(12) United States Patent
Bedjeguelal et al.

(10) Patent No.: US 8,889,711 B2
(45) Date of Patent: Nov. 18, 2014

(54) PYRAZOLOPYRIDINE DERIVATIVES AS ANTICANCER AGENT

(75) Inventors: Karim Bedjeguelal, Toulouse (FR); Rémi Rabot, Toulouse (FR); El Bachir Kaloun, Roquettes (FR); Patrice Mayer, Toulouse (FR); Arnaud Marchand, Korbeek-Lo (BE); Nicolas Rahier, Ayguesvives (FR); Philippe Schambel, Castres (FR); Hugues Bienayme, Saint Symphorien d'Ozon (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 147 days.

(21) Appl. No.: 13/500,757

(22) PCT Filed: Oct. 13, 2010

(86) PCT No.: PCT/EP2010/065346
§ 371 (c)(1),
(2), (4) Date: Jun. 9, 2012

(87) PCT Pub. No.: WO2011/045344
PCT Pub. Date: Apr. 21, 2011

(65) Prior Publication Data
US 2012/0245170 A1 Sep. 27, 2012

Related U.S. Application Data

(60) Provisional application No. 61/254,285, filed on Oct. 23, 2009.

(30) Foreign Application Priority Data

Oct. 13, 2009 (FR) ...................... 09 57140

(51) Int. Cl.
*C07D 471/02* (2006.01)
*C07D 491/02* (2006.01)
*C07D 498/02* (2006.01)
*A61K 31/44* (2006.01)

(52) U.S. Cl.
USPC .......................... 514/303; 546/119

(58) Field of Classification Search
USPC .......................... 546/119; 514/303
See application file for complete search history.

(56) References Cited

U.S. PATENT DOCUMENTS

| | | | |
|---|---|---|---|
| 4,822,799 | A | 4/1989 | Kathawala |
| 2006/0004003 | A1 | 1/2006 | Abe et al. |
| 2007/0032515 | A1 | 2/2007 | Anand et al. |
| 2010/0113415 | A1 | 5/2010 | Rajapakse et al. |

FOREIGN PATENT DOCUMENTS

| WO | 03068773 | * | 8/2003 |
|---|---|---|---|
| WO | WO 2004/014910 | | 2/2004 |
| WO | WO 2007/023105 | | 3/2007 |

OTHER PUBLICATIONS

Quiroga et al., Acta Crystallographica, Section C: Crystal Structure Communications (1999), C55(12), iii, IUC9900168/1-3.*
Quiroga et al., Journal of Heterocyclic Chemistry (2001), 38(1), 53-60.*
Attaby et al., Phosphorus, Sulfur and Silicon and the Related Elements (1997), 126, 27-38.*
Attaby et al., Phosphorus, Sulfur and Silicon and the Related Elements (1996), 119, 257-270.*
S. Abdel-Mohsen et al., *A convenient synthesis of pyrrolo[2,3-b]pyridines and pyrido[2',3':5,4]pyrrolo[2,3-d]pyrimidines*, 139 Monatsh Chem 1233-1240 (2008).
F. Attaby et al., *Reactions with Cyanothioacetamide Derivatives: Synthesis and Reactions of Some Pyrazolo[3,4-b]Pyridine Derivatives*, 73 Phosphorus, Sulfur, and Silicon 127-135 (1992).
F. Attaby et al., *Reactions with Pyridinethione Derivatives: Synthesis and Characterization of Thienyl[2,3-b]Pyridine, Pyridol[2'3':4,5]Thieno[2,3-b]Pyridazine, Pyrido[2'3':4,5]Thieno[2-3-b]-Pyrimidinone, Pyrazolino[3'4':4,5]Thieno[2,3-b]Pyridine and Aminopyrazolo[3,4-b]Pyridine Derivatives*, 126 Phosphorus, Sulfur, and Silicon 27-38 (1997).
M. Chioua et al., *Synthesis and biological evaluation of 3,6-diamino-1H-pyrazolo[3,4-b]pyridine derivatives as protein kinase inhibitors*, 19 Bioorganic & Medicinal Chemistry Letters 4566-4569 (2009).
R. Clay et al., *A Safe, Economical Method for the Preparation of β-Oxo Esters*, 3 Synthesis 290-292 (1993).
J. Cobo et al., *Synthesis and Structural Analysis of 5-Cyanodihydropyrazolo[3,4-b]pyridines*, 38 Heterocyclic Chem 53-60 (2001).
Am Gasco et al., *Benzofurazanyl- and benzofuroxanyl-1,4-dihydropyridines: synthesis, structure and calcium entry blocker activity*, 31 Eur J Med Chem 3-10 (1996).
J. Grossert et al., *The Alkylation of an α, α'-dianion in a β-Ketosulphone Leading to the Preparation of Axial 2-Substituted Thiane-1,1-dioxides*, 40(7) Tetrahedron 1135-1140 (1984).
T. Higashino et al., *Studies on Pyrazolo[3,4-d]pyrimidine Derivatives. V.1) On the Transformation of 1H-Pyrazolo[3-4-d]pyrimidines into 1H-Pyrazolo[3,4-b]pyridines*, 25(4) Chemical & Pharmaceutical Bulletin 535-542 (Apr. 1997).
C. Ibarra et al., *One-Pot Synthesis of β-Keto Sulfones and β-Keto Sulfoxides from Carboxylic Acids*, 54 J. Org. Chem. 5620-5623 (1989).
M. Jachak et al., *Friedländer Condensation of 5-aminopyrazole-4-carbaldehydes with Reactive α-Methylene Ketones: Synthesis of Pyrazolo[3,4-b]pyridines*, 42 J. Heterocyclic Chem 1311-1319 (2005).

(Continued)

*Primary Examiner* — Niloofar Rahmani
(74) *Attorney, Agent, or Firm* — Buchanan Ingersoll & Rooney PC

(57) ABSTRACT

The present invention concerns compounds of following general formula (I): (Formula I) and their pharmaceutically acceptable salts, their method of preparation and their uses, notably as anticancer agent.

(I)

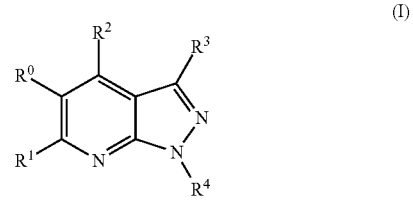

19 Claims, No Drawings

(56) References Cited

OTHER PUBLICATIONS

M. Jachak et al., *Synthesis of Pyrazolo[3,4-b]pyridines Using Ammonium Acetate as Green Reagent in Multi-component Reactions*, 45 J. Heterocyclic Chem 1221-1224 (2008).

Z. Kalme et al., *Reactions of Nucleophilic Substitution of 4-aryl-5-Carbomethoxy-6-Methyl-2-Chloro-3-Cyanopyridines*, 28(12) Chemistry of Heterocyclic Compounds 1411-1415 (1992).

P. Magdolen et al., *Ultrasound effect on the synthesis of 4-alkyl-(aryl)aminobenzaldehydes*, 57 Tetrahedron 4781-4785 (2001).

A. Meyers et al., *Nucleophilic Annulations of Aromatics. Novel Route to Benzo-Fused Ring Systems via Oxazoline Activation*, 46 J. Org. Chem. 483-788 (1981).

V. Nenaidenko et al., *New Synthesis of 3-Aryl-5-amino-1H-pyrazoles*, 40(10) Russian Journal of Organic Chemistry 1518-1520 (2004).

Y. Otomaru at al., *Preparation of an Amphiphilic Resin-Supported BINAP Ligand and Its Use for Rhodium-Catalyzed Asymmetric 1,4-Addition of Phenylboronic Acid in Water*, 6(19) Org. Lett. 3357-3359 (2004).

M. Palanki et al., *Development of Prodrug 4-Chloro-3-(5-methyl-3-{[4-(2-pyrrolidin-1-ylethoxy)phenyl]amino}-1,2,4-benzotriazin-7-yl)phenyl Benzoate (TG100801): A Topically Administered Therapeutic Candidate in Clinical Trials for the Treatment of Age-Related Macular Degeneration*, 51 J. Med. Chem. 1546-1559 (2008).

D. Prim et al., *Convenient Amination of Weakly Activated Thiophenes, Furans and Selenophenes in Aqueous Media*, 55 Tetrahedron 6511-6526 (1999).

U. Rao et al., *Claisen Rearrangement of Aryl Propargyl Ethers in Poly(Ethylene Glycol)—A Remarkable Substituent and Solvent Effect*, 24(45) Tetrahedron Letters 5023-5024 (1983).

I. Sircar et al., *Cardiotonic Agents. 2. Synthesis and Structure-Activity Relationships of 4,5-Dihydro-6-[4-(1H-imidazol-l-yl)phenyl]-3(2H)-pyridazinones: A New Class of Positive Inotropic Agents*, 28 J. Med. Chem. 1405-1413 (1985).

S. Vieth et al., *Furylvinylhalogenides, XII [1]: Reactions of β-Chloro-α-cyano-β-(5-nitrofur-2-yl)-acrylic Acid Derivatives with Malonic Acid Derivatives*, 122 Monatshefte Für Chemie 1035-1045 (1991).

J. Witherington et al., *6-Aryl-pyrazolo[3,4-b]pyridines: Potent Inhibitors of Glycogen Synthase Kinase-3 (GSK-3)*, 13 Bioorganic & Medicinal Chemistry Letters 3055-3057 (2003).

G. Zhu et al., *Design and synthesis of pyridine-pyrazolopyridine-based inhibitors of protein kinase B/akt*, 15 Bioorganic & Medicinal Chemistry 2441-2452 (2007).

* cited by examiner

PYRAZOLOPYRIDINE DERIVATIVES AS ANTICANCER AGENT

CROSS-REFERENCE TO RELATED APPLICATIONS

This application is a U.S. National Stage pursuant to 35 U.S.C. §371 of International Patent Application PCT/EP2010/065346, filed on Oct. 13, 2010, and published as WO 2011/045344 on Apr. 21, 2011, which claims priority to U.S. Provisional Patent Application Ser. No. 61/254,285, filed on Oct. 23, 2009, and French Patent Application 0957140, filed on Oct. 13, 2009, all of which are incorporated herein by reference in their entireties for all purposes.

The present invention concerns pyrazolopyridine derivatives, their therapeutic use notably for cancer treatment, and their method of synthesis.

Protein kinases are enzymes which play a key role in cell signal transduction, and are involved in physiological processes such as cell proliferation, mitosis, differentiation, cell invasion and mobility, or apoptosis. These enzymes are considered to play a major role during the different stages of tumour development, and therefore form important pharmaceutical targets for the treatment of cancers.

Receptor tyrosine kinases (RTKs) form a particular class of protein kinases amongst which mention may be made inter alia of: ALK, EGFR, HER2, PDGFR, KIT, VEGFR, IGFR, FGFR, TRK, AXL, MER, MET, RON and RET. In this sub-family, ALK is considered to be a particularly relevant target since able to give rise to activating chromosome translocation, generating tumorigenesis.

Several cases of chromosome translocations involving ALK and related to cancer pathologies, have already been documented. For example, the fusion protein NPM-ALK is associated with Anaplastic Large Cell Lymphoma (ALCL) for which optimal treatment remains to be developed. Similarly, the fusion protein EML4-ALK is associated with tumoral development in a sub-population of patients suffering from non-small cell lung cancer. Mutant forms of ALK have also been observed in neuroblastoma.

The compounds of the present invention therefore have the property of inhibiting or modulating the enzymatic activity of protein kinases, e.g. ALK, and therefore can be used as medicinal product, for example for the treatment of various diseases notably proliferative diseases such as cancer, inflammation or disorders of the central nervous system.

A particular subject of the invention is therefore a compound of following general formula (I):

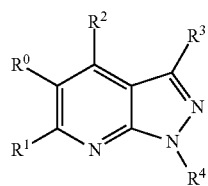

(I)

or a pharmaceutically acceptable salt thereof,
wherein:
$R^0$ is a —CN, —$CO_2H$, —$CONH_2$—$CO_2$—(($C_1$-$C_6$)alkyl), —$SO_2$—(($C_1$-$C_6$)alkyl), —$NO_2$, or —C(=NH)$CH_3$ group,
$R^1$ is a halogen atom such as a chlorine atom, or a $NHR^{20}$, $OR^{21}$, $SR^{21}$, ($C_1$-$C_6$)alkyl, aryl, heteroaryl, aryl-($C_1$-$C_6$))alkyl, heterocycle, or aryl-carbonyloxy group, and preferably is a halogen atom such as a chlorine atom, or a $NHR^{20}$, $SR^{21}$, ($C_1$-$C_6$)alkyl, aryl, heteroaryl, aryl-($C_1$-$C_6$))alkyl, heterocycle, or aryl-carbonyloxy group,
the aryl and heteroaryl rings of said group being optionally substituted with one or more groups chosen from among a halogen atom and a —OH, —CN, —$NO_2$, —$NH_2$, —$CO_2H$, ($C_1$-$C_6$)alkyl optionally substituted with an OH group, ($C_1$-$C_6$)alcoxy, ($C_1$-$C_6$)haloalkyl, ($C_1$-$C_6$)haloalcoxy, aryl, aryloxy, aryl-($C_1$-$C_6$)alkyl, aryl-($C_1$-$C_6$)alcoxy, heteroaryl, heterocycle, —$CO_2$—(($C_1$-$C_6$)alkyl), aryl-carbonyloxy, —NH—(($C_1$-$C_6$)alkyl), and —$NHSO_2$—(($C_1$-$C_6$)alkyl) group; and/or being optionally fused to a heterocycle, and
the heterocycle rings of the whole being optionally substituted with one or more groups chosen from among an oxo(=O) group and a ($C_1$-$C_6$)-alkyl group,
$R^2$ is a hydrogen atom, a ($C_1$-$C_6$)-alkyl, aryl, heteroaryl, cycloalkyl, heterocycle, aryl-($C_1$-$C_6$)alkyl, aryl-($C_1$-$C_6$)alkenyl, —$X^1$-heterocycle, -cycloalkyl-$X^2$-heterocycle, and -cycloalkyl-(($C_1$-$C_6$)alkyl)-OH group,
the aryl and heteroaryl rings of said group being optionally substituted with one or more groups chosen from among a halogen atom, a group OH; $NO_2$; $CO_2H$; CN; $CONH_2$; $SO_3H$; ($C_1$-$C_6$)alkyl optionally substituted with an OH group; ($C_1$-$C_6$)alkynyl optionally substituted with an $NR^{25}R^{26}$ group; ($C_1$-$C_6$)alcoxy; aryl optionally substituted with $NH_2$ and/or $SO_2NH_2$; heteroaryl; heterocycle; aryl-($C_1$-$C_6$)alkyl; heteroaryl-($C_1$-$C_6$)alkyl; heterocycle-($C_1$-$C_6$)alkyl; aryl-($C_1$-$C_6$)alcoxy; heteroaryl-($C_1$-$C_6$)alcoxy; heterocycle-($C_1$-$C_6$)alcoxy; $NR^{10}R^{11}$; and —$X^3$—($C_1$-$C_6$)alkyl)$NR^{12}R^{13}$; and/or being optionally fused to a heterocycle,
the heterocycle rings of the whole being optionally substituted with one or more groups chosen from among OH; ($C_1$-$C_6$)alkyl optionally substituted with OH or $NR^{27}R^{28}$ such as $NH_2$; $CO_2$—(($C_1$-$C_6$)alkyl); heterocycle optionally substituted with a ($C_1$-$C_6$)alkyl group; and $NR^{14}R^{15}$,
$R^3$ is a hydrogen atom, a group $NH_2$; $NO_2$; $CO_2H$; ($C_1$-$C_6$) alkyl optionally substituted with a group $OR^{22}$ or $NR^{23}R^{24}$; CONH—($C_1$-$C_6$)alkyl); CONH—(($C_1$-$C_6$) alkyl)-heterocycle; aryl; heteroaryl; heterocycle; aryl-($C_1$-$C_6$)alkyl; —NH-aryl; or —NH-heteroaryl,
the aryl and heteroaryl rings of said group being optionally substituted with one or more groups chosen from among a halogen atom; a $NO_2$; $CO_2H$; $NR^{16}R^{17}$; aryl; ($C_1$-$C_6$)alkyl; ($C_1$-$C_6$)haloalkyl; ($C_1$-$C_6$)alcoxy; —$CO_2$—($C_1$-$C_6$)alkyl; and heterocycle group, and
the heterocycle rings of the whole being optionally substituted with a ($C_1$-$C_6$)alkyl; ($C_1$-$C_6$)alcoxy; or —NH—($C_1$-$C_6$)alkyl group, and
$R^4$ is a hydrogen atom, a ($C_1$-$C_6$)alkyl group such as methyl or tert-butyl, or an aryl group such as phenyl, and preferably is a hydrogen atom,
wherein:
$X^1$ and $X^2$ are each independently —CO—, —CONH— or —CONH—($C_1$-$C_6$)alkyl),
$X^3$ is a single bond, an oxygen atom, a sulphur atom, a NH or N—(($C_1$-$C_6$)alkyl) group,
$R^{10}$, $R^{11}$, $R^{14}$, $R^{15}$, $R^{18}$, $R^{19}$, and $R^{23}$ to $R^{28}$ are each independently a hydrogen atom or a ($C_1$-$C_6$)alkyl group,
$R^{12}$ and $R^{13}$ are each independently a hydrogen atom or a ($C_1$-$C_6$)alkyl group; or form together, with the nitrogen atom bearing them, a heteroaromatic or a heterocycle optionally substituted with a ($C_1$-$C_6$)alkyl group, $R^{16}$ and $R^{17}$ are each independently a hydrogen atom or a ($C_1$-$C_6$)alkyl group optionally substituted with a group $NR^{18}R^{19}$, $R^{20}$ is a hydrogen atom or a ($C_1$-$C_6$)alkyl, aryl, or aryl-($C_1$-$C_6$)alkyl group, and $R^{21}$ and $R^{22}$ are each independently a hydrogen atom or ($C_1$-$C_6$-alkyl), aryl, or heteroaryl group, the aryl and heteroaryl rings of said group being optionally substituted with one or more groups chosen from among a halogen atom, a group OH, CN, $NO_2$, $NH_2$, $CO_2H$, ($C_1$-$C_6$)alkyl, ($C_1$-$C_6$)alcoxy, ($C_1$-$C_6$)haloalkyl, ($C_1$-$C_6$)haloalcoxy, aryl, aryloxy, aryl-($C_1$-$C_6$)alkyl, aryl-($C_1$-$C_6$)alcoxy, heteroaryl, heterocycle, $CO_2$—(($C_1$-$C_6$)alkyl); NH—(($C_1$-$C_6$)alkyl), and $NHSO_2$—(($C_1$-$C_6$)alkyl); and/or being optionally fused to a heterocycle, and the heterocycle rings of the whole being optionally substituted with a group oxo(=O) and/or ($C_1$-$C_6$) alkyl, with the exclusion of the following compounds:

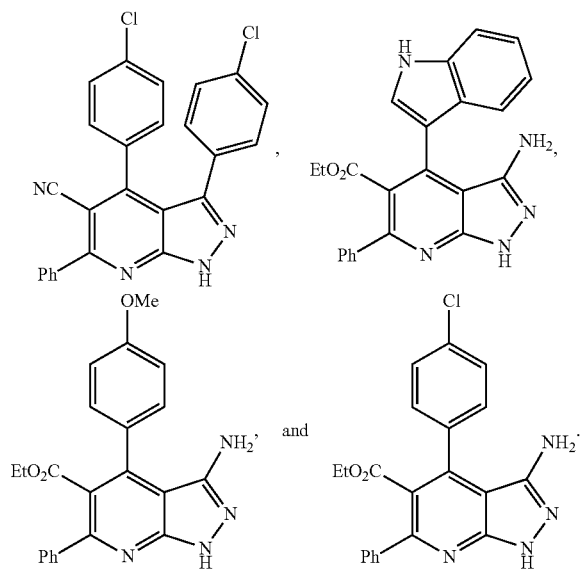

The excluded compounds are described in the following documents: J. Quiroga et al. J. Heterocyclic Chem. 2001, 38, 53-60; Fawzy A. Attaby and Azza M. Abd El Fattah Phosphorus, Sulfur and Silicon 1996, 119, 257-270; and Phosphorus, Sulfur and Silicon 1997, 126, 27-38. However, none of these documents describes any biological activity of these compounds.

In the present invention, by "pharmaceutically acceptable" is meant what can be used to prepare a pharmaceutical composition which is generally safe, non-toxic and neither biologically nor otherwise undesirable and which is acceptable for veterinary use and for human pharmaceutical use.

By "pharmaceutically acceptable salts" of a compound is meant salts which are pharmaceutically acceptable, as defined herein, and which have the desired pharmacological activity of the parent compound. Such salts comprise:

(1) the hydrates and solvates, (2) the acid addition salts formed with organic acids, such as formic acid, or inorganic acids such as hydrochloric acid or hydrobromic acid, or (3) the salts formed when an acid proton present in the parent compound is either replaced by a metallic ion e.g. an alkaline metal ion, an alkaline-earth metal ion or an aluminium ion; or is coordinated with an organic or inorganic base such as potassium hydroxide or sodium hydroxide.

By "halogen atom", is meant, in the meaning of the present invention, fluorine, chlorine, bromine and iodine atoms.

By "($C_1$-$C_6$)alkyl" group, is meant, in the meaning of the present invention, a saturated, linear or branched hydrocarbon chain comprising 1 to 6, preferably 1 to 4, carbon atoms. As an example, the following groups may be cited: methyl, ethyl, propyl, isopropyl, butyl, isobutyl, sec-butyl, tert-butyl, pentyle, and hexyl.

By "($C_2$-$C_6$)alkenyl" group, is meant, in the meaning of the present invention, a linear or branched hydrocarbon chain comprising at least one double bond and containing 2 to 6 carbon atoms. As an example mention may be made of the ethenyl and allyl groups.

By "($C_2$-$C_6$)alkynyl" group, is meant, in the meaning of the present invention, a linear or branched hydrocarbon chain comprising at least one ripple bond and containing 2 to 6 carbon atoms. As an example mention may be made of the ethynyl and propynyl groups.

By "($C_1$-$C_6$)alcoxy" group, is meant, in the meaning of the present invention, a ($C_1$-$C_6$)alkyl group such as defined above, linked to the remainder of the molecule via an oxygen atom. For example mention may be of the groups: methoxy, ethoxy, propoxy, isopropoxy, butoxy and tert-butoxy.

By "($C_1$-$C_6$)halooalkyl" group, is meant, in the meaning of the present invention, a ($C_1$-$C_6$)alkyl group such as defined above in which one or more hydrogen atoms have been replaced by a halogen atom as defined above. This may be in particular a $CF_3$ group.

By "($C_1$-$C_6$)haloalcoxy" group, is meant in the meaning of the present invention, a ($C_1$-$C_6$)haloalkyl group such as defined above, linked to the remainder of the molecule via an oxygen atom.

By "aryl", is meant, in the meaning of the present invention, an aromatic group preferably comprising 6 to 10 carbon atoms and containing one or more fused cycles, such as a phenyl or naphtyl group. Advantageously it is phenyl.

By "aryloxy group", is meant, in the meaning of the present invention, any aryl group such as defined above, linked to the molecule via an oxygen atom. It may be in particular a phenyloxy group.

By "heteroaryl" or "heteroaromatic", is meant, in the meaning of the present invention, an aromatic group comprising 5 to 10 cyclic atoms including one or more heteroatoms, advantageously 1 to 4 and more advantageously 1 or 2, such as sulphur, nitrogen or oxygen atoms for example, the other cyclic atoms being carbon atoms. Examples of heteroaryl groups are the furyl, thienyl, pyrrolyl, pyridinyl, pyrimidinyl, pyrazolyl, imidazolyl, triazolyl, tetrazolyl, or indyl groups.

By "heterocycle", is meant, in the meaning of the present invention, a 3- to 7-membered cycle saturated or unsaturated but not aromatic, and containing one or more, advantageously 1 to 4, more advantageously 1 or 2, heteroatoms such as sulphur, nitrogen or oxygen atoms for example. These may be particularly the pyrrolidinyl, piperidinyl, piperazinyl, or morpholinyl groups.

By "cycloalkyl" group, is meant, in the meaning of the present invention, a cyclic saturated hydrocarbon chain comprising 3 to 7 cyclic carbon atoms. Examples are the cyclopropyl, cyclopentyl, cyclohexyl, and cycloheptyl groups.

By "aryl-($C_1$-$C_6$)alkyl", is meant, in the meaning of the present invention, an aryl group such as defined above, linked to the remainder of the molecule via a $(C_1\text{-}C_6)$alkyl chain such as defined above. As an example, the benzyl group can be cited.

By "aryl-$(C_1\text{-}C_6)$alkenyl", is meant, in the meaning of the present invention, an aryl group such as defined above, linked to the remainder of the molecule via a $(C_1\text{-}C_6)$alkenyl chain such as defined above. As an example, mention may be made of the phenyl-ethenyl group.

By "aryl-$(C_1\text{-}C_6)$alcoxy", is meant, in the meaning of the present invention, an aryl-$(C_1\text{-}C_6)$alkyl group such as defined above, linked to the remainder of the molecule via an oxygen atom. As an example, the benzyloxy group can be mentioned.

By "heteroaryl-$(C_1\text{-}C_6)$alkyl", is meant, in the meaning of the present invention, a heteroaryl group such as defined above, linked to the remainder of the molecule via a $(C_1\text{-}C_6)$ alkyl chain such as defined above.

By "heteroaryl-$(C_1\text{-}C_6)$alcoxy", is meant, in the meaning of the present invention, a heteroaryl-$(C_1\text{-}C_6)$alkyl group such as defined above, linked to the remainder of the molecule via an oxygen atom.

By "heterocycle-$(C_1\text{-}C_6)$alkyl", is meant, in the meaning of the present invention, a heterocycle group such as defined above, linked to the remainder of the molecule via a $(C_1\text{-}C_6)$ alkyl chain such as defined above.

By "heterocycle-$(C_1\text{-}C_6)$alcoxy", is meant, in the meaning of the present invention, a heterocycle-$(C_1\text{-}C_6)$alkyl group such as defined above, linked to the remainder of the molecule via an oxygen atom.

By "arylcarbonyloxy", is meant, in the meaning of the present invention, an aryl group such as defined above, linked to the molecule via a —C(O)O— group. As an example, the phenyl-carbonyloxy group can be cited.

According to a particular embodiment:

$R^0$ is a —CN, —$CO_2H$, —$CONH_2$—$CO_2$—(($C_1$-$C_6$) alkyl), —$SO_2$—(($C_1$-$C_6$)alkyl), —$NO_2$, or —C(=NH) $CH_3$ group, $R^1$ is a halogen atom such as a chlorine atom, or a $NHR^{20}$, $OR^{21}$, $SR^{21}$, $(C_1$-$C_6)$alkyl, aryl, heteroaryl, aryl-($C_1$-$C_6$))alkyl, heterocycle, or aryl-carbonyloxy group, and preferably is a halogen atom such as a chlorine atom, or a $NHR^{20}$, $SR^{21}$, $(C_1$-$C_6)$alkyl, aryl, heteroaryl, aryl-($C_1$-$C_6$))alkyl, heterocycle, or aryl-carbonyloxy group, the aryl and heteroaryl rings of said group being optionally substituted with one or more groups chosen from among a halogen atom and a —OH, —CN, —$NO_2$, —$NH_2$, —$CO_2H$, $(C_1$-$C_6)$alkyl, $(C_1$-$C_6)$alcoxy, $(C_1$-$C_6)$haloalkyl, $(C_1$-$C_6)$haloalcoxy, aryl, aryloxy, aryl-$(C_1$-$C_6)$alkyl, aryl-$(C_1$-$C_6)$alcoxy, heteroaryl, heterocycle, —$CO_2$—(($C_1$-$C_6$)alkyl), —NH—(($C_1$-$C_6$) alkyl), and —$NHSO_2$—(($C_1$-$C_6$)alkyl) group; and/or being optionally fused to a heterocycle, and the heterocycle rings of the whole being optionally substituted with one or more groups chosen from among an oxo(=O) group and a $(C_1$-$C_6)$-alkyl group, $R^2$ is a hydrogen atom, a $(C_1$-$C_6)$-alkyl, aryl, heteroaryl, cycloalkyl, heterocycle, aryl-($C_1$-$C_6$)alkyl, aryl-($C_1$-$C_6$) alkenyl, —$X^1$-heterocycle, -cycloalkyl-$X^2$-heterocycle, and -cycloalkyl-(($C_1$-$C_6$)alkyl)-OH group, the aryl and heteroaryl rings of said group being optionally substituted with one or more groups chosen from among a halogen atom, a group OH; $NO_2$; $CO_2H$; CN; $CONH_2$; $SO_3H$; $(C_1$-$C_6)$alkyl optionally substituted with an OH group; $(C_1$-$C_6)$alcoxy; aryl optionally substituted with $SO_2NH_2$; heteroaryl; heterocycle; aryl-($C_1$-$C_6$)alkyl; heteroaryl-($C_1$-$C_6$)alkyl; heterocycle-($C_1$-$C_6$)alkyl; aryl-($C_1$-$C_6$)alcoxy; heteroaryl-($C_1$-$C_6$)alcoxy; heterocycle-($C_1$-$C_6$)alcoxy; $NR^{10}R^{11}$; and —$X^3$—(($C_1$-$C_6$)alkyl)$NR^{12}R^{13}$; and/or being optionally fused to a heterocycle, the heterocycle rings of the whole being optionally substituted with one or more groups chosen from among OH; $(C_1$-$C_6)$alkyl optionally substituted with OH or $NH_2$; $CO_2$—(($C_1$-$C_6$)alkyl); heterocycle optionally substituted with a $(C_1$-$C_6)$alkyl group; and $NR^{14}R^{15}$, $R^3$ is a hydrogen atom, a group $NH_2$; $NO_2$; $CO_2H$; $(C_1$-$C_6)$ alkyl optionally substituted with a group $OR^{22}$ or $NR^{23}R^{24}$; CONH—(($C_1$-$C_6$)alkyl); CONH—(($C_1$-$C_6$) alkyl)-heterocycle; aryl; heteroaryl; heterocycle; aryl-($C_1$-$C_6$)alkyl; —NH-aryl; or —NH-heteroaryl, the aryl and heteroaryl rings of said group being optionally substituted with one or more groups chosen from among a halogen atom; a $NO_2$; $CO_2H$; $NR^{16}R^{17}$; aryl; $(C_1$-$C_6)$alkyl; $(C_1$-$C_6)$haloalkyl; $(C_1$-$C_6)$alcoxy; —$CO_2$—($C_1$-$C_6$)alkyl; and heterocycle group, and the heterocycle rings of the whole being optionally substituted with a $(C_1$-$C_6)$alkyl; $(C_1$-$C_6)$alcoxy; or —NH—($C_1$-$C_6$)alkyl group, and $R^4$ is a hydrogen atom, a $(C_1$-$C_6)$alkyl group such as methyl or tert-butyl, or an aryl group such as phenyl, and preferably is a hydrogen atom.

Advantageously, $R^0$ is a —CN; —$CO_2H$; —$CO_2$—(($C_1$-$C_6$)alkyl); —$SO_2$(($C_1$-$C_6$)alkyl) group; in particular a —CN or —$CO_2$—(($C_1$-$C_6$)alkyl) group such as COOEt; for example a CN group.

$R^1$ is advantageously an aryl group such as phenyl or naphtyl, or a heteroaryl group such as furyl, thienyl, pyrrole, indolyl, benzoimidazolyl, indazolyl or benzotriazolyl, and is preferably an aryl group such as phenyl, said group being optionally substituted with one or more groups chosen from among a halogen atom, a OH, CN, $NO_2$, $NH_2$, $CO_2H$, $(C_1$-$C_6)$alkyl optionally substituted with an OH group, $(C_1$-$C_6)$alcoxy, $(C_1$-$C_6)$haloalkyl, $(C_1$-$C_6)$haloalcoxy, aryl, aryloxy, aryl-($C_1$-$C_6$)alkyl, aryl-($C_1$-$C_6$)alcoxy, heteroaryl, heterocycle, $CO_2$—(($C_1$-$C_6$)alkyl), aryl-carbonyloxy, NH—(($C_1$-$C_6$)alkyl), and $NHSO_2$—(($C_1$-$C_6$)alkyl) group; and notably chosen from among a halogen atom, a OH, CN, $NO_2$, $NH_2$, $CO_2H$, $(C_1$-$C_6)$alkyl, $(C_1$-$C_6)$alcoxy, $(C_1$-$C_6)$ haloalkyl, $(C_1$-$C_6)$haloalcoxy, aryl, aryloxy, aryl-($C_1$-$C_6$) alkyl, aryl-($C_1$-$C_6$)alcoxy, heteroaryl, heterocycle, $CO_2$—(aryl), NH—(($C_1$-$C_6$)alkyl), and $NHSO_2$—$_{((C_1}$-$C_6)$alkyl) group; and in particular chosen from among a halogen atom, a group OH, $(C_1$-$C_6)$alcoxy such as methoxy, $(C_1$-$C_6)$alkyl such as methyl and $(C_1$-$C_6)$halogenalkyl such as $CF_3$.

In particular, $R^2$ is an aryl or heteroaryl group, said group being optionally substituted with one or more groups chosen from among a halogen atom, a group OH; $NO_2$; $CO_2H$; CN; $CONH_2$; $SO_3H$; $(C_1$-$C_6)$alkyl optionally substituted with an OH group; $(C_1$-$C_6)$alkynyl optionally substituted with an $NR^{25}R^{26}$ group; $(C_1$-$C_6)$alcoxy; aryl optionally substituted with $NH_2$ and/or $SO_2NH_2$; heteroaryl; heterocycle; aryl-($C_1$-$C_6$)alkyl; heteroaryl-($C_1$-$C_6$)alkyl; heterocycle-($C_1$-$C_6$)alkyl; aryl-($C_1$-$C_6$)alcoxy; heteroaryl-($C_1$-$C_6$)alcoxy; heterocycle-($C_1$-$C_6$)alcoxy; $NR^{10}R^{11}$; and —$X^3$—(($C_1$-$C_6$)alkyl)$NR^{12}R^{13}$; and/or being optionally fused to a heterocycle, the heterocycle rings of the whole being optionally substituted with one or more groups chosen from among OH; $(C_1$-$C_6)$alkyl optionally substituted with OH or $NR^{27}R^{28}$; $CO_2$—(($C_1$-$C_6$)alkyl); heterocycle optionally substituted with a $(C_1$-$C_6)$alkyl group; and $NR^{14}R^{15}$.

Advantageously, $R^2$ is an aryl or heteroaryl group, said group being optionally substituted with one or more groups chosen from among a halogen atom, a group OH; $NO_2$; $CO_2H$; CN; $CONH_2$; $SO_3H$; $(C_1$-$C_6)$alkyl optionally substituted with an OH group; $(C_1-C_6)$alcoxy; aryl optionally substituted with $SO_2NH_2$; heteroaryl; heterocycle; aryl-$(C_1-C_6)$alkyl; heteroaryl-$(C_1-C_6)$alkyl; heterocycle-$(C_1-C_6)$alkyl; aryl-$(C_1-C_6)$alcoxy; heteroaryl-$(C_1-C_6)$alcoxy; heterocycle-$(C_1-C_6)$alcoxy; $NR^{10}R^{11}$; and —$X^3$—$((C_1-C_6)$alkyl)$NR^{12}R^{13}$; and/or being optionally fused to a heterocycle, the heterocycle rings of the whole being optionally substituted with one or more groups chosen from among OH; $(C_1-C_6)$alkyl optionally substituted with OH or $NH_2$; $CO_2$—$((C_1-C_6)$alkyl); heterocycle optionally substituted with a $(C_1-C_6)$alkyl group; and $NR^{14}R^{15}$.

Advantageously, $R^3$ is a hydrogen atom, a group $NH_2$, $(C_1-C_6)$alkyl group such as methyl, aryl such as phenyl, or heteroaryl such as furanyl, thienyl, pyridinyl, isoxazolyl, thiazolyl or oxadiazolyl, the aryl and heteroaryl rings being optionally substituted with one or more groups chosen from among a halogen atom or a $NO_2$, $CO_2H$, $NR^{16}R^{17}$, aryl, $(C_1-C_6)$alkyl, $(C_1-C_6)$haloalkyl, $(C_1-C_6)$alcoxy, $CO_2$—$(C_1-C_6)$alkyl, and heterocyle group, the heterocycle rings being optionally substituted with a $(C_1-C_6)$alkyl, $(C_1-C_6)$alcoxy, or NH—$(C_1-C_6)$alkyl group.

More advantageously, $R^3$ is a hydrogen atom, a $NH_2$, $(C_1-C_6)$alkyl, aryl, or heteroaryl group, and advantageously a hydrogen atom, a $NH_2$, methyl, phenyl, thienyl, or furanyl group.

Preferably $R^4$ is a hydrogen atom.

According to one particular embodiment, the compound of the invention is a compound of general formula (I) or one of its pharmaceutically acceptable salts in which:

$R^0$ is a —CN, —$CO_2H$, —$CO_2$—$((C_1-C_6)$alkyl), or —$SO_2$$((C_1-C_6)$alkyl) group; for example a —CN or —$CO_2$$((C_1-C_6)$alkyl) group such as —COOEt; for example —CN, $R^1$ is a halogen atom such as a chlorine atom, or a group: $NHR^{20}$, $OR^{21}$, $(C_1-C_6)$alkyl, aryl, heteroaryl, aryl-$(C_1-C_6)$alkyl, or heterocycle; for example an aryl group such as phenyl or naphtyl, or a heteroaryl group such as furyl, thienyl, pyrrole, indolyl, benzoimidazolyl, indazolyl or benzotriazolyl; for example phenyl, the aryl and heteroaryl rings of said group being optionally substituted with one or more groups chosen from among a halogen atom, a group —OH, —CN, —$NO_2$, —$NH_2$, —$CO_2H$, $(C_1-C_6)$alkyl, $(C_1-C_6)$alcoxy, $(C_1-C_6)$haloalkyl such as $CF_3$, aryl-$(C_1-C_6)$alcoxy such as phenylalcoxy, heteroaryl, heterocycle, —$CO_2$—$((C_1-C_6)$alkyl) such as —$CO_2$—$CH_3$, aryl-carbonyloxy such as phenylcarbonyloxy, —NH$((C_1-C_6)$alkyl, and —$NHSO_2$—$((C_1-C_6)$alkyl); in particular chosen from among a halogen atom, a group —OH, —CN, —$NO_2$, —$NH_2$, —$CO_2H$, $(C_1-C_6)$alkyl, $(C_1-C_6)$alcoxy, $(C_1-C_6)$haloalkyl such as $CF_3$, aryl-$(C_1-C_6)$alcoxy such as phenylalcoxy, heteroaryl, heterocycle, —$CO_2$—$((C_1-C_6)$alkyl) such as —$CO_2$—$CH_3$, —NH$((C_1-C_6)$alkyl, and —$NHSO_2$—$((C_1-C_6)$alkyl); for example from among a halogen atom and a group —OH, $(C_1-C_6)$alcoxy such as methoxy, $(C_1-C_6)$alkyl such as methyl, and $(C_1-C_6)$haloalkyl such as $CF_3$, and/or the aryl and heteroaryl rings of said group being optionally fused to a heterocycle, the heterocycle rings of the whole being optionally substituted with one or more groups chosen from among an oxo(=O) and $(C_1-C_6)$alkyl group, $R^2$ is a hydrogen atom, a $(C_1-C_6)$alkyl; aryl; heteroaryl; aryl-$(C_1-C_6)$alkyl; aryl-$(C_1-C_6)$alkenyl; —$X^1$-heterocycle; -cycloalkyl-$X^2$-heterocycle and -cycloalkyl-$((C_1-C_6)$alkyl)-OH group, the aryl and heteroaryl rings of said group being optionally substituted with one or more groups chosen from among a halogen atom, a group OH; $NO_2$; $CO_2H$; CN; $CONH_2$; $SO_3H$; $(C_1-C_6)$alkyl optionally substituted with a OH group; $(C_1-C_6)$alkynyl optionally substituted with an $NR^{25}R^{26}$ group; $(C_1-C_6)$alcoxy; aryl optionally substituted with $NH_2$ and/or $SO_2NH_2$; heterocycle; heteroaryl-$(C_1-C_6)$alkyl; heterocycle-$(C_1-C_6)$alkyl; heterocycle-$(C_1-C_6)$alcoxy; $NR^{10}R^{11}$; and —$X^3$—$((C_1-C_6)$alkyl)-$NR^{12}R^{13}$; and/or being optionally fused to a heterocycle; and notably the aryl and heteroaryl rings of said group being optionally substituted with one or more groups chosen from among a halogen atom, a group OH; $NO_2$; $CO_2H$; CN; $CONH_2$; $SO_3H$; $(C_1-C_6)$alkyl optionally substituted with a OH group; $(C_1-C_6)$alcoxy; aryl optionally substituted with $SO_2NH_2$; heterocycle; heteroaryl-$(C_1-C_6)$alkyl; heterocycle-$(C_1-C_6)$alkyl; heterocycle-$(C_1-C_6)$alcoxy; $NR^{10}R^{11}$; and —$X^3$—$((C_1-C_6)$alkyl)-$NR^{12}R^{13}$; and/or being optionally fused to a heterocycle, the heterocycle rings of the whole being optionally substituted with one or more groups chosen from among OH; $(C_1-C_6)$alkyl optionally substituted with OH or $NR^{27}R^{28}$ such $NH_2$; $CO_2$—$((C_1-C_6)$alkyl); heterocycle optionally substituted with a $(C_1-C_6)$alkyl group; and $NR^{14}R^{15}$;

$R^3$ is a hydrogen atom, a group $NH_2$, $NO_2$, $(C_1-C_6)$alkyl, CONH—$((C_1-C_6)$alkyl), CONH—$((C_1-C_6)$alkyl)-heterocycle, aryl, heteroaryl, heterocycle, aryl-$(C_1-C_6)$alkyl, or —NH-heteroaryl; for example a hydrogen atom, a group $NH_2$, $(C_1-C_6)$alkyl (such as methyl), aryl (such as phenyl), or heteroaryl (such as furanyl, thienyl, pyridinyl, isoxazolyl, thiazolyl, or oxadiazolyl, for example furanyl or thienyl), the aryl and heteroaryl rings of said group being optionally substituted with one or more groups chosen from among a halogen atom, a group $NO_2$, $CO_2H$, $NR^{16}R^{17}$, aryl such as phenyl, $(C_1-C_6)$alkyl, $(C_1-C_6)$haloalkyl, $(C_1-C_6)$alcoxy, —$CO_2$—$(C_1-C_6)$alkyl, and heterocycle, the heterocycle rings of the whole being optionally substituted with a $(C_1-C_6)$alkyl, $(C_1-C_6)$alcoxy or —NH—$(C_1-C_6)$alkyl group, and $R^4$ is a hydrogen atom, a $(C_1-C_6)$alkyl group (such as methyl or tert-butyl) or an aryl group such as phenyl; for example it is a hydrogen atom, wherein:

$X^1$ and $X^2$ are each independently —CO—, —CONH— or —CONH—$((C_1-C_6)$alkyl), $X^3$ is a single bond, an oxygen atom, a sulphur atom or N—$((C_1-C_6)$alkyl), $R^{10}$, $R^{11}$, $R^{14}$, $R^{15}$, $R^{18}$, $R^{19}$ and $R^{23}$ and $R^{28}$ are each independently a hydrogen atom or a $(C_1-C_6)$alkyl group, $R^{12}$ and $R^{13}$ are each independently a hydrogen atom or a $(C_1-C_6)$alkyl group; or form together, with the nitrogen atom bearing them, a heterocycle, $R^{16}$ and $R^{17}$ are each independently a hydrogen atom or a $(C_1-C_6)$alkyl group optionally substituted with a $NR^{18}R^{19}$ group, $R^{18}$ and $R^{19}$ are each independently a hydrogen atom or a $(C_1-C_6)$alkyl group, $R^{20}$ is a hydrogen atom or a $(C_1-C_6)$alkyl, aryl, or aryl-$(C_1-C_6)$alkyl group, and $R^{21}$ is a hydrogen atom or a $(C_1-C_6)$alkyl, aryl, or heteroaryl group, the aryl and heteroaryl rings of said group being optionally substituted with one or more groups chosen from among a halogen atom, a group OH, CN, NO$_2$, NH$_2$, CO$_2$H, (C$_1$-C$_6$)alkyl, (C$_1$-C$_6$)alcoxy, (C$_1$-C$_6$)haloalkyl, (C$_1$-C$_6$)haloalcoxy, aryl, aryloxy, aryl-(C$_1$-C$_6$)alkyl, aryl-(C$_1$-C$_6$)alcoxy, hétéroaryle, heterocycle, CO$_2$—((C$_1$-C$_6$)alkyl), NH—((C$_1$-C$_6$)alkyl), and NHSO$_2$—((C$_1$-C$_6$)alkyl), and/or being optionally fused to a heterocycle, the heterocycle rings of the whole being optionally substituted with an oxo(=O) and/or (C$_1$-C$_6$)alkyl group.

According to another particular embodiment, the compounds of the invention may meet the following formula (Ia):

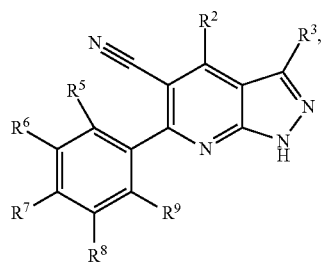

(Ia)

or a pharmaceutically acceptable salt thereof, wherein:

R$^2$ and R$^3$ are such as defined previously, and

R$^5$, R$^6$, R$^7$, R$^8$, and R$^9$ are each independently a hydrogen atom, a halogen atom, a group OH; CN; NO$_2$; NH$_2$; CO$_2$H; (C$_1$-C$_6$)alkyl optionally substituted with an OH group; (C$_1$-C$_6$)alcoxy; (C$_1$-C$_6$)haloalkyl; (C$_1$-C$_6$)haloalcoxy; aryl; aryloxy; aryl-(C$_1$-C$_6$)alkyl; aryl-(C$_1$-C$_6$)alcoxy; heteroaryl; heterocycle; CO$_2$—((C$_1$-C$_6$)alkyl); aryl-carbonyloxy; NH—((C$_1$-C$_6$)alkyl), and NHSO$_2$—((C$_1$-C$_6$)alkyl); and notably are each independently a hydrogen atom, a halogen atom, a group OH; CN; NO$_2$; NH$_2$; CO$_2$H; (C$_1$-C$_6$)alkyl; (C$_1$-C$_6$)alcoxy; (C$_1$-C$_6$)haloalkyl; (C$_1$-C$_6$)haloalcoxy; aryl; aryloxy; aryl-(C$_1$-C$_6$)alkyl; aryl-(C$_1$-C$_6$)alcoxy; heteroaryl; heterocycle; CO$_2$—(C$_1$-C$_6$)alkyl); NH—((C$_1$-C$_6$)alkyl), and NHSO$_2$—((C$_1$-C$_6$)alkyl); and in particular are each independently a hydrogen atom, a halogen atom, a group OH, (C$_1$-C$_6$)alcoxy such as methoxy, (C$_1$-C$_6$)alkyl such as methyl, or (C$_1$-C$_6$)halogenalkyl such as CF$_3$.

The compounds of the invention may in particular be chosen from among the compounds cited in following Table 1:

TABLE I

| 1 | 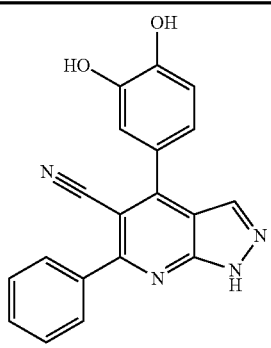 |
|---|---|

TABLE I-continued

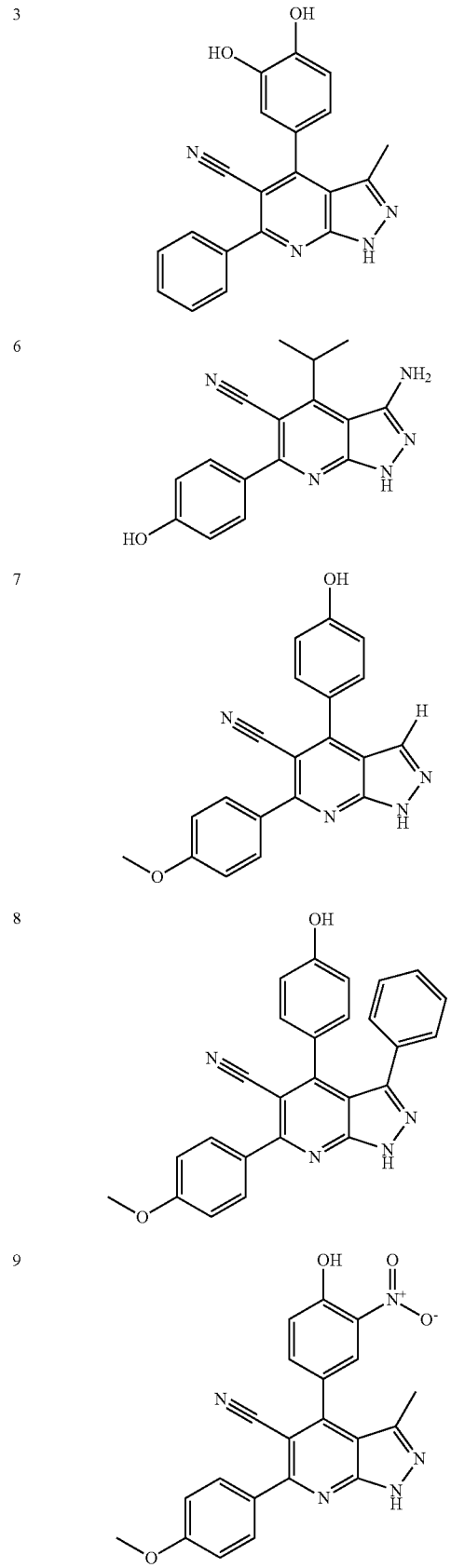

TABLE I-continued
| | |
|---|---|
| 10 | 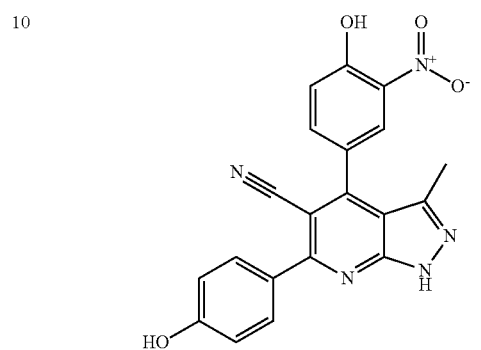 |
| 11 | 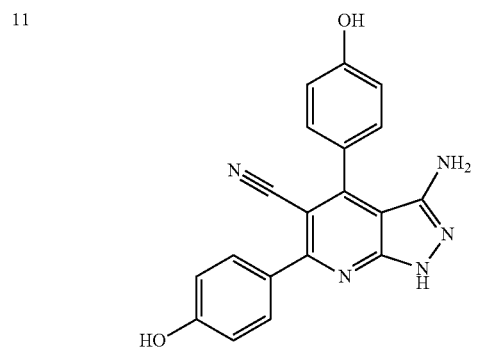 |
| 12 | 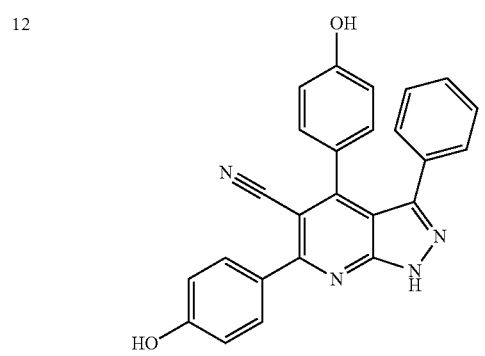 |
| 13 | 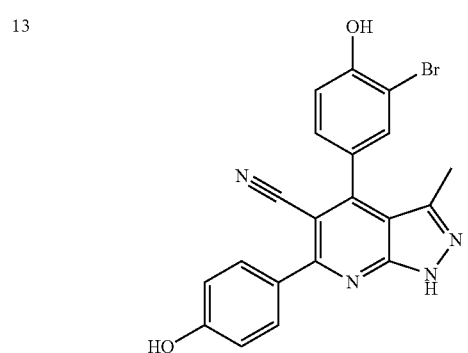 |
| 14 | 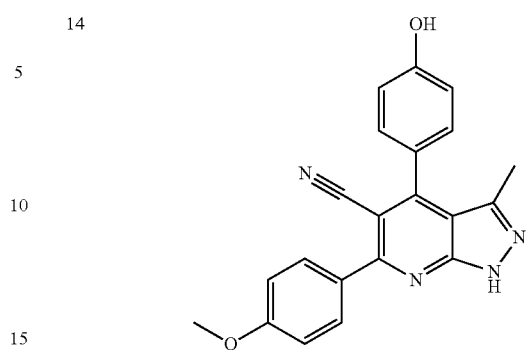 |
| 15 | 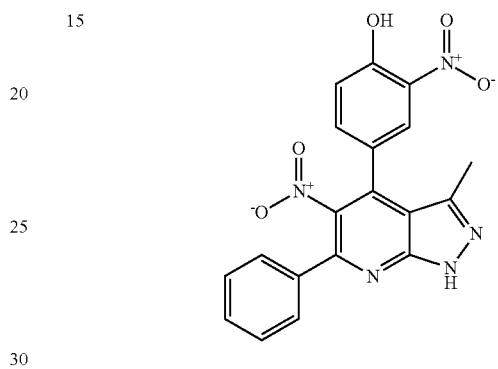 |
| 16 | 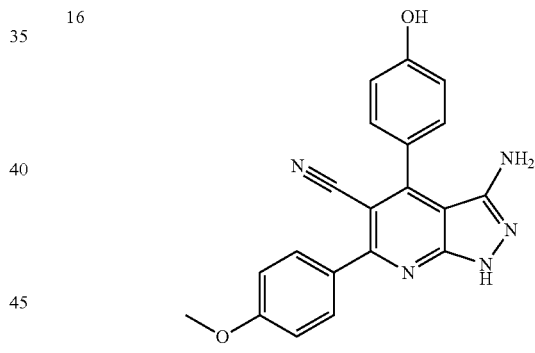 |
| 17 | 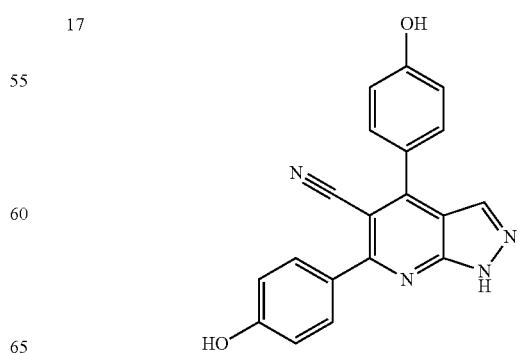 |

TABLE I-continued
| | | | |
|---|---|---|---|
| 18 | 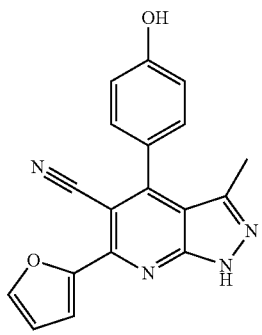 [SMILES: Cc1n[nH]c2nc(-c3ccco3)c(C#N)c(-c3ccc(O)cc3)c12] | 22 | 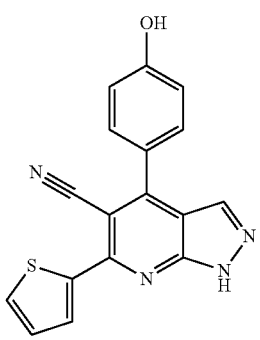 |
| 19 | 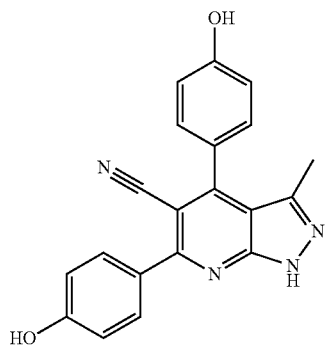 [SMILES: Cc1n[nH]c2nc(-c3ccc(O)cc3)c(C#N)c(-c3ccc(O)cc3)c12] | 23 | 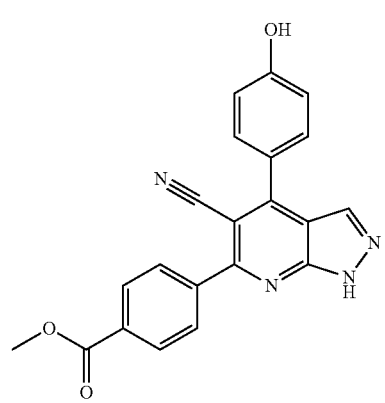 |
| 20 | 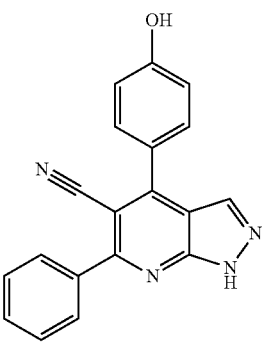 [SMILES: N#Cc1c(-c2ccccc2)nc2[nH]ncc2c1-c1ccc(O)cc1] | 24 | 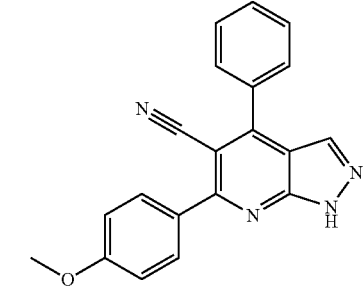 |
| 21 | 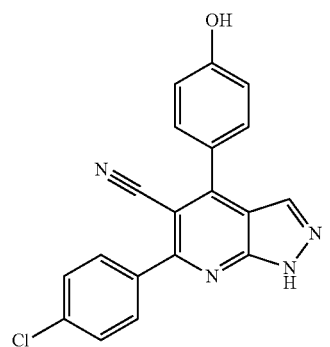 [SMILES: N#Cc1c(-c2ccc(Cl)cc2)nc2[nH]ncc2c1-c1ccc(O)cc1] | 25 | 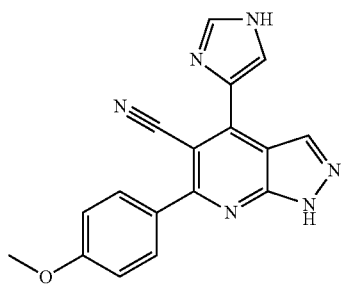 [SMILES: COc1ccc(-c2nc3[nH]ncc3c(-c3c[nH]cn3)c2C#N)cc1] |

TABLE I-continued
| 26 | 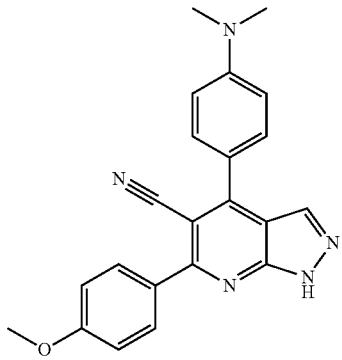 [SMILES: COc1ccc(-c2nc3[nH]ncc3c(-c3ccc(N(C)C)cc3)c2C#N)cc1] | 31 | 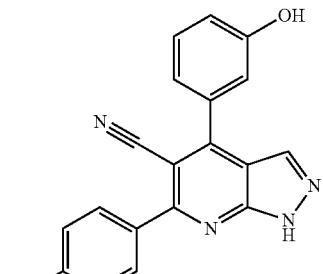 |
| 27 | 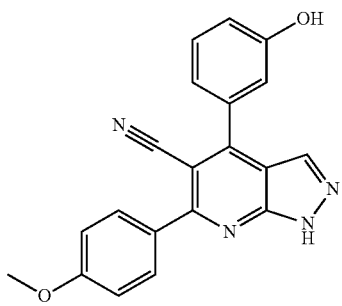 [SMILES: COc1ccc(-c2nc3[nH]ncc3c(-c3cccc(O)c3)c2C#N)cc1] | 32 | 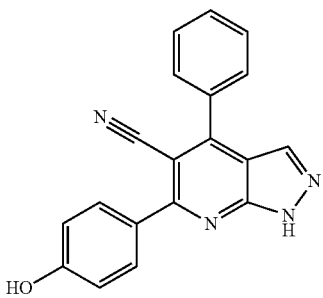 |
| 28 | 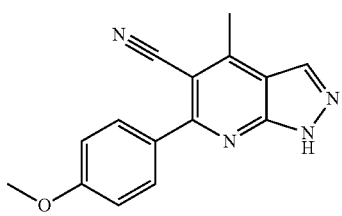 [SMILES: COc1ccc(-c2nc3[nH]ncc3c(C)c2C#N)cc1] | 33 | 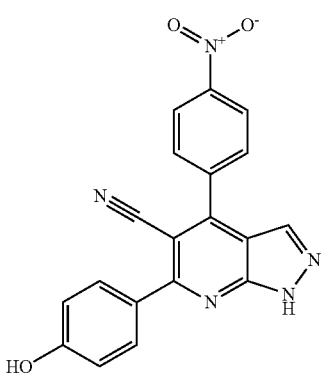 [SMILES: N#Cc1c(-c2ccc(O)cc2)nc2[nH]ncc2c1-c1ccc([N+](=O)[O-])cc1] |
| 29 | 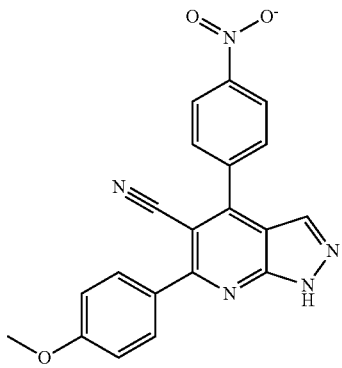 | 34 | 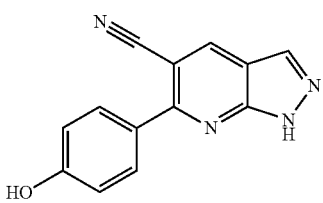 [SMILES: N#Cc1cc2cn[nH]c2nc1-c1ccc(O)cc1] |
| 30 | 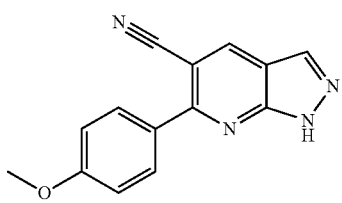 | 35 | 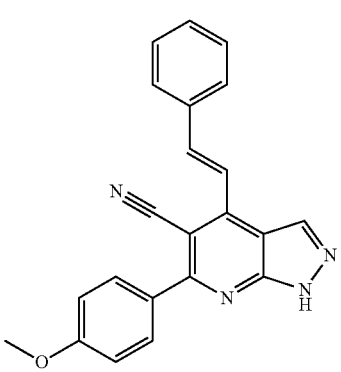 |

TABLE I-continued
| | | | |
|---|---|---|---|
| 36 | 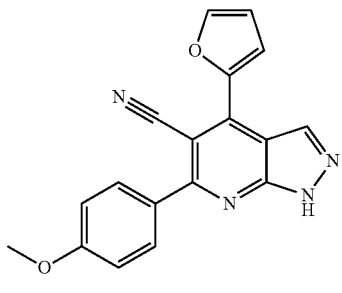 [SMILES: COc1ccc(-c2nc3[nH]ncc3c(-c3ccco3)c2C#N)cc1] | 41 | 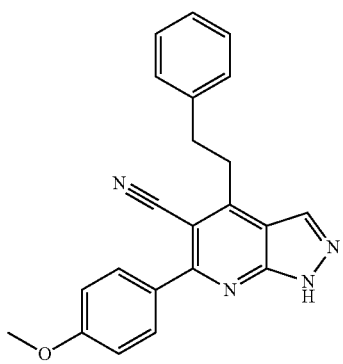 |
| 37 | 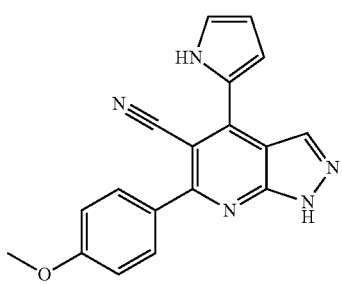 | 42 | 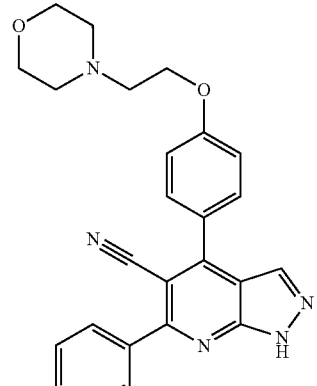 |
| 38 | 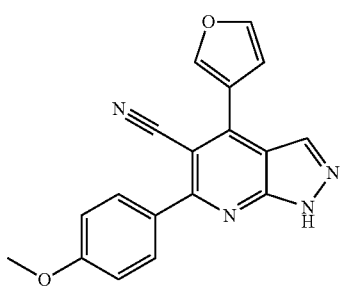 [SMILES: COc1ccc(-c2nc3[nH]ncc3c(-c3ccoc3)c2C#N)cc1] | 43 | 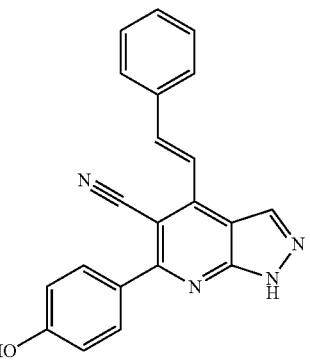 |
| 39 | 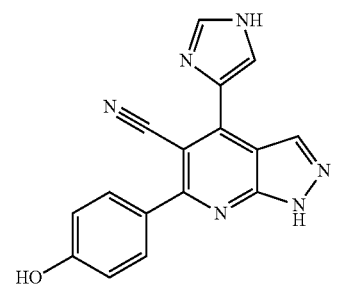 [SMILES: N#Cc1c(-c2ccc(O)cc2)nc2[nH]ncc2c1-c1c[nH]cn1] | 44 | 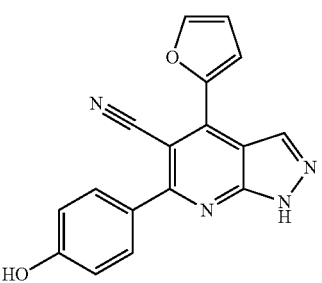 |
| 40 | 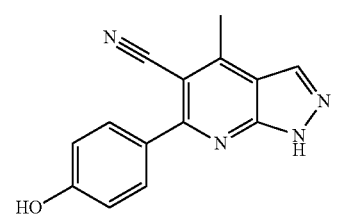 [SMILES: Cc1c(C#N)c(-c2ccc(O)cc2)nc2[nH]ncc12] | | |

TABLE I-continued
| | |
|---|---|
| 45 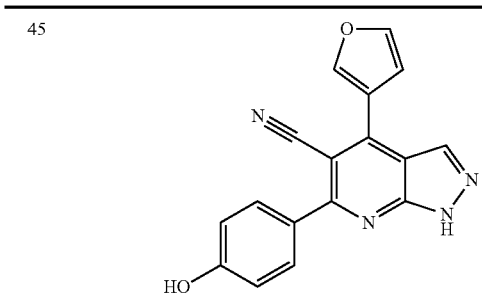 | 50 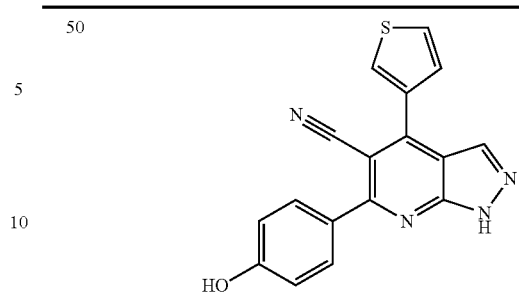 |
| 46 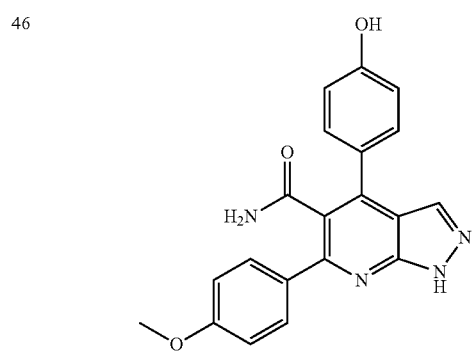 | 51 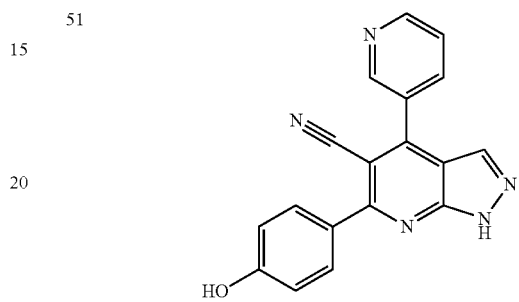 |
| 47 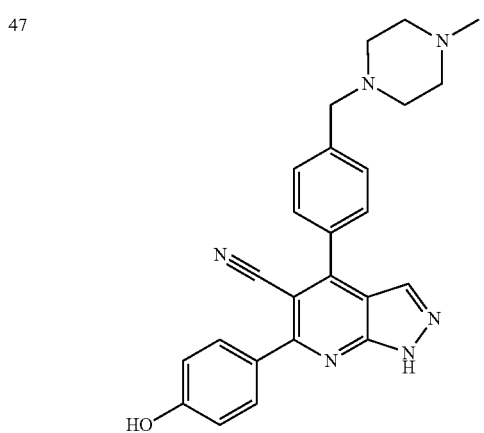 | 52 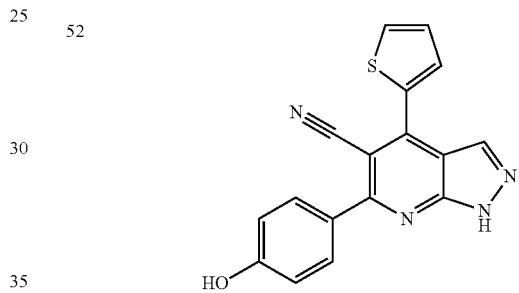 |
| 48 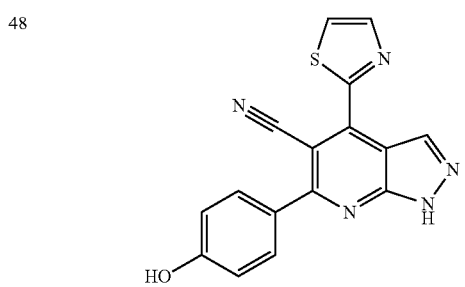 | 53 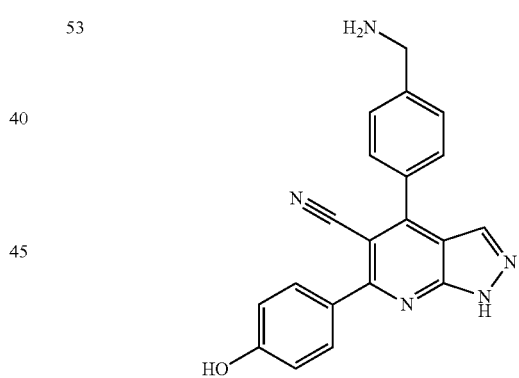 |
| 49 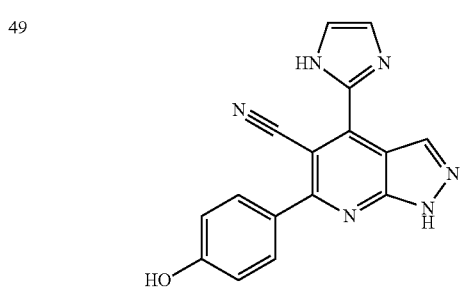 | 54 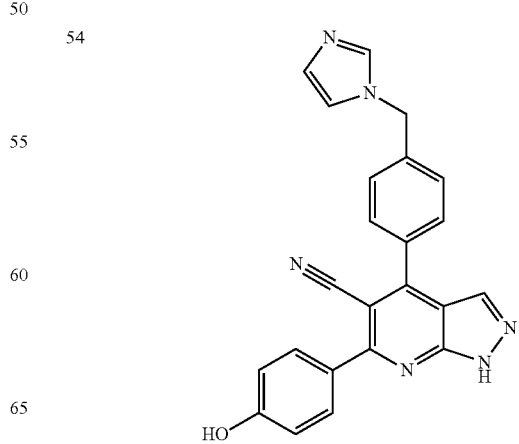 |

TABLE I-continued
| | |
|---|---|
| 55 | 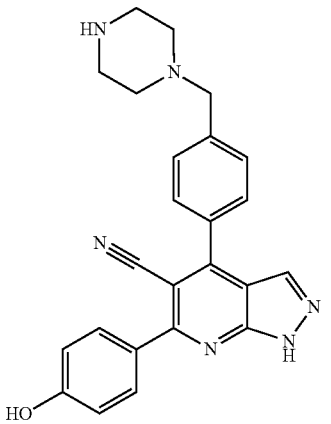 [SMILES: N#Cc1c(-c2ccc(O)cc2)nc2[nH]ncc2c1-c1ccc(CN2CCNCC2)cc1] |
| 56 | 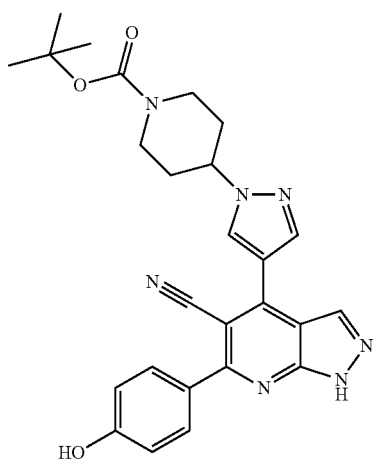 [SMILES: CC(C)(C)OC(=O)N1CCC(n2cc(-c3c(C#N)c(-c4ccc(O)cc4)nc4[nH]ncc34)cn2)CC1] |
| 57 | 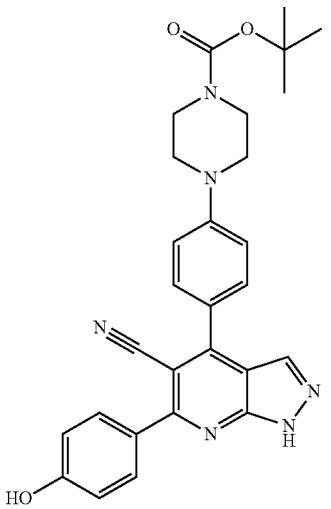 [SMILES: CC(C)(C)OC(=O)N1CCN(c2ccc(-c3c(C#N)c(-c4ccc(O)cc4)nc4[nH]ncc34)cc2)CC1] |
| 58 | 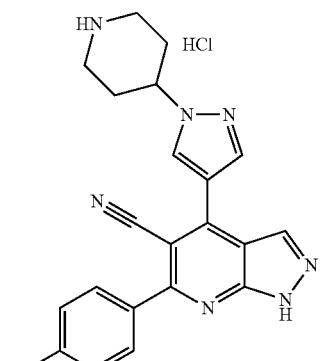 |
| 59 | 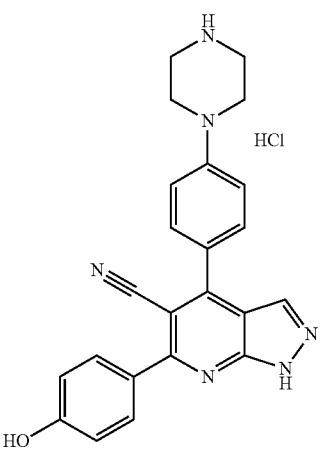 [SMILES: N#Cc1c(-c2ccc(O)cc2)nc2[nH]ncc2c1-c1ccc(N2CCNCC2)cc1 ; Cl] |
| 60 | 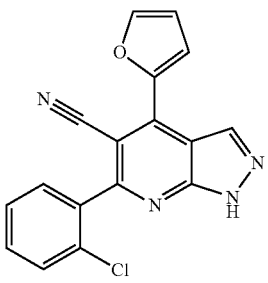 [SMILES: N#Cc1c(-c2ccccc2Cl)nc2[nH]ncc2c1-c1ccco1] |
| 61 | 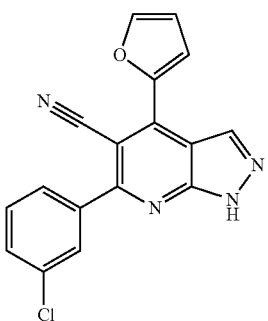 [SMILES: N#Cc1c(-c2cccc(Cl)c2)nc2[nH]ncc2c1-c1ccco1] |

TABLE I-continued
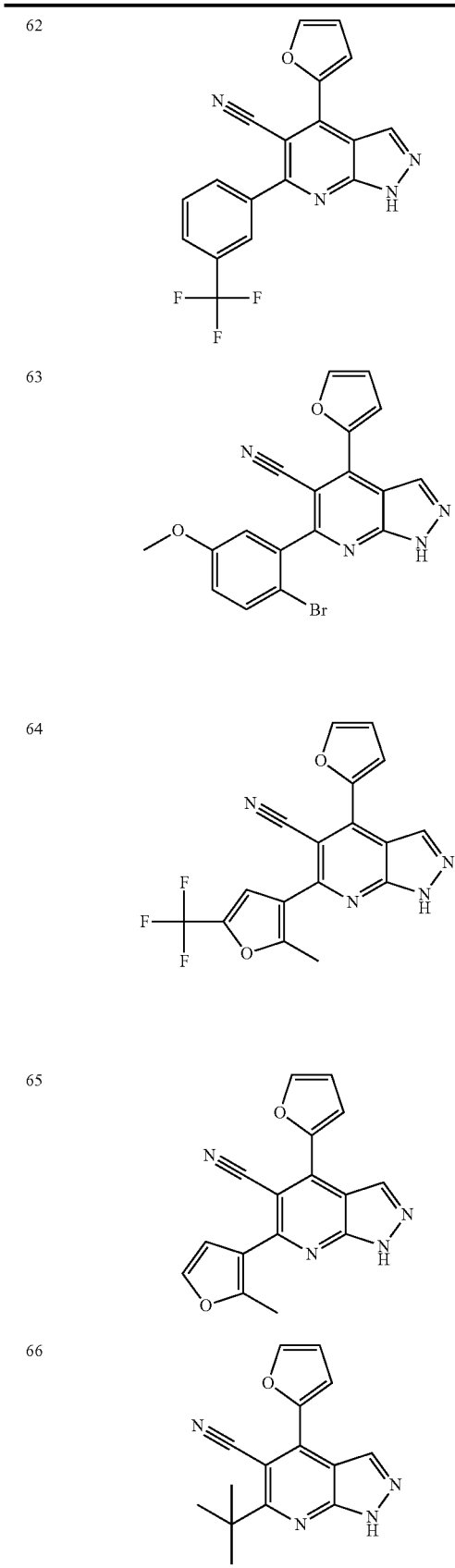
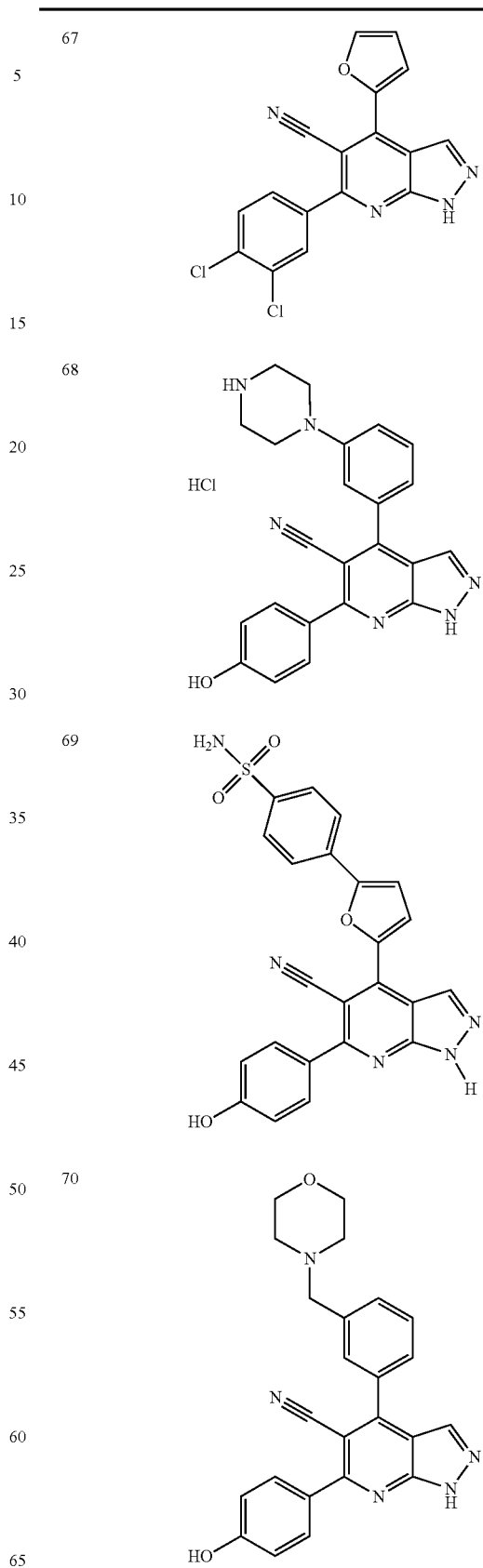

TABLE I-continued
| 71 | 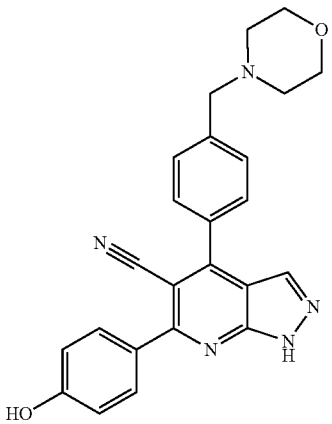 [SMILES: N#Cc1c(-c2ccc(O)cc2)nc2[nH]ncc2c1-c1ccc(CN2CCOCC2)cc1] |
| 72 | 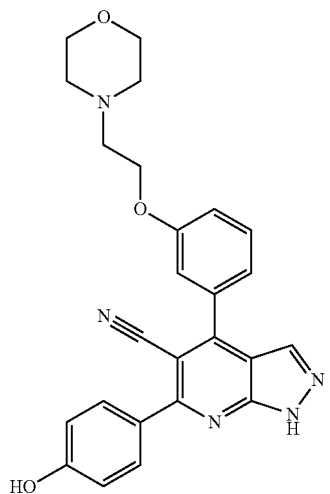 [SMILES: N#Cc1c(-c2ccc(O)cc2)nc2[nH]ncc2c1-c1cccc(OCCN2CCOCC2)c1] |
| 73 | 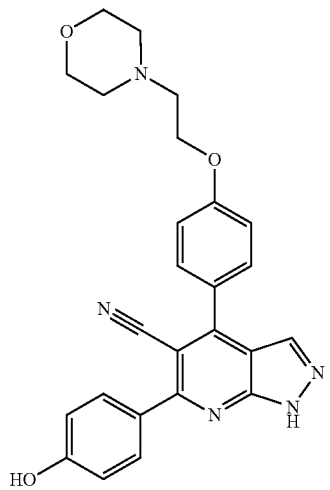 [SMILES: N#Cc1c(-c2ccc(O)cc2)nc2[nH]ncc2c1-c1ccc(OCCN2CCOCC2)cc1] |
| 74 | 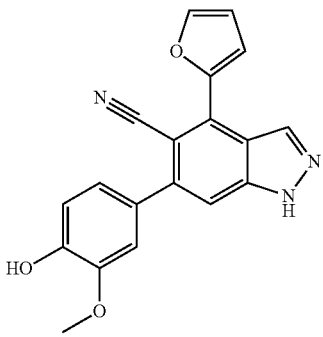 [SMILES: COc1cc(-c2cc3[nH]ncc3c(-c3ccco3)c2C#N)ccc1O] |
| 75 | 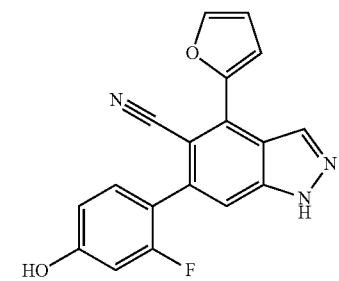 |
| 76 | 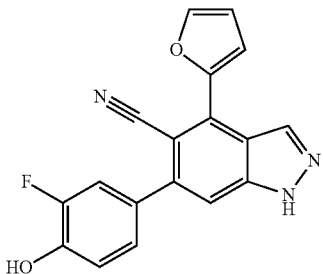 |
| 77 | 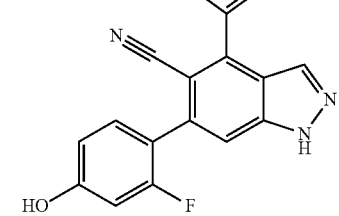 |
| 78 | 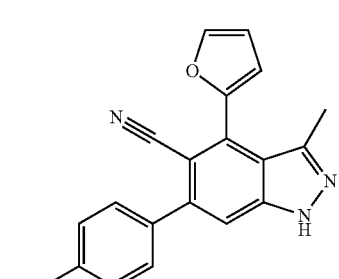 |

TABLE I-continued
| 79 | 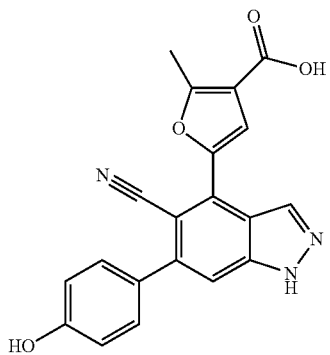 [SMILES: Cc1oc(-c2c(C#N)c(-c3ccc(O)cc3)cc3[nH]ncc23)cc1C(=O)O] |
| --- | --- |
| 80 | 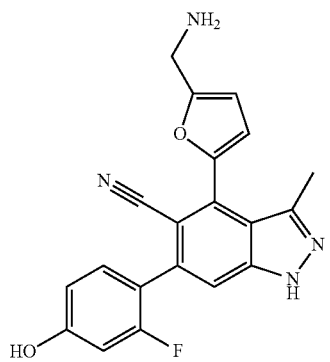 [SMILES: Cc1n[nH]c2cc(-c3ccc(O)cc3F)c(C#N)c(-c3ccc(CN)o3)c12] |
| 81 | 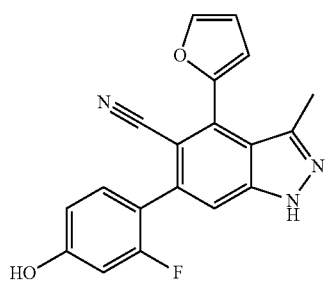 [SMILES: Cc1n[nH]c2cc(-c3ccc(O)cc3F)c(C#N)c(-c3ccco3)c12] |
| 82 | 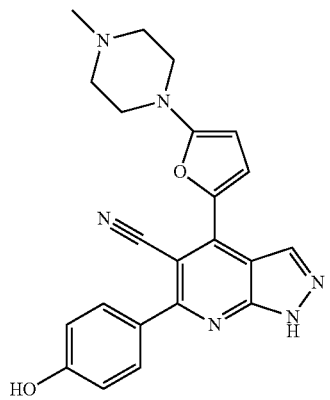 [SMILES: CN1CCN(c2ccc(-c3c(C#N)c(-c4ccc(O)cc4)nc4[nH]ncc34)o2)CC1] |
TABLE I-continued
| 83 | 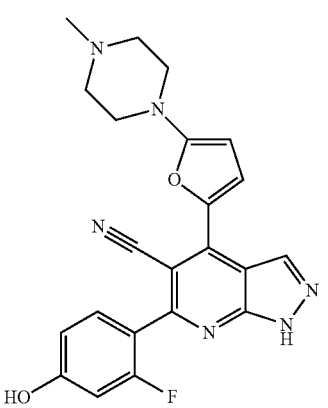 [SMILES: CN1CCN(c2ccc(-c3c(C#N)c(-c4ccc(O)cc4F)nc4[nH]ncc34)o2)CC1] |
| --- | --- |
| 84 | 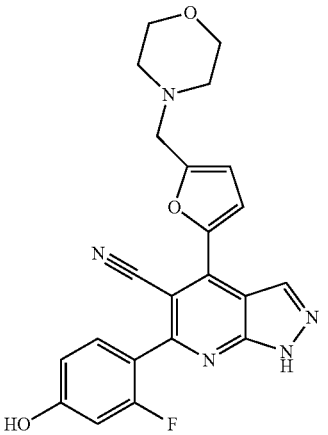 [SMILES: N#Cc1c(-c2ccc(O)cc2F)nc2[nH]ncc2c1-c1ccc(CN2CCOCC2)o1] |
| 85 | 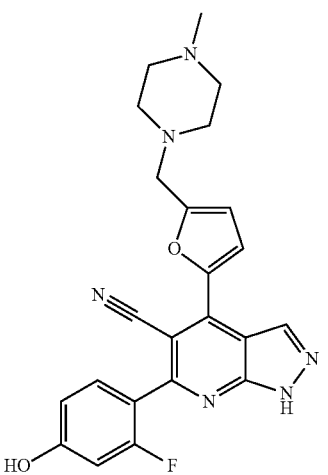 [SMILES: CN1CCN(Cc2ccc(-c3c(C#N)c(-c4ccc(O)cc4F)nc4[nH]ncc34)o2)CC1] |

TABLE I-continued
| | |
|---|---|
| 86 | 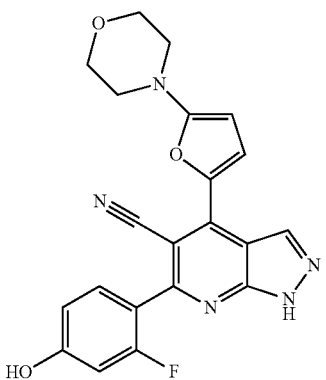 [SMILES: N#Cc1c(-c2ccc(O)cc2F)nc2[nH]ncc2c1-c1ccc(N2CCOCC2)o1] |
| 87 | 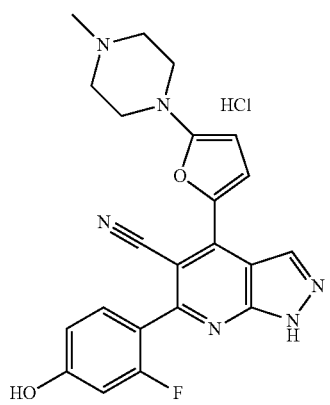 [SMILES: CN1CCN(c2ccc(-c3c(C#N)c(-c4ccc(O)cc4F)nc4[nH]ncc34)o2)CC1 ; Cl] |
| 88 | 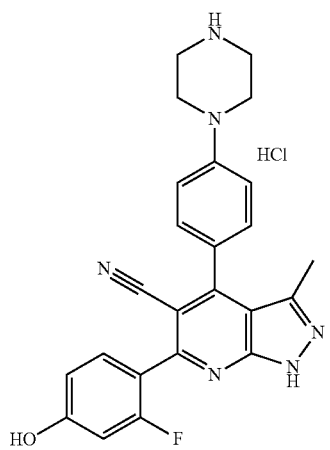 [SMILES: Cc1n[nH]c2nc(-c3ccc(O)cc3F)c(C#N)c(-c3ccc(N4CCNCC4)cc3)c12 ; Cl] |
| 89 | 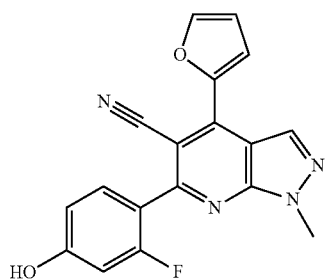 [SMILES: Cn1ncc2c(-c3ccco3)c(C#N)c(-c3ccc(O)cc3F)nc21] |
| 90 | 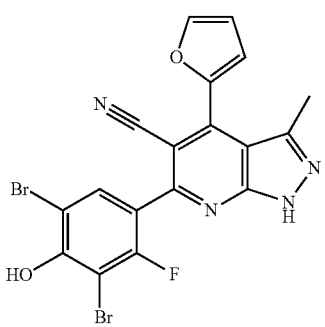 [SMILES: Cc1n[nH]c2nc(-c3cc(Br)c(O)c(Br)c3F)c(C#N)c(-c3ccco3)c12] |
| 91 | 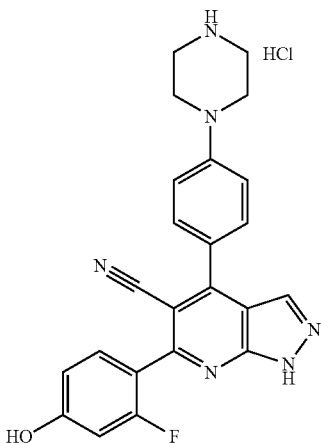 [SMILES: N#Cc1c(-c2ccc(O)cc2F)nc2[nH]ncc2c1-c1ccc(N2CCNCC2)cc1 ; Cl] |
| 92 | 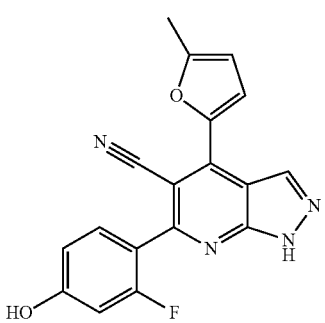 [SMILES: Cc1ccc(-c2c(C#N)c(-c3ccc(O)cc3F)nc3[nH]ncc23)o1] |
| 93 | 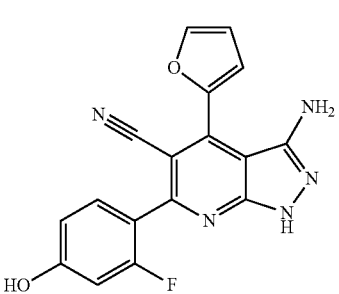 [SMILES: N#Cc1c(-c2ccc(O)cc2F)nc2[nH]nc(N)c2c1-c1ccco1] |

TABLE I-continued
| 94 | 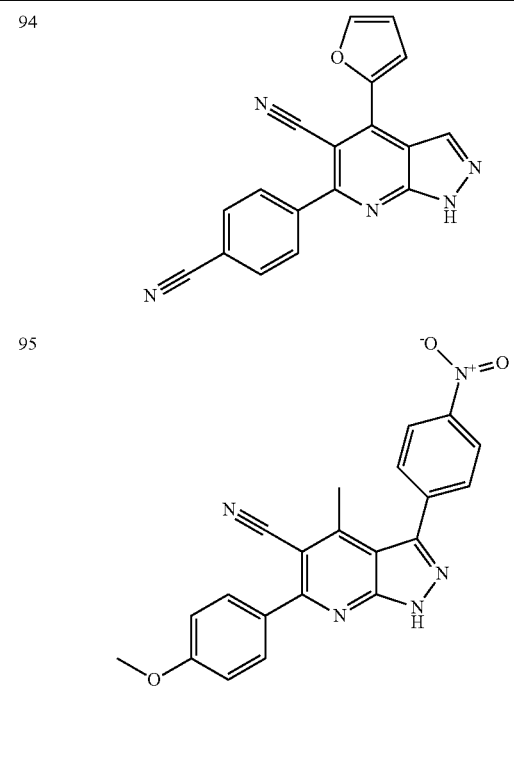 |
| 95 | |
| 96 | |
| 97 | 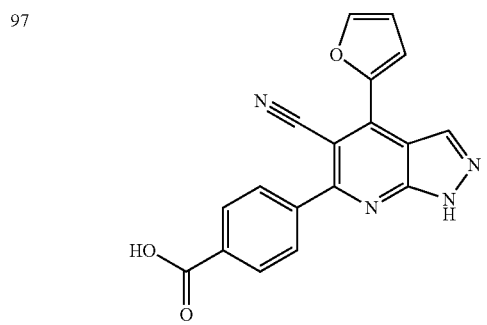 |
TABLE I-continued
| 98 | 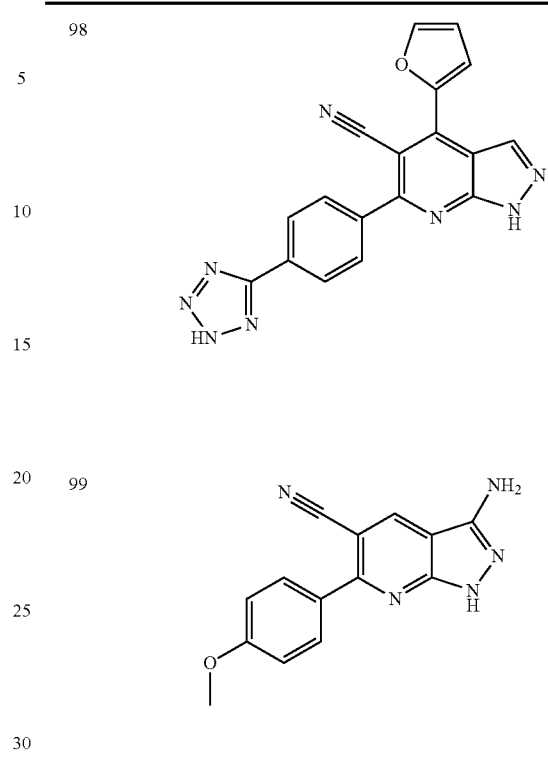 |
| 99 | |
| 100 | 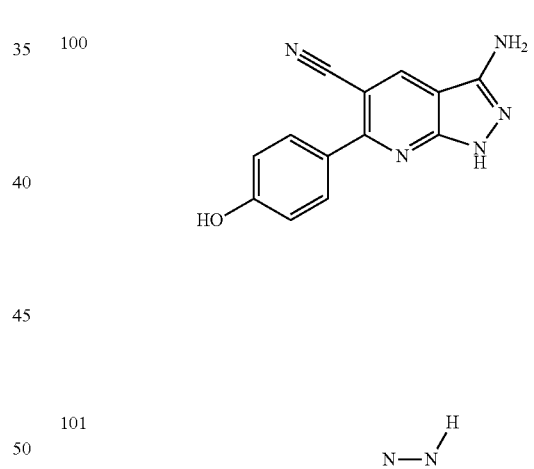 |
| 101 | |

TABLE I-continued
102 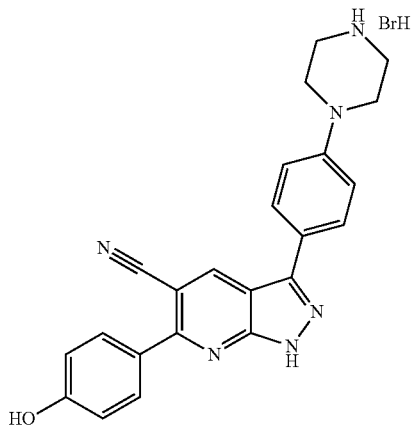 [SMILES: Br ; N#Cc1cc2c(-c3ccc(N4CCNCC4)cc3)n[nH]c2nc1-c1ccc(O)cc1]
103 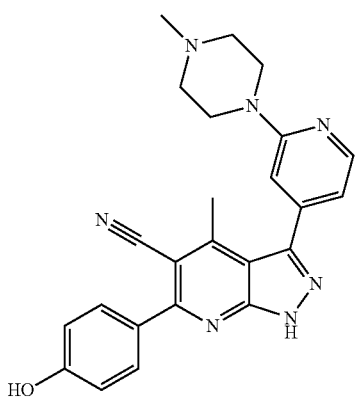 [SMILES: Cc1c(C#N)c(-c2ccc(O)cc2)nc2[nH]nc(-c3ccnc(N4CCN(C)CC4)c3)c12]
104 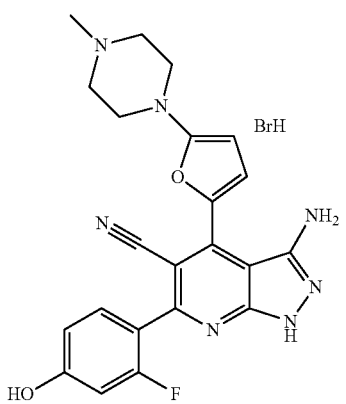 [SMILES: CN1CCN(c2ccc(-c3c(C#N)c(-c4ccc(O)cc4F)nc4[nH]nc(N)c34)o2)CC1 ; Br]
105 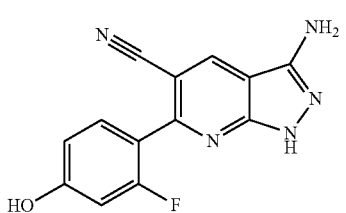 [SMILES: N#Cc1cc2c(N)n[nH]c2nc1-c1ccc(O)cc1F]
106 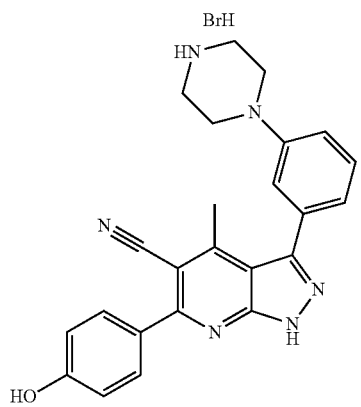 [SMILES: Br ; Cc1c(C#N)c(-c2ccc(O)cc2)nc2[nH]nc(-c3cccc(N4CCNCC4)c3)c12]
107 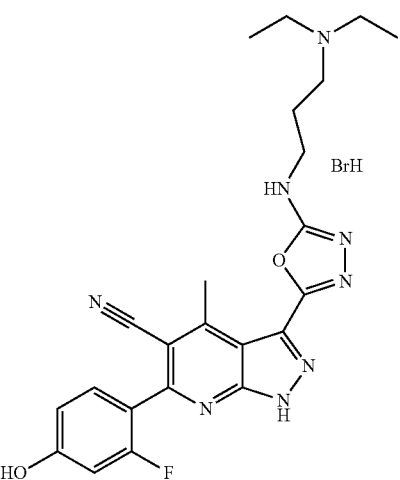 [SMILES: CCN(CC)CCCNc1nnc(-c2n[nH]c3nc(-c4ccc(O)cc4F)c(C#N)c(C)c23)o1 ; Br]
108 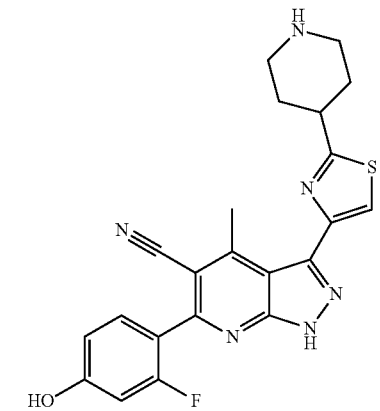 [SMILES: Cc1c(C#N)c(-c2ccc(O)cc2F)nc2[nH]nc(-c3csc(C4CCNCC4)n3)c12]

TABLE I-continued
| 109 | 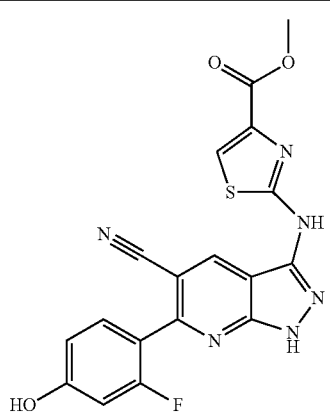 |
| --- | --- |
| 110 | 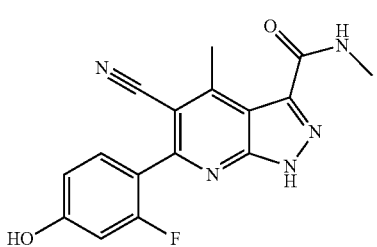 [SMILES: CNC(=O)c1n[nH]c2nc(-c3ccc(O)cc3F)c(C#N)c(C)c12] |
| 111 | 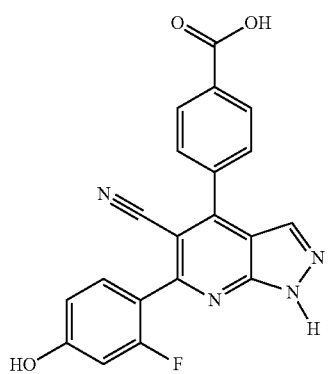 [SMILES: N#Cc1c(-c2ccc(O)cc2F)nc2[nH]ncc2c1-c1ccc(C(=O)O)cc1] |
| 112 | 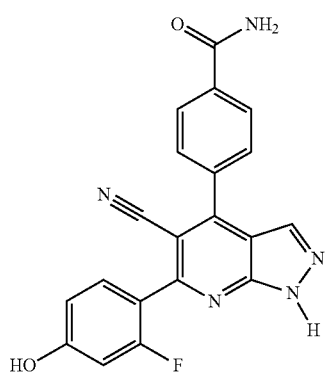 |
| 113 | 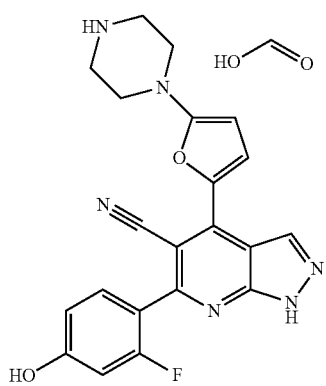 |
| 114 | 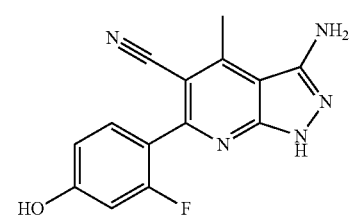 [SMILES: Cc1c(C#N)c(-c2ccc(O)cc2F)nc2[nH]nc(N)c12] |
| 115 | 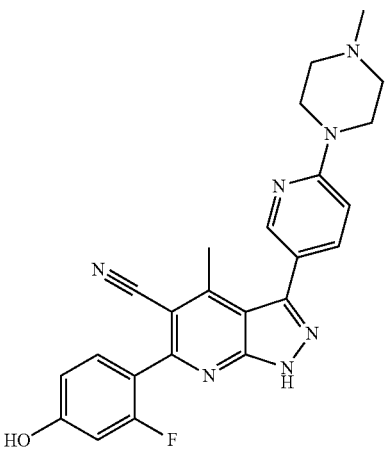 [SMILES: Cc1c(C#N)c(-c2ccc(O)cc2F)nc2[nH]nc(-c3ccc(N4CCN(C)CC4)nc3)c12] |
| 116 | 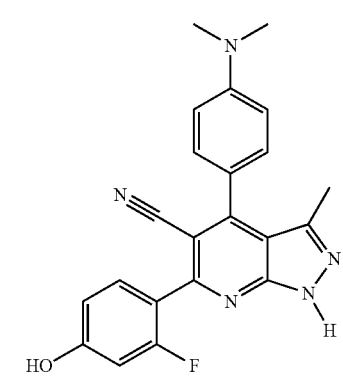 [SMILES: Cc1n[nH]c2nc(-c3ccc(O)cc3F)c(C#N)c(-c3ccc(N(C)C)cc3)c12] |

TABLE I-continued
| 117 | 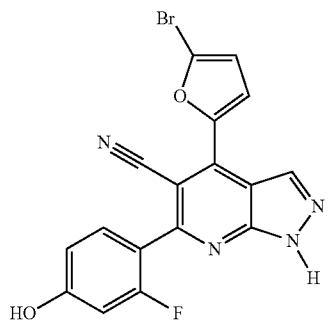 [SMILES: N#Cc1c(-c2ccc(O)cc2F)nc2[nH]ncc2c1-c1ccc(Br)o1] |
| --- | --- |
| 118 | 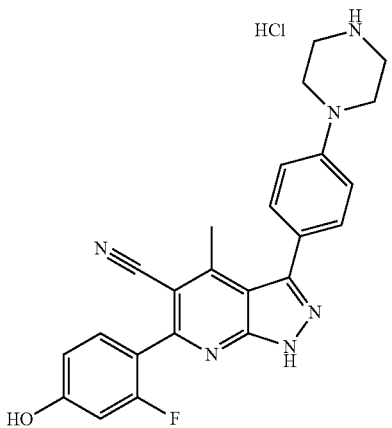 [SMILES: Cl ; Cc1c(C#N)c(-c2ccc(O)cc2F)nc2[nH]nc(-c3ccc(N4CCNCC4)cc3)c12] |
| 119 | 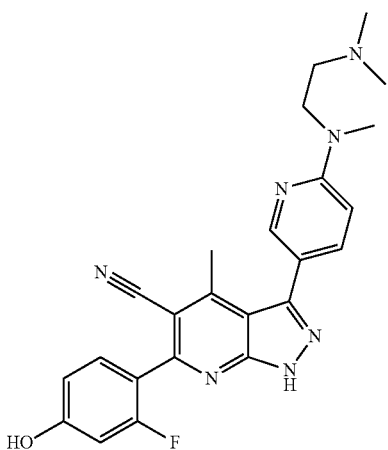 [SMILES: Cc1c(C#N)c(-c2ccc(O)cc2F)nc2[nH]nc(-c3ccc(N(C)CCN(C)C)nc3)c12] |
| 120 | 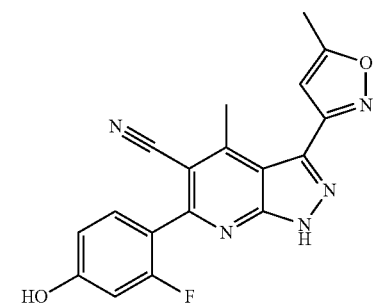 [SMILES: Cc1cc(-c2n[nH]c3nc(-c4ccc(O)cc4F)c(C#N)c(C)c23)no1] |
TABLE I-continued
| 121 | 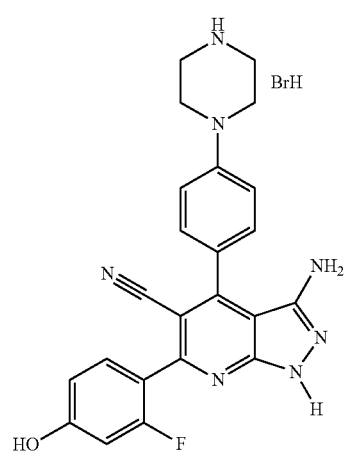 [SMILES: N#Cc1c(-c2ccc(O)cc2F)nc2[nH]nc(N)c2c1-c1ccc(N2CCNCC2)cc1 ; Br] |
| --- | --- |
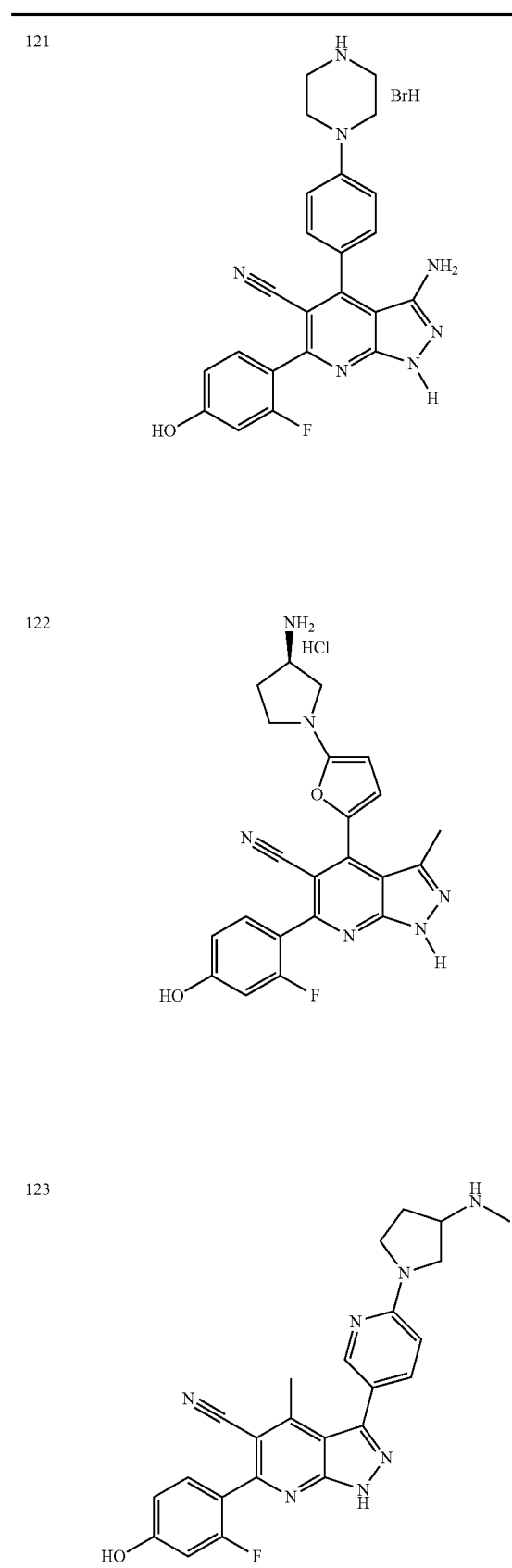

TABLE I-continued
| | |
|---|---|
| 124 | 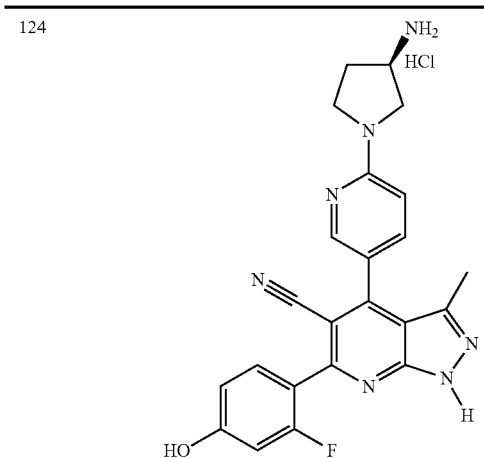 |
| 125 | 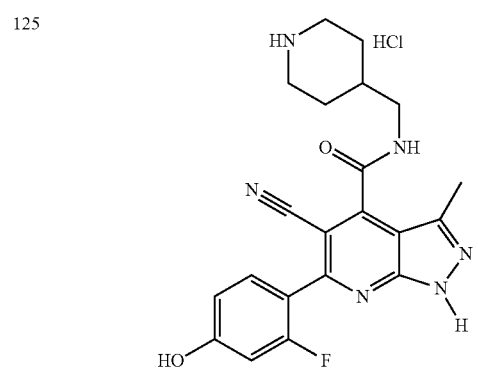 |
| 126 | 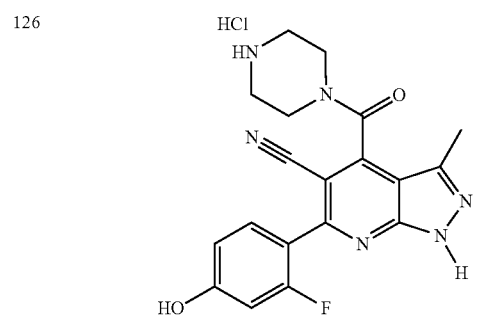 |
| 127 | 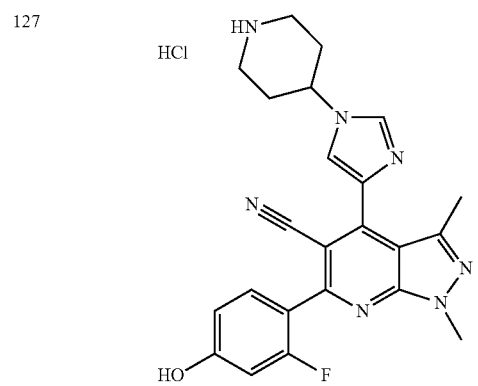 |
| 128 | 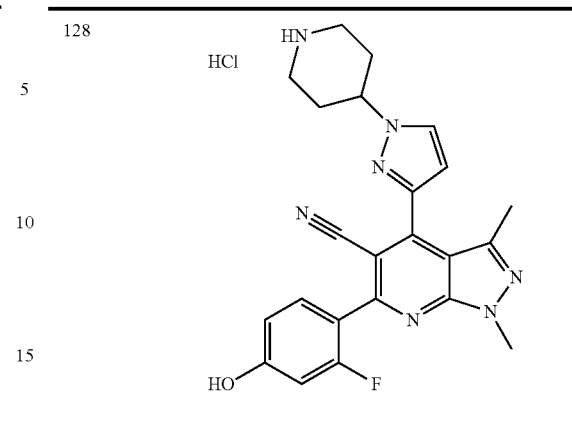 |
| 129 | 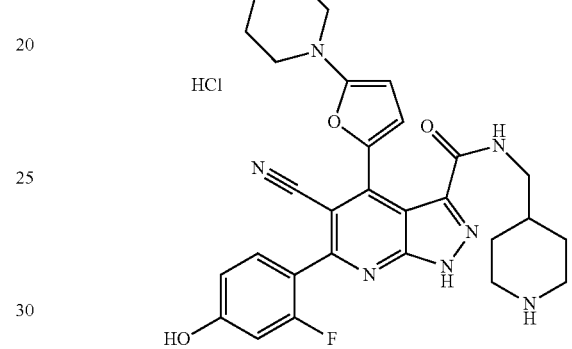 |
| 130 | 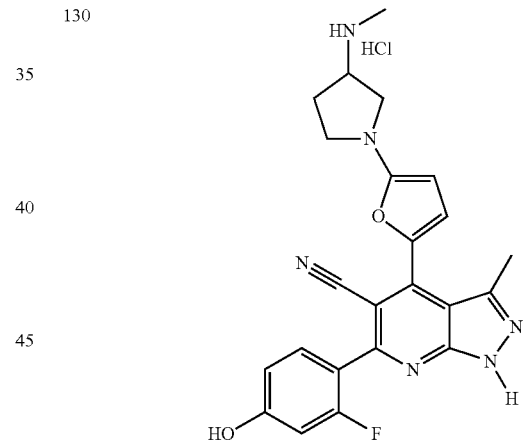 |
| 131 | 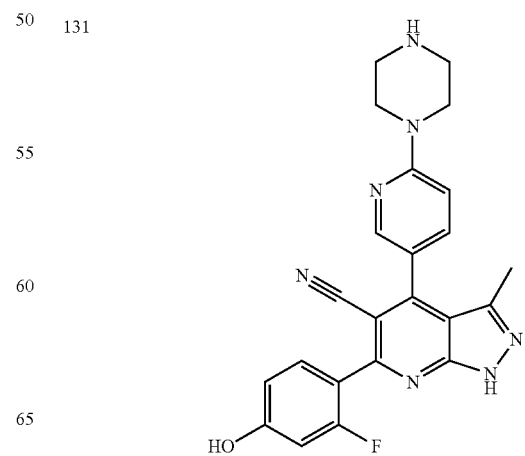 |

TABLE I-continued
132 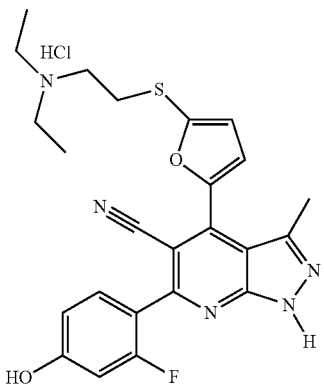 [SMILES: CCN(CC)CCSc1ccc(-c2c(C#N)c(-c3ccc(O)cc3F)nc3[nH]nc(C)c23)o1 ; Cl]
133 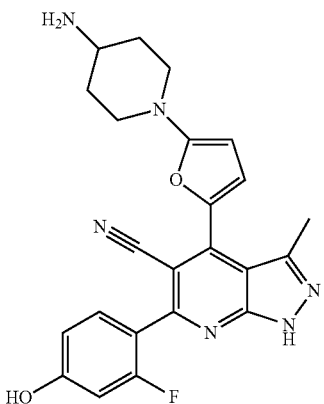 [SMILES: Cc1n[nH]c2nc(-c3ccc(O)cc3F)c(C#N)c(-c3ccc(N4CCC(N)CC4)o3)c12]
134 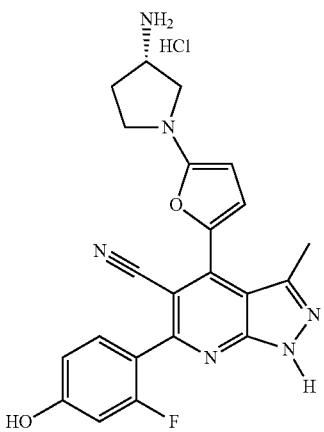 [SMILES: Cc1n[nH]c2nc(-c3ccc(O)cc3F)c(C#N)c(-c3ccc(N4CC[C@H](N)C4)o3)c12 ; Cl]
135 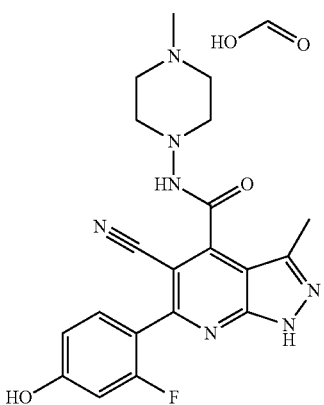
136 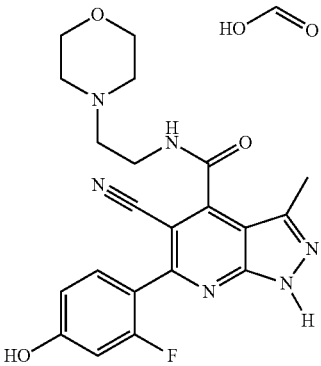 [SMILES: Cc1n[nH]c2nc(-c3ccc(O)cc3F)c(C#N)c(C(=O)NCCN3CCOCC3)c12 ; O=CO]
137 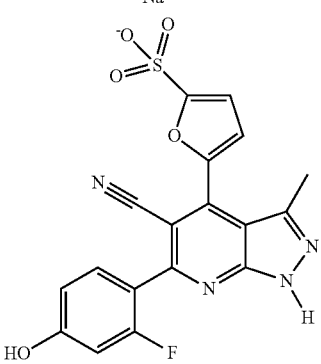
138 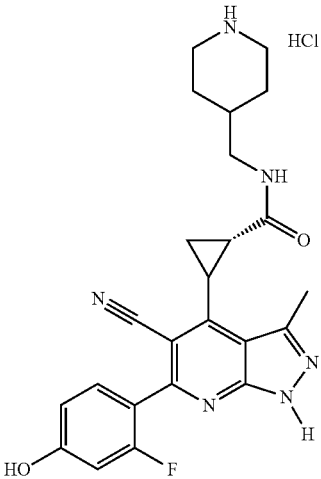 [SMILES: Cc1n[nH]c2nc(-c3ccc(O)cc3F)c(C#N)c(C3C[C@@H]3C(=O)NCC3CCNCC3)c12 ; Cl]
139 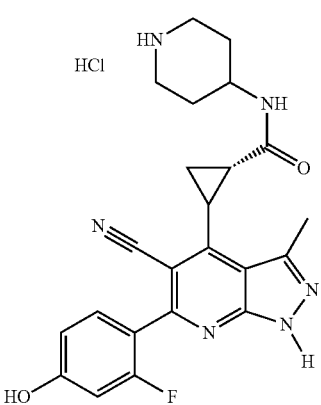 [SMILES: Cc1n[nH]c2nc(-c3ccc(O)cc3F)c(C#N)c(C3C[C@@H]3C(=O)NC3CCNCC3)c12 ; Cl]

TABLE I-continued
140 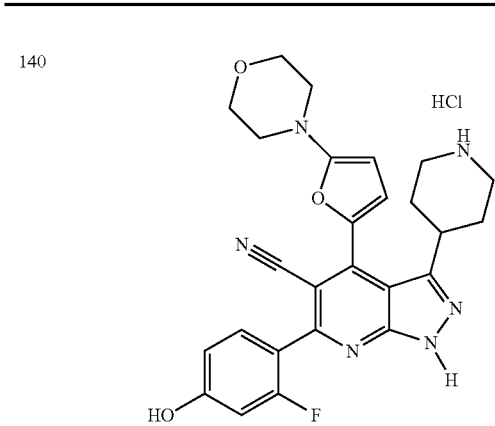
141
142
143 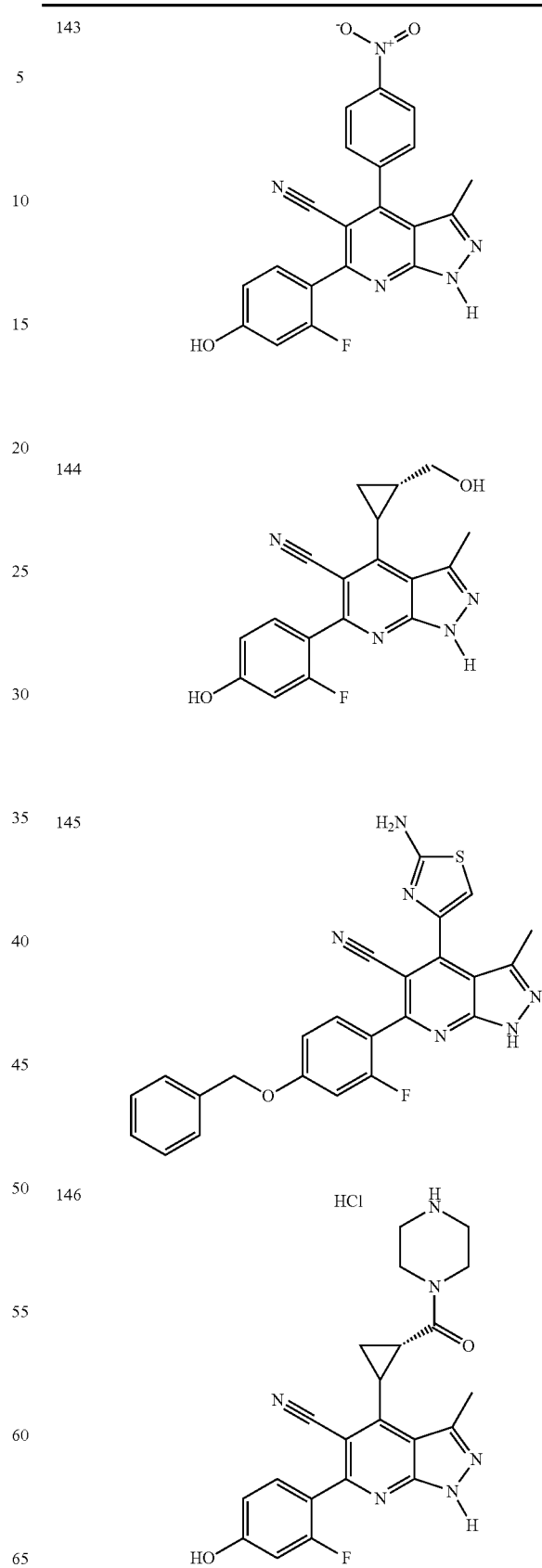
144
145
146

TABLE I-continued
| | |
|---|---|
| 147 | 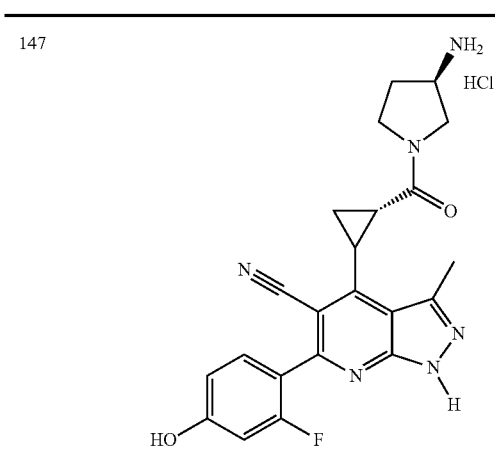 |
| 148 | |
| 149 | 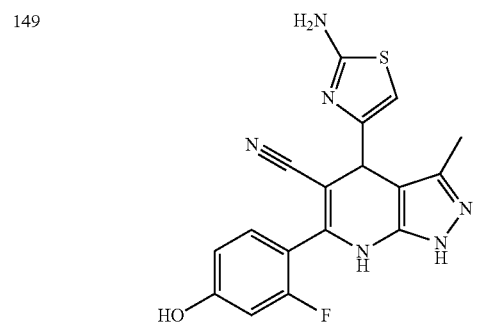 |
| 150 | |
| 151 | 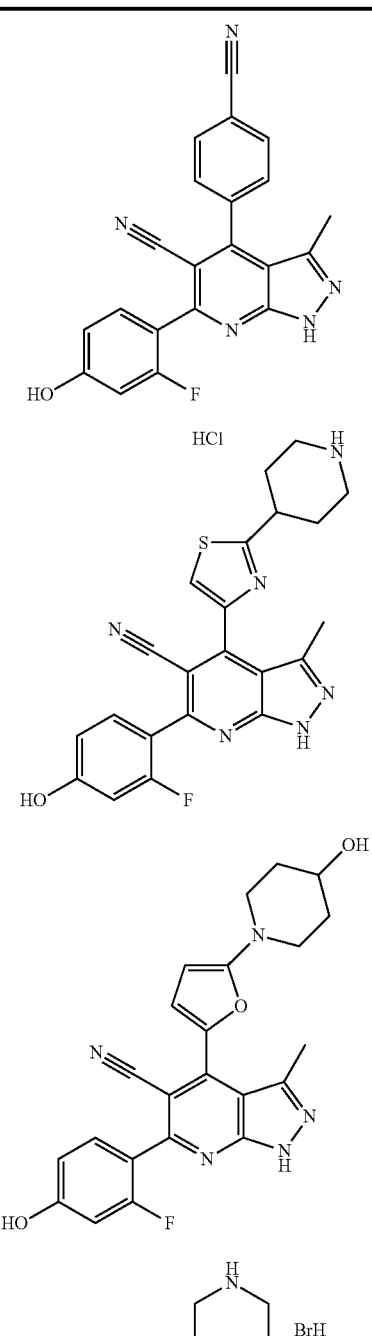 |
| 152 | |
| 153 | |
| 154 | |

TABLE I-continued
| 155 | 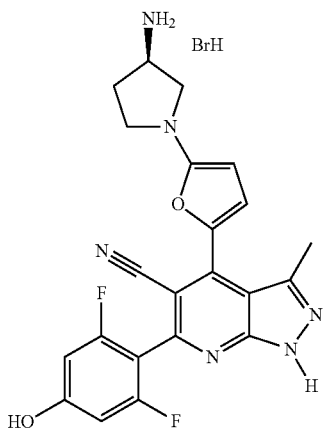 [SMILES: Cc1n[nH]c2nc(-c3c(F)cc(O)cc3F)c(C#N)c(-c3ccc(N4CC[C@@H](N)C4)o3)c12 ; Br] |
| --- | --- |
| 156 | 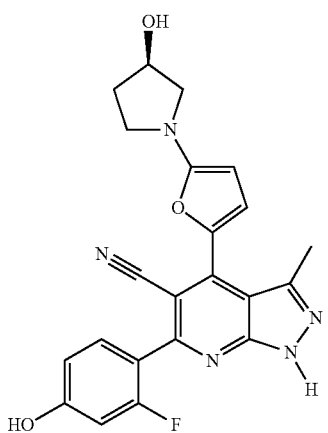 [SMILES: Cc1n[nH]c2nc(-c3ccc(O)cc3F)c(C#N)c(-c3ccc(N4CC[C@@H](O)C4)o3)c12] |
| 157 | 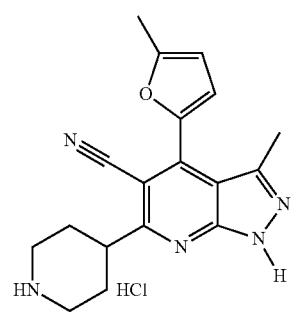 [SMILES: Cc1ccc(-c2c(C#N)c(C3CCNCC3)nc3[nH]nc(C)c23)o1 ; Cl] |
| 158 | 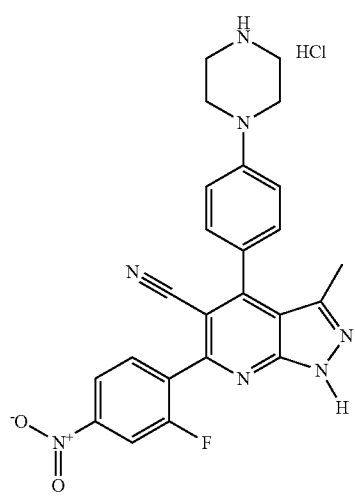 [SMILES: Cc1n[nH]c2nc(-c3ccc([N+](=O)[O-])cc3F)c(C#N)c(-c3ccc(N4CCNCC4)cc3)c12 ; Cl] |
TABLE I-continued
| 159 | 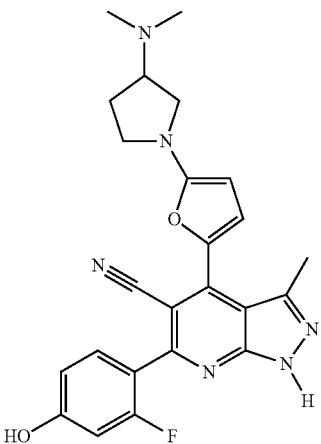 [SMILES: Cc1n[nH]c2nc(-c3ccc(O)cc3F)c(C#N)c(-c3ccc(N4CCC(N(C)C)C4)o3)c12] |
| --- | --- |
| 160 | 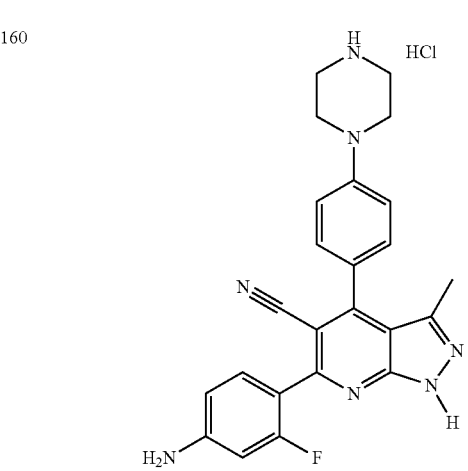 |
| 161 | 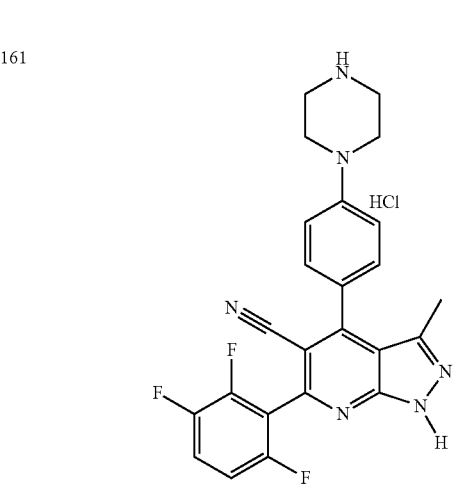 |

TABLE I-continued
| 162 | 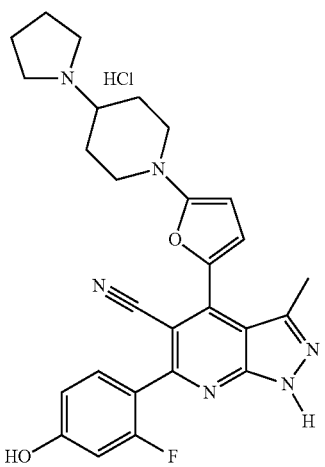 [SMILES: Cc1n[nH]c2nc(-c3ccc(O)cc3F)c(C#N)c(-c3ccc(N4CCC(N5CCCC5)CC4)o3)c12 ; Cl] |
| --- | --- |
| 163 | 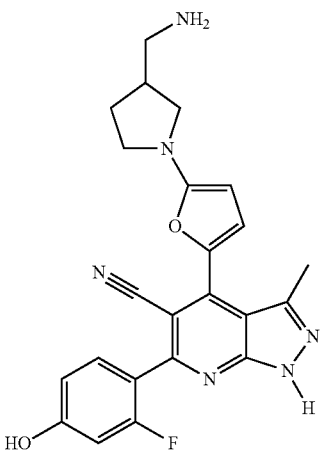 [SMILES: Cc1n[nH]c2nc(-c3ccc(O)cc3F)c(C#N)c(-c3ccc(N4CCC(CN)C4)o3)c12] |
| 164 | 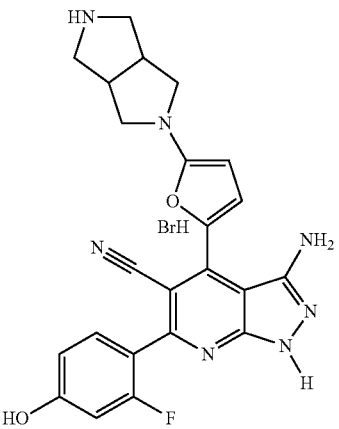 [SMILES: N#Cc1c(-c2ccc(O)cc2F)nc2[nH]nc(N)c2c1-c1ccc(N2CC3CNCC3C2)o1 ; Br] |
TABLE I-continued
| 165 | 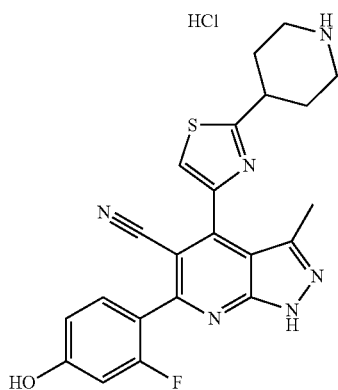 [SMILES: Cl ; Cc1n[nH]c2nc(-c3ccc(O)cc3F)c(C#N)c(-c3csc(C4CCNCC4)n3)c12] |
| --- | --- |
| 166 | 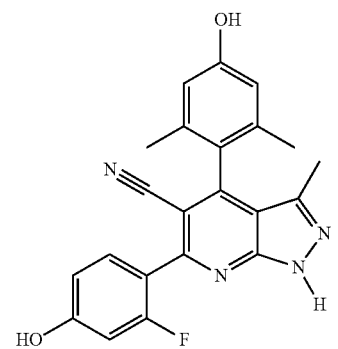 [SMILES: Cc1cc(O)cc(C)c1-c1c(C#N)c(-c2ccc(O)cc2F)nc2[nH]nc(C)c12] |
| 167 | 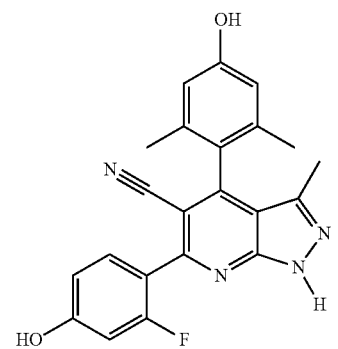 [SMILES: Cc1cc(O)cc(C)c1-c1c(C#N)c(-c2ccc(O)cc2F)nc2[nH]nc(C)c12] |
| 168 | 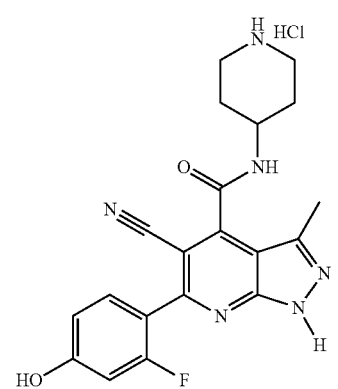 [SMILES: Cl ; Cc1n[nH]c2nc(-c3ccc(O)cc3F)c(C#N)c(C(=O)NC3CCNCC3)c12] |
Note: images 4 spans entries 167 overlapping — see original.

TABLE I-continued
| | |
|---|---|
| 169 | 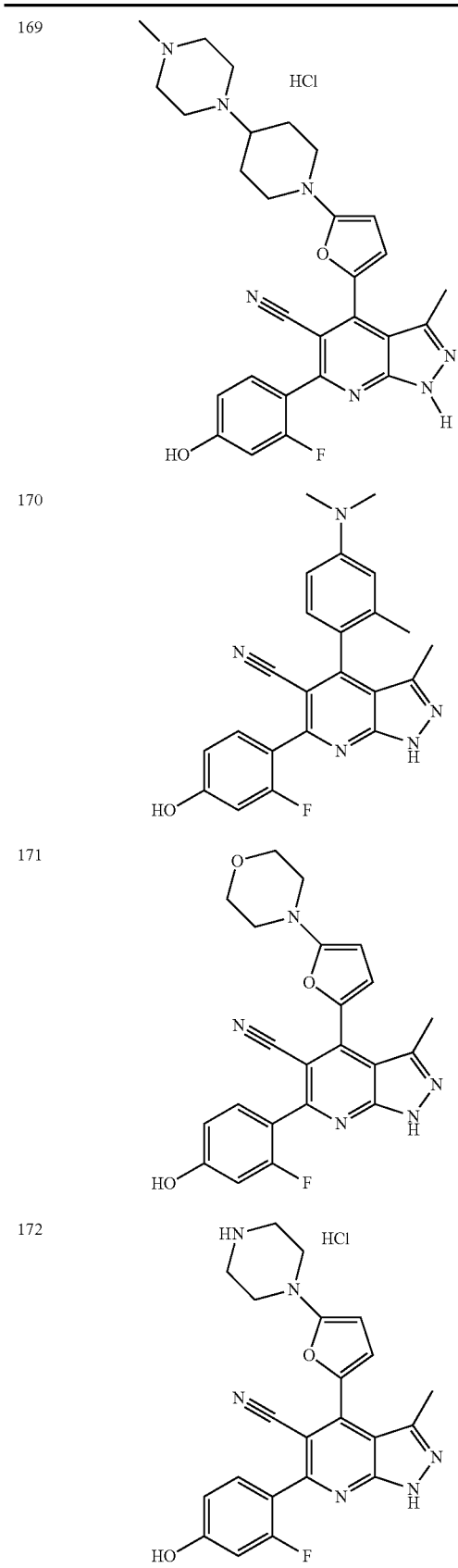 |
| 170 | |
| 171 | |
| 172 | |
TABLE I-continued
| | |
|---|---|
| 173 | 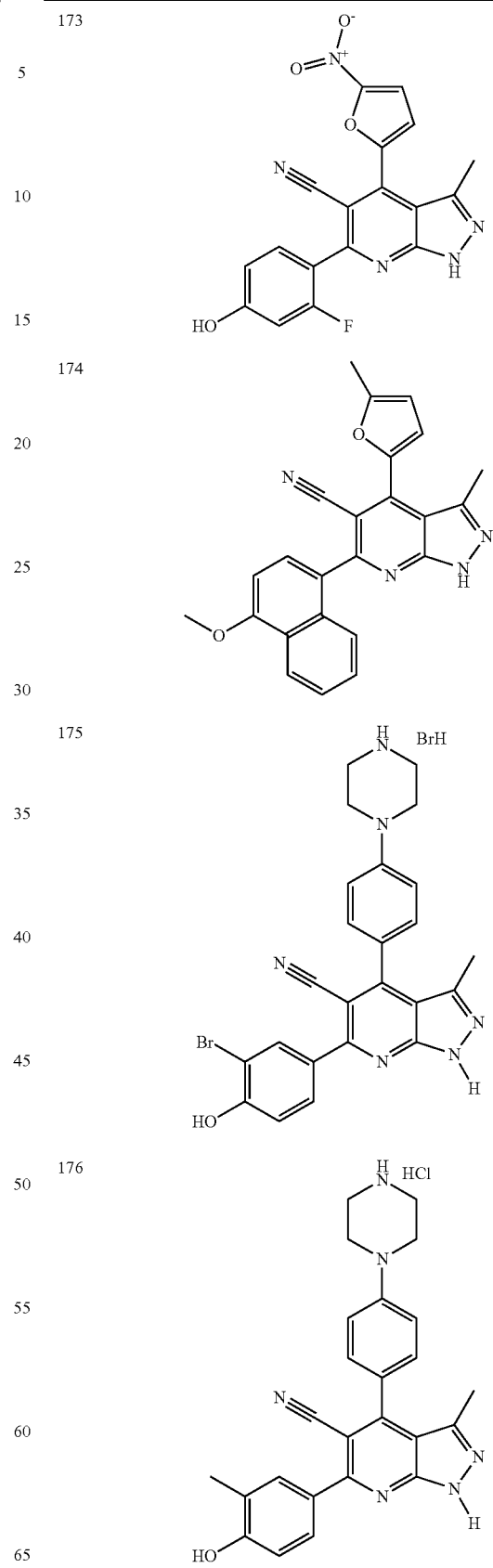 |
| 174 | |
| 175 | |
| 176 | |

TABLE I-continued
| 177 | 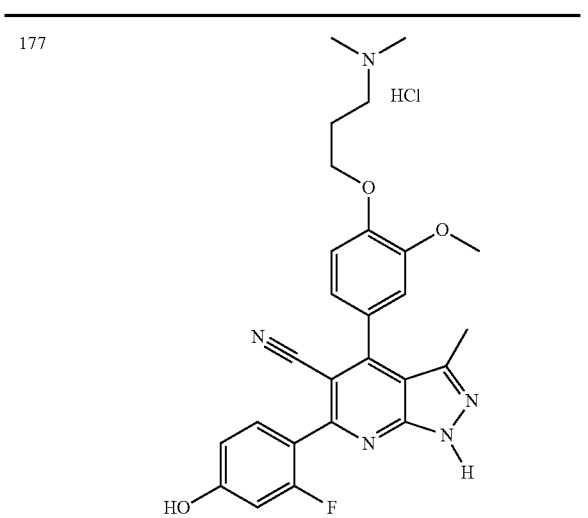 | 180 | 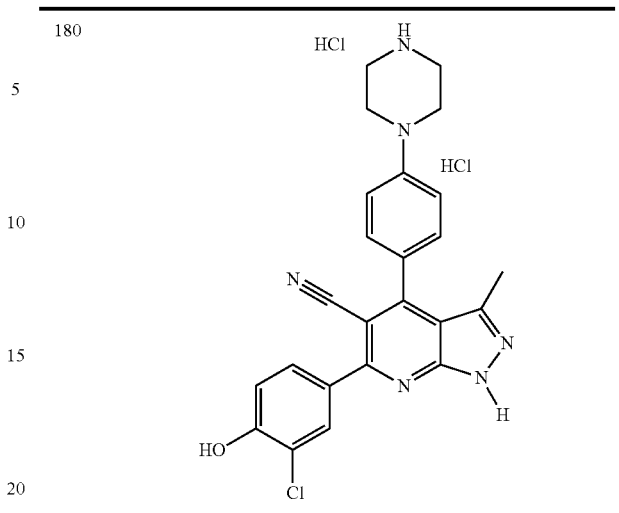 |
| 178 | | 181 | 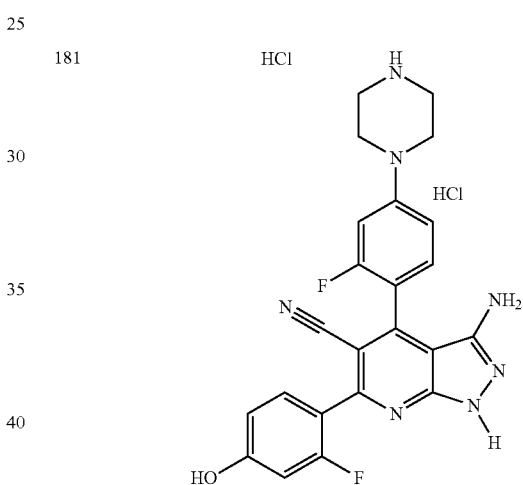 |
| 179 | | 182 | 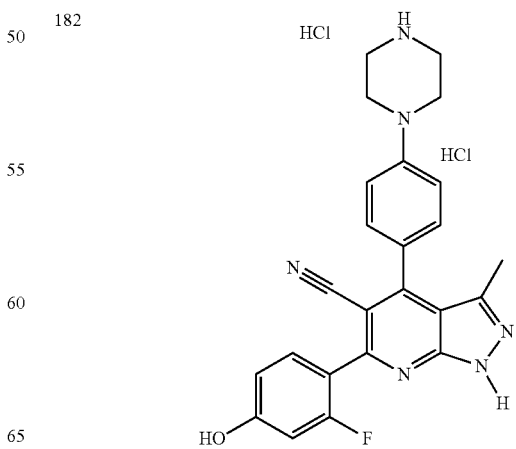 |

TABLE I-continued
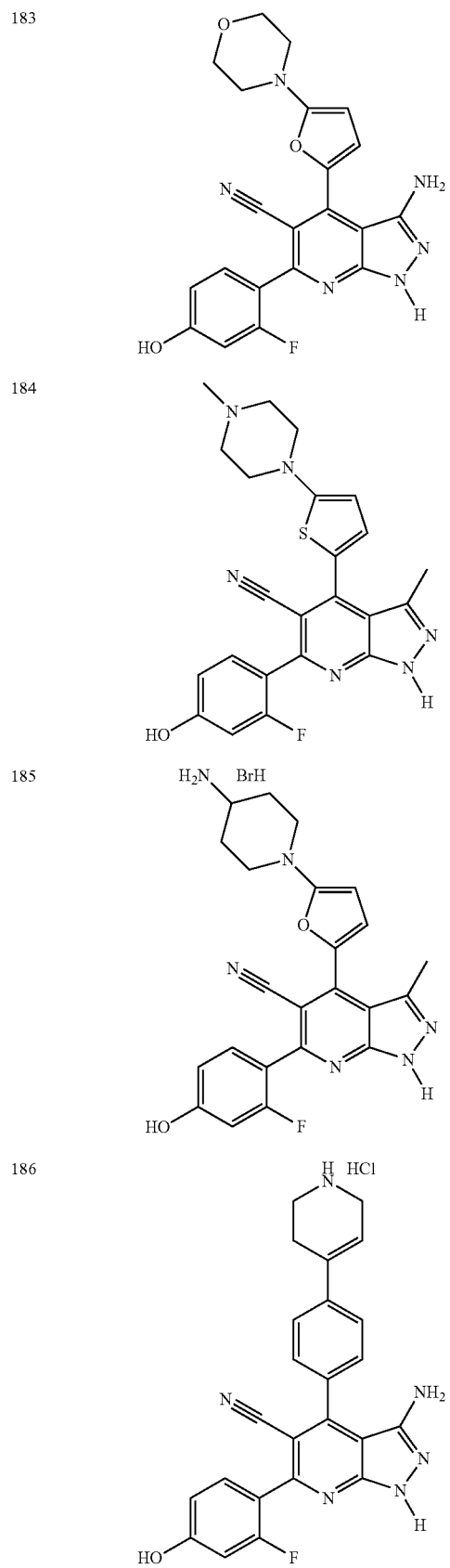
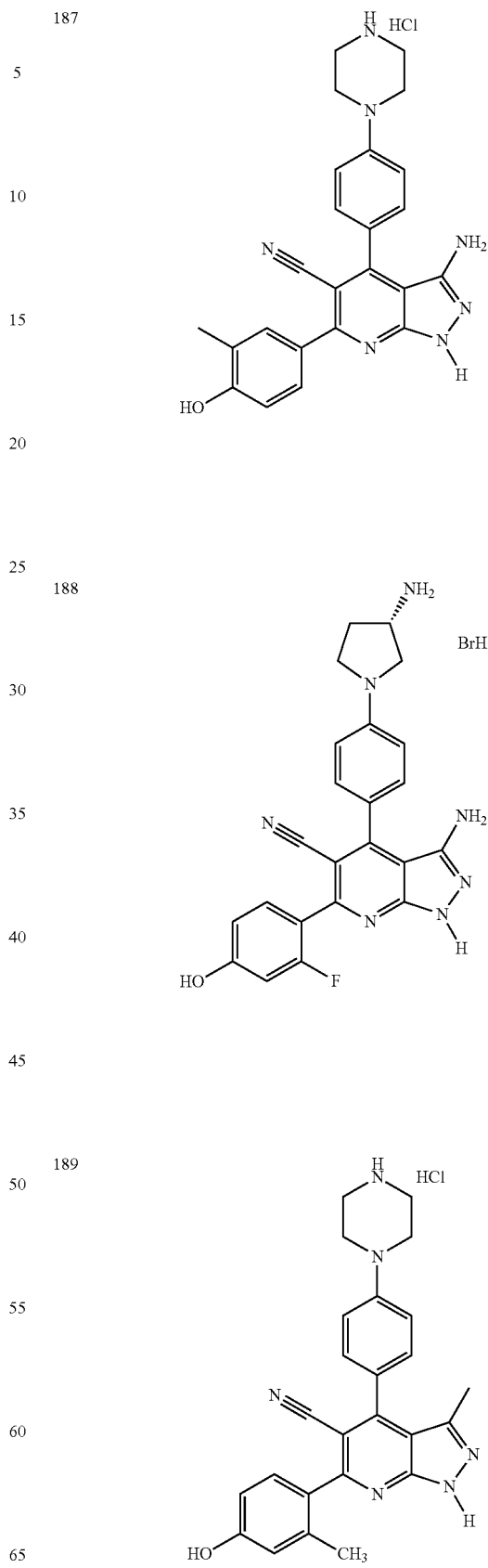

TABLE I-continued
190 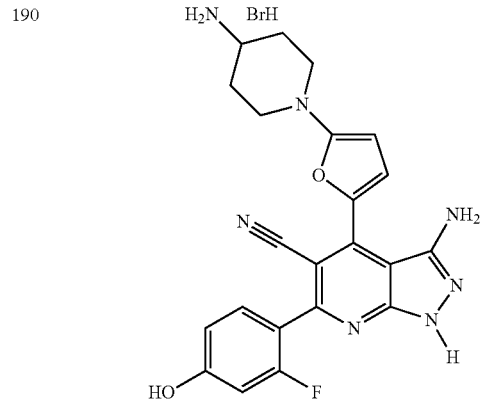
191 
192 
193 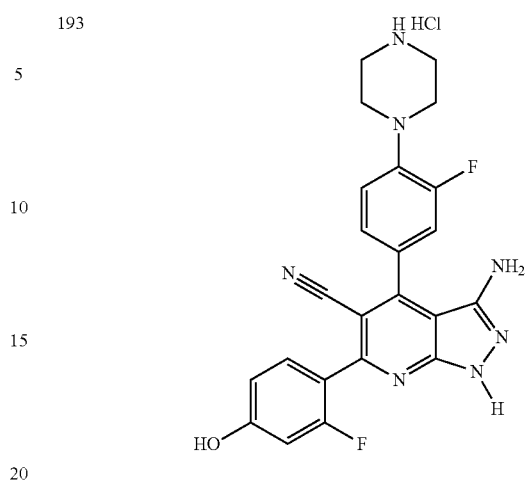
194 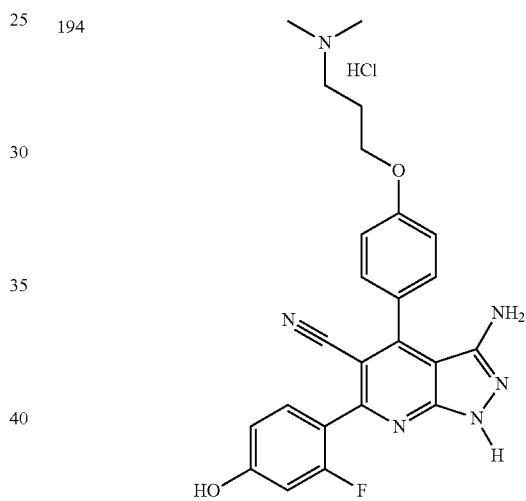
195 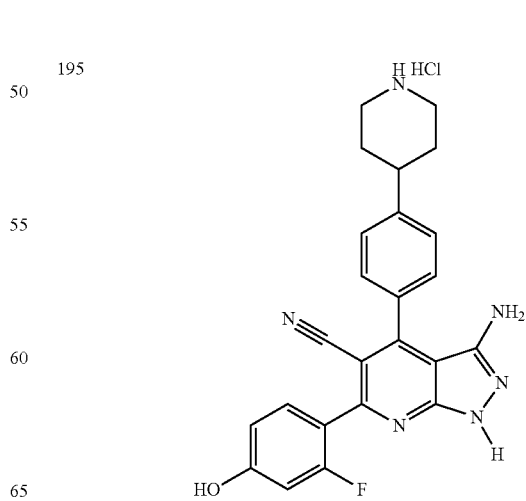

TABLE I-continued
196
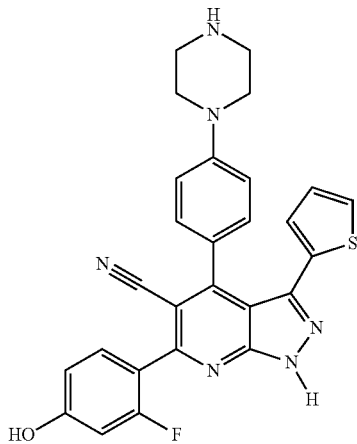 [SMILES: Cl ; N#Cc1c(-c2ccc(O)cc2F)nc2[nH]nc(-c3ccco3)c2c1-c1ccc(N2CCNCC2)cc1]
197 HCl
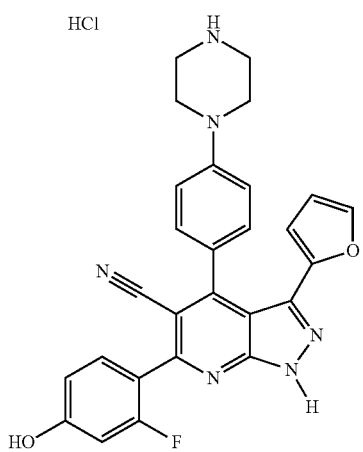
198 HCl
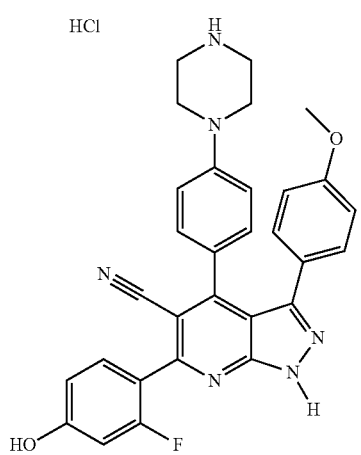 [SMILES: Cl ; COc1ccc(-c2n[nH]c3nc(-c4ccc(O)cc4F)c(C#N)c(-c4ccc(N5CCNCC5)cc4)c23)cc1]
TABLE I-continued
199
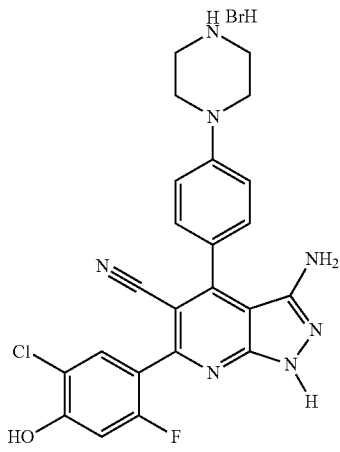 [SMILES: Br ; N#Cc1c(-c2cc(Cl)c(O)cc2F)nc2[nH]nc(N)c2c1-c1ccc(N2CCNCC2)cc1]
200
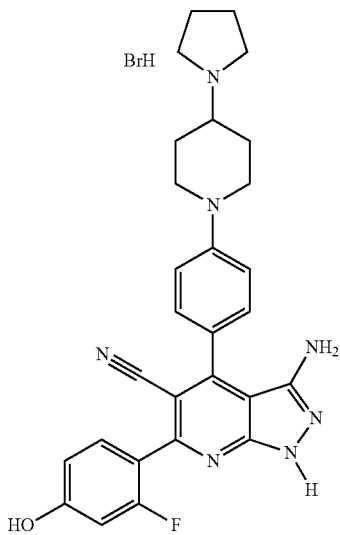 [SMILES: N#Cc1c(-c2ccc(O)cc2F)nc2[nH]nc(N)c2c1-c1ccc(N2CCC(N3CCCC3)CC2)cc1 ; Br]
201
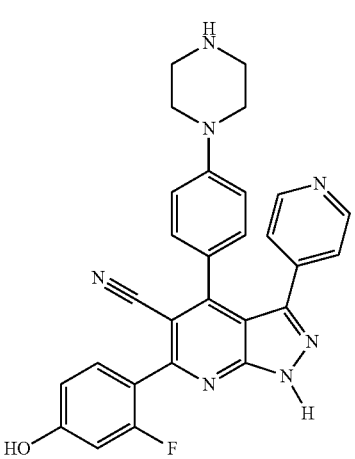 [SMILES: N#Cc1c(-c2ccc(O)cc2F)nc2[nH]nc(-c3ccncc3)c2c1-c1ccc(N2CCNCC2)cc1]

TABLE I-continued
202 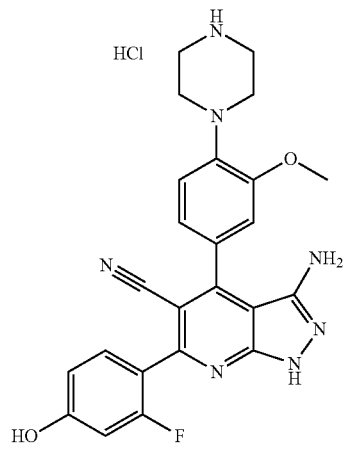 [SMILES: COc1cc(-c2c(C#N)c(-c3ccc(O)cc3F)nc3[nH]nc(N)c23)ccc1N1CCNCC1 ; Cl]
203 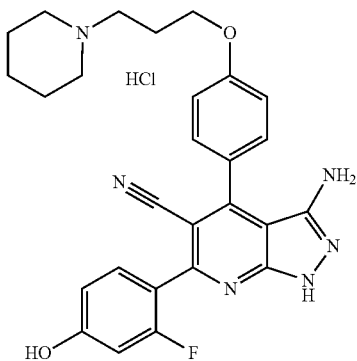 [SMILES: N#Cc1c(-c2ccc(O)cc2F)nc2[nH]nc(N)c2c1-c1ccc(OCCCN2CCCCC2)cc1 ; Cl]
204 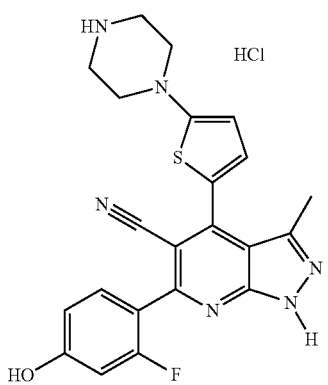 [SMILES: Cc1n[nH]c2nc(-c3ccc(O)cc3F)c(C#N)c(-c3ccc(N4CCNCC4)s3)c12 ; Cl]
205 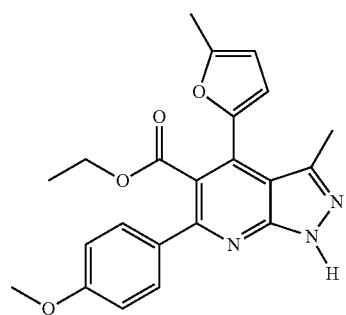 [SMILES: CCOC(=O)c1c(-c2ccc(OC)cc2)nc2[nH]nc(C)c2c1-c1ccc(C)o1]
206 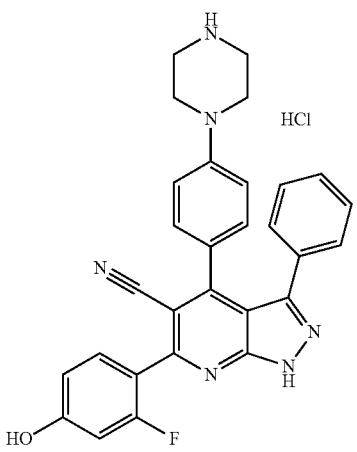 [SMILES: N#Cc1c(-c2ccc(O)cc2F)nc2[nH]nc(-c3ccccc3)c2c1-c1ccc(N2CCNCC2)cc1 ; Cl]
207 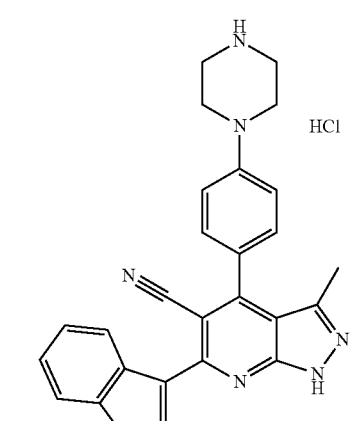
208 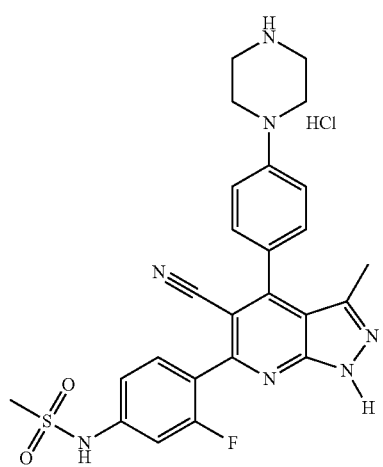 [SMILES: Cc1n[nH]c2nc(-c3ccc(NS(C)(=O)=O)cc3F)c(C#N)c(-c3ccc(N4CCNCC4)cc3)c12 ; Cl]

TABLE I-continued
209 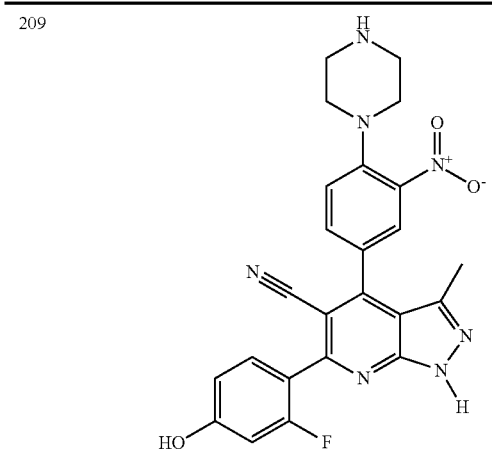
210 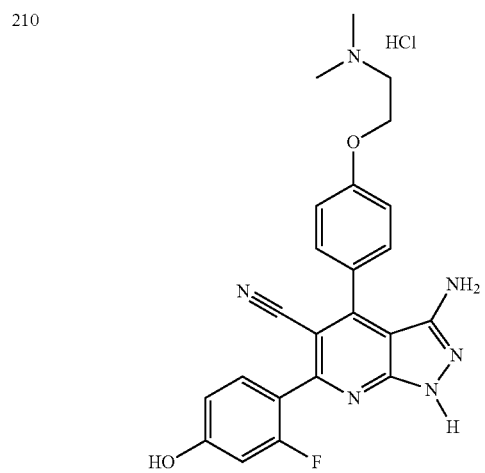
211 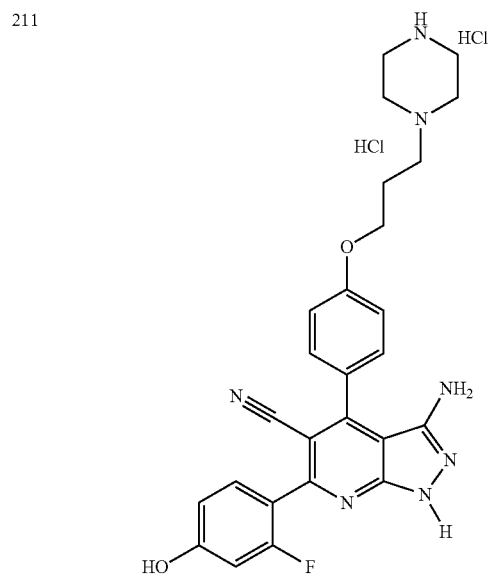
TABLE I-continued
212 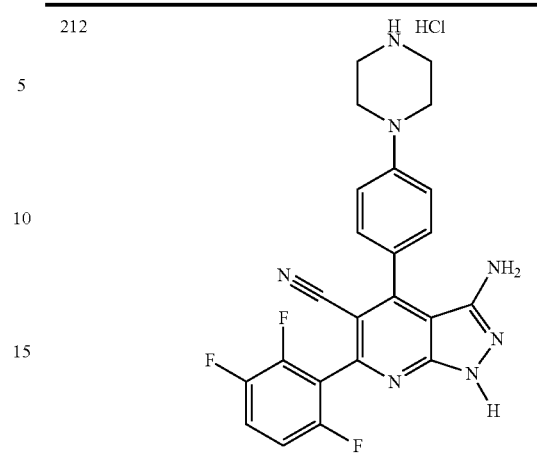
213 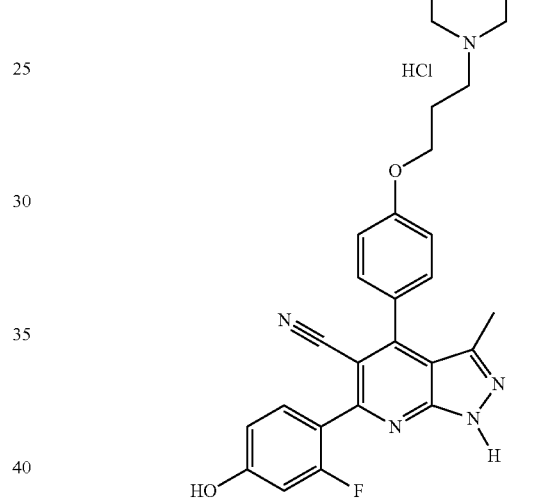
214
215
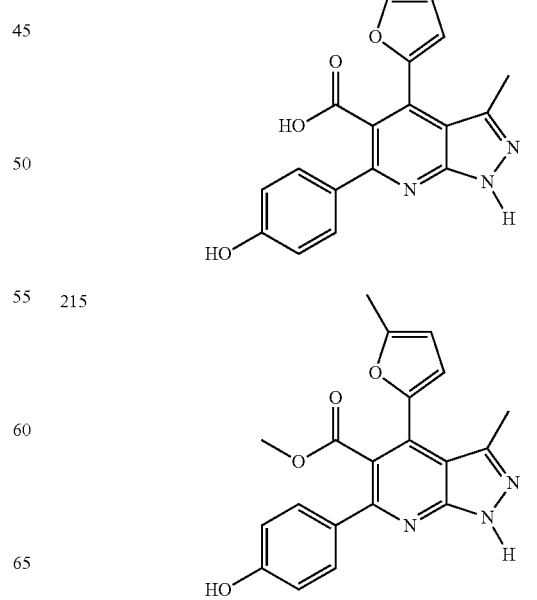

TABLE I-continued
| 216 | 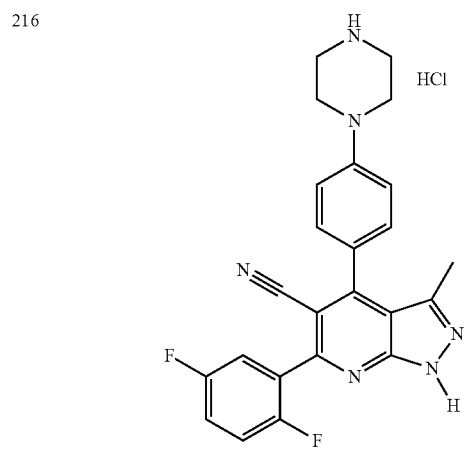 |
| --- | --- |
| 217 | |
| 218 | 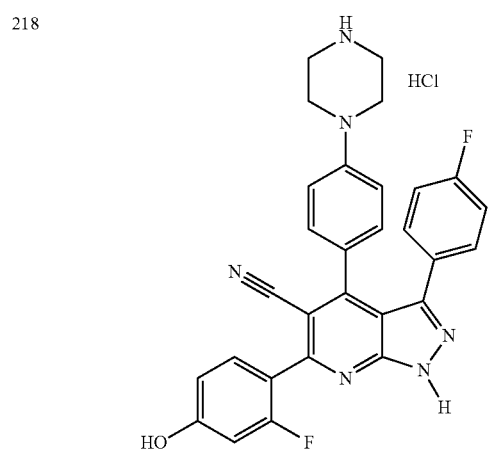 |
TABLE I-continued
| 219 | 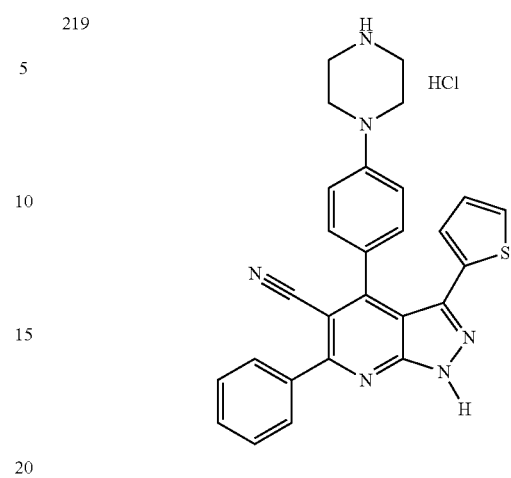 |
| --- | --- |
| 220 | 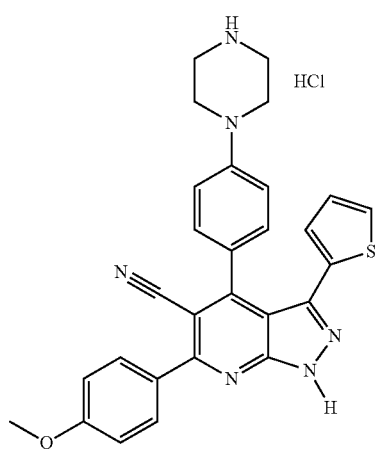 [SMILES: COc1ccc(-c2nc3[nH]nc(-c4cccs4)c3c(-c3ccc(N4CCNCC4)cc3)c2C#N)cc1 ; Cl] |
| 221 | 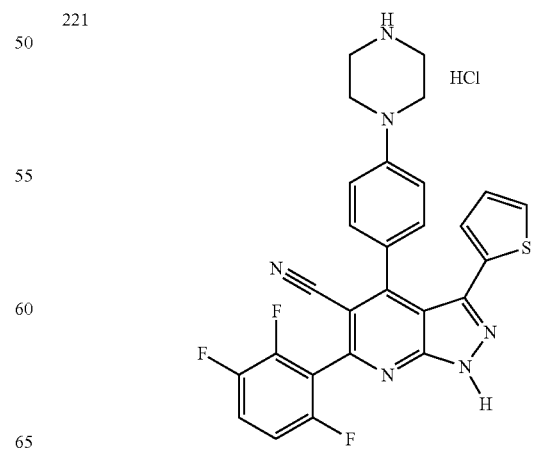 |

TABLE I-continued
222 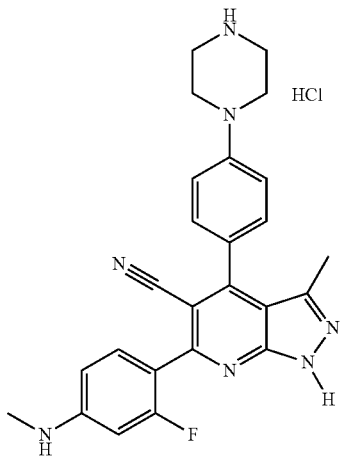 [SMILES: CNc1ccc(-c2nc3[nH]nc(C)c3c(-c3ccc(N4CCNCC4)cc3)c2C#N)c(F)c1 ; Cl]
223 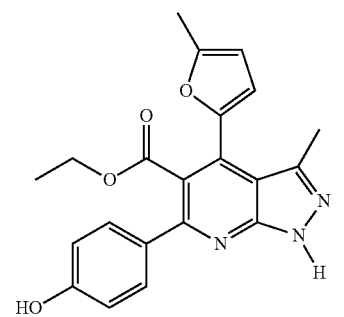 [SMILES: CCOC(=O)c1c(-c2ccc(O)cc2)nc2[nH]nc(C)c2c1-c1ccc(C)o1]
224 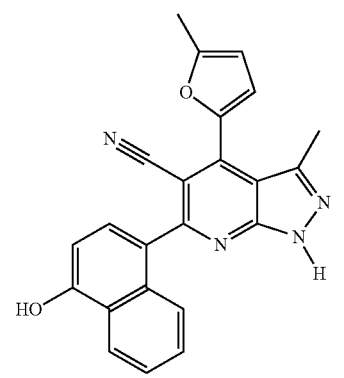 [SMILES: Cc1ccc(-c2c(C#N)c(-c3ccc(O)c4ccccc34)nc3[nH]nc(C)c23)o1]
225 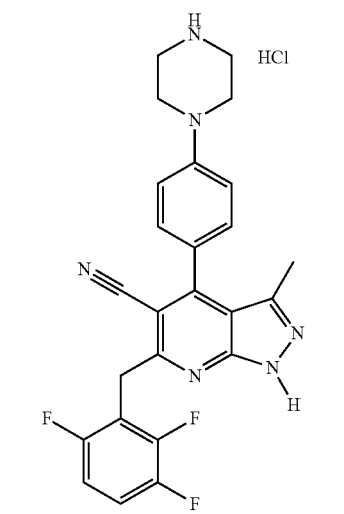 [SMILES: Cc1n[nH]c2nc(Cc3c(F)ccc(F)c3F)c(C#N)c(-c3ccc(N4CCNCC4)cc3)c12 ; Cl]
226 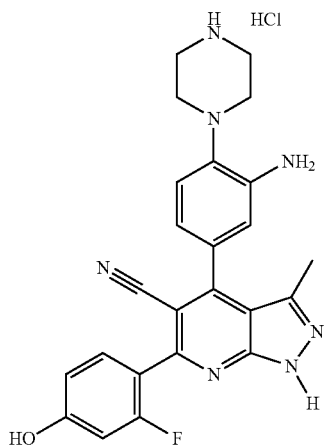 [SMILES: Cl ; Cc1n[nH]c2nc(-c3ccc(O)cc3F)c(C#N)c(-c3ccc(N4CCNCC4)c(N)c3)c12]
227 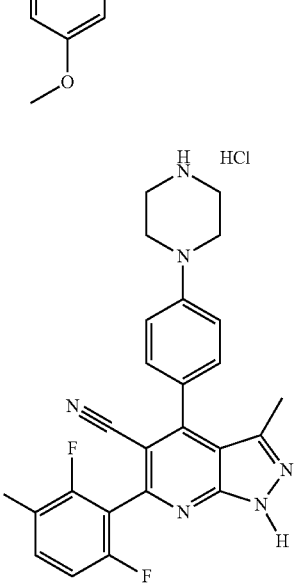
228 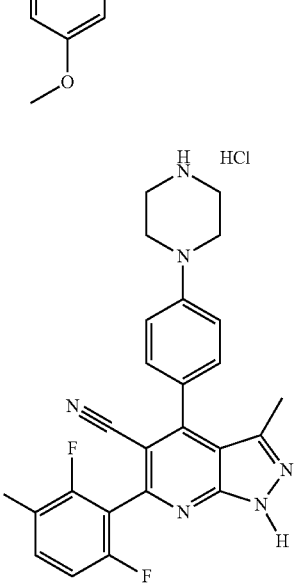

TABLE I-continued
229 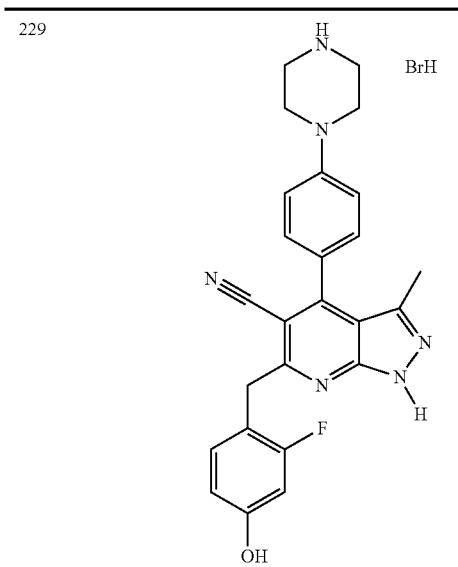
230 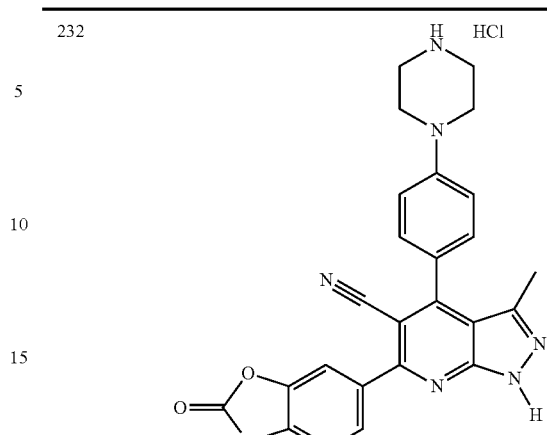
231 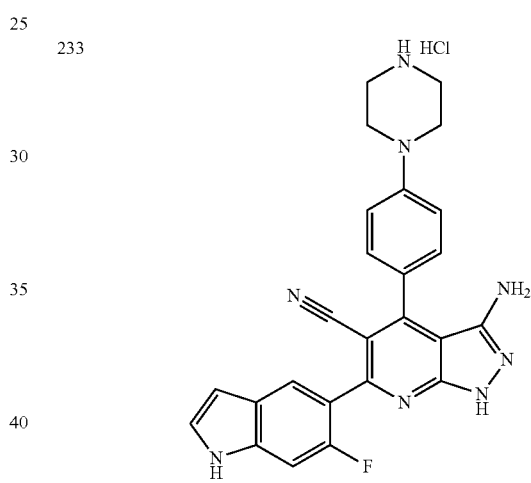
TABLE I-continued
232 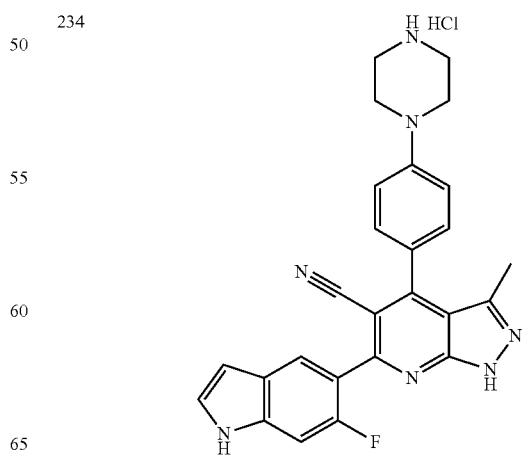
233
234

TABLE I-continued
235 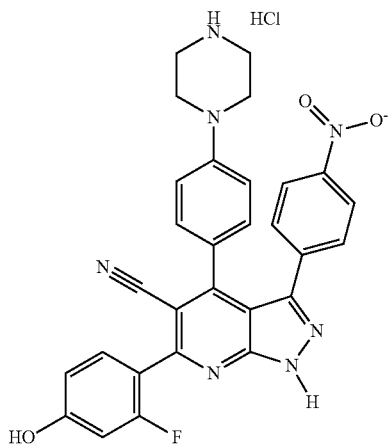
236 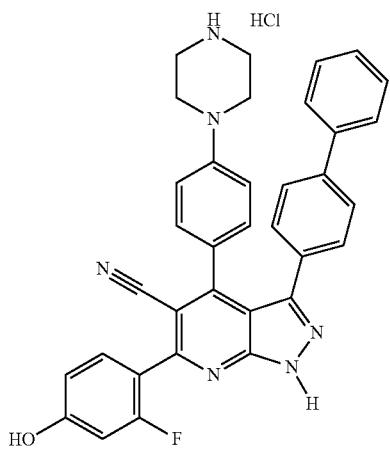 [SMILES: Cl ; N#Cc1c(-c2ccc(O)cc2F)nc2[nH]nc(-c3ccc(-c4ccccc4)cc3)c2c1-c1ccc(N2CCNCC2)cc1]
237 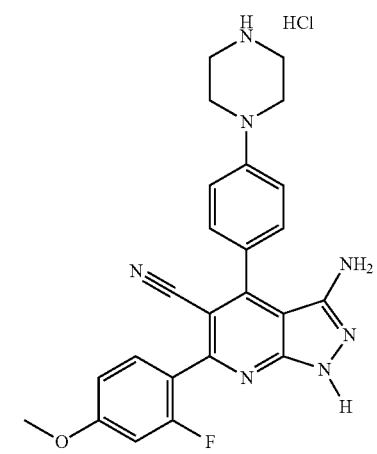 [SMILES: Cl ; COc1ccc(-c2nc3[nH]nc(N)c3c(-c3ccc(N4CCNCC4)cc3)c2C#N)c(F)c1]
TABLE I-continued
238 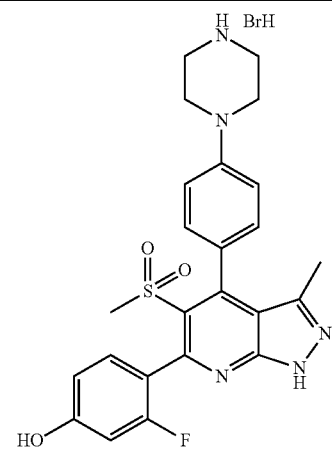
239 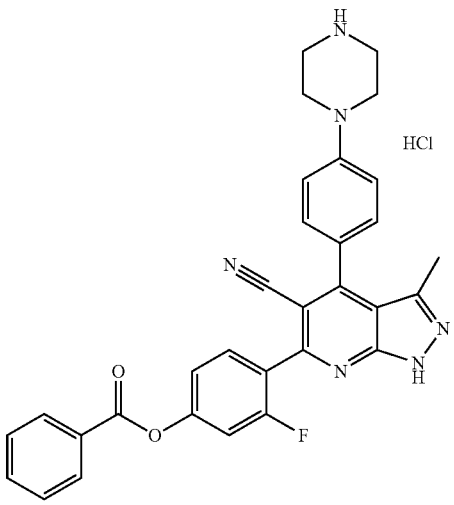 [SMILES: Cc1n[nH]c2nc(-c3ccc(OC(=O)c4ccccc4)cc3F)c(C#N)c(-c3ccc(N4CCNCC4)cc3)c12 ; Cl]
240 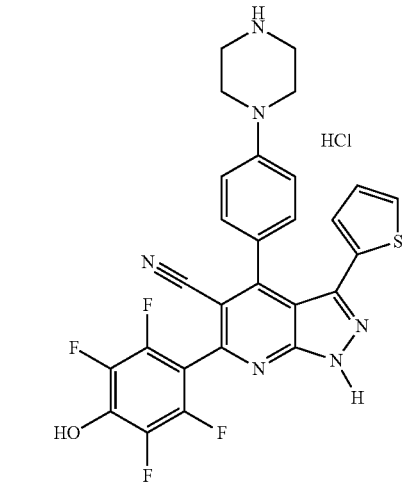 [SMILES: N#Cc1c(-c2c(F)c(F)c(O)c(F)c2F)nc2[nH]nc(-c3cccs3)c2c1-c1ccc(N2CCNCC2)cc1 ; Cl]

TABLE I-continued
242
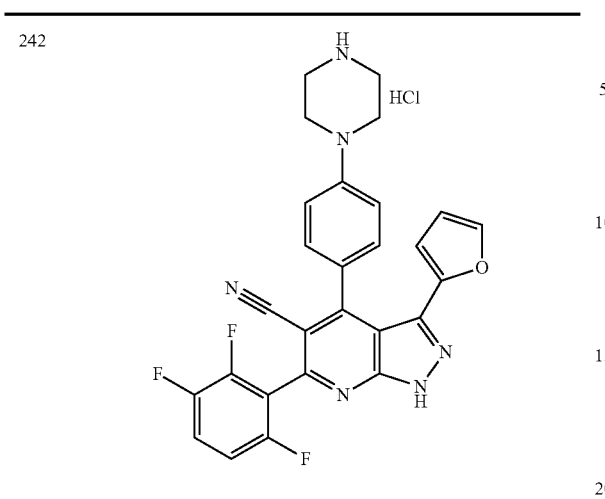
243
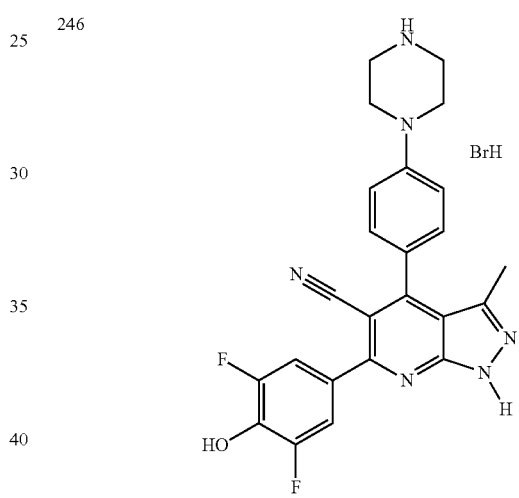
244
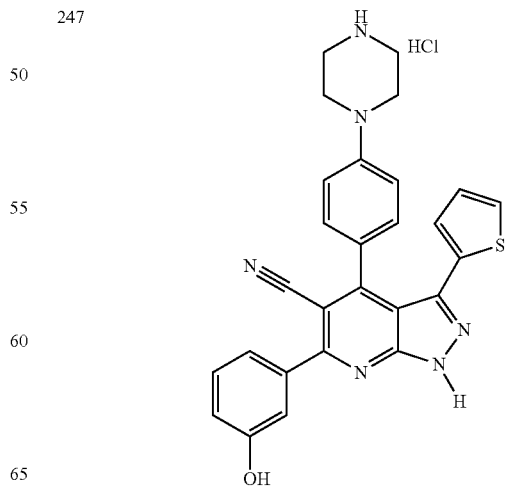
TABLE I-continued
245
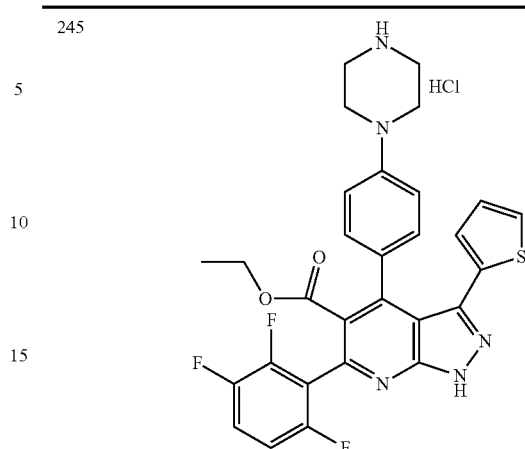
246
247

TABLE I-continued
248 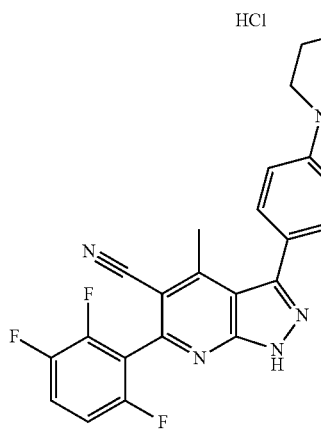
249 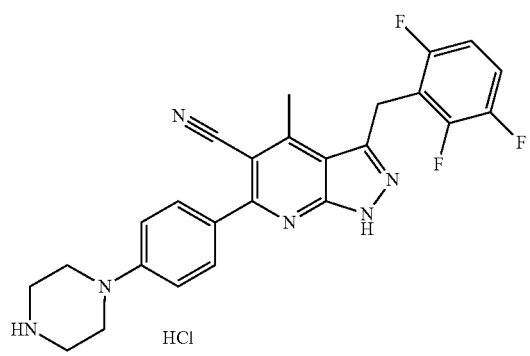 [SMILES: Cc1c(C#N)c(-c2ccc(N3CCNCC3)cc2)nc2[nH]nc(Cc3c(F)ccc(F)c3F)c12 ; Cl]
250 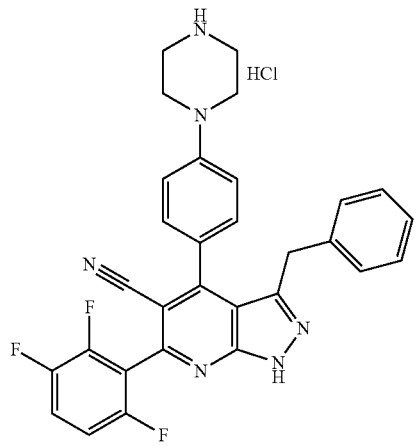 [SMILES: N#Cc1c(-c2c(F)ccc(F)c2F)nc2[nH]nc(Cc3ccccc3)c2c1-c1ccc(N2CCNCC2)cc1 ; Cl]
TABLE I-continued
251 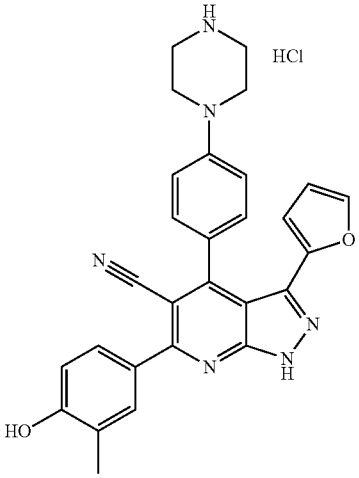 [SMILES: Cc1cc(-c2nc3[nH]nc(-c4ccco4)c3c(-c3ccc(N4CCNCC4)cc3)c2C#N)ccc1O ; Cl]
252 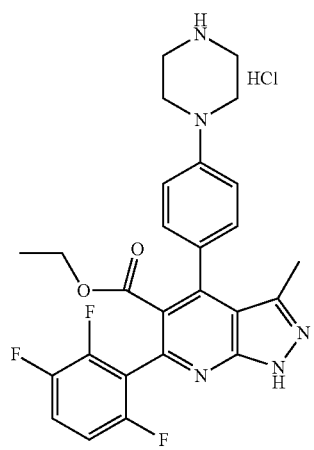 [SMILES: CCOC(=O)c1c(-c2c(F)ccc(F)c2F)nc2[nH]nc(C)c2c1-c1ccc(N2CCNCC2)cc1 ; Cl]
253 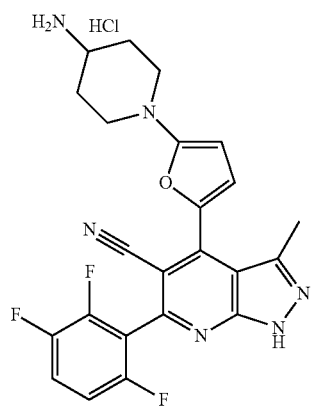 [SMILES: Cc1n[nH]c2nc(-c3c(F)ccc(F)c3F)c(C#N)c(-c3ccc(N4CCC(N)CC4)o3)c12 ; Cl]

TABLE I-continued
254 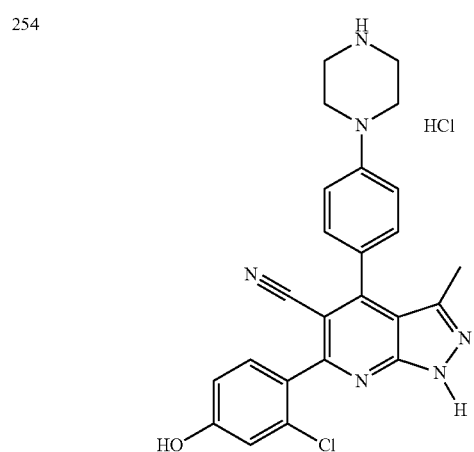
255 
256 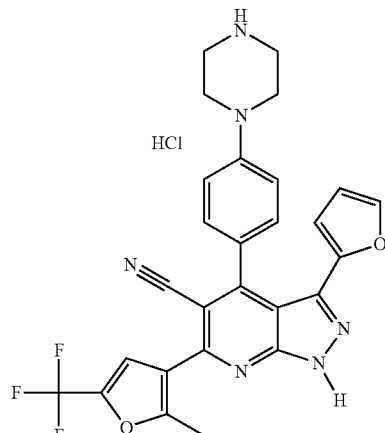
257 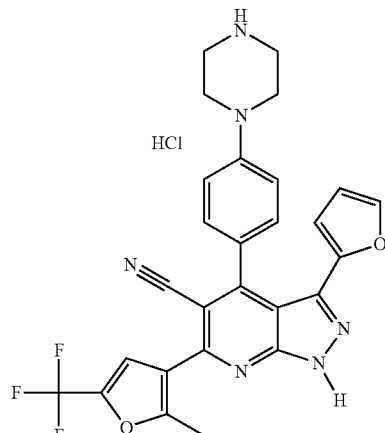
258 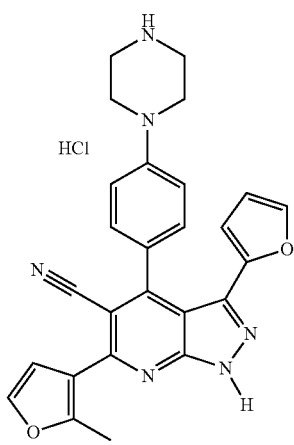 [SMILES: Cc1occc1-c1nc2[nH]nc(-c3ccco3)c2c(-c2ccc(N3CCNCC3)cc2)c1C#N ; Cl]
259 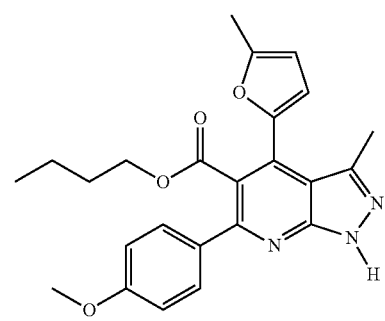 [SMILES: CCCCOC(=O)c1c(-c2ccc(OC)cc2)nc2[nH]nc(C)c2c1-c1ccc(C)o1]
260 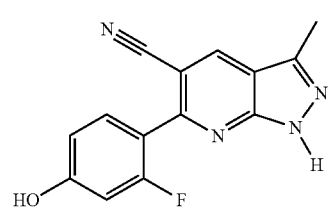 [SMILES: Cc1n[nH]c2nc(-c3ccc(O)cc3F)c(C#N)cc12]

TABLE I-continued
261 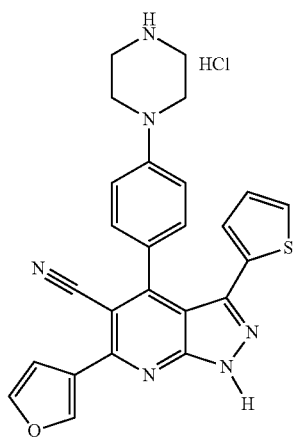 [SMILES: N#Cc1c(-c2ccoc2)nc2[nH]nc(-c3cccs3)c2c1-c1ccc(N2CCNCC2)cc1 ; Cl]
262 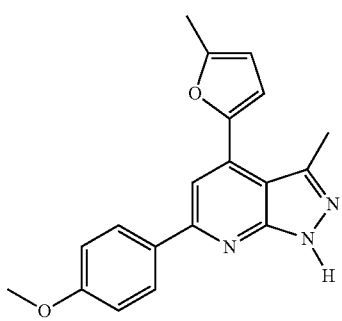 [SMILES: COc1ccc(-c2cc(-c3ccc(C)o3)c3c(C)n[nH]c3n2)cc1]
263 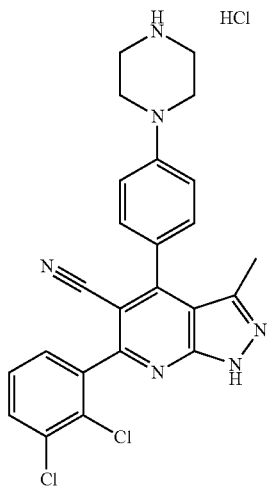
264 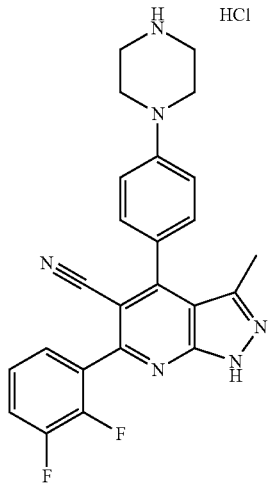
265 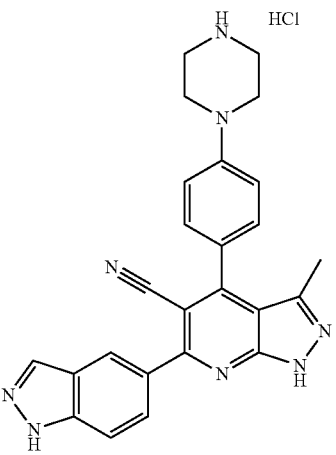 [SMILES: Cl ; Cc1n[nH]c2nc(-c3ccc4[nH]ncc4c3)c(C#N)c(-c3ccc(N4CCNCC4)cc3)c12]
266

TABLE I-continued
267 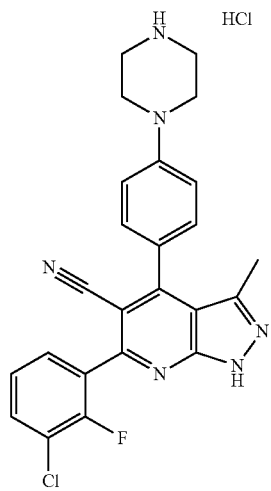 [SMILES: Cl ; Cc1n[nH]c2nc(-c3cccc(Cl)c3F)c(C#N)c(-c3ccc(N4CCNCC4)cc3)c12]
268 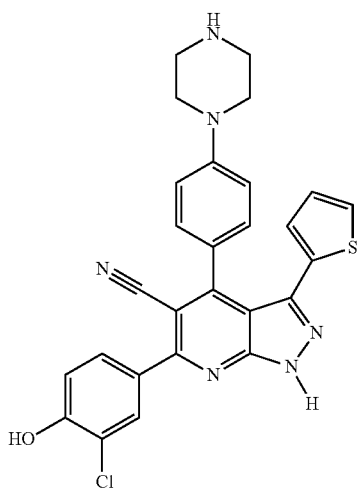 [SMILES: N#Cc1c(-c2ccc(O)c(Cl)c2)nc2[nH]nc(-c3cccs3)c2c1-c1ccc(N2CCNCC2)cc1]
269 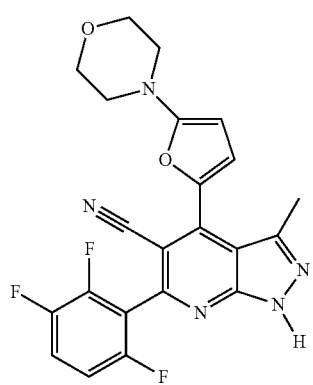 [SMILES: Cc1n[nH]c2nc(-c3c(F)ccc(F)c3F)c(C#N)c(-c3ccc(N4CCOCC4)o3)c12]
TABLE I-continued
270 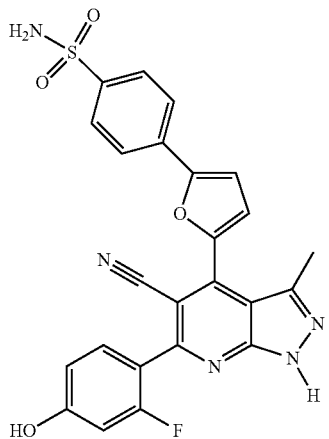 [SMILES: Cc1n[nH]c2nc(-c3ccc(O)cc3F)c(C#N)c(-c3ccc(-c4ccc(S(N)(=O)=O)cc4)o3)c12]
271 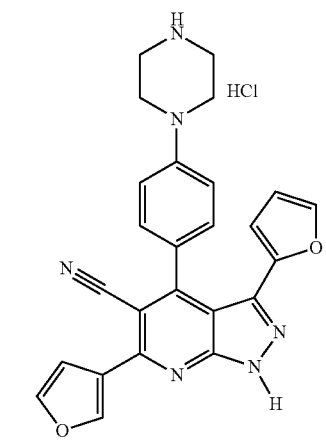 [SMILES: N#Cc1c(-c2ccoc2)nc2[nH]nc(-c3ccco3)c2c1-c1ccc(N2CCNCC2)cc1 ; Cl]
272

US 8,889,711 B2
83
TABLE I-continued
273
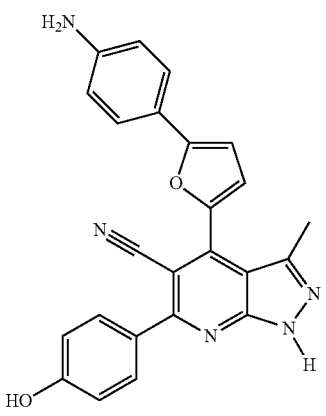 [SMILES: Cc1n[nH]c2nc(-c3ccc(O)cc3)c(C#N)c(-c3ccc(-c4ccc(N)cc4)o3)c12]
274
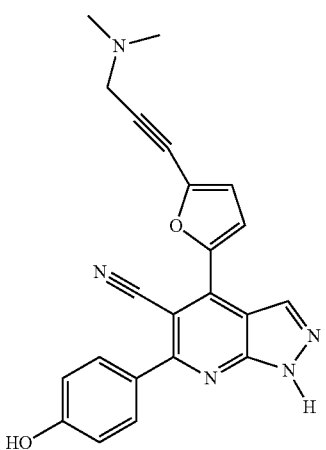 [SMILES: CN(C)CC#Cc1ccc(-c2c(C#N)c(-c3ccc(O)cc3)nc3[nH]ncc23)o1]
275
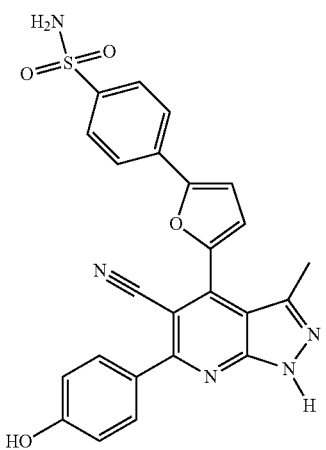 [SMILES: Cc1n[nH]c2nc(-c3ccc(O)cc3)c(C#N)c(-c3ccc(-c4ccc(S(N)(=O)=O)cc4)o3)c12]
84
TABLE I-continued
276
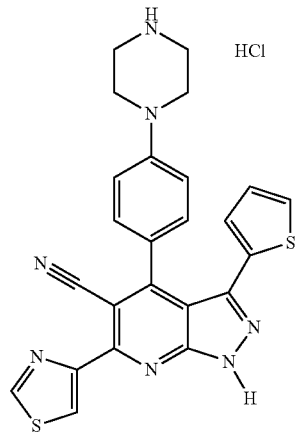 [SMILES: N#Cc1c(-c2cscn2)nc2[nH]nc(-c3cccs3)c2c1-c1ccc(N2CCNCC2)cc1 ; Cl]
277
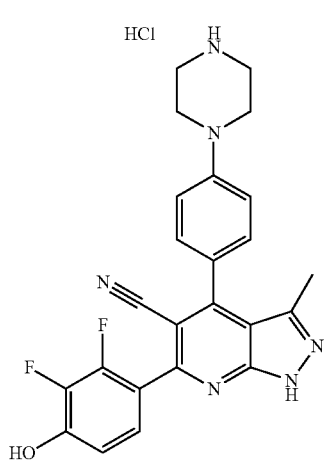 [SMILES: Cl ; Cc1n[nH]c2nc(-c3ccc(O)c(F)c3F)c(C#N)c(-c3ccc(N4CCNCC4)cc3)c12]
278
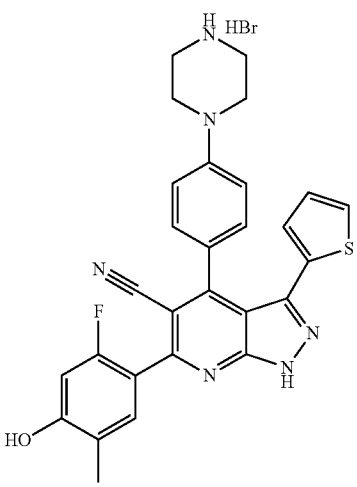 [SMILES: Br ; Cc1cc(-c2nc3[nH]nc(-c4cccs4)c3c(-c3ccc(N4CCNCC4)cc3)c2C#N)c(F)cc1O]

TABLE I-continued
279 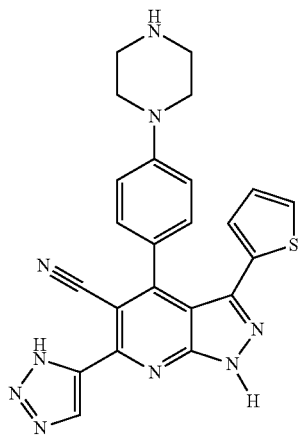 [SMILES: N#Cc1c(-c2cnn[nH]2)nc2[nH]nc(-c3cccs3)c2c1-c1ccc(N2CCNCC2)cc1]
280 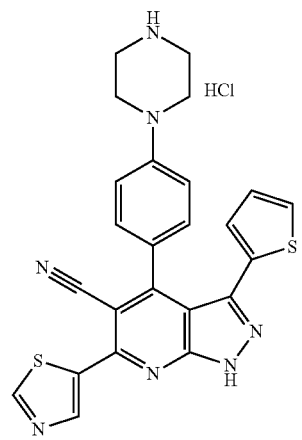 [SMILES: N#Cc1c(-c2cncs2)nc2[nH]nc(-c3cccs3)c2c1-c1ccc(N2CCNCC2)cc1 ; Cl]
281 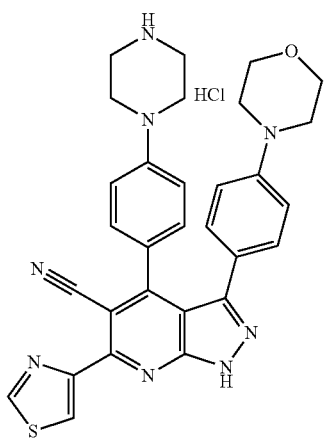 [SMILES: N#Cc1c(-c2cscn2)nc2[nH]nc(-c3ccc(N4CCOCC4)cc3)c2c1-c1ccc(N2CCNCC2)cc1 ; Cl]
TABLE I-continued
282 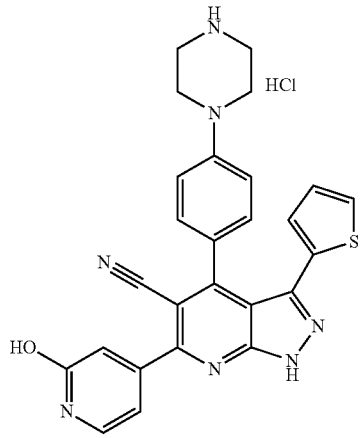 [SMILES: N#Cc1c(-c2ccnc(O)c2)nc2[nH]nc(-c3cccs3)c2c1-c1ccc(N2CCNCC2)cc1 ; Cl]
283 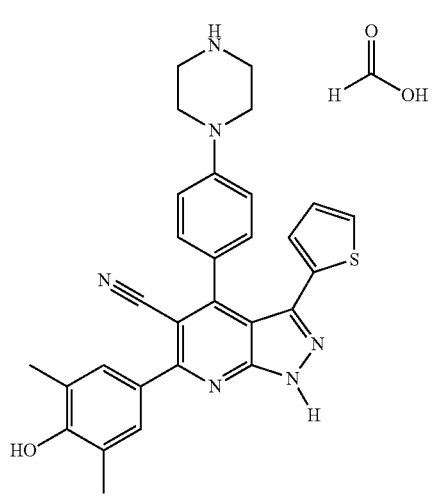 [SMILES: Cc1cc(-c2nc3[nH]nc(-c4cccs4)c3c(-c3ccc(N4CCNCC4)cc3)c2C#N)cc(C)c1O ; O=CO]
284 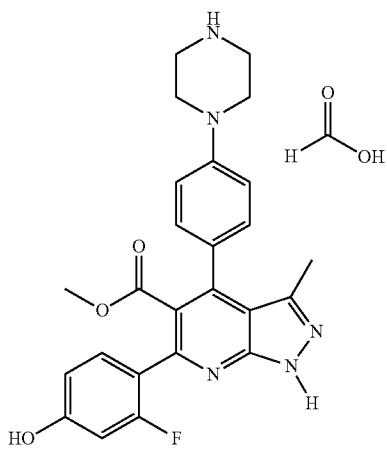

TABLE I-continued
285 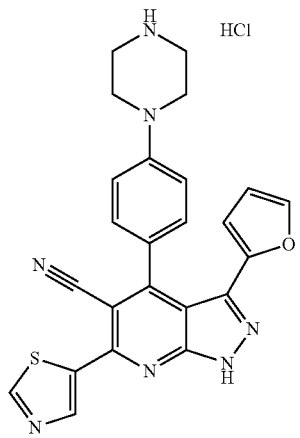 [SMILES: Cl ; N#Cc1c(-c2cncs2)nc2[nH]nc(-c3ccco3)c2c1-c1ccc(N2CCNCC2)cc1]
286 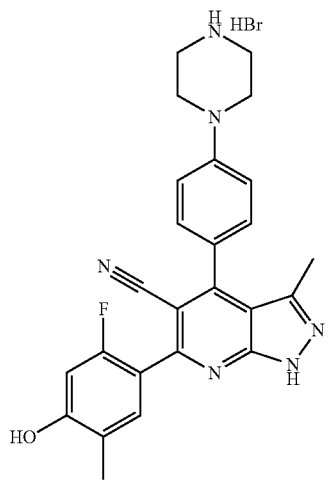 [SMILES: Br ; Cc1cc(-c2nc3[nH]nc(C)c3c(-c3ccc(N4CCNCC4)cc3)c2C#N)c(F)cc1O]
287 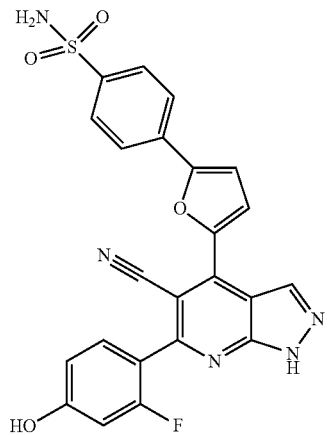 [SMILES: N#Cc1c(-c2ccc(O)cc2F)nc2[nH]ncc2c1-c1ccc(-c2ccc(S(N)(=O)=O)cc2)o1]
TABLE I-continued
288 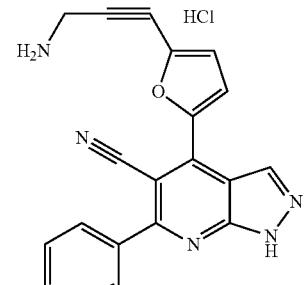
289 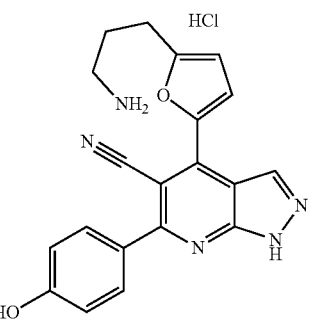
290 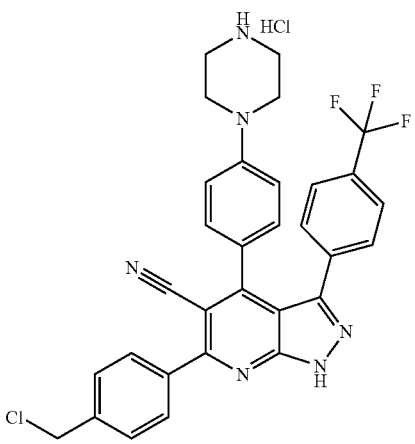 [SMILES: Cl ; N#Cc1c(-c2ccc(CCl)cc2)nc2[nH]nc(-c3ccc(C(F)(F)F)cc3)c2c1-c1ccc(N2CCNCC2)cc1]
291 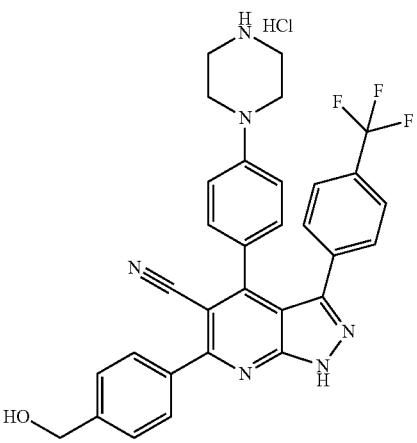 [SMILES: Cl ; N#Cc1c(-c2ccc(CO)cc2)nc2[nH]nc(-c3ccc(C(F)(F)F)cc3)c2c1-c1ccc(N2CCNCC2)cc1]

TABLE I-continued
292 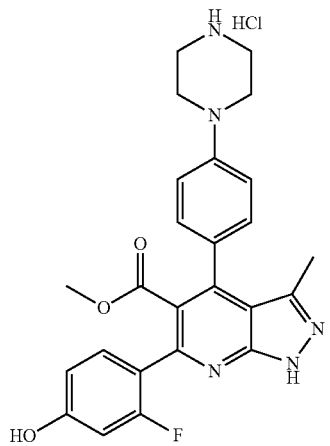 [SMILES: Cl ; COC(=O)c1c(-c2ccc(O)cc2F)nc2[nH]nc(C)c2c1-c1ccc(N2CCNCC2)cc1]
293 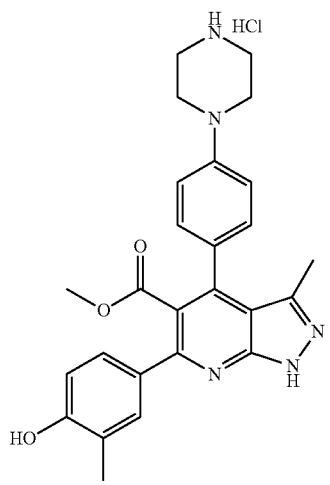 [SMILES: Cl ; COC(=O)c1c(-c2ccc(O)c(C)c2)nc2[nH]nc(C)c2c1-c1ccc(N2CCNCC2)cc1]
294 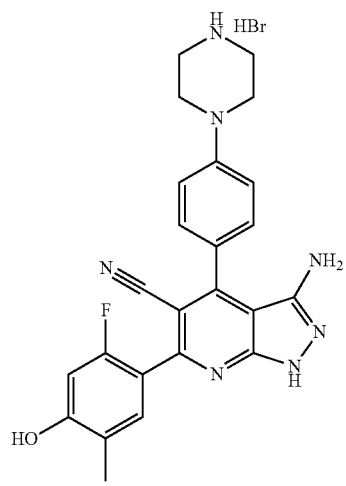 [SMILES: Br ; Cc1cc(-c2nc3[nH]nc(N)c3c(-c3ccc(N4CCNCC4)cc3)c2C#N)c(F)cc1O]
TABLE I-continued
295 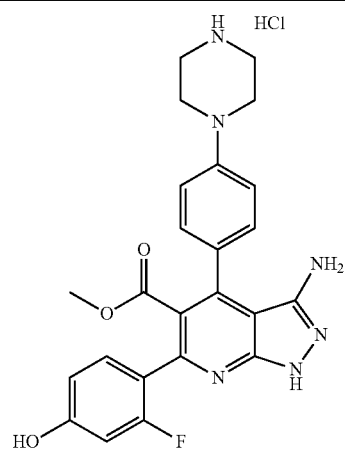
296 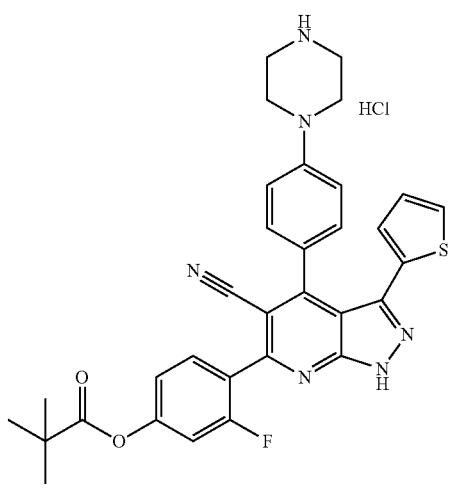 [SMILES: CC(C)(C)C(=O)Oc1ccc(-c2nc3[nH]nc(-c4cccs4)c3c(-c3ccc(N4CCNCC4)cc3)c2C#N)c(F)c1 ; Cl]
297 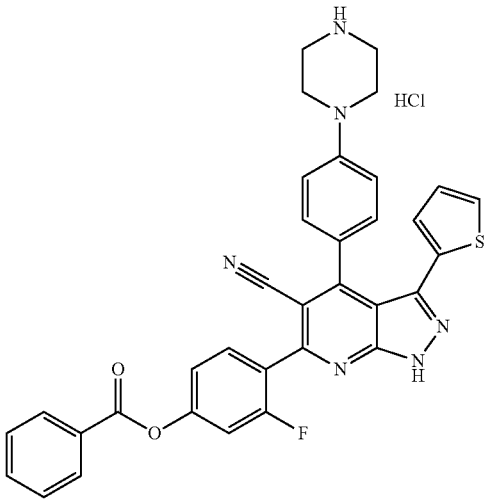 [SMILES: N#Cc1c(-c2ccc(OC(=O)c3ccccc3)cc2F)nc2[nH]nc(-c3cccs3)c2c1-c1ccc(N2CCNCC2)cc1 ; Cl]

TABLE I-continued
| | |
|---|---|
| 298 | 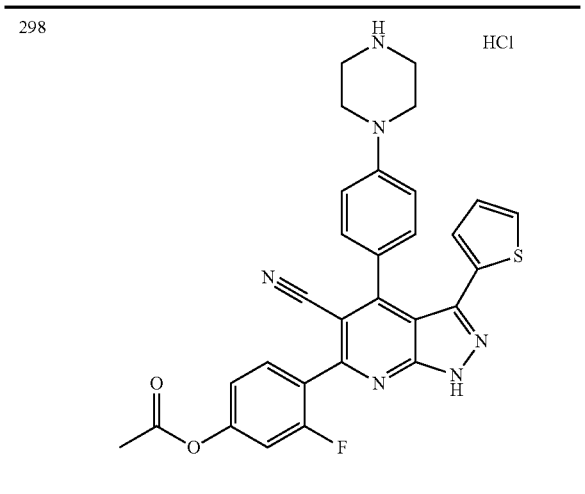 |
| 299 | 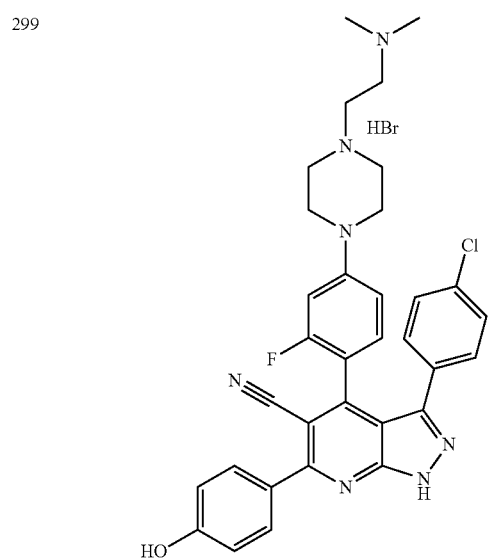 |
| 300 | 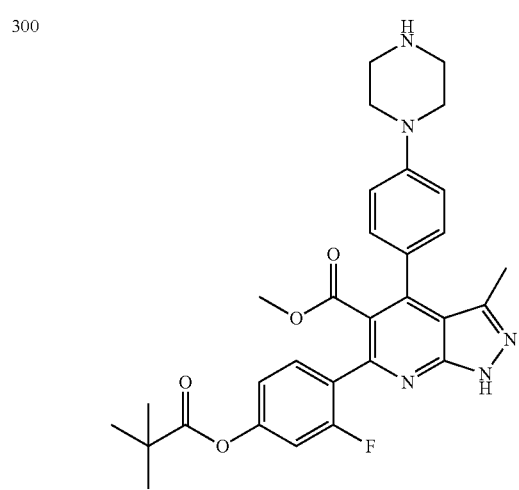 |
| 301 | 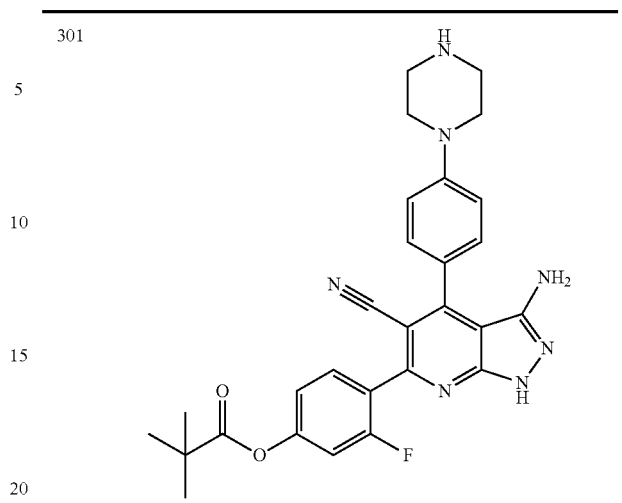 |
| 302 | 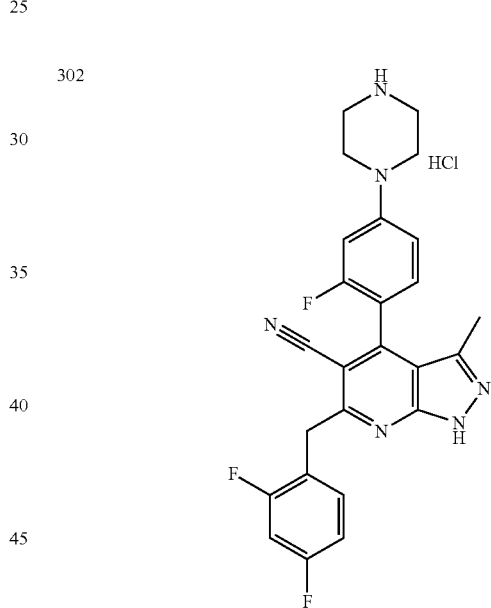 |
| 303 | 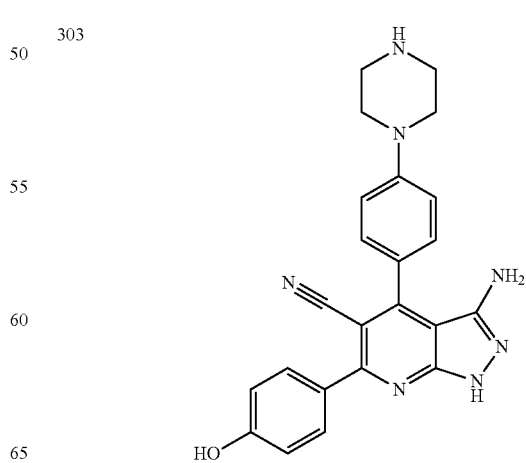 |

TABLE I-continued
304 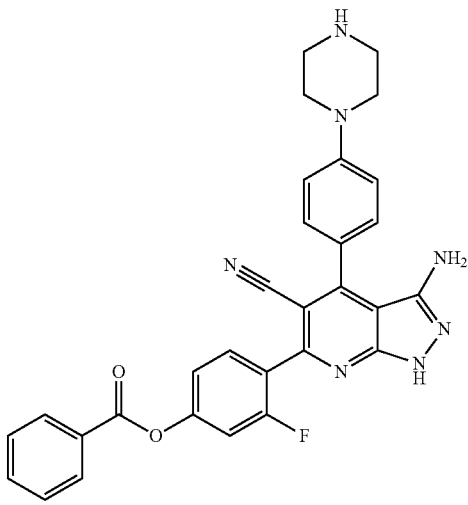 [SMILES: N#Cc1c(-c2ccc(OC(=O)c3ccccc3)cc2F)nc2[nH]nc(N)c2c1-c1ccc(N2CCNCC2)cc1]
305 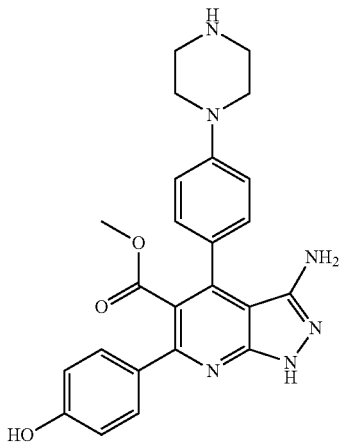 [SMILES: COC(=O)c1c(-c2ccc(O)cc2)nc2[nH]nc(N)c2c1-c1ccc(N2CCNCC2)cc1]
306 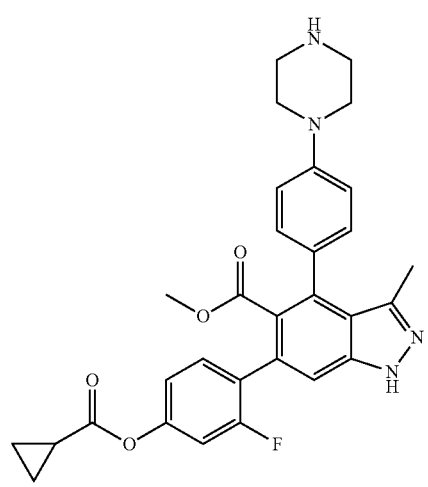 [SMILES: COC(=O)c1c(-c2ccc(OC(=O)C3CC3)cc2F)cc2[nH]nc(C)c2c1-c1ccc(N2CCNCC2)cc1]
TABLE I-continued
307 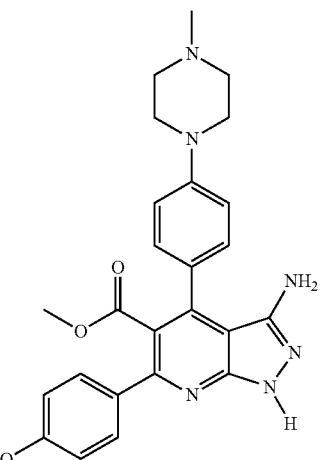
A further subject of the invention is a compound of formula (I) such as defined above, including the following compounds:
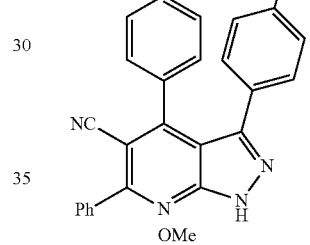 , 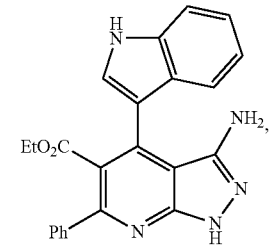
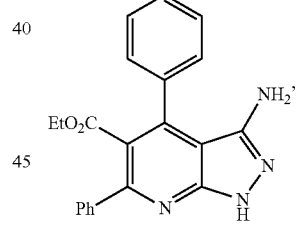 and 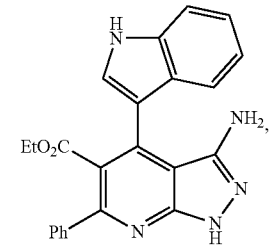
for its use as medicinal product, notably for the treatment of cancer.
The present invention also concerns the use of a compound of formula (I) such as defined above, including the following compounds:
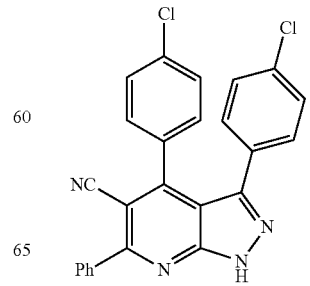 , 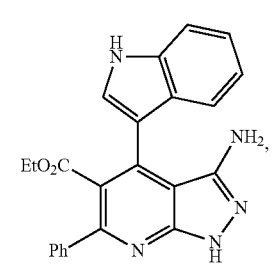

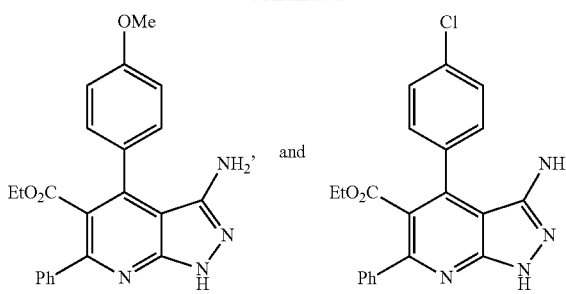

for the manufacture of a medicinal product notably intended for the treatment of cancer.

The present invention also concerns a method to treat cancer, comprising the administration to a person in need thereof of an efficient dose of a compound of formula (I) such as defined above, including the following compounds:

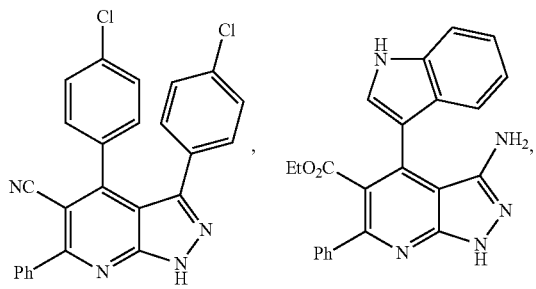

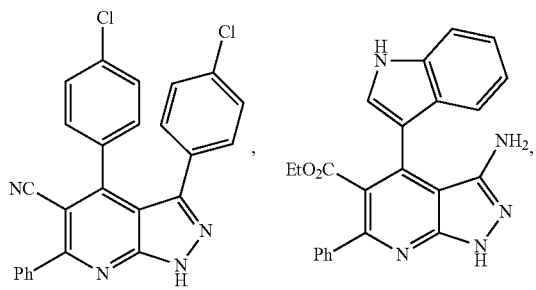

The present invention also concerns a pharmaceutical composition containing at least one compound of formula (I) such as defined above, including the following compounds:

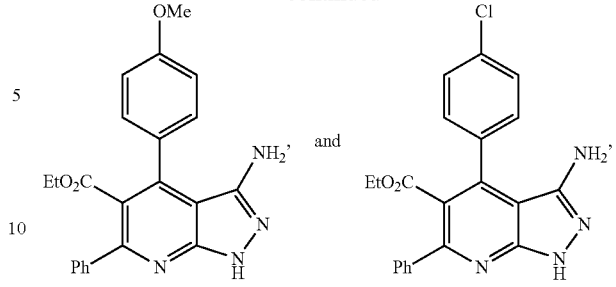

and a pharmaceutically acceptable excipient.

The pharmaceutical compositions of the invention can be formulated in particular for oral administration or for injection, said compositions being intended for mammals, including man.

The active ingredient can be administered in unit administration forms in a mixture with conventional pharmaceutical carriers, to animals and to human beings. The compounds of the invention as active ingredients can be used at doses from 0.01 mg to 1,000 mg per day, given in a single dose per day or administered in several doses throughout the day, for example twice a day in equal doses. The dose administered per day is advantageously between 5 mg and 500 mg, more advantageously between 10 mg and 200 mg. It may be necessary to use doses outside these ranges as can be ascertained by the person skilled in the art.

The pharmaceutical compositions of the invention may further comprise at least one other active ingredient such as an anticancer agent.

A further subject of the present invention is a pharmaceutical composition comprising:
(i) at least one formula (I) compound as defined above, including the following compounds:

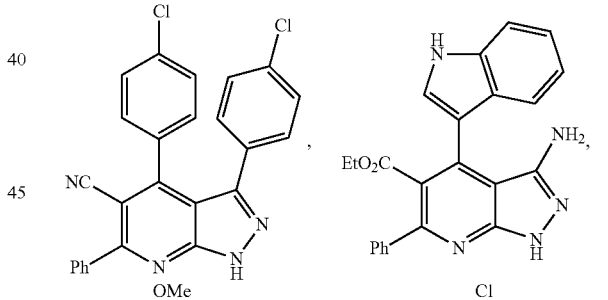

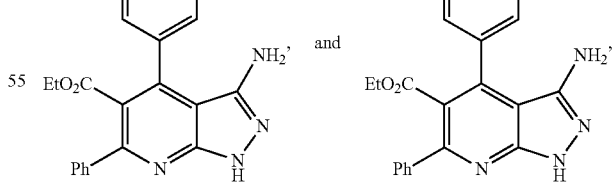

and
(ii) at least one other active ingredient such as an anticancer agent, as combination product for simultaneous, separate or sequential use.

The present invention also concerns a pharmaceutical composition such as defined above for its use as medicinal product notably intended for the treatment of a cancer.

Finally, a further subject of the invention is a method to prepare a formula (I) compound, said method comprising a condensation reaction between: R¹—C(O)—CH₂—R⁰ (II), R²—CHO (III), and

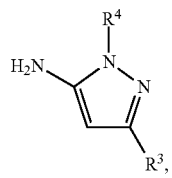

(IV)

to give the following compound (V):

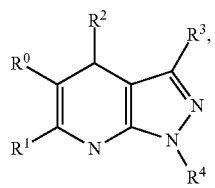

(V)

followed by an oxidation step.

The oxidation reaction can be conducted in the presence of a usual oxidant well known to the person skilled in the art, such as MnO₂, CAN or DDQ.

Additional steps of functionalization, protection, deprotection of the molecule, well known to the person skilled in the art, may be necessary.

In particular, the formula (I) compounds are preferably prepared with R⁰=NO₂, CN, CO₂—((C₁-C₆)alkyl) or SO₂—((C₁-C₆)alkyl). The formula (I) compounds in which R⁰=C(=NH)CH₃ can be prepared from formula (I) compounds in which R⁰=CN by reaction of this group with MeLi in particular (see protocol E18). The formula (I) compounds in which R⁰=CONH₂ can be prepared from formula (I) compounds which R⁰=CN by hydrolysis of this group notably in the presence of phosphoric acid (see protocol E26). The formula (I) compounds in which R⁰=CO₂H can be prepared from the corresponding esters (formula (I) compounds in which R⁰=CO₂—((C₁-C₆)alkyl)) using techniques well known to the person skilled in the art, and in particular under the conditions of protocol E1.

The synthesis of compounds of formula (II), (III), and (IV), when not obtained commercially, are more particularly described in the following examples which are intended to illustrate the invention and not to limit the scope thereof.

EXAMPLES

1—Synthesis of the Compounds of the Invention

The condensation reaction to give pyrazolopyridines can be depicted by the following scheme given by way of indication, bearing in mind that the first step can be obtained following the method described in international application WO 2004/14910 of Mitsubishi.

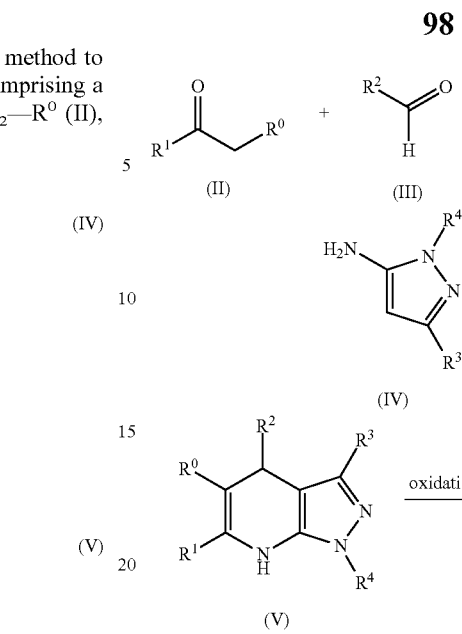

Without the invention being limited to a particular reaction mechanism, it appears that the formation of the compounds according to the present invention takes place following a process involving the three following steps:

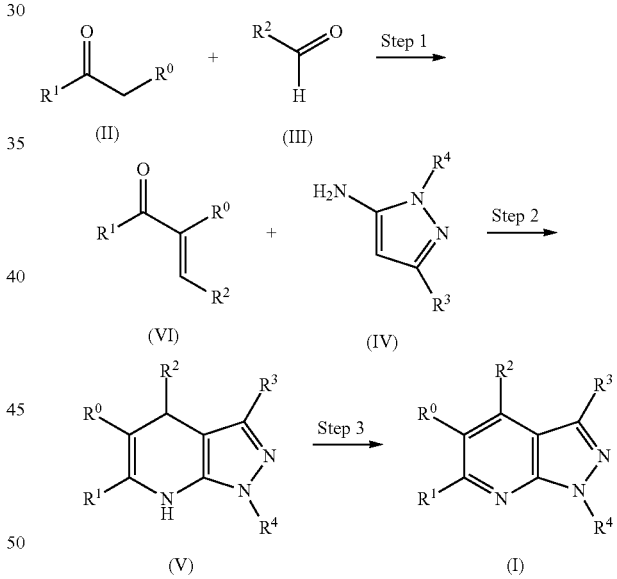

Step 1): Formation of the intermediate of formula (VI) by reaction of a methylene group activated by a electro-attractor group of formula (II) with the aldehyde of formula (III) optionally in the presence of a basic, acid, or metallic catalyst of mineral type such as potassium carbonate. The reaction is conducted in any type of solvent (acetonitrile, butanol, ethanol, etc.) notably at a temperature of between 0° C. and the boiling point of the solvent, and optionally in the presence of molten salt such as NH₄OAc.

Step 2): Cyclizing condensation of the intermediate of formula (VI) with aminopyrazole (IV) under the same conditions as in step 1, to form the dihydropyridine of formula (V).

Step 3): Oxidation of the product optionally in the presence of an oxidant such as MnO$_2$, CAN, DDQ, etc., to give the corresponding pyrazolopyridine in any type of solvent (CH$_2$Cl$_2$, DMSO, etc.) notably at a temperature comprised between 0° C. and the boiling point of the solvent.

Although it is more practical to form the intermediate compounds of formulas (VI) and (V) in situ by reacting together the three starting co-reagents, it is possible without departing from the scope of the invention to prepare the compound of formula (VI) extemporaneously, during a first step, by reaction of the activated methylene compound (II) with the aldehyde (III), then conducting the reaction of this intermediate with the aminopyrazole of formula (IV) under suitable conditions.

A) Synthesis of the Keto-nitriles, Keto-esters and Keto-sulfones of Formula (II)

The starting activated methylene compounds of formula (II) are products well known to the person skilled in the art, and can be prepared using various processes described in the literature.

a) Synthesis of Keto-nitriles

For example, the cyanomethyl derivatives used as starting products for the preparation of pyrazolopyridines can be prepared following the method described in J. Org. Chem, 46, 783, 1981; Eur. J. Med. Chem., 31, 3, 1996; Tetrahedron Lett., 24, 5023, 1983 (whose teaching is incorporated by reference in the present application) by reaction of an ester with acetonitrile in the presence of an organometallic derivative of an alkaline metal, such as the alkyllithiums (N-butyllithium), in an organic solvent such as tetrahydrofuran, at low temperature.

General Procedure A1

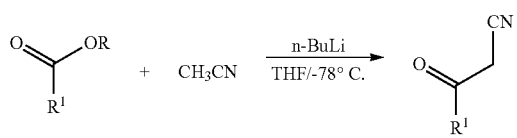

Example of Synthesis Following Procedure A1

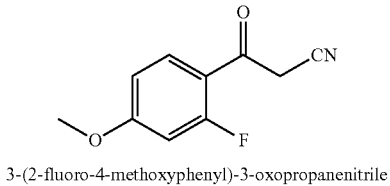

3-(2-fluoro-4-methoxyphenyl)-3-oxopropanenitrile

To a solution of 4.4 g (108.6 mmol, 5.7 ml) of acetonitrile diluted in 50 ml of anhydrous tetrahydrofuran are added dropwise at −78° C. under argon 27.1 ml of a N-butyllithium solution (2.5M in hexane, 67.8 mmol), the reaction mixture is stirred 30 min at −78° C., then 5 g (27.15 mmol) of methyl 2-fluoro-4-methoxybenzoate diluted in 30 ml of tetrahydrofuran are added dropwise at −78° C. to the reaction mixture. This mixture is stirred 2 h at −78° C., then a 1M hydrochloric acid solution is added, and the product is extracted several times with ethyl acetate. The organic phases are combined, dried over magnesium sulfate and concentrated. The solid is triturated in 15 ml of methanol to yield 4.4 g (84%) of 3-(2-fluoro-4-methoxyphenyl)-3-oxopropanenitrile in beige solid form.

LCMS (ESI, m/z): (M+1) 194.2

$^1$H-NMR: $\delta_H$ pm 400 MHz, CDCl$_3$: 7.98 (1H, t, CH$_{arom}$), 6.83 (1H, dd, CH$_{arom}$), 6.68 (1H, dd, CH$_{arom}$), 4.05 (2H, d, CH$_2$), 3.91 (3H, s, CH$_3$).

The compounds below are also obtained following procedure A1:

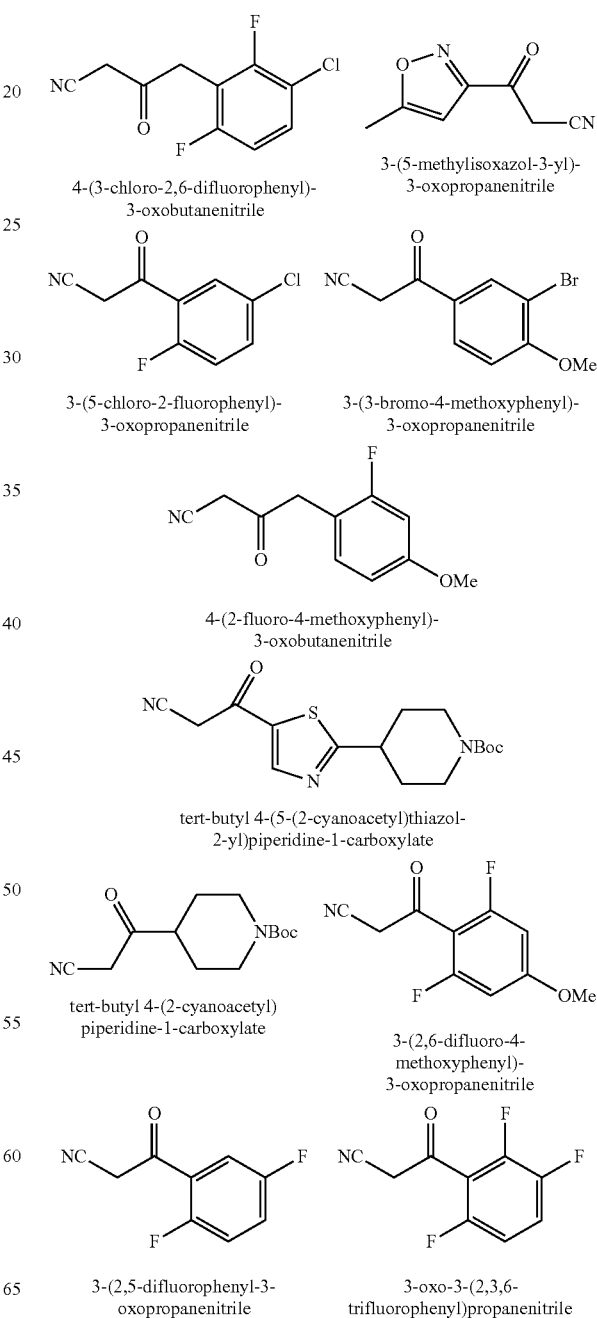

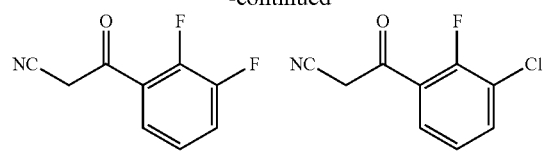

3-(2,3-difluorophenyl)-
3-oxopropanenitrile 3-(3-chloro-2-fluorophenyl)-
3-oxopropanenitrile

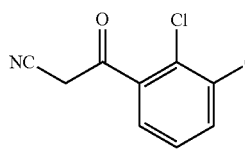

3-(2,3-dichlorophenyl)-
3-oxopropanenitrile

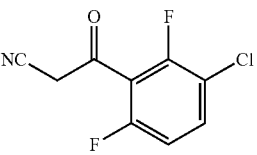

3-(3-chloro-2,6-difluorophenyl)-
3-oxopropanenitrile

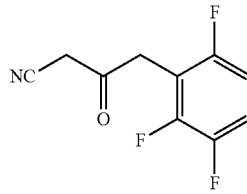

3-oxo-4-(2,3,6-trifluorophenyl)
butanenitrile

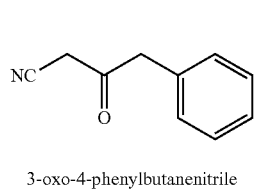

3-oxo-4-phenylbutanenitrile

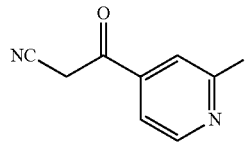

3-(2-chloropyridin-4-yl)-
3-oxopropanenitrile

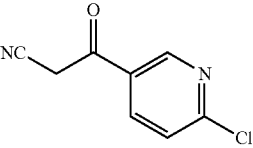

3-(6-chloropyridin-3-yl)-
3-oxopropanenitrile

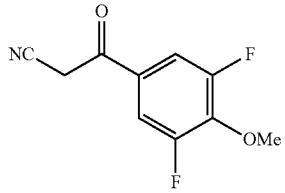

3-(3,5-difluoro-4-methoxphenyl)-
3-oxopropanenitrile

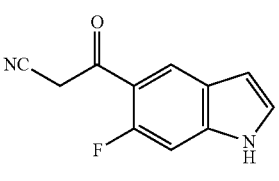

3-(6-fluoro-1H-indol-5-yl)-
3-oxopropanenitrile

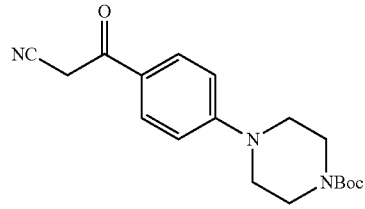

tert-butyl 4-(4-(2-cyanoacetyl)
phenyl)piperazine-
1-carboxylate

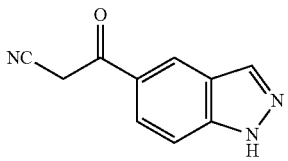

3-(1H-indazol-5-yl)-
3-oxopropanenitrile

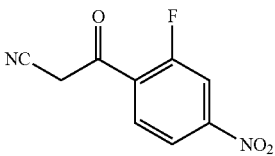

3-(2-fluoro-4-nitrophenyl)-
3-oxopropanenitrile

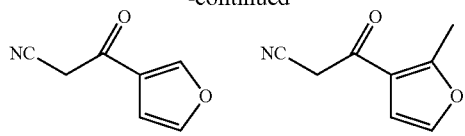

3-(furan-3-yl)-
3-oxopropanenitrile 3-(2-methylfuran-3-yl)-
3-oxopropanenitrile

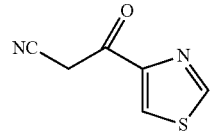

3-oxo-3-thiazol-
4-yl)propanenitrile

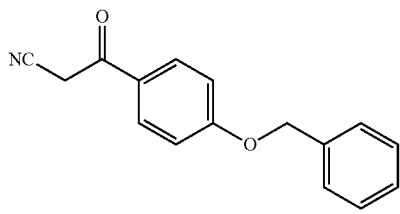

3-(4-(benzyloxy)phenyl)-
3-oxopropanenitrile

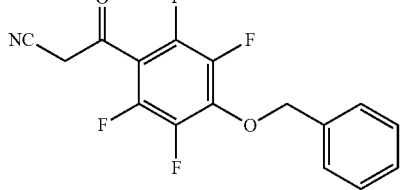

3-(4-(benzyloxy)-2,3,5,6-
tetrafluorophenyl)-3-oxopropanenitrile

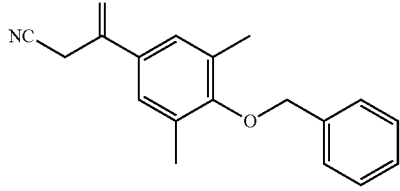

3-(4-(benzyloxy)-3,5-dimethylphenyl)-
3-oxopropanenitrile

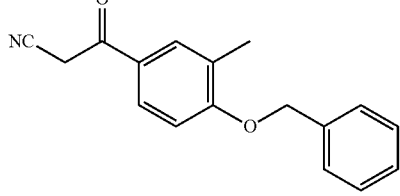

3-(4-(benzyloxy)-3-methylphenyl)-
3-oxopropanenitrile

All the compounds are obtained from the corresponding esters with the exception of the compounds of indole or indazole type which are obtained from an ester previously protected by a silylated protector group (TIPS) or by a Boc group as described below.

Synthesis of
3-(6-fluoro-1H-indol-5-yl)-3-oxopropanenitrile

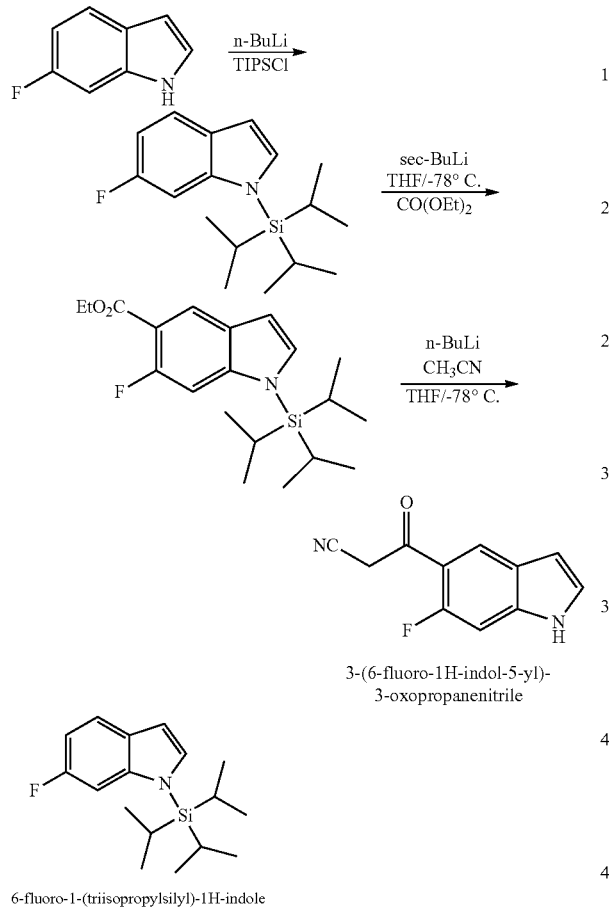

6-fluoro-1-(triisopropylsilyl)-1H-indole

To a solution of 400 mg (2.96 mmol) of 6-fluoroindole dissolved in 6 ml of anhydrous tetrahydrofuran are added dropwise at −78° C. under argon 1.18 ml of a N-butyllithium solution (2.5M in hexane, 2.96 mmol). The reaction mixture is stirred for 5 min at −78° C., then 634 µL (2.96 mmol) of triisopropylsilane chloride are added dropwise at −78° C. to the reaction mixture. This mixture is stirred for 20 min at room temperature then water is added. The product is extracted several times with ethyl acetate. The organic phases are combined, dried over magnesium sulfate and concentrated. The residue is purified by chromatography on silica (cyclohexane/ethyl acetate eluent: 99:1) to yield 760 mg (89%) of 6-fluoro-1-triisopropylsilylindole as a colourless oil.

$^1$H-NMR: $\delta_H$ pm 400 MHz, CDCl$_3$: 7.52 (1H, dd, CH$_{arom}$), 7.22 (1H, d, CH$_{arom}$), 7.18 (1H, d, CH$_{arom}$), 6.88 (1H, t, CH$_{arom}$) 6.59 (1H, d, CH$_{arom}$), 1.68 (3H, sept, 3×CH), 1.14 (18H, d, 6×CH$_3$).

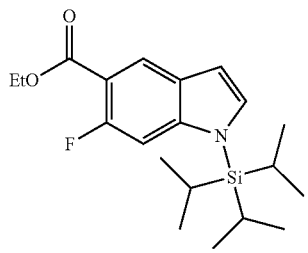

ethyl 6-fluoro-1-(triisopropylsilyl)-1H-indole-5-carboxylate

To a solution of 760 mg (2.61 mmol) of 6-fluoro-1-triisopropylsilylindole dissolved in 6 ml of anhydrous tetrahydrofuran are added dropwise at −78° C. under argon 2.01 ml of a sec-butyllithium solution (1.3M in cyclohexane, 2.01 mmol). The reaction mixture is stirred for 2 h at −78° C. then 500 µL (3.15 mmol) of diethyl carbonate are added dropwise at −78° C. to the reaction mixture. This mixture is stirred for 5 h with a gentle temperature rise then an ammonium chloride saturated aqueous solution is added. The product is extracted several times with ethyl acetate. The organic phases are combined, dried over magnesium sulfate, and concentrated. The residue is purified by chromatography on silica (cyclohexane/ethyl acetate eluent: 97:3) to yield 445 mg (46%) of 5-carboethoxy-6-fluoro-1-triisopropylsilylindole in the form of a colourless oil.

$^1$H-NMR: $\delta_H$ pm 400 MHz, CDCl$_3$: 8.21 (1H, d, CH$_{arom}$), 7.26 (1H, d, CH$_{arom}$), 7.19 (1H, d, CH$_{arom}$), 6.66 (1H, d, CH$_{arom}$) 4.40 (2H, q, CH$_2$), 1.67 (3H, sept, 3×CH), 1.41 (3H, t, CH$_3$), 1.14 (18H, d, 6×CH$_3$).

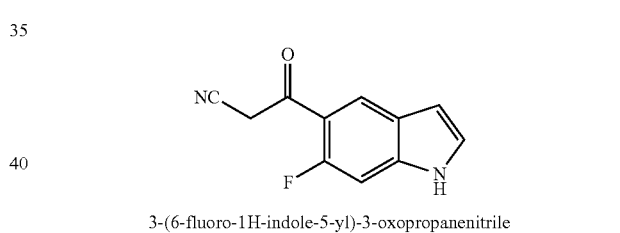

3-(6-fluoro-1H-indole-5-yl)-3-oxopropanenitrile

To a solution of 690 µL (13.2 mmol) acetonitrile diluted in 10 ml anhydrous tetrahydrofuran are added dropwise at −78° C. under argon 3.3 ml of N-butyllithium solution (2.5M in hexane, 8.25 mmol). The reaction mixture is stirred for 30 min at −78° C. then a solution of 1.2 g (3.3 mmol) of 5-carboethoxy-6-fluoro-1-triisopropylsilylindole dissolved in 3 ml of tetrahydrofuran is added dropwise at −78° C. to the reaction mixture. This mixture is stirred 2 h at −78° C. then a 1M hydrochloric acid solution is added, and the product is extracted several times with ethyl acetate. The organic phases are combined before adding 3.5 ml of a tetrabutylammonium fluoride solution (1M in tetrahydrofuran). The reaction mixture is stirred for 30 min at room temperature then water is added. The product is extracted several times with ethyl acetate. The organic phases are combined, dried over magnesium sulfate, and concentrated. The residue is purified by chromatography on silica (cyclohexane/ethyl acetate eluent: 4:6) to yield 318 mg (48%) of 3-(1H-indazol-5-yl)-3-oxopropanenitrile in the form of a white solid.

¹H-NMR: δ_H pm 400 MHz, DMSO: 11.58 (1H, sl, NH), 8.17 (1H, s, CH_arom), 7.48 (1H, s, CH_arom), 7.28 (1H, d, CH_arom) 6.62 (1H, s, CH_arom), 4.61 (2H, s, CH₂).

Synthesis of
3-(1H-indazol-5-yl)-3-oxopropanenitrile

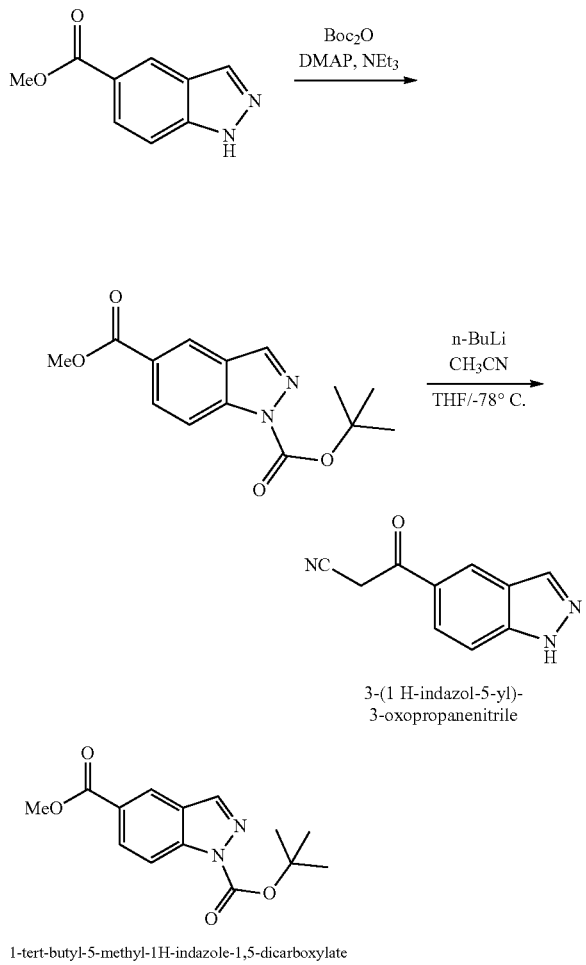

1-tert-butyl-5-methyl-1H-indazole-1,5-dicarboxylate

To a solution of 735 mg (4.17 mmol) of 5-carbomethoxy-indazole dissolved in 20 ml of tetrahydrofuran are respectively added 824 μL (6.26 mmol) of triethylamine, 102 mg (0.834 mmol) of 4-dimethylamino-pyridine. The solution is cooled over an ice bath before adding 1.09 g (5 mmol) of di-tert-butyl dicarbonate. The reaction mixture is stirred at room temperature for 3 h, then diluted with a saturated sodium chloride aqueous solution. The product is extracted several times with ethyl acetate. The organic phases are combined, dried over magnesium sulfate, filtered, and evaporated. The residue is triturated in a minimum amount of methanol and the solid is filtered to yield 650 mg (57%) of 1-tert-butyl-5-methyl-1H-indazole-1,5-dicarboxylate in the form of a brown solid.

¹H-NMR: δ_H pm 400 MHz, DMSO: 8.56-8.52 (2H, m, CH_arom), 8.18-8.15 (2H, m, CH_arom), 3.90 (3H, s, CH₃), 1.65 (9H, s, 3×CH₃).

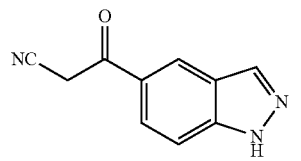

3-(1H-indazol-5-yl)-3-oxopropanenitrile

To a solution of 788 μL (14.8 mmol) of acetonitrile diluted in 10 ml of anhydrous tetrahydrofuran are added dropwise at −65° C. under argon 5.76 ml of N-butyllithium solution (1.6M in hexane, 9.22 mmol). The reaction mixture is stirred 30 min at −65° C., then a solution of 650 mg (3.69 mmol) of 1-tert-butyl 5-methyl-1H-indazole-1,5-dicarboxylate dissolved in 20 ml tetrahydrofuran is added dropwise at −78° C. to the reaction mixture. The mixture is stirred 5 h at −65° C., then water is added and the product is extracted several times with ethyl acetate. The organic phases are combined, dried over magnesium sulfate and concentrated. The residue is purified by chromatography on silica (cyclohexane/ethyl acetate eluent: 7:3 to 5:5) to yield 300 mg (44%) of 3-(1H-indazol-5-yl)-3-oxopropanenitrile in the form of a light brown solid.

¹H-NMR: δ_H pm 400 MHz, DMSO: 13.5 (1H, sl, NH), 8.48 (1H, s, CH_arom), 8.30 (1H, s, CH_arom), 7.88 (1H, d, CH_arom), 7.63 (1H, d, CH_arom), 4.79 (2H, sl, CH₂).

General Procedure A2

These same products can be prepared in two steps by forming an α-halo-ketone intermediate from the corresponding ketone in the presence of a halogenating agent such as dibromine or CuBr₂, followed by cyanation with KCN or trimethylsilyl cyanide (TMSCN).

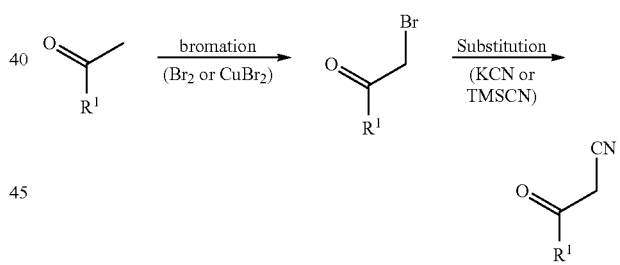

Example of Synthesis Following Procedure A2 in
Two Steps

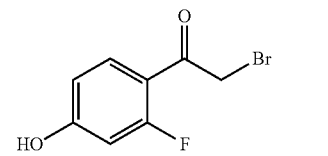

2-bromo-1-(2-fluoro-4-hydroxyphenyl)ethanone

To a solution of 5 g (32.44 mmol) of 1-(2-fluoro-4-hydroxyphenyl)ethanone dissolved in 140 ml of anhydrous dioxane are added dropwise 5.7 g (35.68 mmol, 1.83 ml) of dibromine at 0° C. under argon. The reaction mixture is brought to 70° C.

for 3 h. The solvent is concentrated by vacuum evaporation and the solid is recrystallized in 40 ml of 1,2-dichloroethane to yield 5.67 g (75%) of 2-bromo-1-(2-fluoro-4-hydroxyphenyl)ethanone in the form of a violet solid.

LCMS (ESI, m/z): (M−1) 233.2

$^1$H-NMR: $\delta_H$ pm 400 MHz, DMSO: 11.02 (1H, s, OH), 7.81 (1H, t, $CH_{arom}$), 6.74 (1H, dd, $CH_{arom}$), 6.67 (1H, dd, $CH_{arom}$) 4.70 (2H, d, $CH_2$).

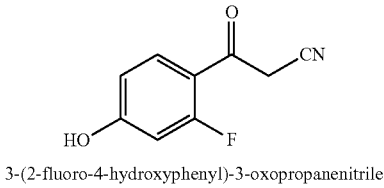 [SMILES: N#CCC(=O)c1ccc(O)cc1F]

3-(2-fluoro-4-hydroxyphenyl)-3-oxopropanenitrile

To a solution of 2.5 g (10.73 mmol) of 2-bromo-1-(2-fluoro-4-hydroxyphenyl)ethanone in 100 ml of acetonitrile are respectively added 1.2 g (11.8 mmol) of trimethylsilyl cyanide and 12.3 ml (12.3 mmol) of tetrabutyl-ammonium fluoride solution (1M in THF). The reaction mixture is stirred at room temperature for 16 h then diluted with an aqueous solution saturated with sodium chloride. The product is extracted several times with ethyl acetate. The organic phases are combined, dried over magnesium sulfate, filtered, then evaporated. The residue is purified by chromatography on silica (cyclohexane/ethyl acetate eluent: 5:5) to give 1.2 g (62%) of 3-(2-fluoro-4-hydroxyphenyl)-3-oxopropanenitrile in the form of a yellow solid.

LCMS (ESI, m/z): (M−1) 178.2

$^1$H-NMR: $\delta_H$ pm 400 MHz, DMSO: 11.09 (1H, s, OH), 7.79 (1H, t, $CH_{arom}$), 6.75 (1H, dd, $CH_{arom}$), 6.66 (1H, dd, $CH_{arom}$) 4.49 (2H, s, $CH_2$).

The compounds below are also obtained following procedure A2:

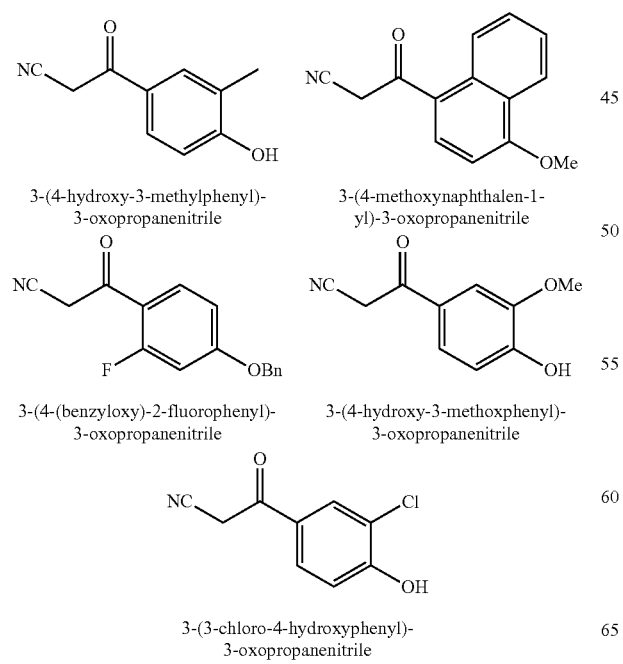

3-(4-hydroxy-3-methylphenyl)-3-oxopropanenitrile 3-(4-methoxynaphthalen-1-yl)-3-oxopropanenitrile 3-(4-(benzyloxy)-2-fluorophenyl)-3-oxopropanenitrile 3-(4-hydroxy-3-methoxphenyl)-3-oxopropanenitrile 3-(3-chloro-4-hydroxyphenyl)-3-oxopropanenitrile

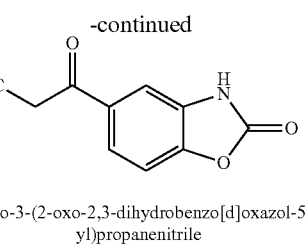

3-oxo-3-(2-oxo-2,3-dihydrobenzo[d]oxazol-5-yl)propanenitrile

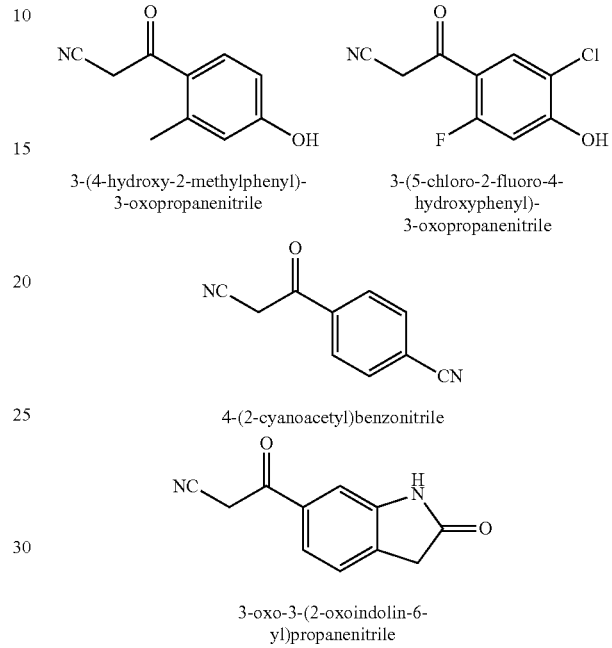

3-(4-hydroxy-2-methylphenyl)-3-oxopropanenitrile 3-(5-chloro-2-fluoro-4-hydroxyphenyl)-3-oxopropanenitrile 4-(2-cyanoacetyl)benzonitrile 3-oxo-3-(2-oxoindolin-6-yl)propanenitrile b) Synthesis of the Keto-esters The keto-esters used as starting material to obtain pyrazolopyridines can be prepared following the method described in the literature by Clay Ronald J., Synthesis, 1993, 3, 290-2 (whose teaching is incorporated in the present application by reference).

General Procedure A3

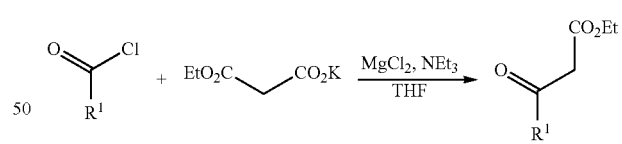

Example of Synthesis Following Procedure A3

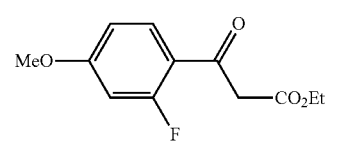

ethyl 3-(2-fluoro-4-methoxyphenyl)-3-oxopropanoate

To a solution of 12.34 g (72.5 mmol) of potassium 3-ethoxy-3-oxopropanoate in suspension in 150 ml anhydrous acetonitrile are added at −0° C. under argon 10.11 ml (72.5 mmol) of triethylamine and 8.28 g (87 mmol) of magnesium (II) chloride. The reaction mixture is stirred for 5 h at room temperature, then at 0° C. a solution of 5.47 g (29 mmol) of 2-fluoro-4-methoxybenzoyl chloride dissolved in 30 ml of acetonitrile is added as well as 4.45 ml (31.9 mmol) of triethylamine. The reaction mixture is stirred for 18 h at room temperature then a 1M hydrochloric acid solution is added until the suspension disappears. The product is extracted several times with ethyl acetate. The organic phases are combined, dried over magnesium sulfate, and concentrated. The residue is purified by chromatography on silica (cyclohexane/ethyl acetate eluent: 85:15) to yield 5.46 g (78%) of ethyl 3-(2-fluoro-4-methoxyphenyl)-3-oxopropanoate in the form of a yellow oil which crystallizes over time.

$^1$H-NMR: $\delta_H$ pm 400 MHz, DMSO: 7.94 (1H, t, $CH_{arom}$), 6.77 (1H, dd, $CH_{arom}$), 6.60 (1H, dd, $CH_{arom}$), 4.21 (2H, q, $CH_2$) 3.93 (2H, d, $CH_2$), 3.86 (3H, s, $CH_3$), 1.26 (3H, t, $CH_3$).

The compound below was also obtained following procedure A3:

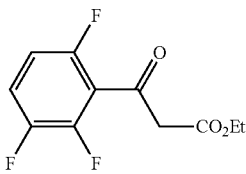

ethyl 3-oxo-3-(2,3,6-trifluorophenyl)propanoate

General Procedure A4

(By analogy with Sircar, I.; Duell, B. L.; Bodowski, G.; Bristol, J. A.; Evans, D. B., J. Med. Chem., 1985, 28, 1405-1413).

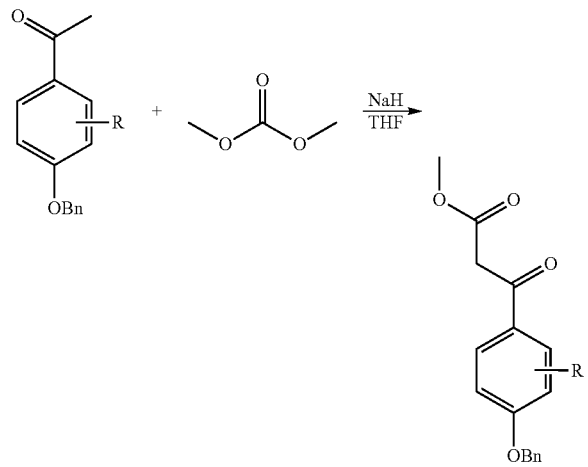

Example of Synthesis Following Procedure A4

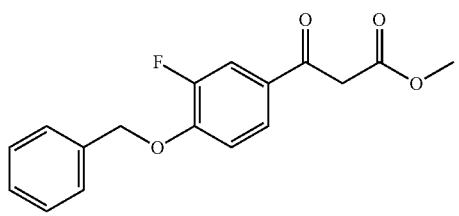

methyl 3-(4-benzyloxy)-3-fluorophenyl)-3-oxopropanoate

To a suspension of 0.64 g (22.8 mmol) of sodium hydride in anhydrous THF (12 ml) are added 5.00 g (22.3 mmol) of 1-[4-(benzyloxy)-2-fluorophenyl]ethanone in THF (43 ml). The reaction mixture is stirred at room temperature for 1 h. Next, 2.17 g (24.1 mmol) of dimethyl carbonate are added. The mixture is then refluxed for 18 h. After cooling, 100 ml of water is added and the solution is brought to pH 6 through the addition of acetic acid. The aqueous phase is extracted several times with ethyl acetate. The organic phases are combined, dried over sodium sulfate, filtered, and evaporated. The residue is purified by chromatography on silica (cyclohexane/ethyl acetate eluent: 6:4) to yield 2.00 g (30%) of methyl 3-(4-benzyloxy)-2-fluorophenyl)-3-oxopropanoate in the form of a grey solid.

LCMS (ESI, m/z): (M−1) 301.01 c) Synthesis of the Keto-sulfones

The keto-sulfones used as starting material to obtain the pyrazolopyridines can be prepared following the method inspired from the literature by Ibarra C. Alvarez et al, Journal of Organic Chemistry, 1989, 54(23), 5620-3 (whose teaching is incorporated in the present application by reference).

General Procedure A5

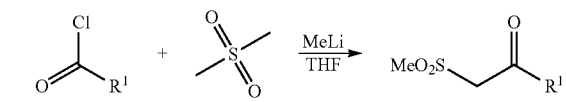

[$SO_2Me_2$ can be replaced by $SO_2Me((C_1-C_6)alkyl)$ to obtain keto-sulfones with alkyl substituents other than methyl by following the protocol described in Jeffrey et al, Tetrahedron 1984, 40, 1135-1140].

Example of Synthesis Following Procedure A5

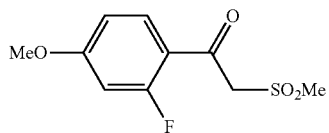

1-(2-fluoro-4-methoxyphenyl)-2-(methylsulfonyl)ethanone

To a solution of 4.15 g (44.07 mmol) of dimethylsulfone in 140 ml of anhydrous tetrahydrofuran are added dropwise at −10° C. under argon 24 ml of methyllithium solution (1.6M in diethyl ether, 38.2 mmol). The reaction mixture is stirred for 15 min at room temperature, the reaction mixture is then cooled to −60° C. A solution of 5.54 g (29.38 mmol) of 2-fluoro-4-methoxybenzoyl chloride dissolved in 60 ml of tetrahydrofuran is then added dropwise to the reaction mixture. This mixture is stirred for 4 h at between −60° C. and 0° C., then a 1M hydrochloric acid solution is added. The product is extracted several times with ethyl acetate. The organic phases are combined, dried over magnesium sulfate and concentrated. The residue is triturated in minimum methanol and the solid is filtered to yield 3.33 g (46%) of 1-(2-fluoro-4-methoxyphenyl)-2-(methylsulfonyl)ethanone in the form of a white solid.

$^1$H-NMR: $\delta_H$ pm 400 MHz, DMSO: 7.90 (1H, t, $CH_{arom}$), 7.03-6.90 (2H, m, $CH_{arom}$), 4.93 (2H, s, $CH_2$), 3.88 (3H, s, $CH_3$) 3.13 (3H, s, $CH_3$).

B) Synthesis of the Formula (III) Aldehydes

The starting formula (III) aldehydes are products well known to the person skilled in the art, and can be prepared using various methods described in the literature. Below a description is given of the aldehydes and their methods of preparation which are not described in the literature and used in the present invention.

General Procedure B1

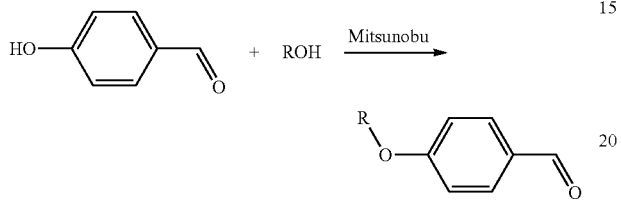

Example of Synthesis Following Procedure B1

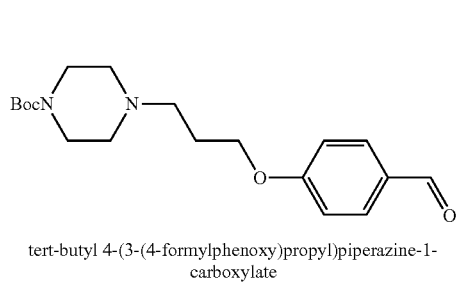 [SMILES: CC(C)(C)OC(=O)N1CCN(CCCOc2ccc(C=O)cc2)CC1]

tert-butyl 4-(3-(4-formylphenoxy)propyl)piperazine-1-carboxylate

To 0.5 g (2.05 mmol) of tert-butyl 4-(3-hydroxypropyl)piperazine-1-carboxylate, 0.3 g (2.46 mmol) of 4-hydroxybenzaldehyde and 1 g (3.07 mmol) of resin-supported triphenyl-phosphine (3 mmol/g of resin) diluted in 14.5 ml of anhydrous tetrahydrofuran, is added dropwise at 0° C. under argon 0.614 ml (3.07 mmol) of diisopropyldiazene-1,2-dicarboxylate. The reaction mixture is stirred at room temperature for 20 h. The solid is filtered then rinsed in dichloromethane. The filtrate is concentrated and diluted in a sodium hydroxide solution (1M) and the product is extracted several times with ethyl acetate. The organic phases are combined, dried over magnesium sulfate, and concentrated. The residue is purified by chromatography on silica (cyclohexane/ethyl acetate eluent: 4:6 to 100% ethyl acetate) to yield 0.58 g of tert-butyl 4-(3-(4-formylphenoxy)propyl)piperazine-1-carboxylate in the form of a colourless oil.

LCMS (ESI, m/z): (M+1) 348.9

$^1$H-NMR: $\delta_H$ pm 400 MHz, DMSO: 9.87 (1H, s, CHO), 7.86 (2H, d, $CH_{arom}$), 7.12 (2H, d, $CH_{arom}$), 4.13 (2H, t, $CH_2$), 3.28-3.31 (4H, m, $2CH_2$), 2.44 (2H, t, $CH_2$), 2.31-2.34 (4H, m, $2CH_2$), 1.91 (2H, q, $CH_2$), 1.40 (9H, s, $3CH_3$).

The compounds below are obtained with procedure B1:

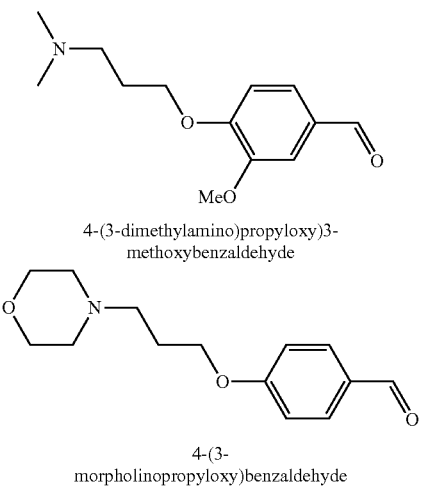

4-(3-dimethylamino)propyloxy)3-methoxybenzaldehyde 4-(3-morpholinopropyloxy)benzaldehyde General Procedure B2

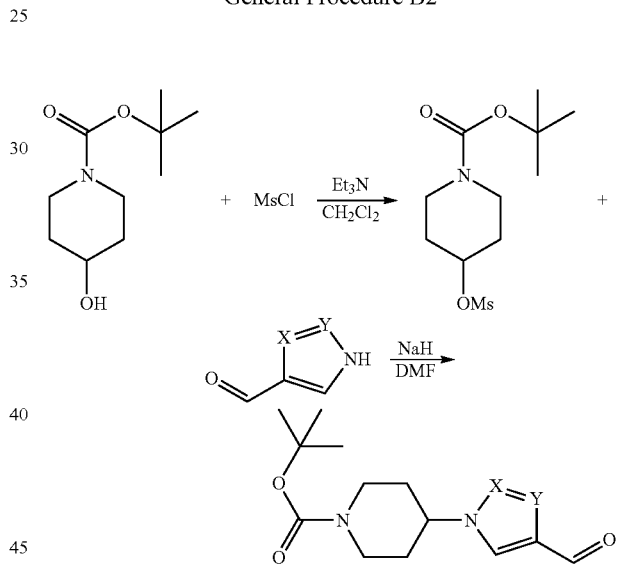

Examples of Synthesis Following Procedure B2 in 2 Steps

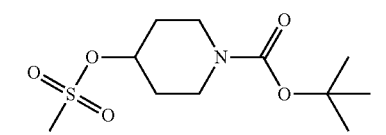

tert-butyl 4-(methylsulfonyloxy)piperidine-1-carboxylate

To 1 g (4.97 mmol) of tert-butyl 4-hydroxypiperidine-1-carboxylate diluted in 12.5 ml of anhydrous dichloro-methane are added dropwise at 0° C. 718 µl, of triethylamine (4.97 mmol), then 385 µL (4.97 mmol) methanesulfonyl chloride and finally 6 mg (49.6 µmol) of 4-dimethylamino-pyridine (DMAP). The solution is stirred at room temperature for 20 h, then water is added and the product is extracted several times with dichloromethane. The organic phases are combined, dried over magnesium sulfate, and concentrated to yield 1.39 g of tert-butyl 4-(methylsulfonyloxy)piperidine-1-carboxylate in the form of white solid.

$^1$H-NMR: $\delta_H$ pm 400 MHz, CDCl$_3$: 4.89-4.94 (1H, m, CH), 3.71-3.76 (2H, m, CH$_2$), 3.31-3.37 (2H, m, CH$_2$), 3.07-3.08 (3H, m, CH$_3$), 1.95-2.04 (2H, m, CH$_2$), 1.81-1.89 (2H, m, CH$_2$), 1.50 (9H, s, 3CH$_3$).

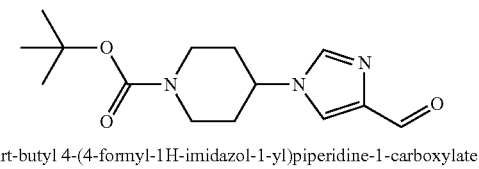

tert-butyl 4-(4-formyl-1H-imidazol-1-yl)piperidine-1-carboxylate

To 137 mg of imidazole-4-carboxaldehyde diluted in 2 ml of anhydrous dimethylformamide under argon are added portionwise at 0° C. 63 mg of sodium hydride (60% in mineral oil). The reaction mixture is stirred for 45 min at 0° C. then 400 mg of tert-butyl 4-(methylsulfonyloxy)piperidine-1-carboxylate are added portionwise, and the solution is brought to 100° C. for 15 h. Water is added and the product is extracted several times with ethyl acetate. The organic phases are combined, washed with sodium chloride saturated aqueous solution, dried over magnesium sulfate, and concentrated. The residue is purified by chromatography on silica (cyclohexane/ethyl acetate eluent: 2:8 to 100% ethyl acetate) to yield 92 mg of tert-butyl 4-(4-formyl-1H-imidazol-1-yl)piperidine-1-carboxylate in the form of a colourless oil.

LCMS (ESI, m/z): (M+1) 280.4

$^1$H-NMR: $\delta_H$ pm 400 MHz, CDCl$_3$: 9.90 (1H, s, CHO), 7.70 (1H, d, CH$_{arom}$), 7.66 (1H, d, CH$_{arom}$), 4.28-4.39 (2H, m, CH$_2$), 4.12-4.20 (1H, m, CH), 2.85-2.92 (2H, m, CH$_2$), 2.11-2.15 (2H, m, CH$_2$), 1.81-1.92 (2H, m, CH$_2$), 1.50 (9H, s, 3CH$_3$).

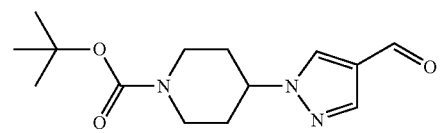

tert-butyl 4-(4-formyl-1H-pyrazol-1-yl)piperidine-1-carboxylate

LCMS (ESI, m/z): (M+1) 224.3 (-tBu)

$^1$H-NMR: $\delta_H$ pm 400 MHz, CDCl$_3$: 9.88 (1H, s, CHO), 8.00 (1H, s, CH$_{arom}$), 7.99 (1H, s, CH$_{arom}$), 4.23-4.36 (3H, m, CH, CH$_2$), 2.85-2.97 (2H, m, CH$_2$), 2.16-2.20 (2H, m, CH$_2$), 1.88-1.98 (2H, m, CH$_2$), 1.49 (9H, s, 3CH$_3$).

Special Procedure B3

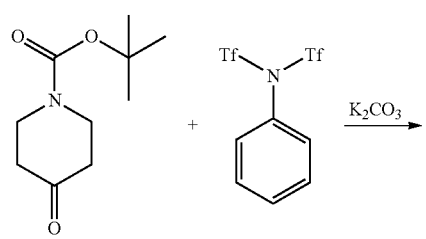

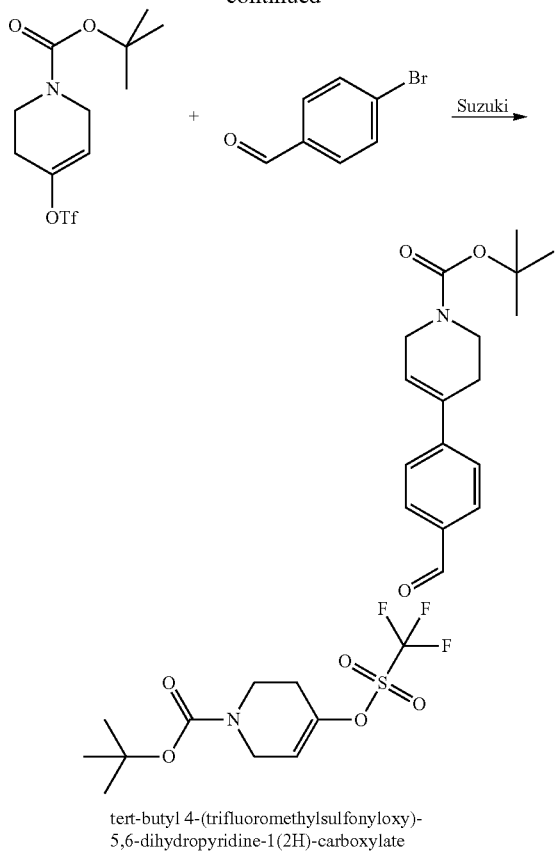

tert-butyl 4-(trifluoromethylsulfonyloxy)-5,6-dihydropyridine-1(2H)-carboxylate

To 3 ml (2M, 6.02 mmol) of lithium diisopropylamide diluted in 20 ml of anhydrous tetrahydrofuran is added dropwise at −78° C. under an inert atmosphere 1 g (5.02 mmol) of tert-butyl 4-oxopiperidine-1-carboxylate. The solution is stirred 10 min at −78° C., then 1.97 g (5.52 mmol) of 1,1,1-trifluoro-N-phenyl-N-(trifluoromethylsulfonyl)-methanesulfonamide diluted in 5 ml of anhydrous tetrahydrofuran are added dropwise at −78° C. The solution is stirred for 1 h at −78° C., for 4 h at room temperature, then trapped with a potassium carbonate saturated solution. The product is extracted several times with diethyl ether. The organic phases are combined, washed with 1M sodium hydroxide solution, with water, dried over magnesium sulfate, and concentrated. The residue is purified by chromatography on silica (cyclohexane/ethyl acetate eluent: 8:2) to yield 0.63 g of tert-butyl 4-(trifluoromethylsulfonyloxy)-5,6-dihydropyridine-1(2H)-carboxylate in the form of a yellow oil.

$^1$H-NMR: $\delta_H$ pm 400 MHz, DMSO: 6.01-6.04 (1H, m, CH), 3.98-4.00 (2H, m, CH$_2$), 3.55 (2H, t, CH$_2$), 2.40-2.43 (2H, m, CH$_2$), 1.42 (9H, s, 3CH$_3$).

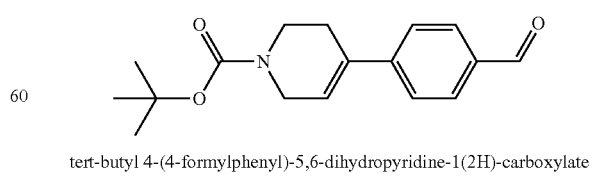

tert-butyl 4-(4-formylphenyl)-5,6-dihydropyridine-1(2H)-carboxylate

To 400 mg (2.67 mmol) of 4-formyl-phenylboronic acid diluted in a dimethoxyethane/water mixture (40 ml/4 ml) are respectively added 1.33 g (5.78 mmol) of tert-butyl 4-(trifluoromethylsulfonyloxy)-5,6-dihydropyridine-1(2H)-carboxylate, 154 mg (0.133 mmol) of palladium tetrakistriphenylphosphine and 1.74 g (5.34 mmol) of cesium carbonate. The solution is purged under argon then stirred at 80° C. for 18 h and filtered on Celite with ethyl acetate. The filtrate is washed with water, then with sodium chloride saturated solution, dried over magnesium sulfate, and concentrated. The residue is purified by chromatography on silica (cyclohexane/ethyl acetate eluent: 85:15 to 70:30) to yield 677 mg of tert-butyl 4-(4-formylphenyl)-5,6-dihydropyridine-1(2H)-carboxylate in the form of a yellow oil.

$^1$H-NMR: $\delta_H$ pm 400 MHz, DMSO: 9.99 (1H, s, CHO), 7.89 (2H, d, CH$_{arom}$), 7.67 (2H, d, CH$_{arom}$), 6.38-6.41 (1H, m, CH), 4.03-4.06 (2H, m, CH$_2$), 3.56 (2H, t, CH$_2$), 2.52-2.54 (2H, m, CH$_2$), 1.44 (9H, s, 3CH$_3$).

General Procedure B4

(Procedure described by Peter Magdolen et al, Tetrahedron, 2001, 57, 4781-5).

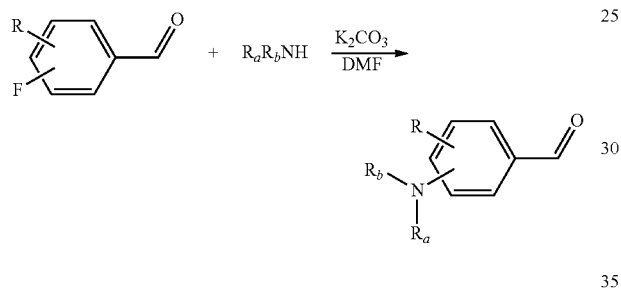

Example of Synthesis Following Procedure B4

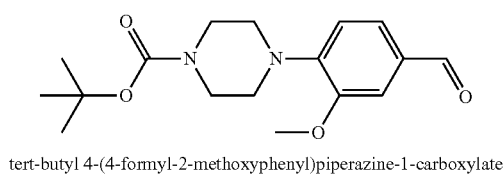 [SMILES: COc1cc(C=O)ccc1N1CCN(C(=O)OC(C)(C)C)CC1]

tert-butyl 4-(4-formyl-2-methoxyphenyl)piperazine-1-carboxylate

To 400 mg (2.60 mmol) of 4-fluoro-3-methoxybenzaldehyde diluted in 10 ml of dimethylsulfoxide are respectively added 483 mg (2.60 mmol) of tert-butyl piperazine-1-carboxylate, then 394 mg (2.85 mmol) of potassium carbonate. The solution is heated to 90° C. for 40 h, then water is added and the product is extracted several times with ethyl acetate. The organic phases are combined, dried over magnesium sulfate, and concentrated. The residue obtained is purified by chromatography on silica (cyclohexane/ethyl acetate eluent: 8:2) to yield 425 mg of tert-butyl 4-(4-formyl-2-methoxyphenyl)piperazine-1-carboxylate in the form of a colourless oil.

LCMS (ESI, m/z): (M+1) 321.1

$^1$H-NMR: $\delta_H$ pm 400 MHz, DMSO: 9.84 (1H, s, CHO), 7.50 (1H, dd, CH$_{arom}$), 7.38 (1H, d, CH$_{arom}$), 7.05 (1H, d, CH$_{arom}$), 3.87 (3H, s, CH$_3$), 3.45-3.48 (4H, m, 2CH$_2$), 3.08-3.11 (4H, m, 2CH$_2$), 1.43 (9H, s, 3CH$_3$).

The following compounds are obtained with procedure B4:

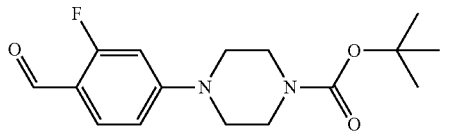

tert-butyl 4-(3-fluoro-4-formylphenyl)piperazine-1-carboxylate

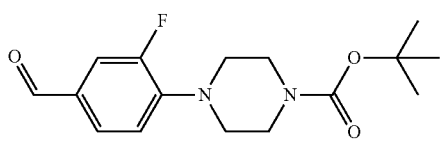

tert-butyl 4-(2-fluoro-4-formylphenyl)piperazine-1-carboxylate

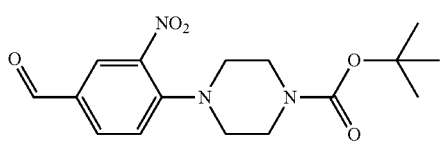

tert-butyl 4-(2-nitro-4-formylphenyl)piperazine-1-carboxylate

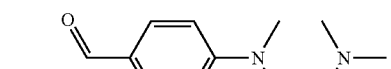

4-((2-(dimethylamino)ethyl)(methyl)amino)benzaldehyde

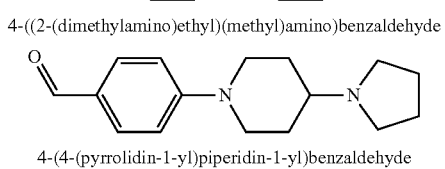

4-(4-(pyrrolidin-1-yl)piperidin-1-yl)benzaldehyde

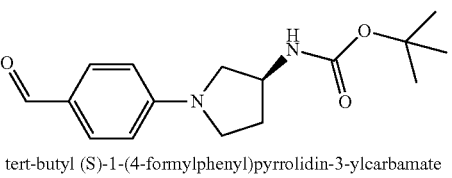

tert-butyl (S)-1-(4-formylphenyl)pyrrolidin-3-ylcarbamate

General Procedure B5

(By analogy with Prim, D. and Kirrsch, G., Tetrahedron, 1999, 55, 1405-1413).

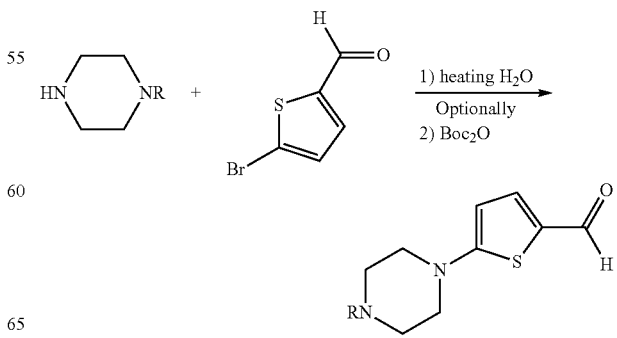

Example of Synthesis Following Procedure B5

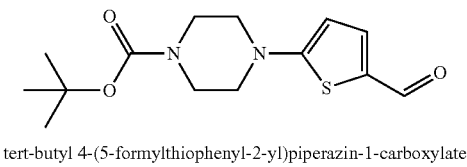 [SMILES: CC(C)(C)OC(=O)N1CCN(c2ccc(C=O)s2)CC1]

tert-butyl 4-(5-formylthiophenyl-2-yl)piperazin-1-carboxylate

A suspension of 1.09 g (5.7 mmol) of 5-bromothiophene-2-carboxaldehyde and 3.19 g (17.1 mmol) of tert-butyl piperazine-1-carboxylate in 30 ml of water is heated under reflux for 48 h. The aqueous phase is extracted three times with methylene chloride. The organic phases are combined, dried over sodium sulfate, filtered, and evaporated. The residue is purified by chromatography on silica (MeOH gradient in dichloromethane: 5 to 10%) to yield 0.80 g (70%) of 5-(piperazin-1-yl)thiophene-2-carboxaldehyde in the form of a blue-grey solid.

To a solution of 0.80 g (4.08 mmol) of 5-(piperazin-1-yl)thiophene-2-carboxaldehyde in ethanol (45 ml) is added 0.71 g (4.08 mmol) of Boc$_2$O. The mixture is stirred at room temperature for 24 h. Next, the mixture is evaporated, dissolved in 100 ml of water, and the aqueous phase is extracted three times with ethyl acetate. The organic phases are combined, washed with sodium chloride saturated solution, dried over sodium sulfate, filtered, and evaporated to yield 1.21 g (100%) of tert-butyl 4-(5-formylthiophen-2-yl)piperazine-1-carboxylate.

$^1$H-NMR: $\delta_H$ pm 400 MHz, DMSO: 9.51 (1H, s, CHO), 7.73 (1H, d, CH$_{arom}$), 6.38 (1H, d, CH$_{arom}$), 3.49-3.47 (4H, m, CH$_2$), 3.36-3.34 (4H, m, CH$_2$), 1.40 (9H, s, t-Bu).

The compound below was also obtained with procedure B5:

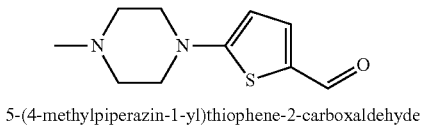

5-(4-methylpiperazin-1-yl)thiophene-2-carboxaldehyde

Particular Procedure B6

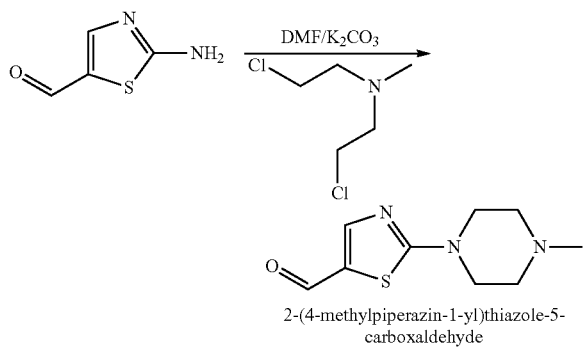

2-(4-methylpiperazin-1-yl)thiazole-5-carboxaldehyde

In a 25 ml flask are added 0.5 g of 2-aminothiazole-5-carboxaldehyde, 1.35 g of K$_2$CO$_3$ in 5 ml of DMF. After dissolution, 0.901 g of 2-chloro-N-(2-chloroethyl)-N-methylethanamine hydrochloride are added. The mixture is left at room temperature for 1 h then heated to 90° C. for 5 h. Next, the mixture is evaporated, dissolved in 100 ml of water, and the aqueous phase is extracted three times with ethyl acetate. The organic phases are combined, washed with sodium chloride saturated solution, dried over sodium sulfate, filtered, and evaporated to yield 420 mg (50%) of 2-(4-methylpiperazin-1-yl)thiazole-5-carboxaldehyde.

$^1$H-NMR: $\delta_H$ pm 400 MHz, DMSO: 9.70 (1H, s), 8.13 (1H, s), 3.60 (4H, m), 2.43 (4H, m), 2.24 (3H, s).

General Procedure B7

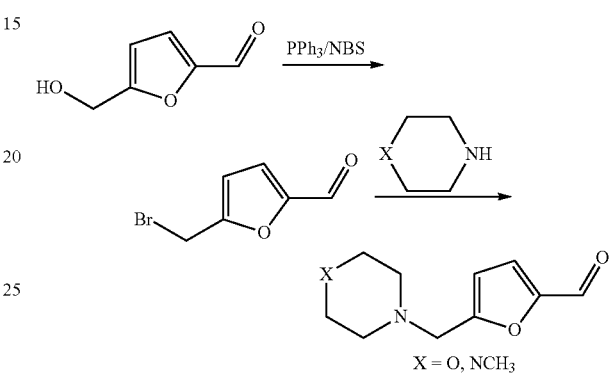

X = O, NCH$_3$

Example of Synthesis Following Procedure B7

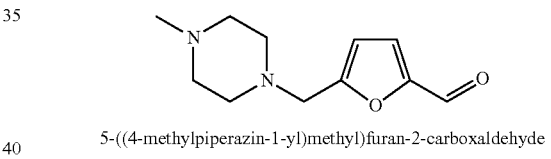

5-((4-methylpiperazin-1-yl)methyl)furan-2-carboxaldehyde

To a solution of 3.4 g (26.7 mmol) of 5-(hydroxymethyl)furan-2-carboxaldehyde and 7.78 g (29.4 mmol) of triphenylphosphine in 300 ml of dichloromethane at −5° C. are added 5.28 g (29.4 mmol) of N-bromosuccinimide in 10 min. The mixture is stirred at −5° C. for 30 min. The mixture is then concentrated and the residue is purified by chromatography on silica (cyclohexane/AcOet: 7:3) to yield 4.38 g (87%) of 5-(bromomethyl)furan-2-carboxaldehyde in the form of a brown solid.

To a solution of 0.20 g (1.1 mmol) of 5-(bromomethyl)furan-2-carboxaldehyde in anhydrous dioxane (10 ml) are added 261 µL (0.24 g, 2.3 mmol) of 1-methylpiperazine. The mixture is stirred at room temperature for 30 min. The precipitate formed is filtered and rinsed with dioxane. The filtrate is concentrated, dissolved in dichloromethane, and washed in water. The organic phase is dried over magnesium sulfate, filtered, and concentrated. The residue obtained is purified by chromatography on silica (eluent: 7N NH$_4$OH in MeOH/CH$_2$Cl$_2$, 5:95) to yield 0.12 g (55%) of 5-((4-methylpiperazine-1-yl)methyl)furan-2-carboxaldehyde in the form of an orange solid.

$^1$H-NMR: $\delta_H$ pm 400 MHz, CDCl$_3$: 9.57 (1H, d, CHO), 7.19 (1H, d, CH$_{arom}$), 6.44 (1H, d, CH$_{arom}$), 3.64 (2H, s, NCH$_2$), 2.54 (4H, m, 2NCH$_2$), 2.45 (4H, d, 2NCH$_2$), 2.26 (3H, s, NCH$_3$).

The compound below is also obtained with procedure B7:

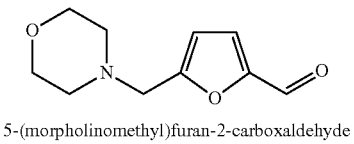 [SMILES: O=Cc1ccc(CN2CCOCC2)o1]

5-(morpholinomethyl)furan-2-carboxaldehyde

C) Synthesis of the Formula (IV) Amino-pyrazoles

The starting formula (IV) aminopyrazoles are products well known to the person skilled in the art and can be prepared using various methods described in the literature. Below, a description is given of aminopyrazoles and their methods of preparation which are not described in the literature and are used in the present invention.

General Procedure C1

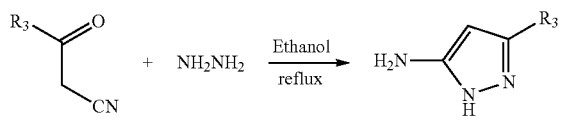

Example of Synthesis Following Procedure C1

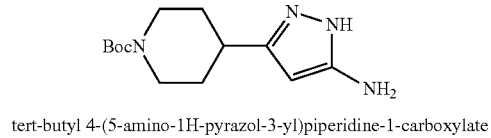 [SMILES: CC(C)(C)OC(=O)N1CCC(c2cc(N)[nH]n2)CC1]

tert-butyl 4-(5-amino-1H-pyrazol-3-yl)piperidine-1-carboxylate

To 1 g (3.96 mmol) of tert-butyl 4-(2-cyanoacetyl)piperidine-1-carboxylate obtained following procedure A2 diluted in 10 ml of ethanol, are added 992 mg (19.82 mmol) of hydrazine hydrate. The solution is refluxed for 3 h, and the solvent is concentrated to yield 1 g of tert-butyl 4-(5-amino-1H-pyrazol-3-yl)piperidine-1-carboxylate.

$^1$H-NMR: $\delta_H$ pm 400 MHz, CDCl$_3$: 5.47 (1H, s, CH$_{arom}$), 4.12-4.23 (2H, m, CH$_2$), 3.19 (2H, sl, NH$_2$), 2.78-2.86 (2H, m, CH$_2$), 2.68-2.75 (1H, m, CH), 1.89-1.94 (2H, m, CH$_2$), 1.53-1.64 (2H, m, CH$_2$), 1.49 (9H, s, 3CH$_3$).

The compounds below can also be obtained following procedure C1:

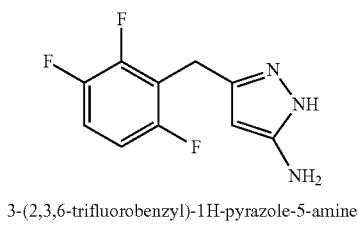

3-(2,3,6-trifluorobenzyl)-1H-pyrazole-5-amine

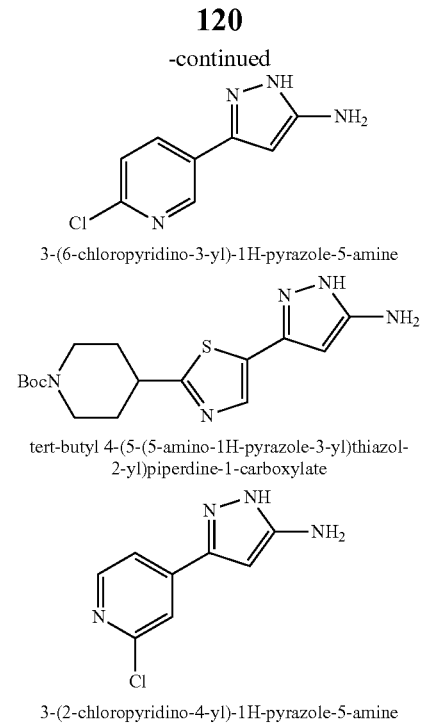

3-(6-chloropyridino-3-yl)-1H-pyrazole-5-amine tert-butyl 4-(5-(5-amino-1H-pyrazole-3-yl)thiazol-2-yl)piperdine-1-carboxylate 3-(2-chloropyridino-4-yl)-1H-pyrazole-5-amine 3-(5-methylisoxazo-3-yl)-1H-pyrazole-5-amine

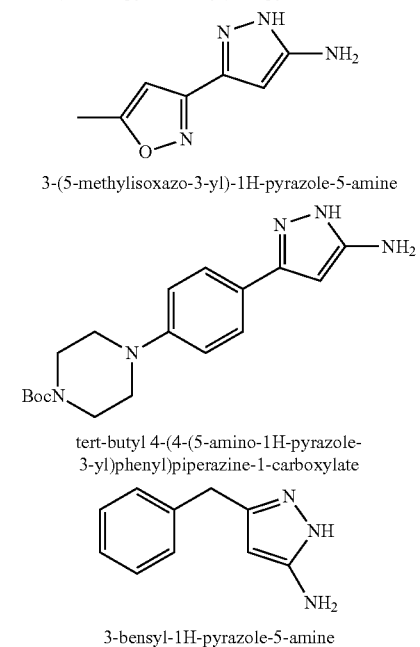

tert-butyl 4-(4-(5-amino-1H-pyrazole-3-yl)phenyl)piperazine-1-carboxylate 3-bensyl-1H-pyrazole-5-amine General Procedure C2

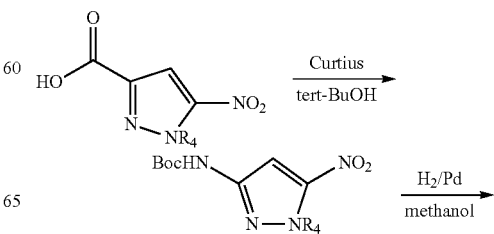

-continued

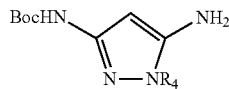

Example of Synthesis Using Procedure C2 in 2 Steps

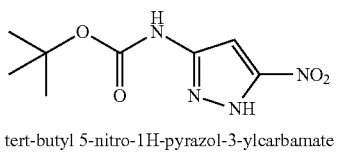 [SMILES: CC(C)(C)OC(=O)Nc1cc([N+](=O)[O-])[nH]n1]

tert-butyl 5-nitro-1H-pyrazol-3-ylcarbamate

To 10 g (63.66 mmol) of 5-nitro-1H-pyrazole-3-carboxylic acid are respectively added 39 ml of tert-butanol, 27.44 ml (127.3 mmol) of diphenylphosphorazidate and 17.7 ml (127.32 mmol) of triethylamine. The solution is refluxed for 8 h, then an aqueous solution saturated with potassium carbonate is added until reaching pH 8, and the product is extracted several times with ethyl acetate. The organic phases are combined, dried over magnesium sulfate, and concentrated. The residue obtained is triturated in methanol to give 4.38 g of tert-butyl 5-nitro-1H-pyrazol-3-ylcarbamate in the form of a yellow solid. The filtrate is concentrated and purified by chromatography on silica (cyclohexane/ethyl acetate eluent: 7:3) to yield an additional 1.49 g of tert-butyl 5-nitro-1H-pyrazol-3-ylcarbamate in the form of a yellow solid.

LCMS (ESI, m/z): (M−1) 227.2

$^1$H-NMR: $\delta_H$ pm 400 MHz, DMSO: 13.47 (1H, sl, NH), 10.35 (1H, sl, NH), 6.46 (1H, s, $CH_{arom}$), 1.49 (9H, s, $3CH_3$).

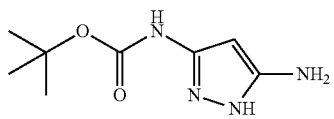

tert-butyl 5-amino-1H-pyrazol-3-ylcarbamate

To 5.88 g (25.77 mmol) of tert-butyl 5-nitro-1H-pyrazol-3-ylcarbamate diluted in 145 ml of methanol, are added under inert atmosphere 600 mg of palladium on charcoal (10%), then the reaction mixture is stirred under hydrogen atmosphere for 24 h. The solution is filtered on Celite and rinsed with ethyl acetate. The filtrate is concentrated to yield 4.93 g of tert-butyl 5-amino-1H-pyrazol-3-ylcarbamate in the form of a grey solid.

LCMS (ESI, m/z): (M+1) 199.2

$^1$H-NMR: $\delta_H$ pm 400 MHz, DMSO: 10.70 (1H, sl, NH), 9.12 (1H, sl, NH), 5.32 (1H, s, $CH_{arom}$), 4.82 (2H, sl, $NH_2$), 1.42 (9H, s, $3CH_3$).

General Procedure C3

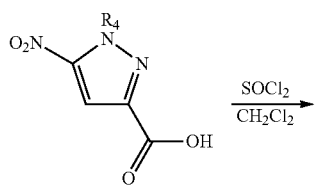

-continued

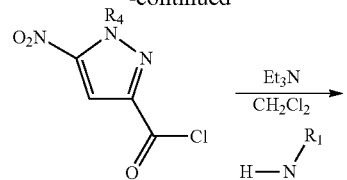

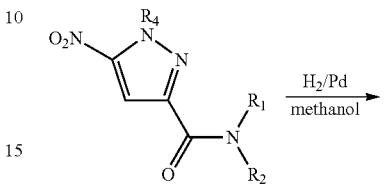

Example of Synthesis Following Procedure C3

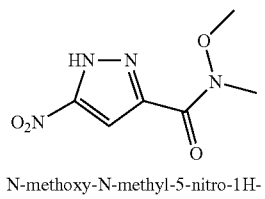

N-methoxy-N-methyl-5-nitro-1H-pyrazol-3-carboxamide

To 20.4 g (130.31 mmol) of 5-nitro-1H-pyrazole-3-carboxylic acid in suspension in 530 ml of 1,2-dichloroethane, are respectively added 28.36 ml (390.93 mmol) of thionyl chloride and 4 ml of dimethylformamide. The suspension is stirred under reflux for 8 h. The reaction mixture is then cooled to room temperature and the precipitate is filtered. The precipitate is re-suspended in 330 ml of dichloromethane after which are successively added 15.25 g (156.37 mmol) of N,O-dimethylhydroxylamine hydrochloride and 39.56 g (390.93 mmol) of triethylamine. The reaction mixture is stirred for 18 h at room temperature, water is added and the product is extracted several times with dichloromethane then with a dichloromethane/methanol mixture (90:10). The organic phases are combined, dried over magnesium sulfate and concentrated to yield 23.88 g of N-methoxy-N-methyl-5-nitro-1H-pyrazol-3-carboxamide in the form of a white solid.

LCMS (ESI, m/z): (M+1) 201.1

$^1$H-NMR: $\delta_H$ pm 400 MHz, DMSO: 14.72 (1H, sl, NH), 7.33 (1H, s, $CH_{arom}$), 3.77 (3H, s, $CH_3$), 3.27 (3H, s, $CH_3$).

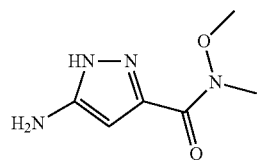

5-amino-N-methoxy-N-methyl-1H-pyrazol-3-carboxamide 6.40 g (32.00 mmol) of N-methoxy-N-methyl-5-nitro-1H-pyrazole-3-carboxamide are dissolved in 500 ml of tetrahydrofuran/methanol mixture (50:50). The solution is purged under argon and 220 mg of palladium on charcoal (10%) are added. The solution is then degassed with hydrogen and stirred under a hydrogen atmosphere for 18 h. After degassing with argon, the solution is filtered on Celite and the solvent is concentrated to yield 5.2 g of 5-amino-N-methoxy-N-methyl-1H-pyrazole-3-carboxamide in the form of a white solid.

LCMS (ESI, m/z): (M+1) 171.07

$^1$H-NMR: $\delta_H$ pm 400 MHz, DMSO: 12.22 (1H, sl, NH), 5.96 (1H, sl, $CH_{arom}$), 4.72 (2H, sl, $NH_2$), 3.37 (3H, s, $CH_3$), 3.31 (3H, s, $CH_3$).

The compounds below are also obtained with procedure C3:

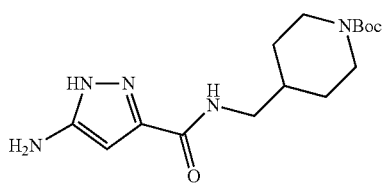

tert-butyl 4-((5-amino-1H-pyrazol-3-carboxamido)methyl)piperidine-1-caroxylate

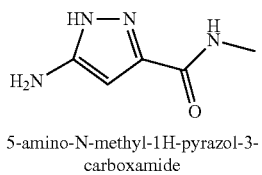

5-amino-N-methyl-1H-pyrazol-3-carboxamide

General Procedure C4

(Method described by V. G. Nenaidenko et al, Russian Journal of Organic Chemistry, 2004, 40(10), 1518-20).

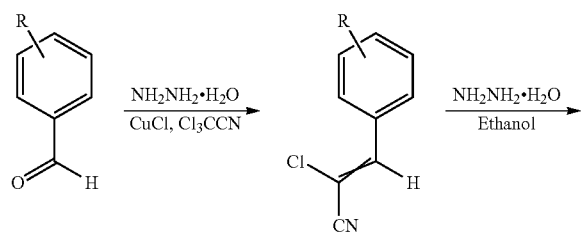

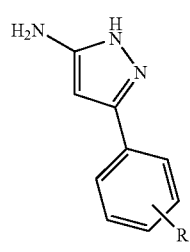

Example of Synthesis Following Procedure C4

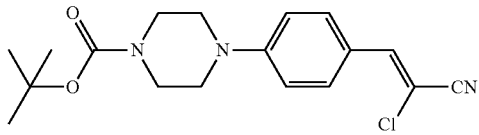

tert-butyl 4-(4-(2-chloro-2-cyanovinyl)phenyl)piperzine-1-carboxylate

To a solution of hydrazine hydrate diluted in 16 ml of dimethylsulfoxide under argon are added dropwise a solution of 4.76 g (16.41 mmol) of tert-butyl 4-(4-formylphenyl)piperazine-1-carboxylate dissolved in 32 ml of dimethylsulfoxide. The reaction mixture is stirred at room temperature for 3 h before being cooled over an ice bath. Then, the successive addition is made of 11.45 ml (82 mmol) of triethylamine, 162 mg of copper (I) chloride and, in 5 min, a solution of 8.23 ml (82 mmol) of trichloroacetonitrile diluted in 16 ml of dimethylsulfoxide. The reaction mixture is stirred at room temperature for 18 h then poured onto an aqueous 0.1N hydrochloric acid solution. The product is extracted several times with dichloromethane. The organic phases are combined, dried over magnesium sulfate, and concentrated. The residue is purified by chromatography on silica (cyclohexane/ethyl acetate eluent: 8:2) to yield 1.52 g (26%) of tert-butyl 4-(4-(2-chloro-2-cyanovinyl)phenyl)piperazine-1-carboxylate in the form of a yellow solid (mixture of the two isomers Z/E).

$^1$H-NMR: $\delta_H$ pm 400 MHz, $CDCl_3$: 7.70 (2H, d, $CH_{arom}$), 7.18 (1H, s, $CH_{arom}$), 6.87 (2H, d, $CH_{arom}$), 3.51-3.45 (4H, m, 2×$CH_2$), 3.35-3.25 (4H, m, 2×$CH_2$), 1.49 (9H, s $C(CH_3)_3$). (33%) 7.62 (2H, d, $CH_{arom}$), 7.21 (1H, s, $CH_{arom}$), 6.87 (2H, d, $CH_{arom}$), 3.51-3.45 (4H, m, 2×$CH_2$), 3.35-3.25 (4H, m, 2×$CH_2$), 1.49 (9H, s, $C(CH_3)_3$). (66%).

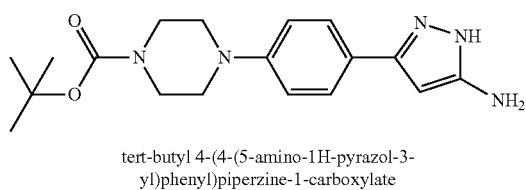 [SMILES: CC(C)(C)OC(=O)N1CCN(c2ccc(-c3cc(N)[nH]n3)cc2)CC1]

tert-butyl 4-(4-(5-amino-1H-pyrazol-3-yl)phenyl)piperzine-1-carboxylate

To 1.52 g (4.37 mmol) of tert-butyl 4-(4-(2-chloro-2-cyanovinyl)phenyl)piperazine-1-carboxylate diluted in 20 ml of ethanol are added 1.06 ml (17.48 mmol) of hydrazine hydrate. The solution is refluxed for 5 h, 20 ml of water are added and the solid is filtered, vacuum dried to yield 1.16 g of tert-butyl 4-(4-(5-amino-1H-pyrazol-3-yl)phenyl)piperazine-1-carboxylate.

$^1$H-NMR: $\delta_H$ pm 400 MHz, DMSO: 11.68 (1H, sl, NH), 7.49 (2H, d, $CH_{arom}$), 6.94 (2H, d, $CH_{arom}$), 5.65 (1H, sl, $CH_{arom}$), 4.62 (2H, sl, $NH_2$), 3.49-3.41 (4H, m, 2×$CH_2$), 3.16-3.07 (4H, m, 2×$CH_2$), 1.42 (9H, s, $C(CH_3)_3$).

The compound below is also obtained with procedure C4:

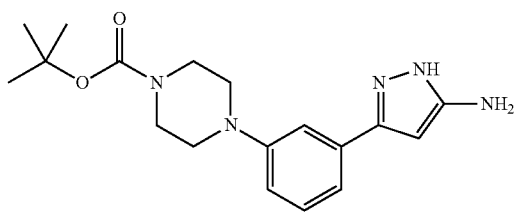

tert-butyl 4-(3-(5-amino-1H-pyrazol-3-yl)phenyl)piperzine-1-carboxylate

D) Synthesis of Formula (I) Pyrazolopyridines (PZPs)

a) Condensation Reaction Between Compounds (II), (III) and (Iv) Followed by Oxidation General Procedure D1

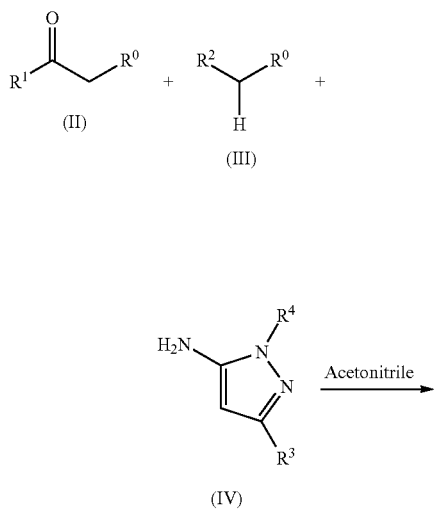

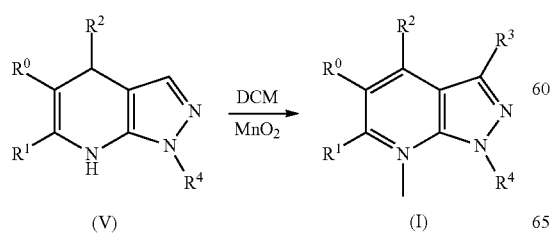

Examples of Synthesis Following Procedure D1

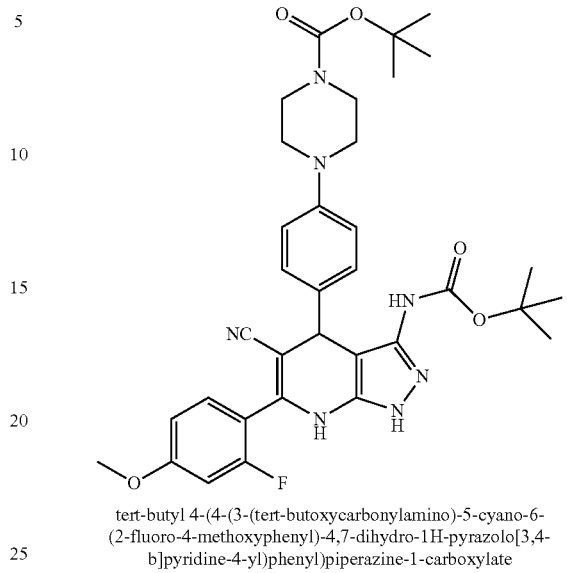

tert-butyl 4-(4-(3-(tert-butoxycarbonylamino)-5-cyano-6-(2-fluoro-4-methoxyphenyl)-4,7-dihydro-1H-pyrazolo[3,4-b]pyridine-4-yl)phenyl)piperazine-1-carboxylate To a solution of 1 g (5.18 mmol) of methyl 2-fluoro-4-methoxybenzoate in 20 ml of acetonitrile are respectively added 1.62 g (5.18 mmol) of tert-butyl 4-(4-formylphenyl)piperazine-1-carboxylate and 1.11 g (5.18 mmol) of tert-butyl 5-amino-1H-pyrazol-3-ylcarbamate. The reaction mixture is refluxed for 8 h. The solution is brought to room temperature, then the solid is filtered and rinsed several times with acetonitrile to yield 2.22 g (66%) of tert-butyl 4-(4-(3-(tert-butoxycarbonylamino)-5-cyano-6-(2-fluoro-4-methoxyphenyl)-4,7-dihydro-1H-pyrazolo[3,4-b]pyridine-4-yl)phenyl)piperazine-1-carboxylate in the form of a yellow solid.

LCMS (ESI, m/z): (M+1) 646.4

$^1$H-NMR: $\delta_H$ pm 400 MHz, DMSO: 11.81 (1H, sl, NH), 9.81 (1H, sl, NH), 9.19 (1H, sl, NH), 7.39 (1H, t, CH$_{arom}$), 7.06 (2H, d, CH$_{arom}$), 6.95 (1H, dd, CH$_{arom}$), 6.86-6.90 (3H, m, CH$_{arom}$), 4.84 (1H, s, CH), 3.83 (3H, s, CH$_3$), 3.43-3.45 (4H, m, 2CH$_2$), 3.05-3.08 (4H, m, 2CH$_2$), 2.08 (18H, s, 6CH$_3$).

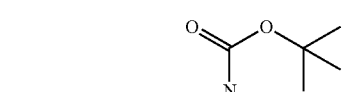

tert-butyl 4-(4-(3-(tert-butoxycarbonylamino)-5-cyano-6-(2-fluoro-4-methoxyphenyl]-1H-pyrazolo[3,4-b]pyridine-4-yl)phenyl)piperazine-1-carboxylate To 2.22 g (3.44 mmol) of tert-butyl 4-(4-(3(tert-butoxycarbonylamino)-5-cyano-6-(2-fluoro-4-methoxyphenyl)-4,7-dihydro-1H-pyrazolo[3,4-b]pyridin-4-yl)phenyl)piperazine-1-carboxylate in solution in 20 ml of dichloromethane are added 1.49 g (17.19 mmol) of manganese oxide. The reaction mixture is sonicated for 5 min then stirred at room temperature for 20 h. It is filtered on silica (cyclohexane/ethyl acetate eluent: 5:5) to yield 2.16 g (97%) of tert-butyl 4-(4-(3-(tert-butoxycarbonylamino)-5-cyano-6-(2-fluoro-4-methoxyphenyl)-1H-pyrazolo[3,4-b]pyridin-4-yl)phenyl)piperazine-1-carboxylate in the form of a yellow solid.

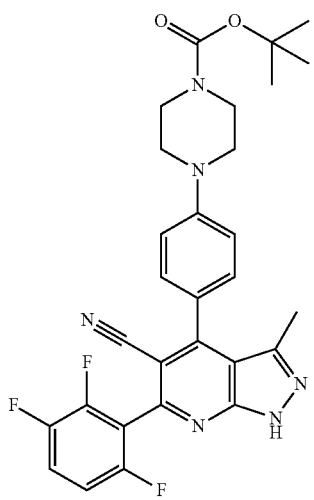

tert-butyl 4-(4-(5-cyano-3-methyl-6-(2,3,6-trifluorophenyl)-1H-pyrazolo[3,4-b]pyridine-4-yl)phenyl)piperazine-1-carboxylate To 2.48 g (4.50 mmol) of tert-butyl 4-(4-(5-cyano-3-methyl-6-(2,3,6-trifluorophenyl)-4,7-dihydro-1H-pyrazolo[3,4-b]pyridin-4-yl)phenyl)piperazine-1-carboxylate diluted in 20 ml of dichloromethane are added 1.96 g (22.5 mmol) of manganese oxide. The reaction mixture is sonicated for 5 min then stirred at room temperature for 18 h. It is next filtered on Celite (cyclohexane/ethyl acetate eluent: 5:5) to yield 1.86 g of tert-butyl 4-(4-(5-cyano-3-methyl-6-(2,3,6-trifluorophenyl)-1H-pyrazolo[3,4-b]pyridin-4-yl)phenyl)piperazine-1-carboxylate in the form of a light yellow solid.

LCMS (ESI, m/z): (M+1) 549.2

$^1$H-NMR: $\delta_H$ pm 400 MHz, DMSO: 14.14 (1H, sl, NH), 7.76-7.85 (1H, m, $CH_{arom}$), 7.54 (2H, d, $CH_{arom}$), 7.41-7.47 (1H, m, $CH_{arom}$), 7.15 (2H, d, $CH_{arom}$), 3.49-3.51 (4H, m, $2CH_2$), 3.30-3.33 (4H, m, $2CH_2$), 2.17 (3H, s, $CH_3$), 1.44 (9H, s, $3CH_3$).

The compounds below are also obtained following procedure D1:

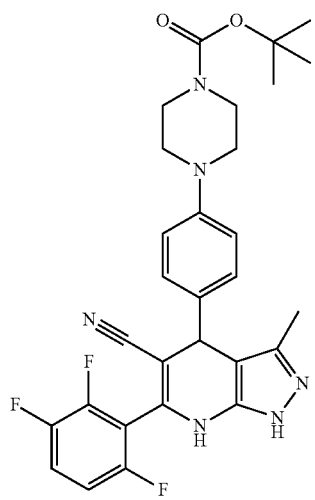

tert-butyl 4-(4-(5-cyano-3-methyl-6-(2,3,6-trifluorophenyl)-4,7-dihydro-1H-pyrazolo[3,4-b]pyridine-4-yl)phenyl)piperazine-1-carboxylate To 1.1 g (5.52 mmol) of 3-oxo-3-(2,3,6-trifluorophenyl)propanenitrile diluted in 20 ml of acetonitrile are respectively added 1.60 g (5.52 mmol) of tert-butyl 4-(4-formylphenyl)piperazine-1-carboxylate and 0.53 g (5.52 mmol) of 3-amino-5-methyl-pyrazole. The reaction mixture is refluxed for 4 h then the solvent is concentrated. The residue is purified by chromatography on silica (cyclohexane/ethyl acetate eluent: 5:5) then the solid obtained is triturated in ethyl acetate and dried to yield 2.48 g (81%) of tert-butyl 4-(4-(5-cyano-3-methyl-6-(2,3,6-trifluorophenyl)-4,7-dihydro-1H-pyrazolo[3,4-b]pyridin-4-yl)phenyl)piperazine-1-carboxylate in the form of a yellow solid.

LCMS (ESI, m/z): (M+1) 551.2

$^1$H-NMR: $\delta_H$ pm 400 MHz, DMSO: 11.98 (1H, sl, NH), 10.13 (1H, sl, NH), 7.67-7.75 (1H, m, $CH_{arom}$), 7.30-7.38 (1H, m, $CH_{arom}$), 7.13 (2H, d, $CH_{arom}$), 6.94 (2H, dd, $CH_{arom}$), 4.91 (1H, s, CH), 3.43-3.46 (4H, m, $2CH_2$), 3.08-3.11 (4H, m, $2CH_2$), 1.83 (3H, s, $CH_3$), 1.42 (9H, s, $3CH_3$).

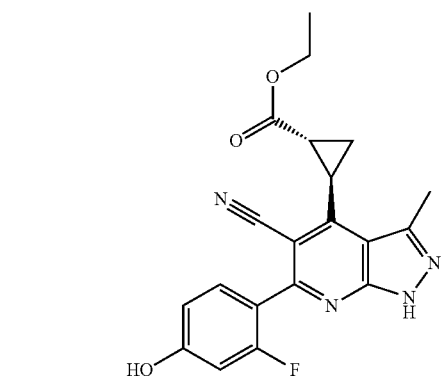

ethyl (1R-2R)-2-(5-cyano-6-(2-fluoro-4-hydroxyphenyl)-3-methyl-1H-pyrazolo[3,4-b]pyridine-4-yl)cyclopropanecarboxylate LCMS (ESI, m/z): (M+1) 381.1

$^1$H-NMR: $\delta_H$ pm 400 MHz, DMSO: 13.83 (1H, sl, NH), 10.42 (1H, sl, OH), 7.41 (1H, dd, $CH_{arom}$), 6.70-6.78 (2H, m, $CH_{arom}$), 4.12-4.24 (2H, m, $CH_2$), 3.07-3.12 (1H, m, CH), 2.66 (3H, s, $CH_3$), 2.29-2.34 (1H, m, $CH_{arom}$), 1.68-1.73 (2H, m, $CH_2$), 1.24 (3H, t, $CH_3$).

129

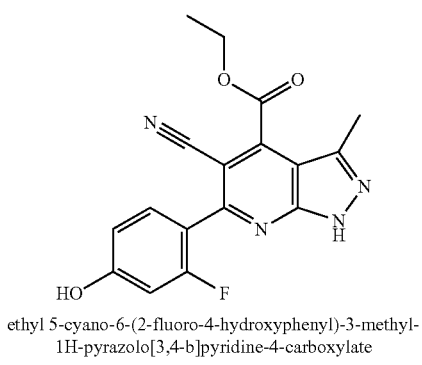 [SMILES: CCOC(=O)c1c(C#N)c(-c2ccc(O)cc2F)nc2[nH]nc(C)c12]

ethyl 5-cyano-6-(2-fluoro-4-hydroxyphenyl)-3-methyl-1H-pyrazolo[3,4-b]pyridine-4-carboxylate ¹H-NMR: δ_H pm 400 MHz, DMSO: 7.48 (1H, dd, CH_arom), 6.79 (1H, dd, CH_arom), 6.74 (1H, dd, CH_arom), 4.56 (2H, q, CH₂), 3.33 (3H, s, CH₃), 1.41 (3H, t, CH₃).

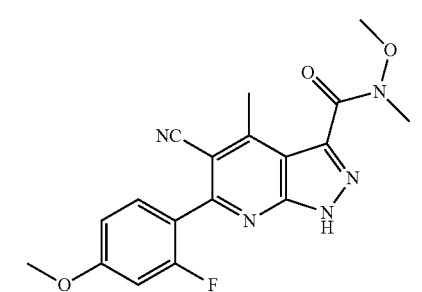

5-cyano-6(2-fluoro-4-methoxyphenyl)-N-methoxy-N-4-dimethyl-1H-pyrazolo[3,4-b]pyridine-3-carboxamide ¹H-NMR: δ_H pm 400 MHz, DMSO: 14.61 (1H, sl, NH), 7.60 (1H, dd, CH_arom), 7.07 (1H, dd, CH_arom), 6.99 (1H, dd, CH_arom), 3.88 (3H, s, CH₃), 3.39 (3H, s, CH₃), 3.33 (3H, s, CH₃), 2.79 (3H, s, CH₃).

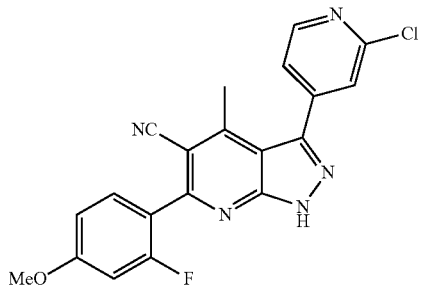

3-(2-chloropyridin-4-yl)-6-(4-methoxyphenyl)-4-methyl-1H-pyrazolo[3,4-b]pyridine-5-carbonitrile ¹H-NMR: δ_H pm 400 MHz, DMSO: 14.63 (1H, sl, NH), 8.59 (1H, d, CH_arom), 7.90-7.88 (1H, m, CH_arom), 7.85 (2H, d, CH_arom), 7.79 (1H, dd, CH_arom), 7.14 (2H, d, CH_arom), 3.87 (3H, s, CH₃), 2.72 (3H, s, CH₃).

130

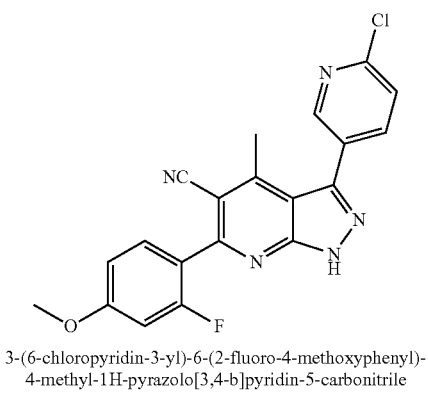 [SMILES: COc1ccc(-c2nc3[nH]nc(-c4ccc(Cl)nc4)c3c(C)c2C#N)c(F)c1]

3-(6-chloropyridin-3-yl)-6-(2-fluoro-4-methoxyphenyl)-4-methyl-1H-pyrazolo[3,4-b]pyridin-5-carbonitrile ¹H-NMR: δ_H pm 400 MHz, DMSO: 14.61 (1H, sl, NH), 8.76 (1H, d, CH_arom), 8.24 (1H, dd, CH_arom), 7.73 (1H, d, CH_arom), 7.59 (1H, t, CH_arom), 7.07 (1H, dd, CH_arom), 6.99 (1H, dd, CH_arom), 3.88 (3H, s, CH₃), 2.67 (3H, s, CH₃).

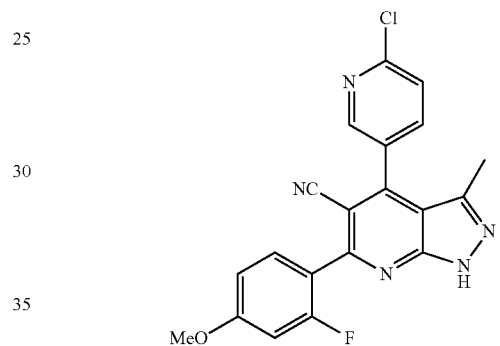

4-(6-chloropyridin-3-yl)-6-(2-fluoro-4-methoxyphenyl)-3-methyl-1H-pyrazolo[3,4-b]pyridine-5-carbonitrile ¹H-NMR: δ_H pm 400 MHz, DMSO: 14.13 (1H, sl, NH), 8.75 (1H, d, CH_arom), 8.25 (1H, dd, CH_arom), 7.83 (1H, d, CH_arom), 7.63 (1H, t, CH_arom), 7.06 (1H, dd, CH_arom), 6.99 (1H, dd, CH_arom), 3.87 (3H, s, CH₃), 2.08 (3H, s, CH₃).

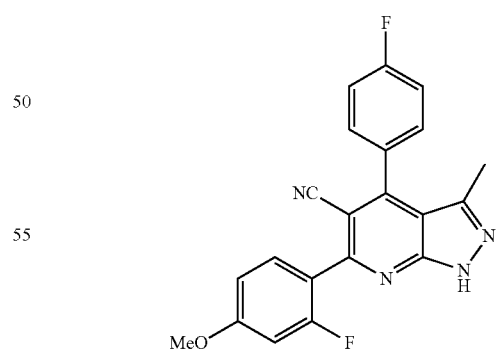

4-(4-fluorophenyl)-6-(methoxyphenyl)-3-methyl-1H-pyrazolo[3,4-b]pyridine-5-carbonitrile ¹H-NMR: δ_H pm 400 MHz, DMSO: 13.91 (1H, sl, NH), 7.87 (2H, d, CH_arom), 7.74-7.67 (2H, m, CH_arom), 7.46 (2H, m, CH_arom), 7.12 (2H, d, CH_arom), 3.85 (3H, s, CH₃), 2.00 (3H, s, CH₃).

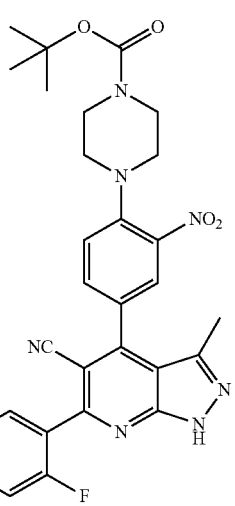

tert-butyl 4-(4-(5-cyano-6-(2-fluoro-4-hydroxyphenyl)-3-methyl-1H-pyrazolo[3,4-b]pyridine-4-yl)-2-nitrophenyl)piperazine-1-carboxylate $^1$H-NMR: $\delta_H$ pm 400 MHz, DMSO: 13.98 (1H, sl, NH), 10.46 (1H, sl, OH), 8.17 (1H, s, CH$_{arom}$), 7.87 (1H, d, CH$_{arom}$), 7.54-7.46 (2H, m, CH$_{arom}$), 6.79 (1H, d, CH$_{arom}$), 6.74 (1H, d, CH$_{arom}$), 3.53-3.43 (4H, m, 2×CH$_2$), 3.21-3.11 (4H, m, 2×CH$_2$), 2.12 (3H, s, CH$_3$), 1.43 (9H, s, 3×CH$_3$).

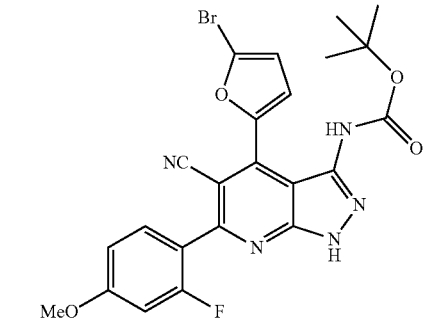

tert-butyl 4-(5-bromofuran-2-yl)-5-cyano-6-(2-fluoro-4-methoxyphenyl)-1H-pyrazolo[3,4-b]pyridine-3-ylcarbamate $^1$H-NMR: $\delta_H$ pm 400 MHz, DMSO: 14.12 (1H, sl, NH), 9.62 (1H, sl, NH), 7.63 (1H, t, CH$_{arom}$), 7.31 (1H, d, CH$_{arom}$), 7.08 (1H, dd, CH$_{arom}$), 6.99 (1H, dd, CH$_{arom}$), 6.95 (1H, d, CH$_{arom}$), 3.88 (3H, s, CH$_3$), 1.30 (9H, s, 3×CH$_3$).

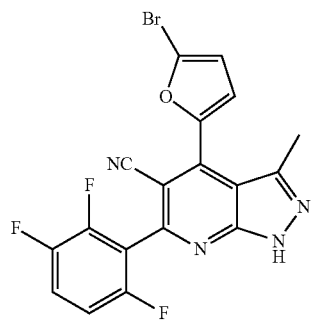

4-(5-bromofuran-2-yl)-3-methyl-6-(2,3,6-trifluorophenyl)-1H-pyrazolo[3,4-b]pyridine-5-carbonitrile $^1$H-NMR: $\delta_H$ pm 400 MHz, DMSO: 14.34 (1H, sl, NH), 7.90-7.74 (1H, m, CH$_{arom}$), 7.52 (1H, s, CH$_{arom}$), 7.51-7.39 (1H, m, CH$_{arom}$), 7.06 (1H, s, CH$_{arom}$), 2.54 (3H, s, CH$_3$).

General Procedure D2

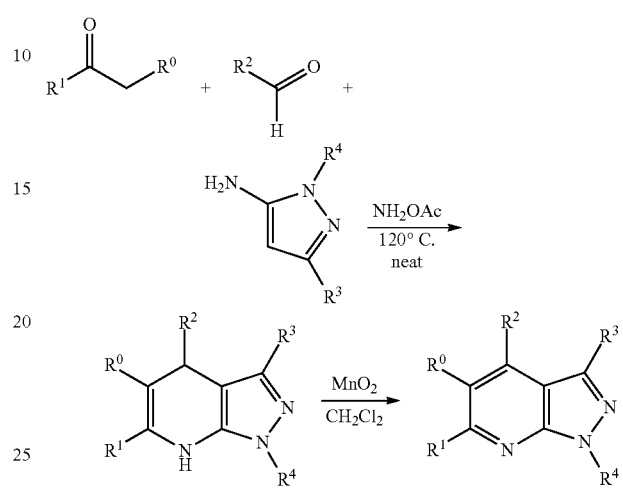

Example of Synthesis Following Procedure D2

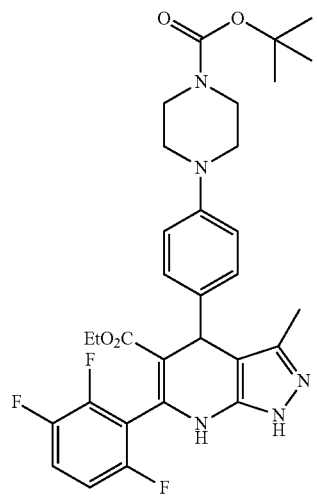

ethyl 4-(4-(4-(tert-butyloxycarbonyl)piperazin-1-yl)phenyl)-3-methyl-6-(2,3,6-trifluorophenyl)-4,7-dihydro-1H-pyrazolo[3,4-b]pyridine-5-carboxylate In a sealed tube are added 1.5 g (6.09 mmol) of ethyl 3-oxo-3-(2,3,6-trifluorophenyl)propanoate, 1.77 g (6.09 mmol) of tert-butyl 4-(4-formylphenyl)piperazine-1-carboxylate, 592 mg (6.09 mmol) of 3-amino-5-methylpyrazole and 1.17 g (15.23 mmol) of ammonium acetate. The mixture is brought to 120° C. neat (i.e. without solvent) for 1 h. The solution is brought to room temperature then the solid is dissolved in a water/ethyl acetate mixture. The phases are separated and the aqueous phase is extracted several times with ethyl acetate. The organic phases are combined, dried over magnesium sulfate, and concentrated. The residue is purified by chromatography on silica (cyclohexane/ethyl acetate eluent: 3:7) to yield 2.27 g (56%) of ethyl 4-(4-(4-(tert-butoxycarbonyl)piperazin-1-yl)phenyl-3-methyl-6-(2,3,6-trifluorophenyl)-4,7-dihydro-1H-pyrazolo[3,4-b]pyridine-5-carboxylate in the form of a light yellow powder which contains 1 eq. of ethyl acetate.

$^1$H-NMR: $\delta_H$ pm 400 MHz, DMSO: 11.77 (1H, sl, NH), 9.68 (1H, d, NH), 7.60-7.48 (1H, m, CH$_{arom}$), 7.22-7.14 (1H, m, CH$_{arom}$), 7.12 (2H, d, CH$_{arom}$), 6.85 (2H, dd, CH$_{arom}$), 5.04 (1H, d, CH), 3.75-3.51 (2H, m, CH$_2$), 3.48-3.39 (4H, m, 2×CH$_2$), 3.07-2.99 (4H, m, 2×CH$_2$), 1.95 (3H, d, CH$_3$), 1.42 (9H, s, 3×CH$_3$), 0.77 (3H, t, CH$_3$).

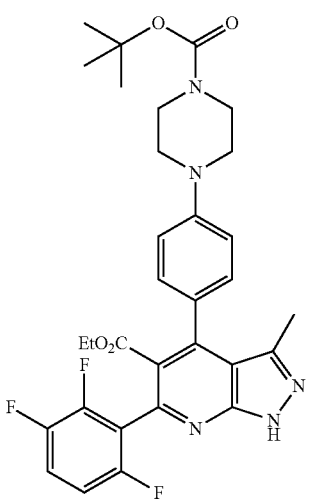

ethyl 4-(4-(4-(tert-butoxycarbonyl)piperazin-1-yl)phenyl)-3-methyl-6-(2,3,6-trifluorophenyl)-1H-pyrazolo[3,4-b]pyridine-5-carboxylate To 2.2 g (3.68 mmol) of ethyl 4-(4-(4-(tert-butoxycarbonyl)piperazin-1-yl)phenyl)-3-methyl-6-(2,3,6-trifluorophenyl)-4,7-dihydro-1H-pyrazolo[3,4-b]pyridine-5-carboxylate in solution in 50 ml of dichloromethane are added 1.6 g (18.41 mmol) of manganese oxide. The reaction mixture is sonicated for 5 min then stirred at room temperature for 20 h. It is filtered on silica (cyclohexane/ethyl acetate eluent: 6:4) to yield 2 g (91%) of ethyl 4-(4-(4-(tert-butoxycarbonyl)piperazin-1-yl)phenyl)-3-methyl-6-(2,3,6-trifluorophenyl)-1H-pyrazolo[3,4-b]pyridine-5-carboxylate in the form of a yellow solid.

LCMS (ESI, m/z): (M+1) 644.4

$^1$H-NMR: $\delta_H$ pm 400 MHz, DMSO: 13.74 (1H, sl, NH), 7.72-7.61 (1H, m, CH$_{arom}$), 7.34-7.24 (3H, m, CH$_{arom}$), 7.06 (2H, d, CH$_{arom}$), 3.77 (2H, q, CH$_2$), 3.51-3.44 (4H, m, 2×CH$_2$), 3.26-3.18 (4H, m, 2×CH$_2$), 2.08 (3H, d, CH$_3$), 1.43 (9H, s, 3×CH$_3$), 0.70 (3H, t, CH$_3$).

General Procedure D3

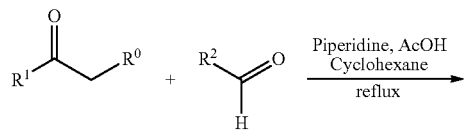

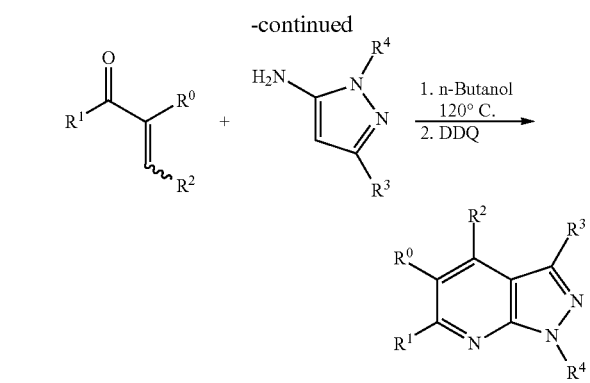

Example of Synthesis Following Procedure D3

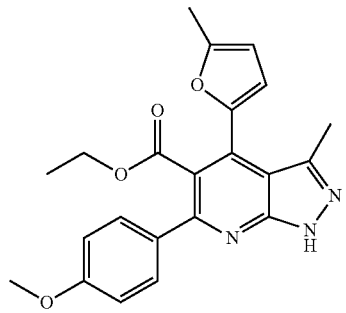

ethyl 6-(4-methoxyphenyl)-3-methyl-4-(5-methylfuran-2-yl)-1H-pyrazolo[3,4-b]pyridine-5-carboxylate In a 100 ml flask surmounted by Dean-Stark apparatus and a condenser are mixed together 3.00 g (13.5 mmol) of ethyl 3-(4-methoxyphenyl)-3-oxopropanoate, 1.06 g (9.6 mmol) of 5-methylfuran-2-carboxaldehyde, 193 µL (1.06 g, 3.4 mmol) of acetic acid and 200 µL (0.17 g, 2.0 mmol) of piperidine in cyclohexane (40 ml). The mixture is refluxed for 3 h. After cooling, the mixture is diluted with 100 ml of ethyl acetate and the mixture is successively washed with water, a saturated NaHCO$_3$ solution and a sodium chloride saturated solution. The organic phase is dried over sodium sulfate, filtered, and concentrated. The ethyl 2-(4-methoxybenzoyl)-3-(5-methylfuran-2-yl)acrylate is used in the following step without purification.

A mixture of 0.76 g (2.41 mmol) of ethyl 2-(4-methoxybenzoyl)-3-(5-methylfuran-2-yl)acrylate and of 0.23 g (2.41 mmol) of 3-amino-5-methyl-pyrazole is heated to 140° C. in 6 ml of n-BuOH for 24 h. The mixture is then cooled to room temperature and 0.55 g (2.4 mmol) of DDQ in 6 ml of THF is added. The mixture is stirred at room temperature for 1 h. The mixture is then poured onto a saturated solution of NaHCO$_3$ then extracted with ethyl acetate. The organic phase is washed in a saturated solution of sodium chloride, dried over sodium sulfate, filtered, and concentrated. The mixture is then purified using reverse-phase HPLC to yield 146 mg (15%) of ethyl 6-(4-methoxyphenyl)-3-methyl-4-(5-methylfuran-2-yl)-1H-pyrazolo[3,4-b]pyridine-5-carboxylate in the form of a yellow solid.

LCMS (ESI, m/z): (M+1) 392.5

$^1$H-NMR: $\delta_H$ pm 400 MHz, DMSO: 13.59 (1H, s, NH), 7.53 (2H, d, CH$_{arom}$), 7.04 (2H, d, CH$_{arom}$), 6.74 (1H, d, CH$_{arom}$), 6.36 (1H, dq, CH$_{arom}$), 4.03 (2H, q, OCH$_2$), 3.81 (3H, s, OCH$_3$), 2.38 (3H, d, CH$_3$), 2.36 (3H, s, CH$_3$), 0.99 (3H, t, CH$_3$).

It is to be noted that the other particular compounds cited in Table I above, and whose synthesis is not explicitly described, are prepared following one of the preceding methods D1, D2 or D3 optionally with a subsequent functionalization step as described below.

b) Subsequent PZP Functionalization Procedures

General Procedure E1: Deprotection of Phenol (Protected by a Methyl)

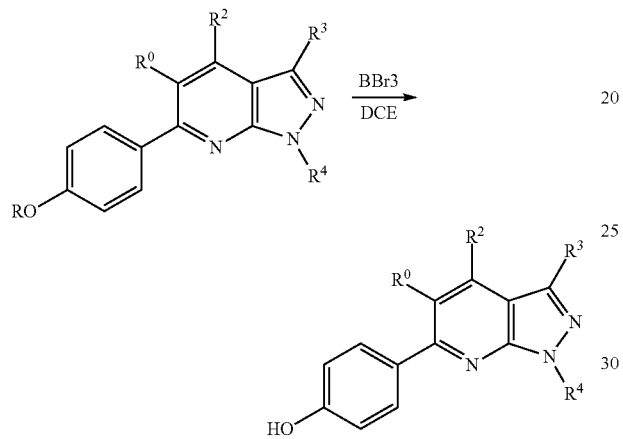

Example of Synthesis Following Procedure E1

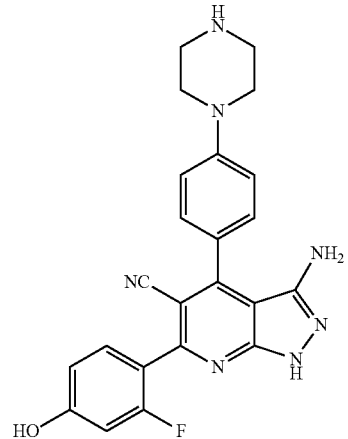

3-amino-6-(2-fluoro-4-hydroxyphenyl)-4-(4-(piperazin-1-yl)phenyl)-1H-pyrazolo[3,4-b]pyridine-5-carbonitrile hydrobromide To 2.15 g (3.34 mmol) of tert-butyl 4-(4-(3-amino-5-cyano-6-(2-fluoro-4-methoxyphenyl)-1H-pyrazolo[3,4-b]pyridin-4-yl)phenyl)piperazine-1-carboxylate, obtained following procedure D1 and diluted in 40 ml of 1,2-dichloroethane are added dropwise at 0° C. 16.7 ml of a tribromoborane solution (1M in dichloromethane, 16.7 mmol). The reaction mixture is brought to 50° C. for 8 h, then methanol is added at 0° C. and the solvents are concentrated. The residue is purified by chromatography on silica (dichloromethane/methanol eluent: 9:1 with dichloromethane/methanol/water: 65:25:4) then hot triturated in methanol to yield 0.84 g (50%) of 3-amino-6-(2-fluoro-4-hydroxyphenyl)-4-(4-(piperazin-1-yl)phenyl)-1H-pyrazolo[3,4-b]pyridine-5-carbonitrile hydrobromide in the form of an orange solid.

LCMS (ESI, m/z): (M+1) 430.4

$^1$H-NMR: δ$_H$ pm 400 MHz, DMSO: 12.96 (1H, sl, NH), 10.29 (1H, sl, OH) 8.75 (2H, sl, NH$_2$), 7.53 (2H, d, 2CH$_{arom}$), 7.46 (1H, t, CH$_{arom}$), 7.22 (2H, d, 2CH$_{arom}$), 6.78-6.70 (2H, m, 2CH$_{arom}$), 4.75 (2H, sl, NH$_2$), 3.55 (4H, m, 2CH$_2$), 3.28 (4H, m, 2CH$_2$).

General Procedure E2: Formation of a Hydrochloride

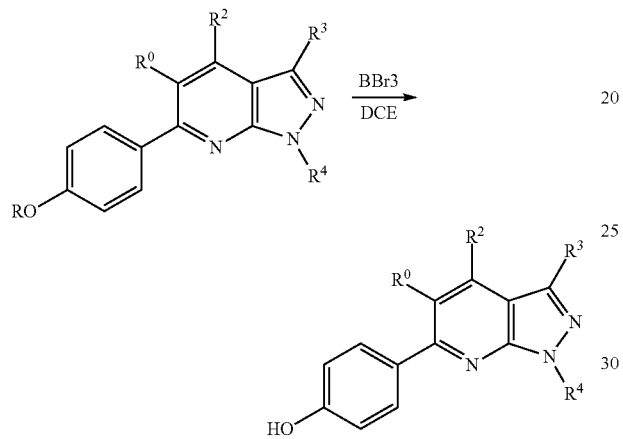

Example of Synthesis Following Procedure E2

3-methyl-4-(4-(piperazin-1-yl)phenyl)-6-(2,3,6-trifluorophenyl)-1H-pyrazolo[3,4-b]pyridine-5-carbonitrile hydrochloride To 1 g (1.82 mmol) of tert-butyl 4-(4-(5-cyano-3-methyl-6-(2,3,6-trifluorophenyl)-1H-pyrazolo[3,4-b]pyridine-4-yl)phenyl)piperazine-1-carboxylate, obtained following procedure D1 and diluted in 10 ml of dioxane, are added 2.28 ml (9.11 mmol) of a hydrochloric acid solution (4M in dioxane). The reaction mixture is stirred for 48 h, then the solid formed is filtered and rinsed several times in an acetonitrile/methanol (95:5) mixture and dried to yield 0.572 g of 3-methyl-4-(4-(piperazin-1-yl)phenyl)-6-(2,3,6-trifluorophenyl)-1H-pyrazolo[3,4-b]pyridine-5-carbonitrile hydrochloride in the form of a beige solid.

LCMS (ESI, m/z): (M+1) 449.0

$^1$H-NMR: δ$_H$ pm 400 MHz, DMSO: 9.36 (2H, sl, NH$_2$), 7.76-7.85 (1H, m, CH$_{arom}$), 7.57 (2H, d, CH$_{arom}$), 7.41-7.47

(1H, m, CH$_{arom}$), 7.20 (2H, d, CH$_{arom}$), 3.56-3.58 (4H, m, 2CH$_2$), 3.22-3.28 (4H, m, 2CH$_2$), 2.16 (3H, s, CH$_3$), 2.21-2.27 (2H, m, CH$_2$).

General Procedure E3: Deprotection of the Phenol (Protected by a Benzyl)

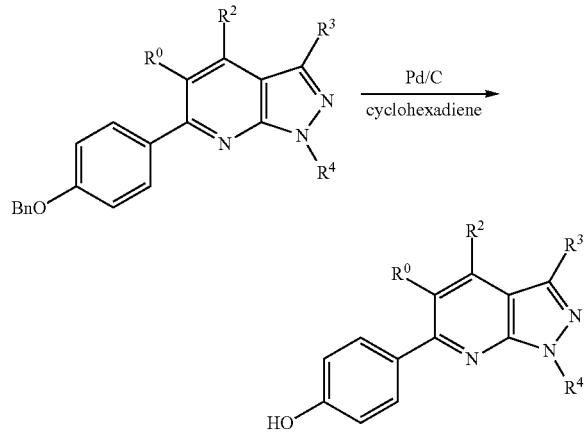

Example of Synthesis Following Protocol E3

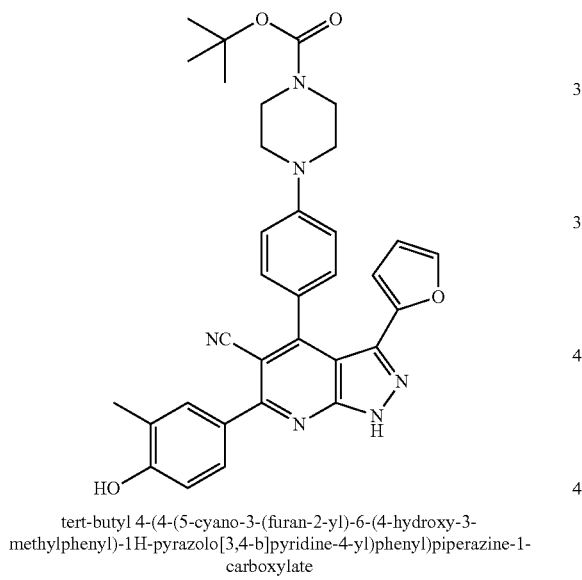

tert-butyl 4-(4-(5-cyano-3-(furan-2-yl)-6-(4-hydroxy-3-methylphenyl)-1H-pyrazolo[3,4-b]pyridine-4-yl)phenyl)piperazine-1-carboxylate To a solution of 2.12 g (3.2 mmol) of tert-butyl 4-(4-(6-(4-(benzyloxy)-3-methylphenyl)-5-cyano-3-(furan-2-yl)-1H-pyrazolo[3,4-b]pyridine-4-yl)phenyl)piperazine-1-carboxylate in a MeOH/CH$_2$Cl$_2$ mixture are added 0.41 g (0.38 mmol) of 10% Pd/C and 3 ml (2.57 g, 32.0 mmol) of 1,4-cyclohexadiene. The mixture is refluxed for 18 h, then 0.41 g (0.38 mmol) of 10% Pd/C and 3 ml (2.57 g, 32.0 mmol) of 1,4-cyclohexadiene are added, and the mixture is refluxed for an additional 24 h, 0.41 g (0.38 mmol) of 10% Pd/C and 3 ml (2.57 g, 32.0 mmol) of 1,4-cyclohexadiene are added and the mixture is again refluxed for 24 h. The mixture is then concentrated, dissolved in dichloromethane, filtered on Celite, then concentrated. The residue is purified by chromatography on silica (MeOH gradient in dichloromethane: 0 to 3%) to give 0.92 g (50%) of tert-butyl 4-(4-(5-cyano-3-(furan-2-yl)-6-(4-hydroxy-3-methylphenyl)-1H-pyrazolo[3,4-b]pyridine-4-yl)phenyl)piperazine-1-carboxylate in the form of yellow crystals.

$^1$H-NMR: δ$_H$ pm 400 MHz, DMSO: 14.39 (1H, sl, NH), 9.92 (1H, sl, OH), 7.68 (1H, d, CH$_{arom}$), 7.62 (1H, dd, CH$_{arom}$), 7.40 (1H, m, CH$_{arom}$), 7.30 (2H, d, CH$_{arom}$), 6.97 (2H, d, CH$_{arom}$), 6.94 (1H, d, CH$_{arom}$), 6.36 (1H, dd, CH$_{arom}$), 5.80 (1H, d, CH$_{arom}$), 3.49 (4H, m, 2CH$_2$), 3.24 (4H, m, 2CH$_2$), 2.22 (3H, s, CH$_3$), 1.44 (9H, s, t-Bu).

General Procedure E4

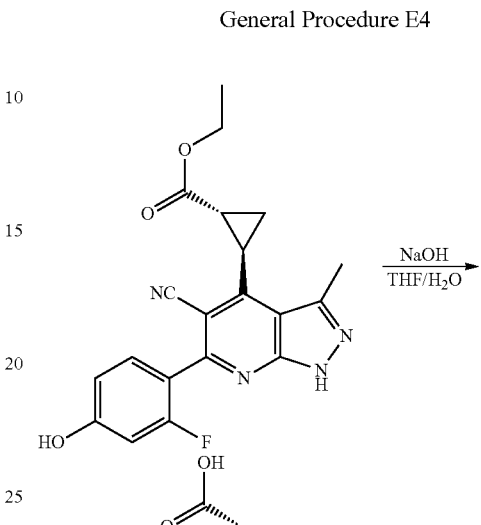

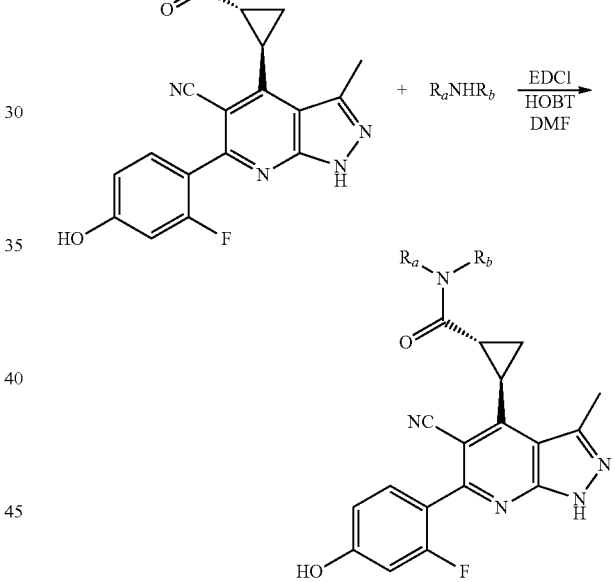

Example of Synthesis Following Procedure E4

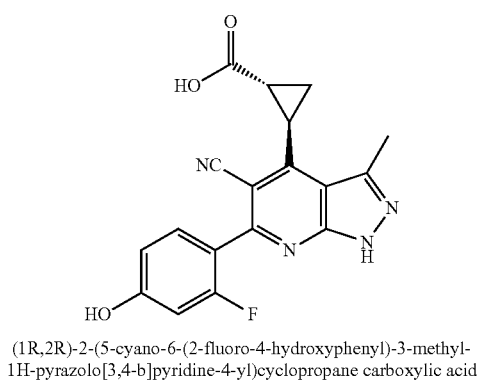 [SMILES: Cc1n[nH]c2nc(-c3ccc(O)cc3F)c(C#N)c([C@@H]3C[C@H]3C(=O)O)c12]

(1R,2R)-2-(5-cyano-6-(2-fluoro-4-hydroxyphenyl)-3-methyl-1H-pyrazolo[3,4-b]pyridine-4-yl)cyclopropane carboxylic acid To 540 mg (1.42 mmol) of ethyl (1R,2R)-2-(5-cyano-6-(2-fluoro-4-hydroxyphenyl)-3-methyl-1H-pyrazolo[3,4-b]pyridine-4-yl)cyclopropane carboxylate obtained following procedure D1 and diluted in 3 ml tetrahydrofuran are added 4.97 ml of aqueous sodium hydroxide solution (4M). The solution is stirred at room temperature for 20 h. The aqueous phase is washed several times with ethyl acetate, then acidified to pH 2 with a hydrochloric acid solution (1M). The product is extracted several times with ethyl acetate, the organic phases are combined, dried over magnesium sulfate and concentrated to give 500 mg of (1R,2R)-2-(5-cyano-6-(2-fluoro-4-hydroxyphenyl)-3-methyl-1H-pyrazolo[3,4-b]pyridine-4-yl)cyclopropane carboxylic acid in the form of a white solid.

LCMS (ESI, m/z): (M+1) 353.1

$^1$H-NMR: $\delta_H$ pm 400 MHz, DMSO: 13.80 (1H, sl, NH), 12.38 (1H, sl, COOH), 1.39 (1H, sl, OH), 7.41 (1H, dd, $CH_{arom}$), 6.77 (1H, dd, $CH_{arom}$), 6.72 (1H, dd, $CH_{arom}$), 3.02-3.07 (1H, m, CH), 2.68 (3H, s, $CH_3$), 2.16-2.21 (1H, m, CH), 1.62-1.69 (2H, m, $CH_2$).

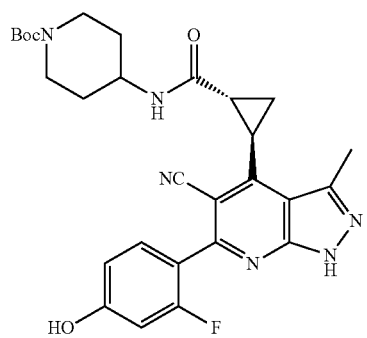

tert-butyl 4-(1R,2R)-2-(5-cyano-6-(2-fluoro-4-hydroxyphenyl)-3-methyl-1H-pyrazolo[3,4-b]pyridin-4-yl)cyclopropanecarboxamido)piperidine-1-carboxylate To 200 mg (0.57 mmol) of (1R,2R)-2-(5-cyano-6-(2-fluoro-4-hydroxyphenyl)-3-methyl-1H-pyrazolo[3,4-b]pyridine-4-yl)cyclopropane carboxylic acid diluted in 4 ml of anhydrous dimethylformamide are added, at 0° C., 121 mg (0.57 mmol) of tert-butyl 4-aminopiperidine-1-carboxylate, 76 mg (0.62 mmol) of N,N-dimethylpyridine-4-amine (DMAP), 110 mg (0.62 mmol of N,N-dimethyl-N-[(methylimino)methylene]propane-1,3-diamine hydrochloride (EDCI) and 84 mg (0.62 mmol) of 1H-benzo[d][1,2,3]triazole-1-ol (HOBT). The reaction mixture is stirred 20 h at room temperature. The solvent is concentrated, water is added and the product extracted several times with ethyl acetate. The organic phases are combined, dried over magnesium sulfate and concentrated. The residue is purified by chromatography on silica (cyclohexane/ethyl acetate eluent: 5:5 to 3:7) to give 158 mg of tert-butyl 4-((1R,2R)-2-(5-cyano-6-(2-fluoro-4-hydroxyphenyl)-3-methyl-1H-pyrazolo[3,4-b]pyridin-4-yl)cyclopropanecarboxamido)piperidine-1-carboxylate in the form of a white solid.

LCMS (ESI, m/z): (M+1) 535.3

$^1$H-NMR: $\delta_H$ pm 400 MHz, DMSO: 13.79 (1H, sl, NH), 10.40 (1H, sl, OH), 8.29 (1H, d, NH), 7.41 (1H, dd $CH_{arom}$), 6.77 (1H, dd, $CH_{arom}$), 6.72 (1H, dd, $CH_{arom}$), 3.81-3.87 (3H, m, $CH_2$, CH), 2.83-2.95 (2H, m, $CH_2$), 2.65 (3H, s, $CH_3$), 2.10-2.14 (1H, m, CH), 1.49-1.76 (5H, m, $2CH_2$, CH), 1.41 (9H, s, $3CH_3$), 1.22-1.34 (2H, m, $CH_2$).

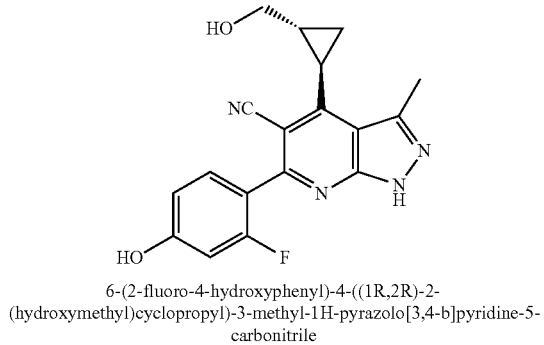 [SMILES: Cc1n[nH]c2nc(-c3ccc(O)cc3F)c(C#N)c([C@@H]3C[C@H]3CO)c12]

6-(2-fluoro-4-hydroxyphenyl)-4-((1R,2R)-2-(hydroxymethyl)cyclopropyl)-3-methyl-1H-pyrazolo[3,4-b]pyridine-5-carbonitrile To 66 mg (1.74 mmol) of LiAlH$_4$ suspended in 3 ml of anhydrous tetrahydrofuran are added under argon at 0° C. 132 mg (0.35 mmol) of ethyl (1R,2R)-2-(5-cyano-6-(2-fluoro-4-hydroxyphenyl)-3-methyl-1H-pyrazolo[3,4-b]pyridine-4-yl)cyclopropane carboxylate obtained following procedure D1. The solution is stirred at room temperature for 2 h, water is added and the product is extracted several times with ethyl acetate. The organic phases are combined, dried over magnesium sulfate and concentrated. The residue is purified by chromatography on silica (cyclohexane/ethyl acetate eluent: 3:7) to give 58 mg of 6-(2-fluoro-4-hydroxyphenyl)-4-((1R,2R)-2-(hydroxymethyl)cyclopropyl)-3-methyl-1H-pyrazolo[3,4-b]pyridine-5-carbonitrile in the form of a white solid.

LCMS (ESI, m/z): (M+1) 339.37

$^1$H-NMR: $\delta_H$ pm 400 MHz, DMSO: 13.71 (1H, sl, NH), 10.42 (1H, sl, OH), 7.40 (1H, dd, $CH_{arom}$), 6.76 (1H, dd, $CH_{arom}$), 6.71 (1H, dd, $CH_{arom}$), 4.73 (1H, sl OH), 3.96-3.90 (1H, m, $CH_2$), 3.47-3.41 (1H, m, $CH_2$), 2.73 (3H, s, $CH_3$), 2.46-4.41 (1H, m, CH), 1.78-1.70 (1H, m, CH), 1.30-1.21 (2H, m, $CH_2$).

The compounds below are obtained following a similar procedure to procedure E4 according to the following reaction scheme:

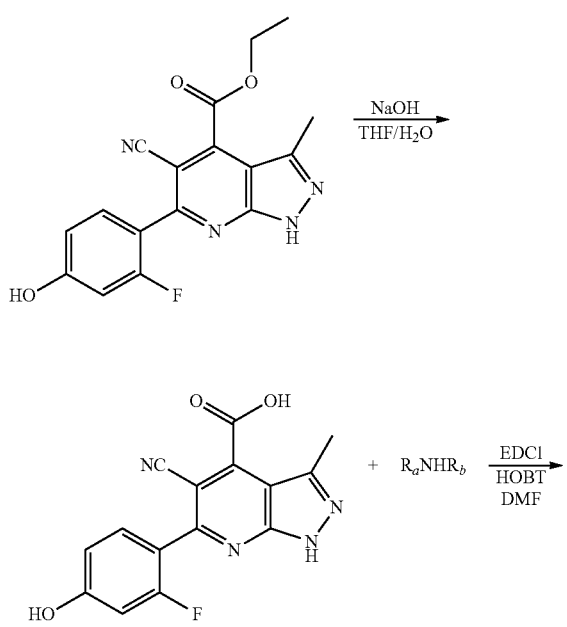

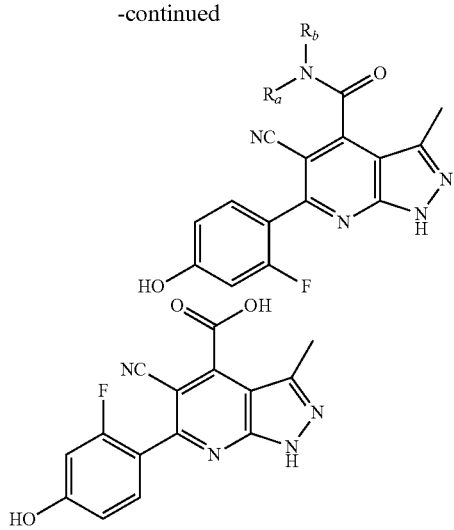

5-cyano-6-(2-fluoro-4-hydroxyphenyl)-3-methyl-1H-pyrazolo[3,4-b]pyridine-4-carboxylic acid To 338 mg (1.42 mmol) of ethyl 5-cyano-6-(2-fluoro-4-hydroxyphenyl)-3-methyl-1H-pyrazolo[3,4-b]pyridine-4-carboxylate obtained following procedure D1 and diluted in 3 ml of tetrahydrofuran are added 4.97 ml of an aqueous sodium hydroxide solution (4M). The solution is stirred at room temperature for 20 h. The aqueous phase is washed several times with ethyl acetate, then acidified to pH 2 with a hydrochloric acid solution (1M). The product is extracted several times with ethyl acetate, the organic phases are combined, dried over magnesium sulfate and concentrated to give 200 mg of 5-cyano-6-(2-fluoro-4-hydroxyphenyl)-3-methyl-1H-pyrazolo[3,4-b]pyridine-4-carboxylic acid in the form of a white solid.

LCMS (ESI, m/z): (M+1) 313.9

$^1$H-NMR: $\delta_H$ pm 400 MHz, DMSO: 14.12 (1H, sl, NH), 10.47 (1H, sl, OH), 7.49 (1H, dd, $CH_{arom}$), 6.80 (1H, dd, $CH_{arom}$), 6.76 (1H, dd, $CH_{arom}$), 2.52 (3H, s, $CH_3$).

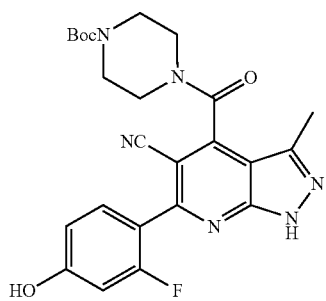

tert-butyl 4-(5-cyano-6-(2-fluoro-4-hydroxyphenyl)-3-methyl-1H-pyrazolo[3,4-b]pyridine-4-carbonyl)piperazine-1-carboxylate To 200 mg (0.57 mmol) of 5-cyano-6-(2-fluoro-4-hydroxyphenyl)-3-methyl-1H-pyrazolo[3,4-b]pyridine-4-carboxylic acid diluted in 4 ml of anhydrous dimethylformamide are added at 0° C. 121 mg (0.57 mmol) of tert-butyl piperazine-1-carboxylate, 76 mg (0.62 mmol) of N,N-dimethylpyridine-4-amine (DMAP), 110 mg (0.62 mmol) of N,N-dimethyl-N-[(methylimino)methylene]propane-1,3-diamine hydrochloride (EDCI) and 84 mg (0.62 mmol) of 1H-benzo[d][1,2,3]triazole-1-ol (HOBT). The reaction mixture is stirred 20 h at room temperature. The solvent is concentrated, water is added and the product extracted several times with ethyl acetate. The organic phases are combined, dried over magnesium sulfate, and concentrated. The residue is purified by chromatography on silica (cyclohexane/ethyl acetate eluent: 5:5 to 3:7) to yield 158 mg of tert-butyl 4-(5-cyano-6-(2-fluoro-4-hydroxyphenyl)-3-methyl-1H-pyrazolo[3,4-b]pyridine-4-carbonyl)piperazine-1-carboxylate in the form of a white solid.

LCMS (ESI, m/z): (M+1) 395.0

$^1$H-NMR: $\delta_H$ pm 400 MHz, DMSO: 14.09 (1H, sl, NH), 10.52 (1H, sl, NH), 9.35 (1H, sl, $CH_{arom}$), 8.78 (1H, dl, NH), 8.58 (1H, sl, NH), 7.46 (1H, dd, $CH_{arom}$), 6.81 (1H, dd, $CH_{arom}$), 6.77 (1H, dd, $CH_{arom}$), 4.22 (1H, m, CH), 3.30-3.33 (2H, m, $CH_2$), 3.06-3.09 (2H, m, $CH_2$), 2.47 (3H, s, $CH_3$), 2.10-2.06 (2H, m, $CH_2$), 1.70-1.80 (2H, m, $CH_2$).

Particular Procedure E5

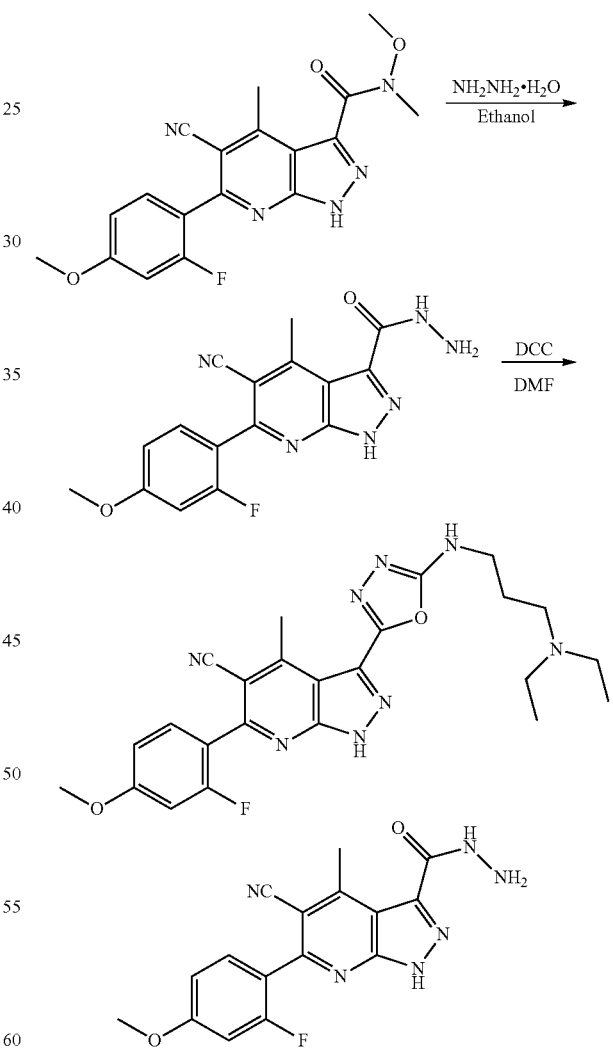

5-cyano-6-(2-fluoro-4-methoxyphenyl)-4-methyl-1H-pyrazolo[3,4-b]pyridine-4-carbohydrazide To 620 mg (1.68 mmol) of 5-cyano-6-(2-fluoro-4-methoxyphenyl)-N-methoxy-N-4-dimethyl-$^1$H-pyrazolo[3,4-b]pyridine-3-carboxamide obtained following procedure D1 dissolved in 2 ml of ethanol are added 0.7 ml (8.39 mmol) of hydrazine hydrate. The solution is refluxed for 5 h, 40 ml of water are added and the product is extracted several times with ethyl acetate. The organic phases are combined, dried over magnesium sulfate, and concentrated. The product is crystallized in methanol to yield 205 mg of 5-cyano-6-(2-fluoro-4-methoxyphenyl)-4-methyl-1H-pyrazolo[3,4-b]pyridine-3-carbohydrazide in the form of a white solid.

LCMS (ESI, m/z): (M+1) 341.1

$^1$H-NMR: $\delta_H$ pm 400 MHz, DMSO: 14.60 (1H, sl, NH), 9.94 (1H, sl, NH), 7.59 (1H, dd, $CH_{arom}$), 7.07 (1H, dd, $CH_{arom}$), 6.98 (1H, dd, $CH_{arom}$), 4.62 (2H, sl, $NH_2$), 3.88 (3H, s, $CH_3$), 3.06 (3H, s, $CH_3$).

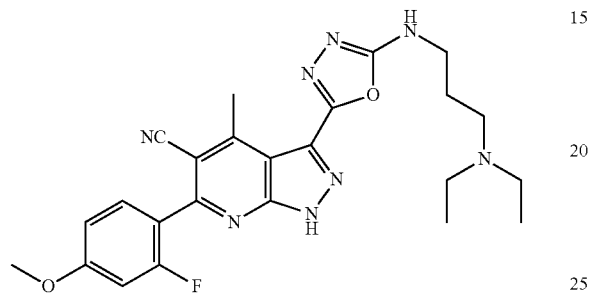

3-(5-(3-(diethylamino)propylamino)-1,3,4-oxadiazol-2-yl)-6-(2-fluoro-4-methoxyphenyl)-4-methyl-1H-pyrazolo[3,4-b]pyridine-5-carbonitrile To 200 mg (0.59 mmol) of 5-cyano-6-(2-fluoro-4-methoxyphenyl)-4-methyl-1H-pyrazolo[3,4-b]pyridine-3-carbohydrazide diluted in 8 ml of dimethylacetamide, are added 101 mg of N,N-diethyl-3-isothiocyanatopropane-1-amine. The reaction mixture is stirred at 65° C. until complete disappearance of the starting product. 224 mg (1.17 mmol) of $N^1$-((ethylimino)methylene)-$N^3$,$N^3$-dimethylpropane-1,3-diamine hydrochloride are added and the solution is stirred at 70° C. for 2 h. 20 ml of water are added and the product is extracted several times with ethyl acetate. The organic phases are combined, dried over magnesium sulfate, and concentrated. The solid is triturated in a diethyl ether/methanol mixture (10:1) to yield 170 mg of 3-(5-(3-(diethylamino)propylamino)-1,3,4-oxadiazol-2-yl)-6-(2-fluoro-4-methoxyphenyl)-4-methyl-1H-pyrazolo[3,4-b]pyridine-5-carbonitrile in the form of a pink solid.

LCMS (ESI, m/z): (M+1) 479.4

$^1$H-NMR: $\delta_H$ pm 400 MHz, DMSO: 7.99 (1H, t, NH), 7.59 (1H, dd, $CH_{arom}$), 7.07 (1H, dd, $CH_{arom}$), 6.99 (1H, dd, $CH_{arom}$), 3.88 (3H, s, $CH_3$), 3.29-3.36 (6H, m, $3CH_2$), 3.19 (3H, s, $CH_3$), 1.70-1.77 (2H, m, $CH_2$), 1.09 (2H, t, $CH_2$), 0.97 (6H, t, $2CH_3$).

General Procedure E6

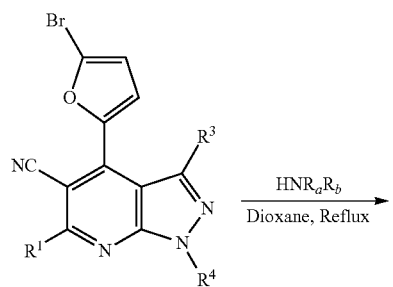

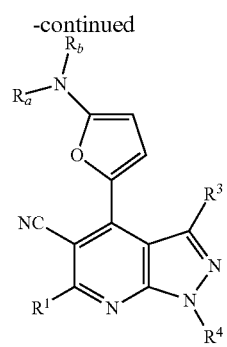

$HNR_aR_b$ = cyclic amine
$R^3$ not NHBoc

Example of Synthesis Following Procedure E6

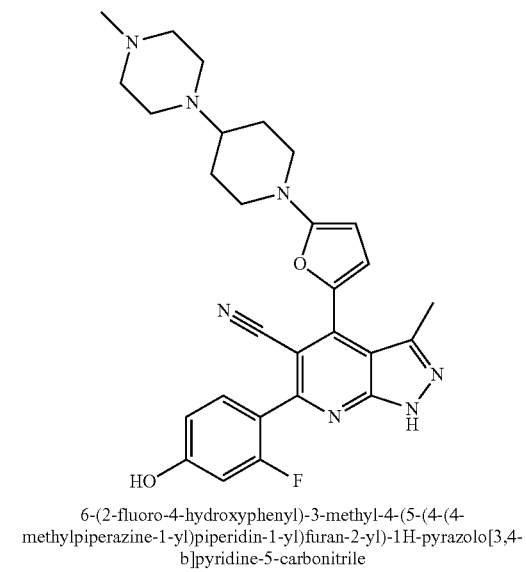 [SMILES: Cc1n[nH]c2nc(-c3ccc(O)cc3F)c(C#N)c(-c3ccc(N4CCC(N5CCN(C)CC5)CC4)o3)c12]

6-(2-fluoro-4-hydroxyphenyl)-3-methyl-4-(5-(4-(4-methylpiperazine-1-yl)piperidin-1-yl)furan-2-yl)-1H-pyrazolo[3,4-b]pyridine-5-carbonitrile A solution of 0.80 g (1.9 mmol) of 4-(5-bromofuran-2-yl)-6-(2-fluoro-4-hydroxyphenyl)-3-methyl-1H-pyrazolo[3,4-b]pyridine-5-carbonitrile and 3.56 g (19.4 mmol) of 1-methyl-4-(piperidin-4-yl)piperazine in 55 ml of anhydrous dioxane is refluxed for 7 days. The mixture is concentrated and the residue is purified by chromatography on silica (MeOH gradient in dichloromethane: 5 to 10%) to yield 0.51 g (51%) of 6-(2-fluoro-4-hydroxyphenyl)-3-methyl-4-(5-(4-(4-methylpiperazine-1-yl)piperidin-1-yl)furan-2-yl)-$^1$H-pyrazolo[3,4-b]pyridine-5-carbonitrile in the form of an orange solid.

LCMS (ESI, m/z); (M+1) 516.25

$^1$H-NMR: $\delta_H$ pm 400 MHz, DMSO: 13.74 (1H, sl, NH), 10.37 (1H, sl, NH), 7.44 (1H, d, $CH_{arom}$), 7.42 (1H, t, $CH_{arom}$), 6.75 (1H, dd, $CH_{arom}$), 6.70 (1H, dd, $CH_{arom}$), 5.71 (1H, d, $CH_{arom}$), 3.85 (2H, dl), 2.96 (2H, td), 2.55 (3H, s, $CH_3$), 2.40 (2H, sl), 2.35-2.22 (3H, m), 2.13 (3H, s, $CH_3$), 1.84 (2H, dl), 1.49 (2H, qd).

General Procedure E7

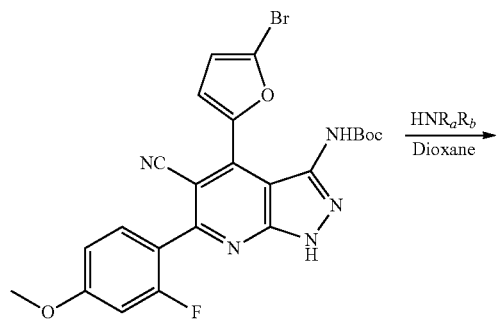

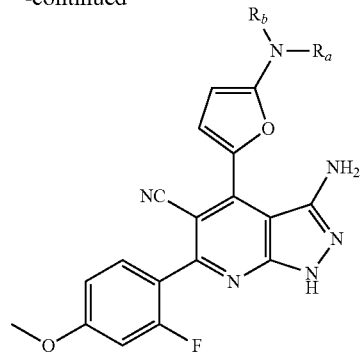

Example of Synthesis Following Procedure E7

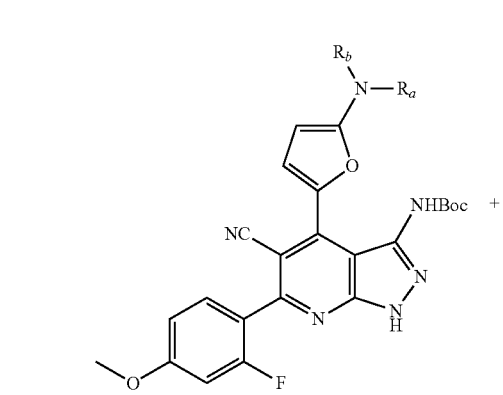

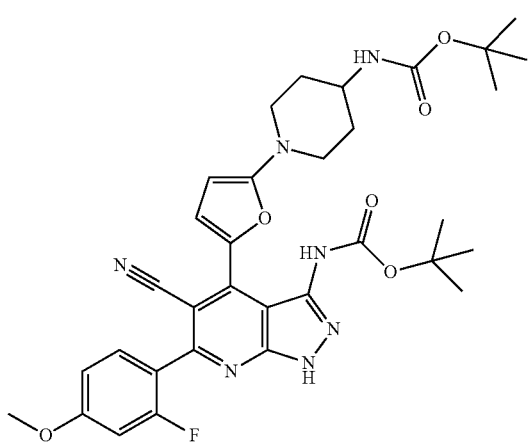

tert-butyl 5-(3-tert-butoxycarbonylamino)-5-cyano-6-(2-fluoro-4-methoxyphenyl)-1H-pyrazolo[3,4-b]pyridine-4-yl)furan-2-yl)piperidine-4-yl carbamate

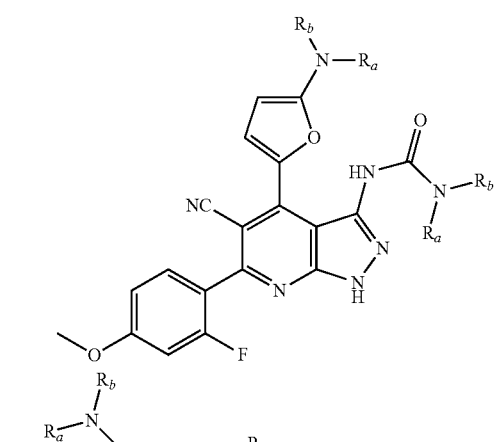

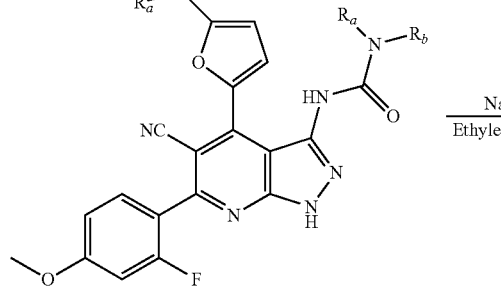

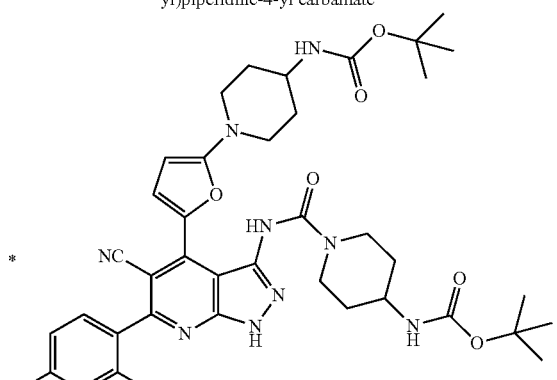

tert-butyl 5-(3-(4-(tert-butoxycarbonylamino)piperidine-1-carboxamido)-5-cyano-6-(2-fluoro-4-methoxyphenyl)-1H-pyrazolo[3,4-b]pyridine-4-yl)furan-2-yl)piperidine-4-yl carbamate To 3.3 g (6.25 mmol) of tert-butyl 4-(5-bromofuran-2-yl)-5-cyano-6-(2-fluoro-4-methoxyphenyl)-1H-pyrazolo[3,4-b]pyridin-3-yl carbamate obtained following procedure D1, in solution in 165 ml of anhydrous dioxane, are added 12.51 g (62.46 mmol) of tert-butyl piperidin-4-yl carbamate. The reaction mixture is stirred at 100° C. for 4 days. A 0.5M aqueous solution of hydrogen chloride is added and the product is extracted several times with ethyl acetate. The organic phases are combined, dried over magnesium sulfate, and concentrated. The residue is purified by chromatography on silica (cyclohexane/ethyl acetate eluent: 6:4) to yield 940 mg (23%) of tert-butyl 5-(3-(tert-butoxycarbonylamino)-5-cyano-6-(2-fluoro-4-methoxyphenyl)-1H-pyrazolo[3,4-b]pyridine-4-yl)furan-2-yl)piperidine-4-yl carbamate in the form of a brown solid, and 2.07 g (43%) of tert-butyl 5-(3-(4-(tert-butoxycarbonylamino)piperidine-1-carboxamido)-5-cyano-6-(2-fluoro-4-methoxyphenyl)-1H-pyrazolo[3,4-b]pyridine-4-yl)furan-2-yl)piperidine-4-yl carbamate in the form of a brown solid.

tert-butyl 5-(3-(tert-butoxycarbonylamino)-5-cyano-6-(2-fluoro-4-methoxyphenyl)-1H-pyrazolo[3,4-b]pyridine-4-yl)furan-2-yl)piperidine-4-yl carbamate.

$^1$H-NMR: $\delta_H$ pm 400 MHz, DMSO: 13.73 (1H, sl, NH), 9.50 (1H, sl, NH), 7.60-7.52 (2H, m, $CH_{arom}$), 7.01 (1H, dd, $CH_{arom}$), 7.00-6.93 (2H, m, NH+$CH_{arom}$), 5.71 (1H, d, $CH_{arom}$), 3.92-3.82 (2H, m, 2×$CH_{pip}$), 3.87 (3H, s, $CH_3$), 3.53-3.42 (1H, m, $CH_{pip}$), 3.12-3.00 (2H, m, 2×$CH_{pip}$), 1.88-1.77 (2H, m, 2×$CH_{pip}$), 1.63-1.40 (2H, m, 2×$CH_{pip}$), 1.40 (9H, s, 3×$CH_3$), 1.30 (9H, s, 3×$CH_3$).

tert-butyl 5-(3-(4-(tert-butoxycarbonylamino)piperidine-1-carboxamido)-5-cyano-6-(2-fluoro-4-methoxyphenyl)-1H-pyrazolo[3,4-b]pyridine-4-yl)furan-2-yl)piperidine-4-yl carbamate $^1$H-NMR: $\delta_H$ pm 400 MHz, DMSO: 13.65 (1H, sl, NH), 8.99 (1H, sl, NH), 7.53 (1H, t, $CH_{arom}$), 7.39 (1H, d, 7.00 (1H, dd, $CH_{arom}$), 6.94 (1H, dd, $CH_{arom}$), 6.95-6.85 (2H, m, 2×NH), 5.77 (1H, d, $CH_{arom}$), 4.02-3.94 (2H, m, 2×$CH_{pip}$), 3.86 (3H, s, $CH_3$), 3.87-3.77 (2H, m, 2×$CH_{pip}$), 3.54-3.39 (2H, m, 2×$CH_{pip}$), 3.09-2.99 (2H, m, 2×$CH_{pip}$), 2.86-2.74 (2H, m, 2×$CH_{pip}$), 1.84-1.67 (4H, m, 4×$CH_{pip}$), 1.52-1.40 (2H, m, 2×$CH_{pip}$), 1.40 (9H, s, 3×$CH_3$), 1.38 (9H, s, 3×$CH_3$), 1.35-1.22 (2H, m, 2×$CH_{pip}$).

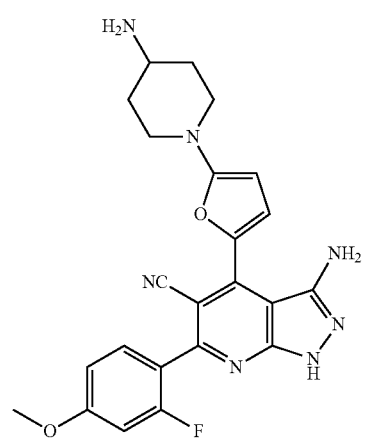

3-amino-4-(5-(4-aminopiperidine-1-yl)furan-2-yl)-6-(2-fluoro-4-methoxyphenyl)-1H-pyrazolo[3,4-b]pyridine-5-carbonitrile To 1 g (1.29 mmol) of tert-butyl 5-(3-(4-(tert-butoxycarbonylamino)piperidine-1-carboxamido)-5-cyano-6-(2-fluoro-4-methoxyphenyl)-1H-pyrazolo[3,4-b]pyridine-4-yl)furan-2-yl)piperidine-4-yl carbamate in solution in 20 ml of ethoxyethanol, are added 2.2 ml (35 mmol) of a 16N aqueous sodium hydroxide solution. The reaction mixture is stirred at 100° C. for 5 h. A 1N aqueous solution of hydrogen chloride (30 ml) is added and the product is extracted several times with ethyl acetate. The organic phases are combined, dried over magnesium sulfate, and concentrated. The residue is purified by chromatography on silica (dichloromethane/methanol/water eluent: 120:25:4) to give 290 mg (50%) of 3-amino-4-(5-(4-aminopiperidine-1-yl)furan-2-yl)-6-(2-fluoro-4-methoxyphenyl)-1H-pyrazolo[3,4-b]pyridine-5-carbonitrile in the form of a brown solid.

$^1$H-NMR: $\delta_H$ pm 400 MHz, DMSO: 7.64 (1H, d, $CH_{arom}$), 7.51 (1H, t, $CH_{arom}$), 6.99 (1H, dd, $CH_{arom}$), 6.92 (1H, dd, $CH_{arom}$), 5.72 (1H, d, $CH_{arom}$), 5.36 (2H, sl, $NH_2$), 3.85 (3H, s, $CH_3$), 3.88-3.76 (2H, m, 2×$CH_{pip}$), 3.52-3.44 (2H, m, $NH_2$), 3.09-2.97 (2H, m, 2×$CH_{pip}$), 2.87-2.77 (1H, m, $CH_{pip}$), 1.86-1.74 (2H, m, 2×$CH_{pip}$), 1.38-1.29 (2H, m, 2×$CH_{pip}$).

General Procedure E8

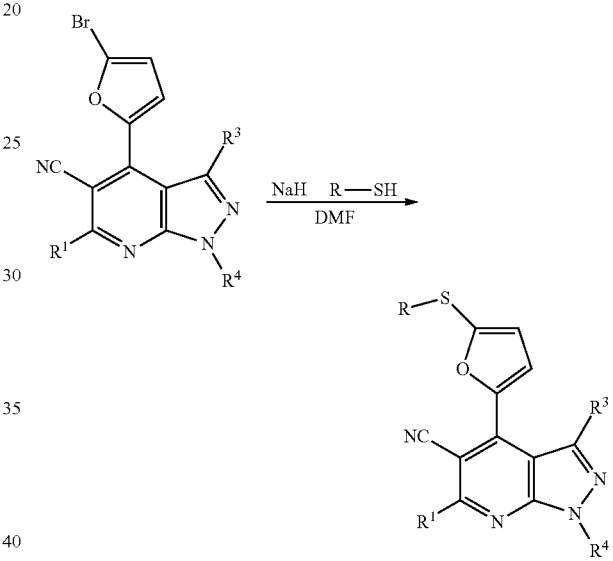

Example of Synthesis Following Procedure E8

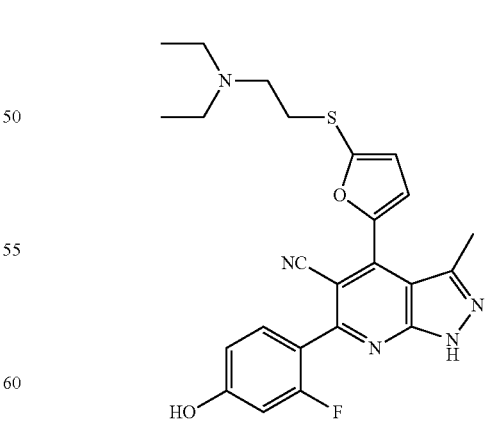

4-(5-(2-(diethylamino)ethylthio)furan-2-yl)-6-(2-fluoro-4-hydroxyphenyl)-3-methyl-1H-pyrazolo[3,4-b]pyridine-5-carbonitrile To a solution of 165 mg (0.96 mmol) of 2-(diethylamino)ethanethiol hydrochloride dissolved in 2.5 ml of anhydrous dimethyl formamide are added 70 mg of sodium hydride (60% in dispersion in oil, 2.9 mmol) and the reaction mixture is stirred 20 min at room temperature. A solution of 200 mg (0.48 mmol) of 4-(5-bromofuran-2-yl)-6-(2-fluoro-4-hydroxyphenyl)-3-methyl-1H-pyrazolo[3,4-b]pyridine-5-carbonitrile obtained following general procedure D1 is dissolved in 2 ml of dimethylformamide and is added dropwise to the reaction mixture. This mixture is stirred 5 h at room temperature, then water is added. The product is extracted several times with ethyl acetate. The organic phases are combined, dried over magnesium sulfate, and concentrated. The residue is purified by chromatography on silica (dichloromethane/methanol eluent: 92:8) to yield 135 mg (60%) of 4-(5-2-(diethylamino)ethylthio)bromofuran-2-yl)-6-(2-fluoro-4-hydroxyphenyl)-3-methyl-1H-pyrazolo[3,4-b]pyridine-5-carbonitrile in the form of an orangish solid.

¹H-NMR: $\delta_H$ pm 400 MHz, DMSO: 14.02 (1H, sl, NH), 10.42 (1H, sl, OH), 7.48 (1H, t, $CH_{arom}$), 7.41 (1H, d, $CH_{arom}$), 6.94 (1H, d, $CH_{arom}$), 6.79 (1H, dd, $CH_{arom}$), 6.74 (1H, dd, $CH_{arom}$), 3.07 (2H, t, $CH_2$), 2.67 (2H, t, $CH_2$), 2.49 (3H, s, $CH_3$), 2.46 (4H, q, 2×$CH_2$), 0.90 (6H, t, 2×$CH_3$).

General Procedure E9

To 210 mg (0.53 μmol) of 3-(6-chloropyridine-3-yl)-6-(2-fluoro-4-methoxyphenol)-4-methyl-1H-pyrazolo[3,4-b]pyridine-5-carbonitrile obtained using procedure D1, in solution in 3 ml of dimethylacetamide, are added 406 μL (3.2 mmol) of N,N,N'-trimethylethylene-diamine. The reaction mixture is stirred at 160° C. for 20 h. Water is added and the product is extracted several times with ethyl acetate. The organic phases are combined, dried over magnesium sulfate, and concentrated. The residue is purified by chromatography on silica (dichloromethane/methanol eluent: 95:5 to 85:15) to give 100 mg (40%) of 3-(6-((2-(dimethylamino-ethyl(methylamino)pyridine-3-yl)-6-(2-fluoro-4-methoxyphenol)-4-methyl-1H-pyrazolo[3,4-b]pyridine-5-carbonitrile in the form of an orange-red solid.

¹H-NMR: $\delta_H$ pm 400 MHz, DMSO: 14.27 (1H, sl, NH), 8.36 (1H, s, $CH_{arom}$), 7.81 (1H, d, $CH_{arom}$), 7.58 (1H, t, $CH_{arom}$), 7.06 (1H, d, $CH_{arom}$), 6.99 (1H, d, $CH_{arom}$), 6.74 (1H, d, $CH_{arom}$), 3.87 (3H, s, $CH_3$), 3.70 (2H, t, $CH_2$), 3.08 (3H, s, $CH_3$), 2.70 (3H, s, $CH_3$), 2.45 (2H, t, $CH_2$), 2.20 (6H, s, 2×$CH_3$).

General Procedure E10

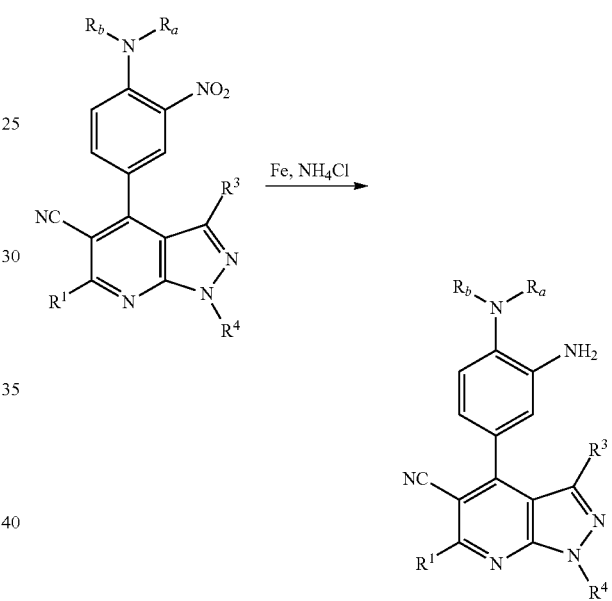

Example of Synthesis Following Procedure E10

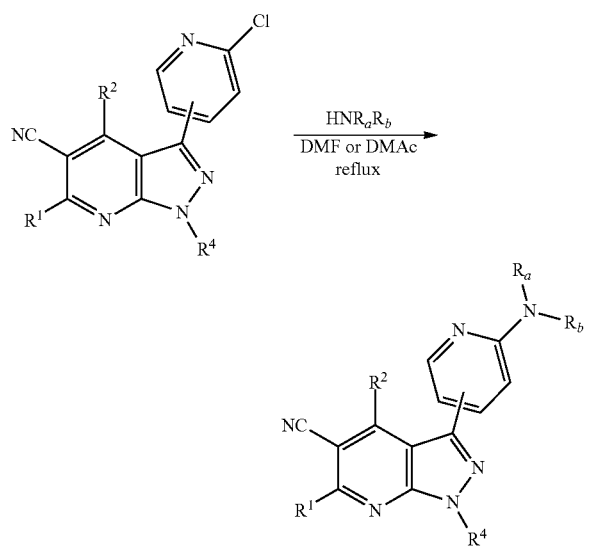

Example of Synthesis Following Procedure E9

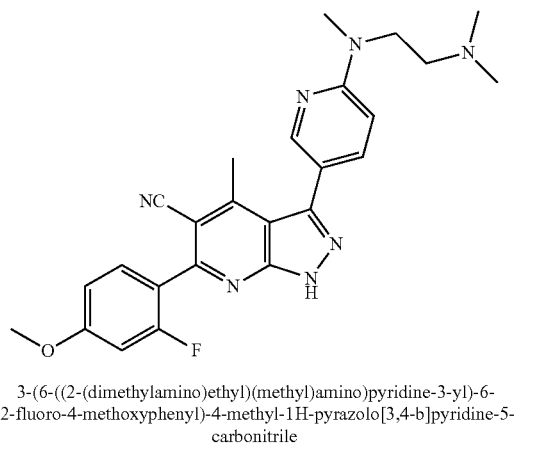

3-(6-((2-(dimethylamino)ethyl)(methyl)amino)pyridine-3-yl)-6-(2-fluoro-4-methoxyphenyl)-4-methyl-1H-pyrazolo[3,4-b]pyridine-5-carbonitrile

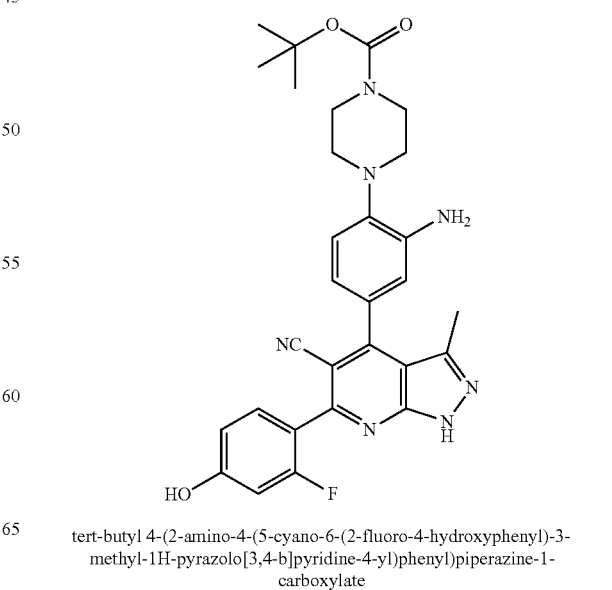

tert-butyl 4-(2-amino-4-(5-cyano-6-(2-fluoro-4-hydroxyphenyl)-3-methyl-1H-pyrazolo[3,4-b]pyridine-4-yl)phenyl)piperazine-1-carboxylate To 680 mg (1.19 μmol) of tert-butyl 4-(2-nitro-4-(5-cyano-6-(2-fluoro-4-hydroxyphenyl)-3-methyl-1H-pyrazolo[3,4-b]pyridine-4-yl)phenyl)piperazine-1-carboxylate obtained following general procedure D1, in solution in 50 ml of dioxane and 50 ml of ethanol are added 662 mg (11.8 mmol) of iron and a solution of 152 mg (2.84 mmol) of ammonium chloride dissolved in 10 ml of water. The reaction mixture is stirred at room temperature for 20 h, then filtered through Celite. The stationary phase is rinsed with an ethanol/tetrahydrofuran mixture (4:1). The filtrate is vacuum evaporated and the residue is purified by chromatography on silica (dichloromethane/methanol eluent: 99:1 to 95:5) to yield 350 mg (54%) of tert-butyl 4-(2-amino-4-(5-cyano-6-(2-fluoro-4-hydroxyphenyl)-3-methyl-1H-pyrazolo[3,4-b]pyridine-4-yl)phenyl)piperazine-1-carboxylate in the form of a yellow solid.

$^1$H-NMR: $\delta_H$ pm 400 MHz, DMSO: 13.91 (1H, sl, NH), 10.43 (1H, sl, OH), 7.48 (1H, t, $CH_{arom}$), 7.05 (1H, d, $CH_{arom}$), 6.85 (1H, s, $CH_{arom}$), 6.80 (1H, d, $CH_{arom}$), 6.75-6.68 (2H, m, $CH_{arom}$), 5.10 (2H, sl, $NH_2$), 3.59-3.49 (4H, m, 2×$CH_2$), 2.95-2.77 (4H, m, 2×$CH_2$), 2.90 (3H, s, $CH_3$), 1.43 (9H, s, 3×$CH_3$).

Particular Procedure E11

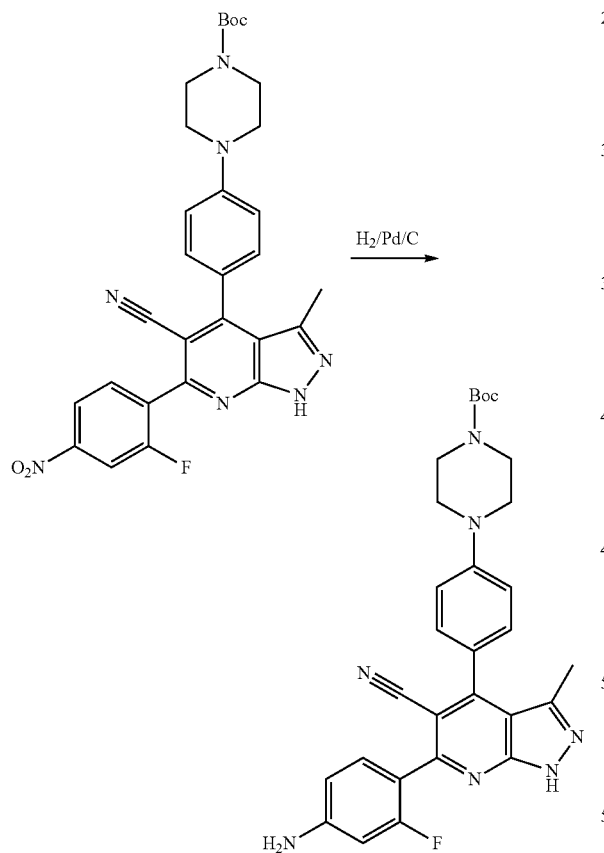

To a solution of 0.15 g (0.27 mmol) of tert-butyl 4-(4-(5-cyano-6-(2-fluoro-4-nitrophenyl)-3-methyl-1H-pyrazolo[3,4-b]pyridin-4-yl)phenyl)piperazine-1-carboxylate in 15 ml of ethanol are added 0.037 g (0.035 mmol) of 10% Pd/C. The mixture is stirred at room temperature for 18 h under hydrogen atmospheric pressure. The mixture is then concentrated, re-dissolved in dichloromethane, filtered through Celite, and concentrated. The residue is purified by chromatography on silica (MeOH gradient in dichloromethane: 0 to 5%) to yield 0.020 g (14%) of tert-butyl 4-(4-(6-(4-amino-2-fluorophenyl)-5-cyano-3-methyl-1H-pyrazolo[3,4-b]pyridin-4-yl)phenyl)piperazine-1-carboxylate in the form of yellow crystals.

$^1$H-NMR: $\delta_H$ pm 400 MHz, DMSO: 14.10 (1H, s, OH), 11.07 (1H, sl, NH), 8.20 (1H, dd, $CH_{arom}$), 7.93 (1H, d, $CH_{arom}$), 7.42 (1H, $CH_{arom}$), 6.90 (1H, dd, $CH_{arom}$), 2.46 (3H, s, $CH_3$).

Particular Procedure E13

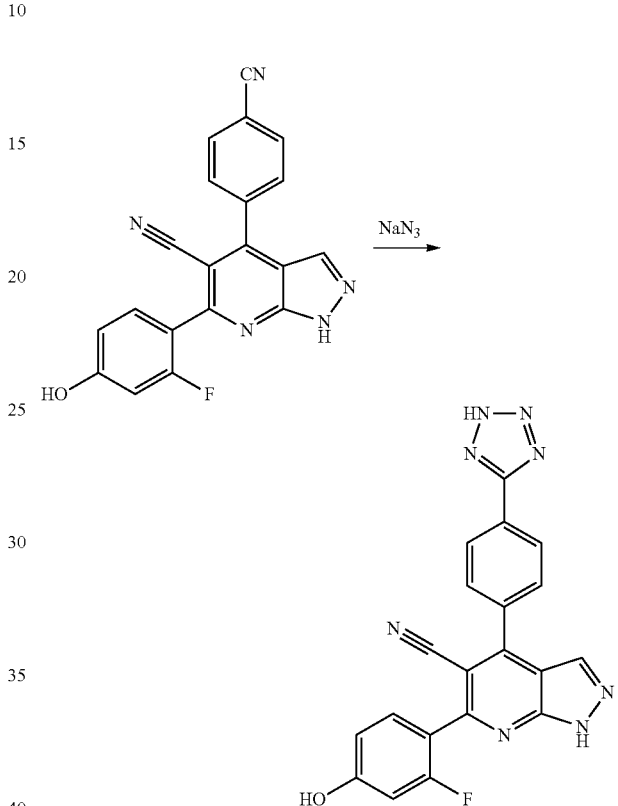

LCMS (ESI, m/z): (M+1) 528.24.

Particular Procedure E12

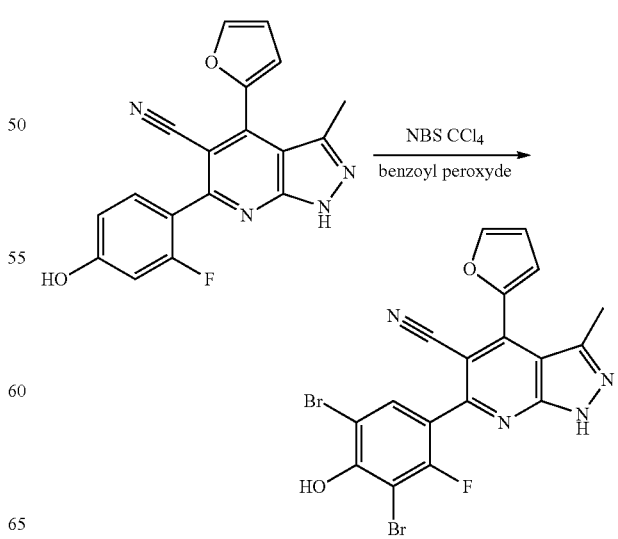

A solution of 97 mg (0.29 mmol) of 6-(2-fluoro-4-hydroxyphenyl)-4-(furan-2-yl)-3-methyl-1H-pyrazolo[3,4-b]pyridine-5-carbonitrile, 52 mg (0.29 mmol) of N-bromosuccinimide (NBS) and 0.7 mg (0.029 mmol) of benzoyl peroxide in 5 ml carbon tetrachloride is refluxed for 1 h30. An additional 104 mg (0.58 mmol) of N-bromosuccinimide and 1.4 mg (0.058 mmol) of benzoyl peroxide are added and the reaction mixture is refluxed for 2 h30. After return to room temperature, the mixture is filtered. The solid obtained is purified by chromatography on silica (methanol gradient in dichloromethane: 0 to 5%) to give 0.098 g (94%) of 6-(3,5-dibromo-2-fluoro-4-hydroxyphenyl)-4-(furan-2-yl)-3-methyl-1H-pyrazolo[3,4-b]pyridine-5-carbonitrile in the form of brown crystals.

LCMS (ESI, m/z): (M+1) 490.91

$^1$H-NMR: $\delta_H$ pm 400 MHz, DMSO: 14.10 (1H, s, OH), 11.07 (1H, sl, NH), 8.20 (1H, dd, $CH_{arom}$), 7.93 (1H, d, $CH_{arom}$), 7.42 (1H, $CH_{arom}$), 6.90 (1H, dd, $CH_{arom}$), 2.46 (3H, s, $CH_3$).

Particular Procedure E13

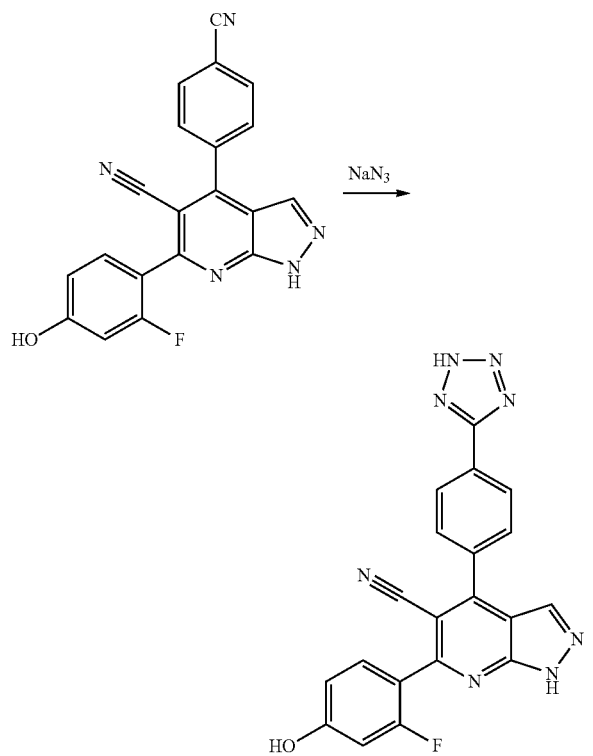

To a solution of 100 mg (0.28 mmol) of 4-(4-cyanophenyl)-6-(2-fluoro-4-hydroxyphenyl)-1H-pyrazolo[3,4-b]pyridine-5-carbonitrile in 5 ml of anhydrous DMF are added 84 mg (1.12 mmol) of sodium azide and 305 μL (366 mg, 1.12 mmol) of tributyltin chloride. The mixture is heated to 130° C. under nitrogen for 8 h. Then 19 mg (0.28 mmol) of sodium azide and 77 μL (92 mg, 0.28 mmol) of tributyltin chloride are added, and the mixture is again heated to 130° C. for 48 h.

After return to room temperature, the mixture is poured onto a water/ice mixture and acidified with a 6N HCl solution. The aqueous phase is extracted once with dichloromethane and twice with chloroform. The organic phase is washed with sodium chloride saturated solution, dried over sodium sulfate, filtered, and concentrated. The solid obtained is then purified by chromatography on silica (methanol gradient in dichloromethane: 15 to 25%) to give 0.032 g (29%) of 4-(4-(2H-tetrazole-5-yl)phenyl)-6-(2-fluoro-4-hydroxyphenyl)-1H-pyrazolo[3,4-b]pyridine-5-carbonitrile in the form of beige crystals.

LCMS (ESI, m/z); (M+1) 399.10

$^1$H-NMR: $\delta_H$ pm 400 MHz, DMSO: 14.41 (1H, s, OH), 10.45 (1H, s, NH), 8.30 (1H, s, $CH_{arom}$), 8.30 (2H, d, $CH_{arom}$), 8.03 (2H, d, $CH_{arom}$), 7.95 (1H, s, NH), 7.55 (1H, t, $CH_{arom}$), 6.81 (1H, dd, $CH_{arom}$), 6.76 (1H, dd, $CH_{arom}$).

Particular Procedure E14

(By analogy with Otomaru, Y., Senda, T., Hayashi, T., Org. Lett., 2004, 6, 3357-3359).

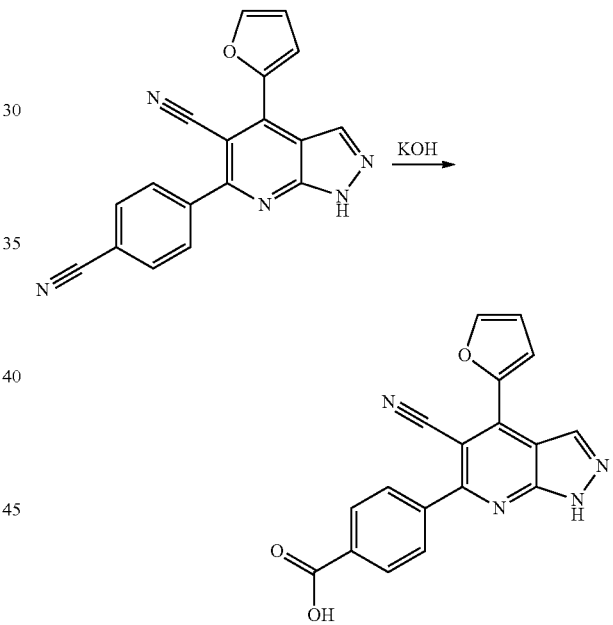

A solution of 0.10 g (0.32 mmol) of 6-(4-cyanophenyl)-4-(furan-2-yl)-1H-pyrazolo[3,4-b]pyridine-5-carbonitrile and 0.22 g (4.0 mmol) of potassium hydroxide in a mixture of 2 ml of dioxane, 2 ml of MeOH, and 0.75 ml of water is refluxed for 24 h. Next, the mixture is cooled, acidified with 1N HCl, then extracted with ethyl acetate and dichloromethane. The organic phase is dried over sodium sulfate, filtered and concentrated to give 0.018 g (17%) of 4-(5-cyano-4-(furan-2-yl)-1H-pyrazolo[3,4-b]pyridine-6-yl)benzoic acid in the form of brown crystals.

LCMS (ESI, m/z): (M+1) 331.08

$^1$H-NMR: $\delta_H$ pm 400 MHz, DMSO: 14.40 (1H, sl, $CO_2H$), 13.22 (1H, sl, NH), 8.72 (1H, s, $CH_{arom}$), 8.25 (1H, dd $CH_{arom}$), 8.12 (2H, d, $CH_{arom}$), 7.96 (2H, d, $CH_{arom}$), 7.87 (1H, dd, $CH_{arom}$), 6.95 (1H, dd, $CH_{arom}$).

Particular Procedure E15

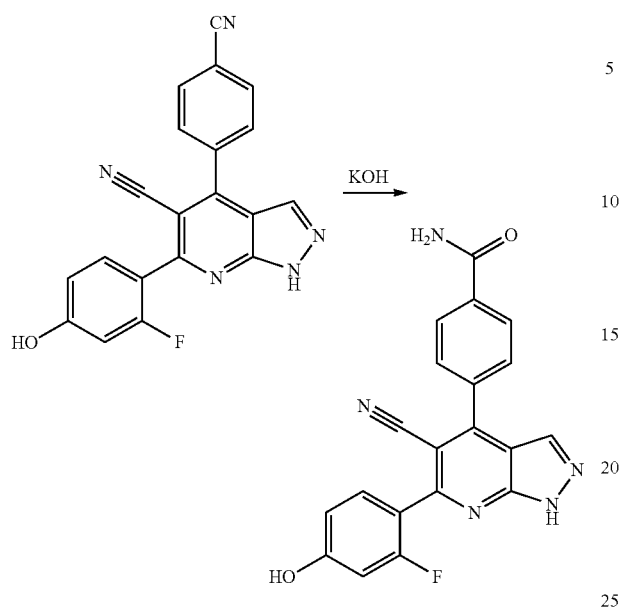

A solution of 0.06 g (0.17 mmol) of 4-(4-cyanophenyl)-6-(2-fluoro-4-hydroxyphenyl)-1H-pyrazolo[3,4-b]pyridine-5-carbonitrile and 0.08 g (1.40 mmol) of potassium hydroxide in 6 ml of tert-butanol is refluxed for 4 h. The mixture is then cooled to room temperature, diluted with water, acidified with 1N HCl, and extracted with dichloromethane. The organic phase is dried over sodium sulfate, filtered, and concentrated. The solid obtained is then purified by chromatography on silica (methanol gradient in dichloromethane: 0 to 10%) to yield 0.019 g (30%) of 4-(5-cyano-6-(2-fluoro-4-hydroxyphenyl)-1H-pyrazolo[3,4-b]pyridine-4-yl)benzamide in the form of yellow crystals.

LCMS (ESI, m/z): (M+1) 374.10

$^1$H-NMR: $\delta_H$ pm 400 MHz, DMSO: 8.22 (1H, s, CH$_{arom}$), 8.19 (1H, s, NH), 8.12 (2H, d, CH$_{arom}$), 7.88 (2H, d, CH$_{arom}$), 7.57 (1H, s, NH), 7.51 (1H, t, CH$_{arom}$), 6.79 (1H, CH$_{arom}$), 6.74 (1H, dd, CH$_{arom}$).

Particular Procedure E16

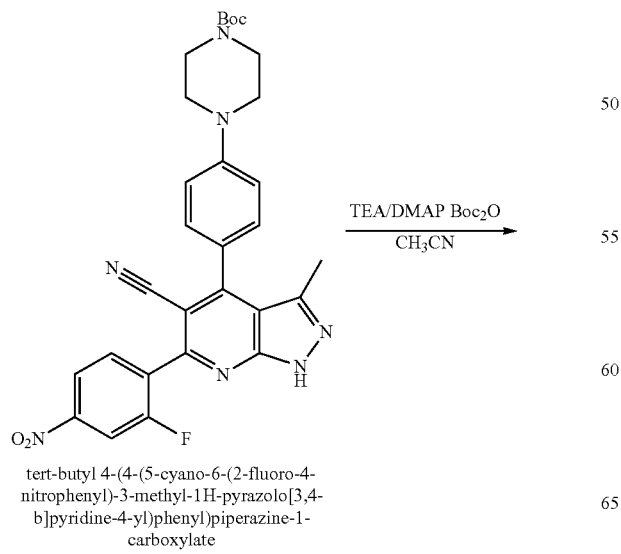

tert-butyl 4-(4-(5-cyano-6-(2-fluoro-4-nitrophenyl)-3-methyl-1H-pyrazolo[3,4-b]pyridine-4-yl)phenyl)piperazine-1-carboxylate -continued

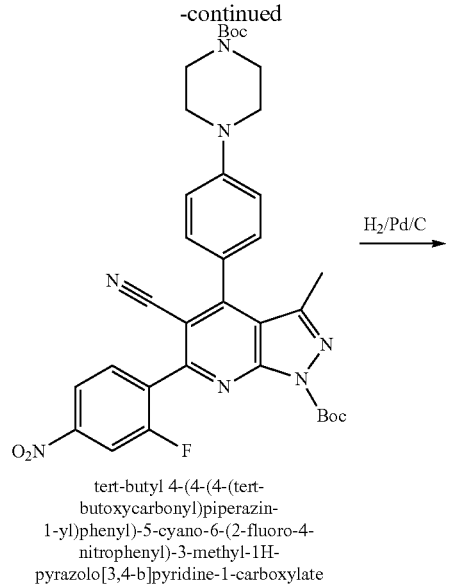

tert-butyl 4-(4-(4-(tert-butoxycarbonyl)piperazin-1-yl)phenyl)-5-cyano-6-(2-fluoro-4-nitrophenyl)-3-methyl-1H-pyrazolo[3,4-b]pyridine-1-carboxylate

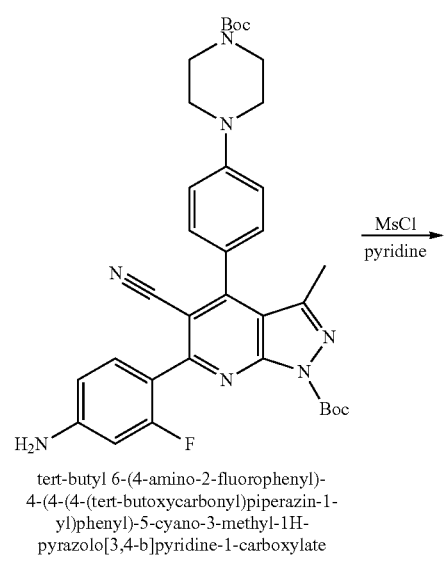

tert-butyl 6-(4-amino-2-fluorophenyl)-4-(4-(4-(tert-butoxycarbonyl)piperazin-1-yl)phenyl)-5-cyano-3-methyl-1H-pyrazolo[3,4-b]pyridine-1-carboxylate

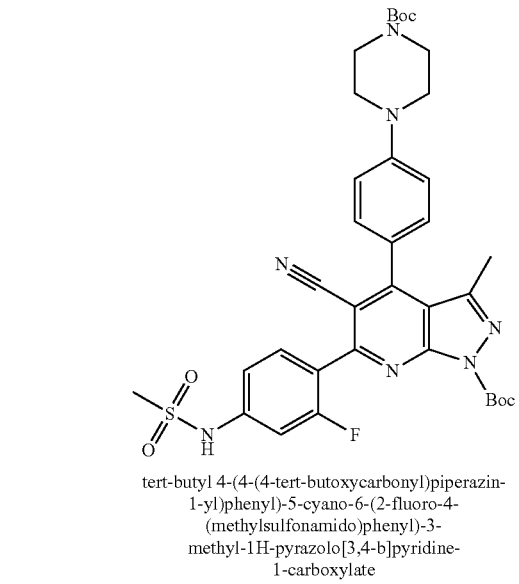 [SMILES: Cc1nn(C(=O)OC(C)(C)C)c2nc(-c3ccc(NS(C)(=O)=O)cc3F)c(C#N)c(-c3ccc(N4CCN(C(=O)OC(C)(C)C)CC4)cc3)c12]

tert-butyl 4-(4-(4-(4-tert-butoxycarbonyl)piperazin-1-yl)phenyl)-5-cyano-6-(2-fluoro-4-(methylsulfonamido)phenyl)-3-methyl-1H-pyrazolo[3,4-b]pyridine-1-carboxylate The diprotected derivative: tert-butyl 4-(4-(4-(tert-butoxy-carbonyl)piperazin-1-yl)phenyl)-5-cyano-6-(2-fluoro-4-nitrophenyl)-3-methyl-1H-pyrazolo[3,4-b]pyridine-1-carboxylate is obtained by analogy with the method of Zhu, G.-D., Gong, J., Gandhi, V. B., Woods, K., Luo, Y., Liu, X., Guan, R., Klinghofer, V., Johnson, E. F., Stoll, V. S., Mamo, M., Li, Q., Rosenberg, S. H., Giranda, V. L., Bioorg. Med. Chem., 2007, 15, 2441-2452. The reduced derivative: tert-butyl 6-(4-amino-2-fluorophenyl)-4-(4-(4-tert-butoxycarbonyl)piperazin-1-yl)phenyl)-5-cyano-3-methyl-1H-pyrazolo[3,4-b]pyridine-1-carboxylate is obtained following general procedure F8. To a solution of 0.60 g (0.96 mmol) of reduced derivative in 2.4 ml of pyridine at 0° C. are added dropwise 110 µL (164 mg, 1.42 mmol) of methanesulfonyl chloride. The mixture is stirred at room temperature for 1 h. It is then concentrated, diluted with water and dichloromethane, washed with water and a saturated sodium chloride solution. The organic phase is dried over magnesium sulfate, filtered, and concentrated. The solid obtained is then purified by chromatography on silica (AcOEt gradient in dichloromethane: 10 to 15%), then purified by reverse-phase HPLC to give 168 mg (25%) of tert-butyl 4-(4-(4-tert-butoxycarbonyl)piperazin-1-yl)phenyl)-5-cyano-6-(2-fluoro-4-(methylsulfonamido)phenyl)-3-methyl-1H-pyrazolo[3,4-b]pyridine-1-carboxylate in the form of a yellow solid. The double deprotection following general procedure E2 yields 0.12 g (94%) of N-(4-(5-cyano-3-methyl-4-(4-piperazine-1-yl)phenyl)-1H-pyrazolo[3,4-b]pyridine-6-yl)-3-fluorophenyl) methane sulfonamide hydrochloride in the form of an orange solid.

LCMS (ESI, m/z): (M+1) 506.1

$^1$H-NMR: $\delta_H$ pm 400 MHz, DMSO: 13.99 (1H, sl, NH), 10.44 (1H, sl, NH), 8.98 (2H, sl, NH$_2$), 7.67 (1H, t, CH$_{arom}$), 7.54 (2H, d, CH$_{arom}$), 7.23-7.14 (4H, m, CH$_{arom}$), 3.54 (4H, m), 3.28 (4H, m), 3.19 (3H, s, CH$_3$), 2.12 (3H, s, CH$_3$).

Particular Procedure E17

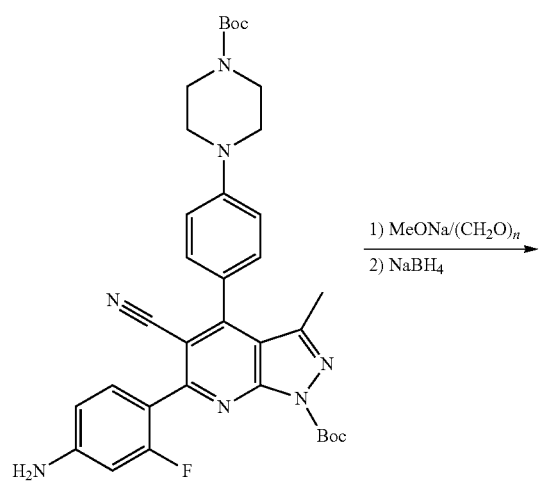

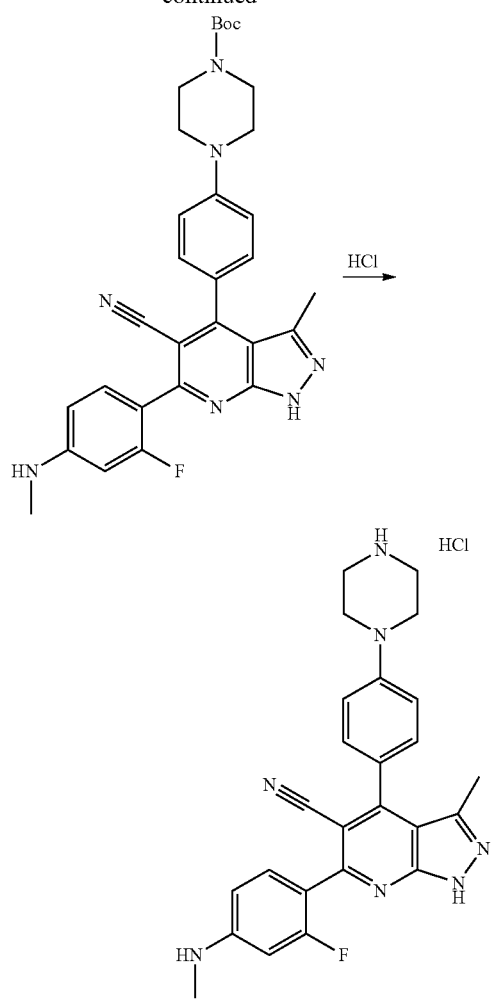

To a solution of 0.20 g (0.32 mmol) of tert-butyl 6-(4-amino-2-fluorophenyl)-4-(4-(4-(tert-butoxycarbonyl)piperazin-1-yl)phenyl)-5-cyano-3-methyl-1H-pyrazolo[3,4-b]pyridine-1-carboxylate in 40 ml of MeOH are added 0.16 mg (2.9 mmol) of sodium methoxide and 0.10 g (3.2 mmol) of paraformaldehyde. The reaction mixture is refluxed for 2 h. The mixture is then cooled, 0.24 g (6.34 mmol) of sodium borohydride is added, and the mixture is refluxed for 1 h. The mixture is then cooled, diluted with iced water, then extracted with dichloromethane. The organic phase is dried over magnesium sulfate, filtered, and concentrated. The solid obtained is then purified by chromatography on silica (methanol gradient in dichloromethane: 1 to 2%) to give 0.036 g (18%) of tert-butyl 4-(4-(5-cyano-6-(2-fluoro-4-(methylamino)phenyl)-3-methyl-1H-pyrazolo[3,4-b]pyridin-4-yl)phenyl)piperazine-1-carboxylate in the form of yellow crystals. Deprotection of the piperazine following general procedure E2 gives 0.02 g (68%) of 6-(2-fluoro-4-(methylamino)phenyl)-3-methyl-4-(4-(piperazine-1-yl)phenyl)-1H-pyrazolo[3,4-b]pyridine-5-carbonitrile hydrochloride in the form of orange crystals.

LCMS (ESI, m/z): (M+1) 442.2

$^1$H-NMR: $\delta_H$ pm 400 MHz, DMSO: 13.81 (1H, sl, NH), 9.16 (1H, sl, NH), 7.50 (2H, d, CH$_{arom}$), 7.38 (1H, t, CH$_{arom}$), 7.18 (2H, d, CH$_{arom}$), 6.52 (1H, dd, CH$_{arom}$), 6.41 (1H, dd CH$_{arom}$), 3.47-3.59 (4H, m), 3.18-3.33 (4H, m), 2.74 (3H, s, NCH$_3$), 2.08 (3H, s, CH$_3$).

General Procedure E18

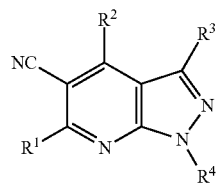

→

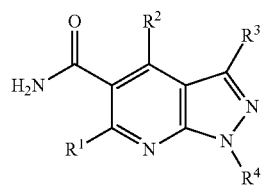

Example of Synthesis Following Procedure E18

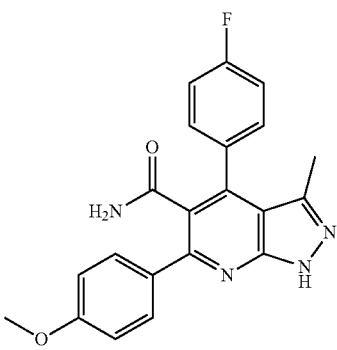

4-(4-fluorophenyl)-6-(4-methoxyphenyl)-3-methyl-1H-pyrazolo[3,4-b]pyridine-5-carboxamide To 140 mg (390 μmol) of 4-(4-fluorophenyl)-6-(4-methoxyphenyl)-3-methyl-1H-pyrazolo[3,4-b]pyridine-5-carbonitrile obtained following general procedure D1, in solution in 2 ml of xylene, are added 1 g of polyphosphoric acid. The reaction mixture is stirred at 110° C. for 20 h. Water is added and the product is extracted several times with ethyl acetate. The organic phases are combined, dried over magnesium sulfate, and concentrated. The residue is purified by chromatography on silica (dichloromethane/methanol eluent: 6:4 then 4:6) to give 52 mg (35%) of 4-(4-fluorophenyl)-6-(4-methoxyphenyl)-3-methyl-1H-pyrazolo[3,4-b]pyridine-5-carboxamide in the form of a yellow solid.

$^1$H-NMR: δ$_H$ pm 400 MHz, DMSO: 13.38 (1H, sl, NH), 7.78 (2H, d CH$_{arom}$), 7.63 (1H, sl, NH), 7.51-7.45 (2H, m, CH$_{arom}$), 7.32 (2H, t, CH$_{arom}$), 7.22 (1H, sl, NH), 7.01 (2H, d, CH$_{arom}$), 3.81 (3H, s, CH$_3$), 1.87 (3H, s, CH$_3$).

Particular Procedure E19

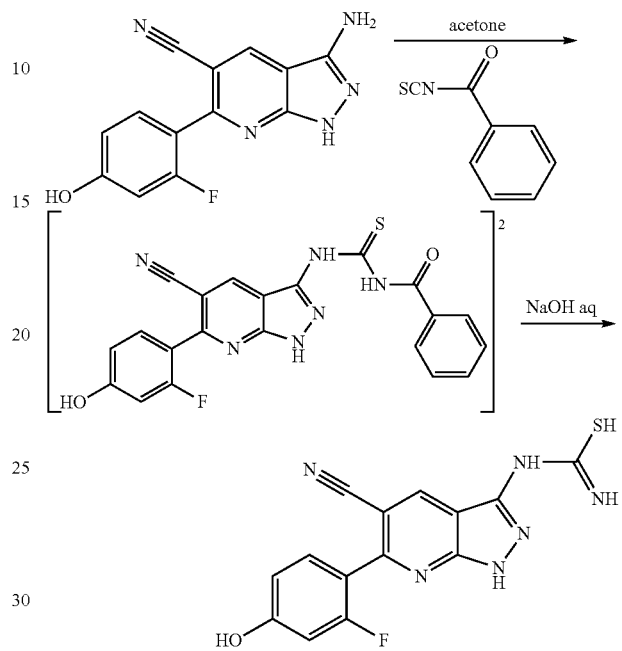

To 85 mg (0.52 mmol) of benzoyl isothiocyanate diluted in 2 ml of acetone are added at 0° C. 140 mg (0.52 mmol) of 3-amino-6-(2-fluoro-4-hydroxyphenyl)-1H-pyrazolo[3,4-b]pyridine-5-carbonitrile obtained following general procedure D1 and diluted in 5 ml of acetone. The solution is stirred for 1 h at 0° C. and for 18 h at room temperature. The solvent is concentrated and the solid is triturated in diethyl ether. This is diluted in an aqueous sodium hydroxide solution (5 wt. %) and the reaction mixture is stirred for 1 h30 at 80° C. A solution of hydrochloric acid (1M) is added at room temperature until the solution reaches a pH in the order of 5. The product is extracted several times with ethyl acetate. The organic phases are combined, dried over magnesium sulfate, and concentrated. The residue obtained is triturated in methanol to yield 76 mg of N-(5-cyano-6-(2-fluoro-4-hydroxyphenyl)-1H-pyrazolo[3,4-b]pyridine-3-yl)carbamimidothioic acid in the form of a yellow solid.

LCMS (ESI, m/z): (M+1) 329.19

$^1$H-NMR: δ$_H$ pm 400 MHz, DMSO: 13.88 (1H, sl, NH), 11.19 (1H, s, NH), 10.48 (1H, s, OH), 9.21 (1H, s, CH$_{arom}$), 9.11 (1H, sl, NH), 9.03 (1H, sl, SH), 7.49 (1H, dd, CH$_{arom}$), 6.80 (1H, dd, CH$_{arom}$), 6.76 (1H, dd, CH$_{arom}$).

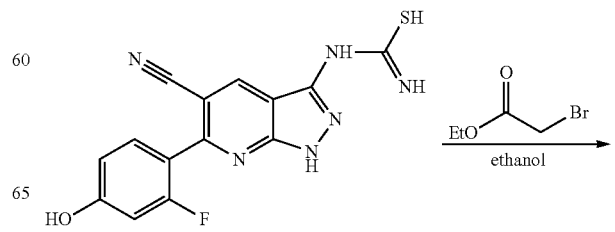

-continued

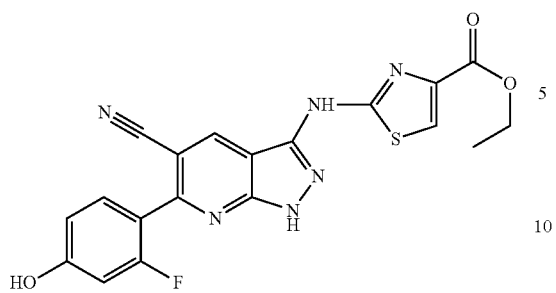

To 66 mg (0.20 mmol) of N-(5-cyano-6-(2-fluoro-4-hydroxyphenyl)-1H-pyrazolo[3,4-b]pyridine-3-yl)carbamimidothioic acid diluted in 2 ml of ethanol are added 57 mg (0.20 mmol, 68%) of ethyl 3-bromo-2-oxopropanoate. The solution is refluxed for 2 h. The solid is filtered, washed with ethanol and dried to give 38 mg of ethyl 2-(5-cyano-6-(2-fluoro-4-hydroxyphenyl)-1H-pyrazolo[3,4-b]pyridine-3-ylamino)thiazole-4-carboxylate in the form of a yellow solid.

LCMS (ESI, m/z): (M+1) 425.23

$^1$H-NMR: $\delta_H$ pm 400 MHz, DMSO: 13.69 (1H, s, NH), 12.31 (1H, sl, NH), 10.46 (1H, sl, OH), 9.01 (1H, s, $CH_{arom}$), 7.98 (1H, s, $CH_{arom}$), 7.49 (1H, dd, $CH_{arom}$), 6.81 (1H, dd, $CH_{arom}$), 6.76 (1H, dd, $CH_{arom}$), 4.29 (2H, q, $CH_2$), 1.32 (3H, t, $CH_3$).

Particular Procedure E20

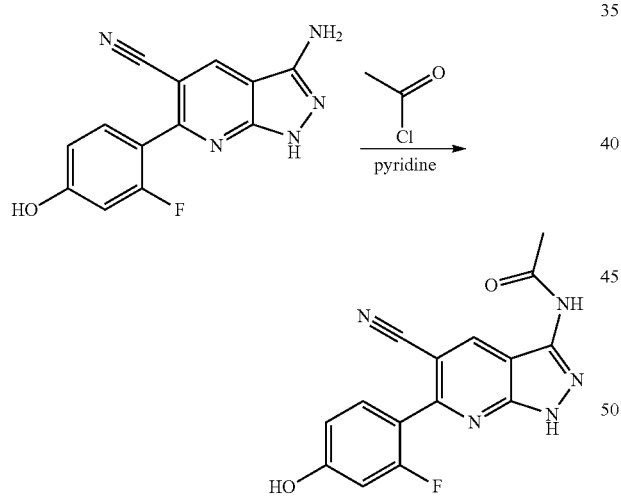

To a mixture of 165 mg (0.66 mmol) of 3-amino-6-(4-hydroxyphenyl)-1H-pyrazolo[3,4-b]pyridine-5-carbonitrile obtained following general procedure D1 and of 180 μL (2.16 mmol) of pyridine diluted in 1.6 ml of anhydrous tetrahydrofuran, are added dropwise at 0° C. 168 mg (2.16 mmol) of acetyl chloride. The solution is stirred under reflux for 4 h, then 655 μL (5M, 3.28 mmol) of sodium hydroxide solution are added, and the mixture is stirred for 1 h30 at 40° C. The tetrahydrofuran is concentrated and the solution is brought to acid pH (in the order of 3/4). The solid is filtered, washed with water, dried, and triturated in ethanol to yield 70 mg of N-(5-cyano-6-(4-hydroxyphenyl)-1H-pyrazolo[3,4-b]pyridine-3-yl)acetamide in the form of a yellow solid.

Particular Procedure E21

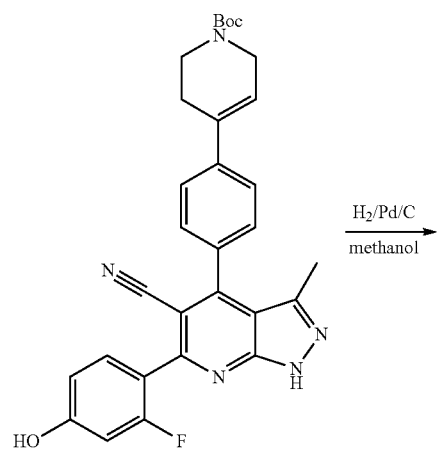

To 96 mg (0.18 mmol) of tert-butyl 4-(4-(5-cyano-6-(2-fluoro-4-hydroxyphenyl)-3-methyl-1H-pyrazolo[3,4-b]pyridine-4-yl)phenyl)piperidine-1-carboxylate prepared following general procedure D1, diluted in 5 ml of methanol and purged under argon, are respectively added 10 mg of 10% palladium on charcoal, then 345 mg (5.48 mmol) of ammonium formate. The reaction is initiated with a heat gun then heated to 40° C. for 18 h. The solution is filtered on Celite, rinsed in ethyl acetate and concentrated. The residue is dissolved in ethyl acetate and again filtered on Celite. The filtrate is concentrated and dried to give 88 mg of tert-butyl 4-(4-(5-cyano-6-(2-fluoro-4-hydroxyphenyl)-3-methyl-1H-pyrazolo[3,4-b]pyridine-4-yl)phenyl)piperidine-1-carboxylate.

LCMS (ESI, m/z): (M+1) 528.2

$^1$H-NMR: $\delta_H$ pm 400 MHz, DMSO: 13.94 (1H, sl, NH), 10.39 (1H, sl, OH), 7.48-7.56 (5H, m, $CH_{arom}$), 6.79 (1H, dd, $CH_{arom}$), 6.73 (1H, dd, $CH_{arom}$), 4.08-4.15 (2H, m, $CH_2$), 2.80-2.89 (3H, m, CH, CH$_2$), 2.01 (3H, s, CH$_3$), 1.84-1.89 (2H, m, CH$_2$), 1.53-1.63 (2H, m, CH$_2$), 1.43 (9H, s, 3CH$_3$).

General Procedure E22

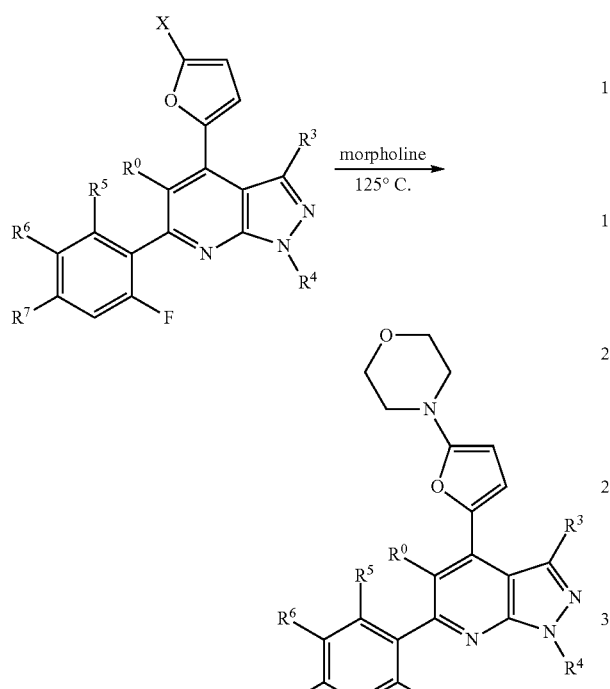

Example of Synthesis Following Procedure E22

3-methyl-4-(5-morpholinofuran-2-yl)-6-(2,3,6-trifluorphenyl)-1H-pyrazolo[3,4-b]pyridine-5-carbonitrile A solution of 2.0 g (5.0 mmol) of 4-(5-chlorofuran-2-yl)-3-methyl-6-(2,3,6-trifluorophenyl)-1H-pyrazolo[3,4-b]pyridine-5-carbonitrile in 11 ml of morpholine is refluxed for 20 h. The mixture is then concentrated, dissolved in dichloromethane and washed three times with 1N hydrochloric acid solution. The organic phase is dried over magnesium sulfate, filtered, and concentrated. The residue obtained is purified by chromatography on silica (ethyl acetate gradient in dichloromethane: 10 to 20%) to give 0.76 g (35%) of 3-methyl-4-(5-morpholinofuran-2-yl)-6-(2,3,6-trifluorphenyl)-1H-pyrazolo[3,4-b]pyridine-5-carbonitrile in the form of yellow crystals.

LCMS (ESI, m/z): (M+1) 440.13

$^1$H-NMR: δ$_H$ pm 400 MHz, DMSO: 13.99 (1H, sl, NH), 7.78 (1H, m, CH$_{arom}$), 7.56 (1H, d, CH$_{arom}$), 7.40 (1H, m, CH$_{arom}$), 5.82 (1H, d, CH$_{arom}$), 3.73 (4H, t, 2CH$_2$), 3.38 (4H, t, 2CH$_2$), 2.60 (3H, s, CH$_3$).

Particular Procedure E23

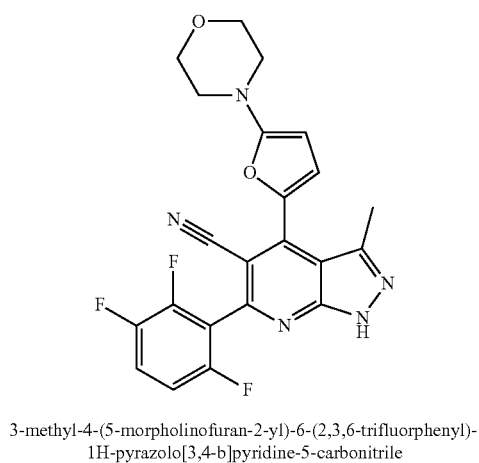 [SMILES: Cc1n[nH]c2nc(-c3c(F)ccc(F)c3F)c(C#N)c(-c3ccc(N4CCOCC4)o3)c12]

To a suspension of 0.066 g (0.10 mmol) of methyl 5-(5-cyano-6-(4-hydroxyphenyl)-1H-pyrazolo[3,4-b]pyridine-4-yl)-2-methylfuran-3-carboxylate in 2 ml of dioxane/water (80:20) are added 0.011 g (0.4 mmol) of lithium hydroxide. The mixture is brought to 50° C. for 5 h. After return to room temperature, the mixture is poured onto 20 ml of iced water and adjusted to pH=1-2 with 0.1N hydrochloric acid solution. The solution is left to stand for 18 h at 4° C. The precipitate obtained is filtered. The residue obtained is purified by preparative reverse-phase HPLC (acetonitrile/water eluent) to yield 3 mg (6%) of 5-(5-cyano-6-(4-hydroxyphenyl)-1H-pyrazolo[3,4-b]pyridine-4-yl)-2-methylfuran-3-carboxylic acid in the form of a yellow solid.

LCMS (ESI, m/z): (M+1) 361.09

$^1$H-NMR: δ$_H$ pm 400 MHz, DMSO: 14.20 (1H, sl, OH), 10.03 (1H, sl, NH), 8.68 (1H, s, CH$_{arom}$), 7.95 (1H, s, CH$_{arom}$), 7.72 (2H, d, CH$_{arom}$), 6.93 (2H, d, CH$_{arom}$), 2.79 (3H, s, CH$_3$).

Particular Procedure E24

(By analogy with M. S. S. Palanki et al, J. Med. Chem., 2008, 51, 6, 1546-1559).

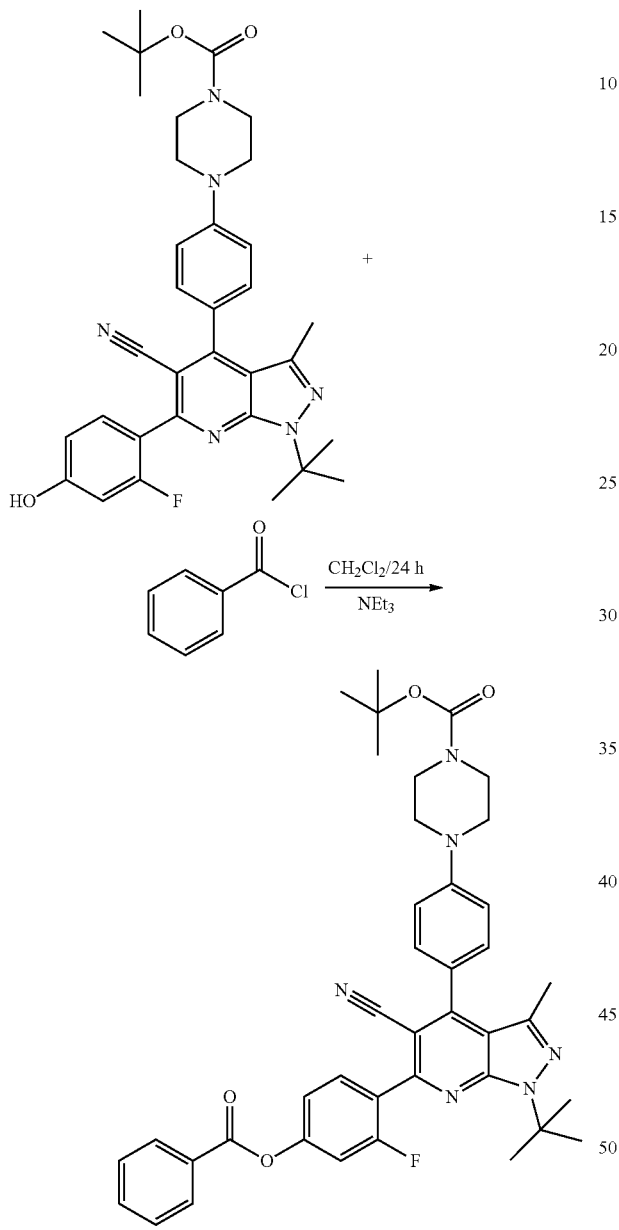

To a solution of 0.33 g (0.56 mmol) of tert-butyl 4-(4-(1-tert-butyl-5-cyano-6-(2-fluoro-4-hydroxyphenyl)-3-methyl-1H-pyrazolo[3,4-b]pyridine-4-yl)phenyl)piperazine-1-carboxylate and 325 µL (0.24 g, 2.3 mmol) of triethylamine in 17 ml of anhydrous dichloromethane are added dropwise 78 µL (0.09 g, 0.67 mmol) of benzoyl chloride. The mixture is stirred at room temperature for 24 h. The mixture is diluted with dichloromethane and washed with water. The aqueous phase is then extracted with dichloromethane. The organic phases are combined, dried over sodium sulfate, and concentrated to give 0.38 g (quantitative) of tert-butyl 4-(4-(6-(4-(benzoyloxy)-2-fluorophenyl)-1-tert-butyl-5-cyano-3-methyl-1H-pyrazolo[3,4-b]pyridine-4-yl)phenyl)piperazine-1-carboxylate which is used in the following step without purification.

LCMS (ESI, m/z): (M+1) 689.32

Particular Procedure E25

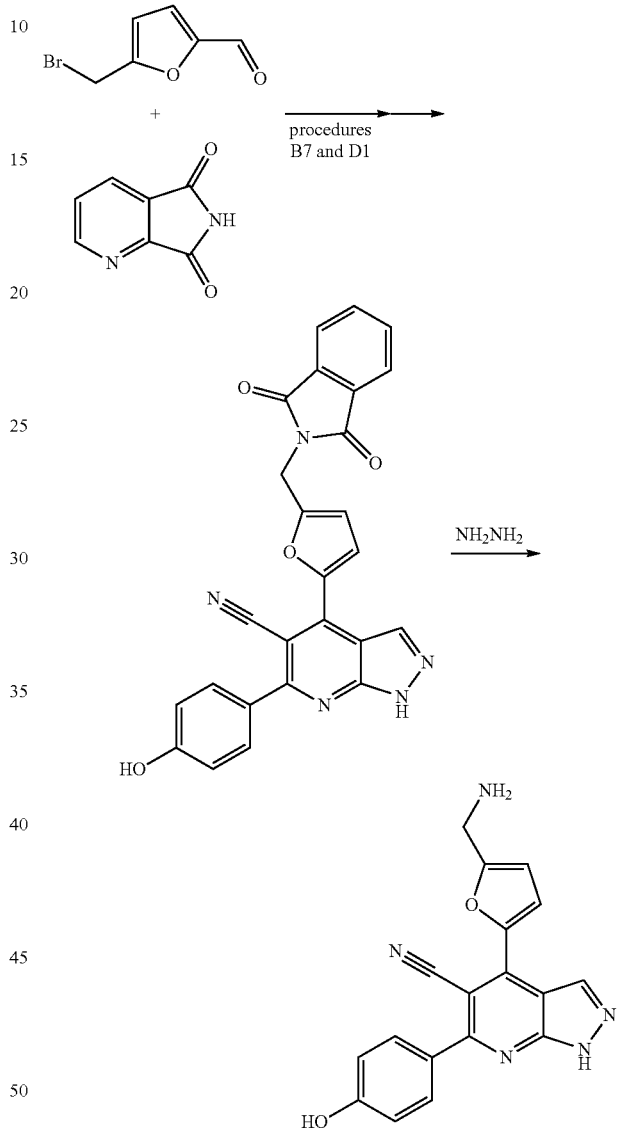

To a suspension of 0.39 g (0.80 mmol) of 4-(5-((1,3-dioxoisoindoline-2-yl)methyl)furan-2-yl)-6-(4-hydroxyphenyl)-1H-pyrazolo[3,4-b]pyridine-5-carbonitrile obtained following the sequences of procedures B7 and D1, in 8 ml of ethanol, are added 368 µL (0.38 g, 7.6 mmol) of hydrazine hydrate. The mixture is refluxed for 3 h. The precipitate obtained is filtered and dissolved in water. The mixture is brought to pH=7-8 with 30% sodium hydroxide and extracted with ethyl acetate. The organic phases are dried over magnesium sulfate, filtered, and concentrated. The residue obtained is purified by silica chromatography (eluent 7N $NH_4OH$ in methanol in dichloromethane: 10:90) to yield 0.057 g (22%) of 4-(5-(aminomethyl)furan-2-yl)-6-(4-hydroxyphenyl)-1H-pyrazolo[3,4-b]pyridine-5-carbonitrile in the form of a yellow solid.

LCMS (ESI, m/z): (M+1) 332.11

$^1$H-NMR: $\delta_H$ pm 400 MHz, DMSO: 8.71 (1H, s, CH$_{arom}$), 7.79 (1H, d, CH$_{arom}$), 7.71 (2H, d, CH$_{arom}$), 6.92 (2H, d, CH$_{arom}$), 6.66 (1H, d, CH$_{arom}$), 3.92 (2H, s, CH$_2$).

Particular Procedure E26

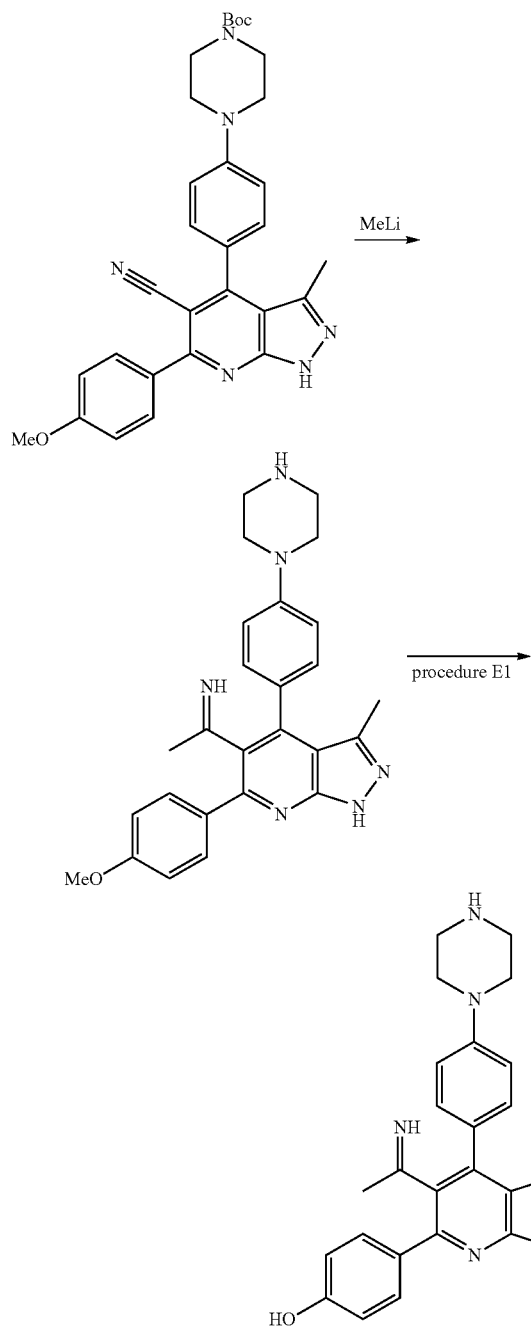

To a solution of 0.6 g (1.246 mmol) of tert-butyl 4-(4-(5-cyano-6-(4-methoxyphenyl)-3-methyl-1H-pyrazolo[3,4-b]pyridine-4-yl)phenyl)piperazine-1-carboxylate in 15 ml of anhydrous tetrahydrofuran at 0° C. are added dropwise under argon a solution of 1.94 ml of methyl lithium (1.6M in hexane, 3.10 mmol). The reaction mixture is stirred 30 minutes at −0° C. then heated to 40° C. for 2 hours. A methanol solution is added at 0° C. and the solvent is concentrated.

The solid obtained (620 mg, yield=90%) of 1-(6-(4-methoxyphenyl)-3-methyl-4-(4-(piperazin-1-yl)phenyl)-1H-pyrazolo[3,4-b]pyridin-5-yl)ethanimine is directly used in the following step without purification following deprotection procedure E1 to yield 62 mg of 4-(5-(1-iminoethyl)-3-methyl-4-(4-(piperazin-1-yl)phenyl)-1H-pyrazolo[3,4-b]pyridin-6-yl)phenol in the form of a beige solid.

LCMS (ESI, m/z): (M+1) 427.10

$^1$H-NMR: $\delta_H$ pm 400 MHz, DMSO: 13.99 (1H, sl, NH), 9.92 (1H, sl, NH), 9.71 (1H, sl, OH), 8.66 (2H, sl, NH), 7.44 (2H, d, CH$_{arom}$), 7.27 (2H, d, CH$_{arom}$), 7.06 (2H, d, CH$_{arom}$), 6.81 (2H, d, CH$_{arom}$), 3.43 (4H, m, 2CH$_2$), 3.26 (4H, m, 2CH$_2$), 2.60 (3H, s, CH$_3$).

II—Biological Results

Test to Measure ALK Kinase Inhibition

A ViewPlate (Packard) is incubated with the GST-PLCγ1 substrate (purified recombinant form) at 0.1 mg/ml in phosphate buffer (PBS pH 7.4)(100 μl/well) for one hour under shaking. The plate is then saturated with a blocking solution containing 5% bovine serum albumin (BSA) (SIGMA) in PBS buffer pH 7.4.

After adding the inhibitor at the desired final concentration (usual range of 30 μM to 10 nM), the reaction is conducted by adding the ALK kinase at 180 ng/ml in 13 mM Tris reaction buffer pH 7.5 (SIGMA); 6.5 mM MgCl$_2$ (MERCK); 0.65 mM DiThioThreitol (DTT) (ACROS); 39 mM sodium β-glycerophosphate (TCI); 0.65 mM sodium orthovanadate (SIGMA) and 250 μM ATP (SIGMA). Incubation is carried out for 30 minutes at 30° C. under shaking.

After three washings under shaking in 0.1% PBS/Tween-20 buffer (SIGMA), an anti-phosphotyrosine antibody coupled with HRP (UBI) diluted to $1/1000^{th}$ in PBS/BSA buffer 5 mg/ml, is incubated for one hour under shaking. After three further washings in 0.1% PBS/Tween-20, the wells are incubated two minutes with 100 μl of SuperSignal ELISA mixture (PIERCE).

The signal is read in luminescent mode using a luminometer (MOLECULAR DEVICES SpectraMax M5e).

Measurement of Inhibition of Cell Proliferation (Karpas):

The antiproliferative activities of the compounds were measured using the ATPlite technique (Perkin Elmer).

The non-adhering cells (karpas 299) are seeded in 96-well plates (300 000 cells/ml) on Day 1 at a concentration compatible with logarithmic growth for 72 hours required for evaluation of the compounds. All the cells are treated on Day 1, then placed in an incubator at 37° C. under 5% CO$_2$ atmosphere. Cell viability is evaluated on Day 4 by assay of released ATP, characteristic of viable cells. The IC$_{50}$ values are determined by non-linear regression on the basis of a sigmoid model of dose/response relationship, Hill's slope coefficient being left variable, performed using GraphPad software sequence with the supplied algorithm.

The results of these two tests obtained with the compounds of the invention are given below:

| Composé | ALK IC$_{50}$ μM(*) | Karpas IC$_{50}$ μM(*) |
|---|---|---|
| 17 | B | C |
| 19 | B | C |
| 44 | A | B |

-continued

| Composé | ALK IC$_{50}$ μM(*) | Karpas IC$_{50}$ μM(*) |
|---|---|---|
| 45 | B | C |
| 47 | C | C |
| 48 | B | C |
| 50 | B | C |
| 52 | B | C |
| 53 | B | C |
| 54 | C | D |
| 59 | B | C |
| 68 | B | C |
| 73 | B | — |
| 74 | B | — |
| 75 | A | B |
| 76 | B | C |
| 77 | B | C |
| 78 | B | C |
| 80 | B | C |
| 81 | A | B |
| 82 | B | C |
| 83 | A | B |
| 84 | B | C |
| 85 | B | C |
| 86 | A | C |
| 87 | A | B |
| 88 | A | B |
| 90 | C | D |
| 91 | A | C |
| 92 | A | B |
| 93 | D | B |
| 96 | B | C |
| 101 | C | C |
| 102 | A | B |
| 103 | B | D |
| 104 | A | C |
| 105 | B | C |
| 106 | B | C |
| 108 | A | C |
| 113 | A | B |
| 114 | B | C |
| 115 | B | C |
| 116 | B | C |
| 117 | A | B |
| 118 | A | C |
| 119 | B | C |
| 120 | B | C |
| 121 | A | C |
| 122 | A | C |
| 123 | B | C |
| 124 | A | C |
| 130 | A | B |
| 131 | B | C |
| 132 | A | D |
| 133 | A | B |
| 134 | A | C |
| 135 | B | D |
| 136 | C | D |
| 137 | B | D |
| 138 | B | D |
| 142 | A | D |
| 143 | C | D |
| 146 | B | D |
| 147 | C | D |
| 148 | C | C |
| 150 | B | D |
| 152 | B | D |
| 153 | A | C |
| 154 | A | B |
| 155 | A | C |
| 156 | A | B |
| 158 | C | D |
| 159 | A | B |
| 160 | C | D |
| 161 | B | D |
| 162 | A | B |
| 163 | A | C |
| 164 | B | D |

-continued

| Composé | ALK IC$_{50}$ μM(*) | Karpas IC$_{50}$ μM(*) |
|---|---|---|
| 165 | B | C |
| 167 | B | C |
| 168 | C | D |
| 169 | A | B |
| 171 | B | B |
| 172 | B | C |
| 175 | B | C |
| 176 | B | B |
| 177 | B | C |
| 178 | A | B |
| 180 | A | B |
| 181 | A | C |
| 182 | A | C |
| 183 | A | C |
| 184 | A | B |
| 185 | A | B |
| 186 | A | C |
| 187 | A | C |
| 188 | A | C |
| 189 | B | C |
| 190 | A | C |
| 191 | A | C |
| 192 | A | C |
| 193 | A | C |
| 194 | A | B |
| 195 | A | C |
| 196 | C | B |
| 197 | A | B |
| 198 | A | B |
| 199 | A | D |
| 200 | A | B |
| 201 | A | D |
| 202 | B | D |
| 203 | B | C |
| 204 | A | B |
| 206 | A | B |
| 208 | C | D |
| 209 | B | C |
| 210 | B | C |
| 211 | B | D |
| 212 | C | D |
| 213 | A | C |
| 215 | A | B |
| 217 | C | C |
| 218 | A | C |
| 219 | C | C |
| 221 | B | C |
| 222 | C | D |
| 223 | A | B |
| 226 | B | C |
| 228 | B | C |
| 230 | B | C |
| 231 | C | C |
| 233 | B | D |
| 234 | B | C |
| 235 | B | C |
| 236 | A | B |
| 238 | B | C |
| 239 | B | B |
| 242 | B | C |
| 244 | A | B |
| 245 | B | C |
| 247 | B | C |
| 248 | C | C |
| 251 | A | B |
| 252 | B | C |
| 253 | B | C |
| 254 | B | C |
| 255 | C | C |
| 256 | A | C |
| 260 | B | C |
| 270 | B | D |
| 271 | B | D |
| 272 | C | C |
| 273 | B | D |

-continued

| Composé | ALK IC$_{50}$ μM$^{(*)}$ | Karpas IC$_{50}$ μM$^{(*)}$ |
|---|---|---|
| 274 | C | C |
| 275 | B | D |
| 276 | D | C |
| 277 | B | D |
| 278 | A | B |
| 279 | C | D |
| 280 | C | C |
| 281 | C | C |
| 282 | C | D |
| 283 | B | C |
| 284 | A | A |
| 285 | A | C |
| 286 | A | B |
| 287 | A | C |
| 288 | C | D |
| 289 | A | B |
| 290 | C | C |
| 291 | C | C |
| 292 | A | A |
| 293 | A | A |
| 294 | A | B |
| 295 | A | B |
| 296 | B | B |
| 297 | B | B |
| 298 | B | D |
| 299 | A | C |
| 300 | A | A |
| 301 | B | D |
| 302 | D | — |
| 303 | C | — |
| 304 | C | — |
| 305 | A | — |
| 306 | A | — |
| 307 | A | — |

(*)A: IC50 < 100 nM; B: 100 nM < IC50 < 1 μM; C: 1 μM < IC50 < 10 μM; D > 10 μM; —: not tested.

Abbreviations:
Boc tert-Butoxycarbonyl
Bn Benzyl
CAN Ceric ammonium nitrate
DCC Dicyclohexylcarbodiimide
DCE 1,1-Dichloroethane
DCM Dichloromethane
DDQ 2,3-Dichloro-5,6-dicyano-1,4-benzoquinone
DMAc N,N-Dimethylacetamide
DMAP N,N-4-Dimethylaminopyridine
DMF Dimethylformamide
DMSO Dimethylsulfoxide
EDCI 1-Ethyl-3(3-dimethylaminopropyl)carbodiimide
ESI Electrospray ionization
HOBT 1-Hydroxybenzotriazole
HPLC High Performance Liquid Chromatography
LCMS Liquid Chromatography coupled with mass spectrometer
MsCl Mesyl chloride
NBS N-Bromosuccinimide
NMR Nuclear Magnetic resonance
Rfx Reflux
TEA Triethylamine
THF Tetrahydrofuran
TIPS Triisopopylsilyl
TMSCN Trimethylsilyl cyanide.

149 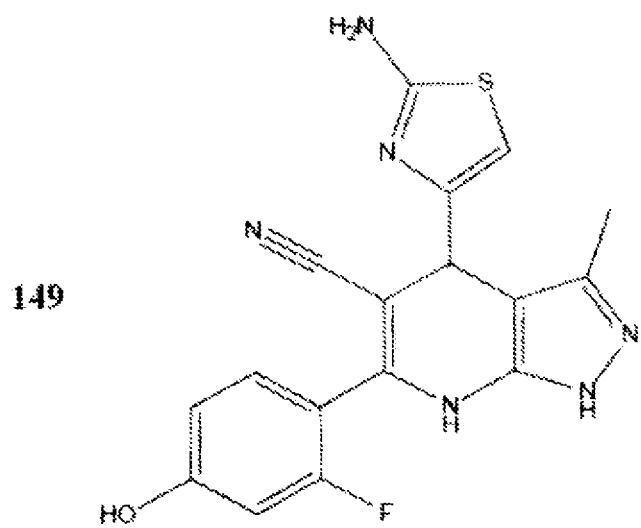

The invention claimed is:
1. A compound of general formula (I)

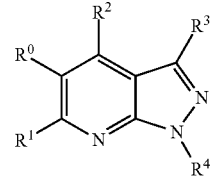

or a pharmaceutically acceptable salt thereof,
wherein:
$R^0$ is a —CN, —CO$_2$H, —CONH$_2$, —CO$_2$-((C$_1$-C$_6$)alkyl), —SO$_2$—((C$_1$-C$_6$)alkyl), —NO$_2$ or —C(=NH)CH$_3$ group,
$R^1$ is an aryl, aryl-(C$_1$-C$_6$))alkyl, or aryl-carbonyloxy group,
the aryl rings of said group being optionally substituted with one or more groups chosen from among a halogen atom, a —OH, —CN, —NO$_2$, —NH$_2$, —CO$_2$H, (C$_1$-C$_6$)alkyl optionally substituted with an OH group, (C$_1$-C$_6$)alcoxy, (C$_1$-C$_6$)haloalkyl, (C$_1$-C$_6$)haloalcoxy, aryl, aryloxy, aryl-(C$_1$-C$_6$)alkyl, aryl-(C$_1$-C$_6$)alcoxy, heteroaryl, heterocycle, —CO$_2$—((C$_1$-C$_6$)alkyl), aryl-carbonyloxy, —NH—((C$_1$-C$_6$)alkyl), and —NHSO$_2$—((C$_1$-C$_6$)alkyl) group; and/or being optionally fused to a heterocycle,
and the heterocycle rings of the whole being optionally substituted with one or more groups chosen from among an oxo(=O) group and a (C$_1$-C$_6$)-alkyl group,
$R^2$ is a (C$_2$-C$_6$)-alkyl, aryl, heteroaryl, cycloalkyl, heterocycle, aryl-(C$_1$-C$_6$)alkyl, aryl-(C$_1$-C$_6$)alkenyl, —X$^1$-heterocycle, -cycloalkyl-X$^2$-heterocycle, and -cycloalkyl-((C$_1$-C$_6$)alkyl-OH group,
the aryl and heteroaryl rings of said group being optionally substituted with one or more groups chosen from among a halogen atom, a group OH; NO$_2$; CO$_2$H; CN; CONH$_2$; SO$_3$H; (C$_1$-C$_6$)alkyl optionally substituted with an OH group; (C$_1$-C$_6$)alkynyl optionally substituted with an NR$^{25}$R$^{26}$ group; (C$_1$-C$_6$)alcoxy; aryl optionally substituted with NH$_2$ and/or SO$_2$NH$_2$; heteroaryl; heterocycle; aryl-(C$_1$-C$_6$)alkyl; heteroaryl-(C$_1$-C$_6$)alkyl; heterocycle-(C$_1$-C$_6$)alkyl; aryl-(C$_1$-C$_6$)alcoxy; heteroaryl-(C$_1$-C$_6$)alcoxy; heterocycle-(C$_1$-C$_6$)alcoxy; NR$^{10}$R$^{11}$; and —X$^3$—((C$_1$-C$_6$)alkyl)NR$^{12}$R$^{13}$; and/or being optionally fused to a heterocycle,
the heterocycle rings of the whole being optionally substituted with one or more groups chosen from among OH; (C$_1$-C$_6$)alkyl optionally substituted with OH or NR$^{27}$R$^{28}$; CO$_2$—((C$_1$-C$_6$)alkyl); heterocycle optionally substituted with a (C$_1$-C$_6$)alkyl group; and NR$^{14}$R$^{15}$,
$R^3$ is a hydrogen atom, a group NH$_2$; NO$_2$; CO$_2$H; (C$_1$-C$_6$) alkyl optionally substituted with a group OR$^{22}$ or NR$^{23}$R$^{24}$; CONH—((C$_1$-C$_6$)alkyl); CONH—((C$_1$-C$_6$)alkyl)-heterocycle; aryl; heteroaryl; heterocycle; aryl-(C$_1$-C$_6$)alkyl; —NH-aryl; or —NH-heteroaryl,
the aryl and heteroaryl rings of said group being optionally substituted with one or more groups chosen from among a halogen atom; a group NO$_2$; CO$_2$H; NR$^{16}$R$^{17}$; aryl; (C$_1$-C$_6$)alkyl; (C$_1$-C$_6$)haloalkyl; (C$_1$-C$_6$)alcoxy; —CO$_2$—(C$_1$-C$_6$)alkyl; and heterocycle, and the heterocycle rings of the whole being optionally substituted with a $(C_1-C_6)$alkyl; $(C_1-C_6)$alcoxy, or —NH—$(C_1-C_6)$alkyl group, and $R^4$ is a hydrogen atom, wherein:

$X^1$ and $X^2$ are each independently —CO—, —CONH— or —CONH—$((C_1-C_6)$alkyl), $X^3$ is a simple bond, an oxygen atom, a sulphur atom, a group NH or N—$((C_1-C_6)$alkyl), $R^{10}$, $R^{11}$, $R^{14}$, $R^{15}$, $R^{18}$, $R^{19}$ and $R^{23}$ to $R^{28}$ are each independently a hydrogen atom or $(C_1-C_6)$alkyl group, $R^{12}$ and $R^{13}$ are each independently a hydrogen atom or a $(C_1-C_6)$alkyl group; or form together, with the nitrogen atom bearing them, a heteroaromatic or a heterocycle optionally substituted with a $(C_1-C_6)$alkyl group, $R^{16}$ and $R^{17}$ are each independently a hydrogen atom or a $(C_1-C_6)$alkyl group optionally substituted with a group $NR^{18}R^{19}$, $R^{20}$ is a hydrogen atom or a $(C_1-C_6)$alkyl, aryl or aryl-$(C_1-C_6)$alkyl group, and $R^{21}$ and $R^{22}$ are each independently a hydrogen atom, or a $(C_1-C_6)$alkyl, aryl, or heteroaryl group, the aryl and heteroaryl rings of said group being optionally substituted with one or more groups chosen from among a halogen atom, a group OH, CN, $NO_2$, $NH_2$, $CO_2H$, $(C_1-C_6)$alkyl, $(C_1-C_6)$alcoxy, $(C_1-C_6)$haloalkyl, $(C_1-C_6)$haloalcoxy, aryl, aryloxy, aryl-$(C_1-C_6)$alkyl, aryl-$(C_1-C_6)$alcoxy, heteroaryl, heterocycle, $CO_2$—$((C_1-C_6)$alkyl); NH—$((C_1-C_6)$alkyl), and $NHSO_2$—$((C_1-C_6)$alkyl); and/or being optionally fused to a heterocycle, and the heterocycle rings of the whole being optionally substituted with a oxo (=O) and/or $(C_1-C_6)$ alkyl group, with the exclusion of the following compounds:

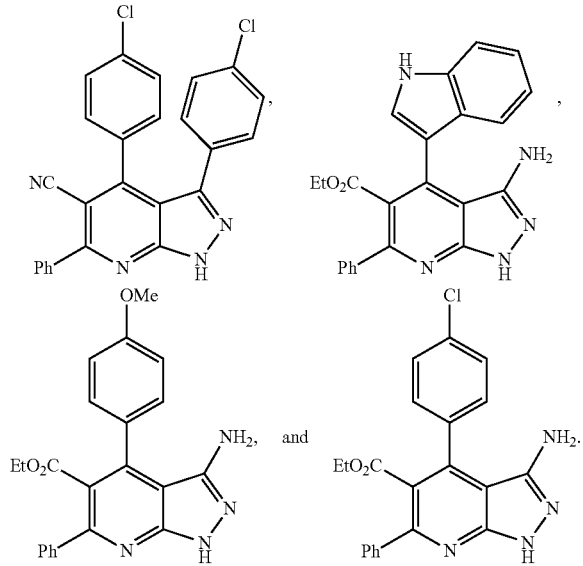

2. The compound according to claim 1, wherein $R^0$ is a CN or $CO_2$—$((C_1-C_6)$alkyl) group.

3. The compound according to claim 1, wherein $R^1$ is an aryl group, said group being optionally substituted with one or more groups chosen from among a halogen atom, a OH, CN, $NO_2$, $NH_2$, $CO_2H$, $(C_1-C_6)$alkyl optionally substituted with an OH group, $(C_1-C_6)$alcoxy, $(C_1-C_6)$haloalkyl, $(C_1-C_6)$haloalcoxy, aryl, aryloxy, aryl-$(C_1-C_6)$alkyl, aryl-$(C_1-C_6)$alcoxy, heteroaryl, heterocycle, —$CO_2$—$((C_1-C_6)$alkyl), aryl-carbonyloxy, —NH—$((C_1-C_6)$alkyl), and $NHSO_2$—$((C_1-C_6)$ group.

4. The compound according to claim 1, wherein $R^2$ is an aryl or heteroaryl group, said group being optionally substituted with one or more groups chosen from among a halogen atom, a group OH; $NO_2$; $CO_2H$; CN; $CONH_2$; $SO_3H$; $(C_2-C_6)$alkyl optionally substituted with an OH group; $(C_1-C_6)$alkynyl optionally substituted with an $NR^{25}R^{26}$ group; $(C_1-C_6)$alcoxy; aryl optionally substituted with $NH_2$ and/or $SO_2NH_2$; heteroaryl; heterocycle; aryl-$(C_1-C_6)$alkyl; heteroaryl-$(C_1-C_6)$alkyl; heterocycle-$(C_1-C_6)$alkyl; aryl-$(C_1-C_6)$alcoxy; heteroaryl-$(C_1-C_6)$alcoxy; heterocycle-$(C_1-C_6)$alcoxy; $NR^{10}R^{11}$; and —$X^3$—$((C_1-C_6)$alkyl)$NR^{12}R^{13}$; and/or being optionally fused to a heterocycle, the heterocycle rings of the whole being optionally substituted with one or more groups chosen from among OH; $(C_1-C_6)$alkyl optionally substituted with OH or $NR^{27}R^{28}$; $CO_2$—$((C_1-C_6)$alkyl); heterocycle optionally substituted with a $(C_1-C_6)$alkyl group; and $NR^{14}R^{15}$.

5. The compound according to claim 1, wherein $R^3$ is a hydrogen atom, a group $NH_2$, $(C_1-C_6)$alkyl, aryl, the aryl and heteroaryl rings being optionally substituted with one or more groups chosen from among a halogen atom, a group: $NO_2$, $CO_2H$, $NR^{16}R^{17}$, aryl, $(C_1-C_6)$alkyl, $(C_1-C_6)$haloalkyl, $(C_1-C_6)$alcoxy, $CO_2$—$(C_1-C_6)$alkyl and heterocyle, the heterocycle ring being optionally substituted with a $(C_1-C_6)$alkyl, $(C_1-C_6)$alcoxy and NH—$(C_1-C_6)$alkyl group.

6. The compound according to claim 1, wherein $R^3$ is a hydrogen atom, a $NH_2$, $(C_1-C_6)$alkyl, aryl, or heteroaryl group.

7. The compound according to claim 1, corresponding to a compound of following formula (Ia):

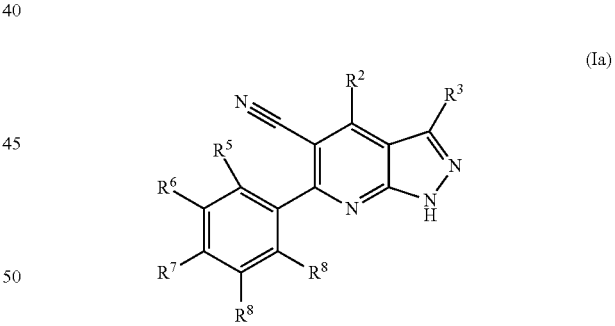

(Ia)

or a pharmaceutically acceptable salt thereof, wherein:

$R^2$ and $R^3$ are as defined in claim 1, and $R^5$, $R^6$, $R^7$, $R^8$, and $R^9$ are each independently a hydrogen atom, a halogen atom, a group OH; CN; $NO_2$; $NH_2$; $CO_2H$; $(C_1-C_6)$alkyl optionally substituted with an OH group; $(C_1-C_6)$alcoxy; $(C_1-C_6)$haloalkyl; $(C_1-C_6)$haloalcoxy; aryl; aryloxy; aryl-$(C_1-C_6)$alkyl; aryl-$(C_1-C_6)$alcoxy; heteroaryl; heterocycle; $CO_2$—$((C_1-C_6)$alkyl); aryl-carbonyloxy; NH—$((C_1-C_6)$alkyl); and $NHSO_2$—$((C_1-C_6)$alkyl).

8. The compound according to claim 1, chosen from among:
1
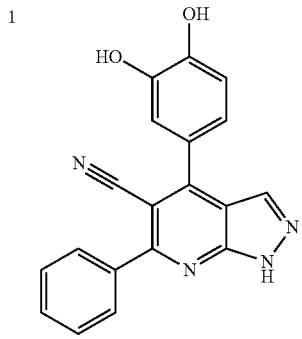
3
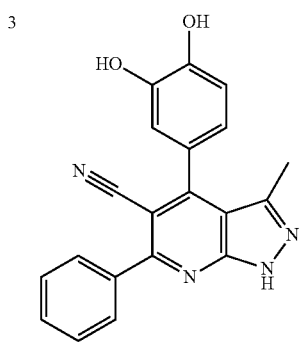
6
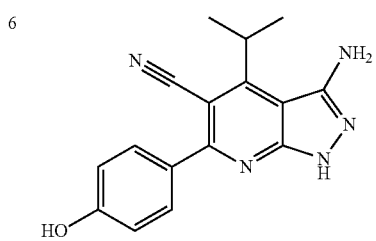
7
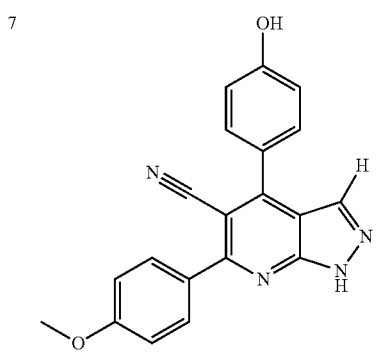
8
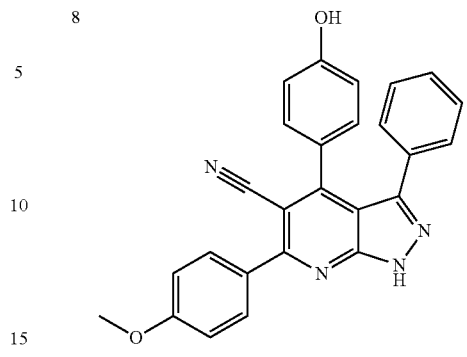
9
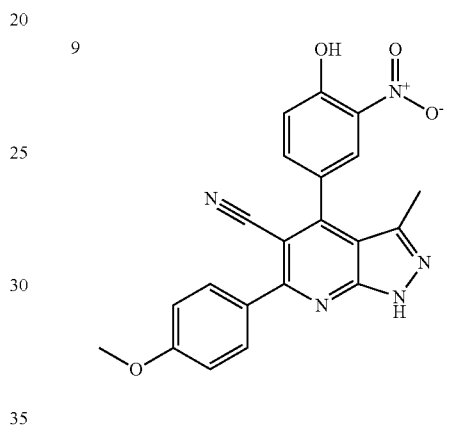
10
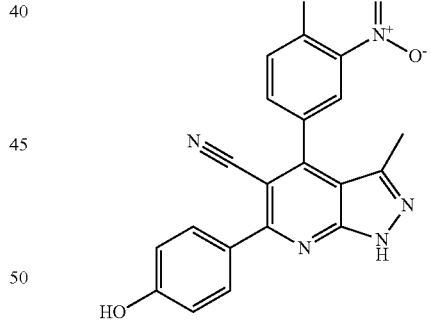
11
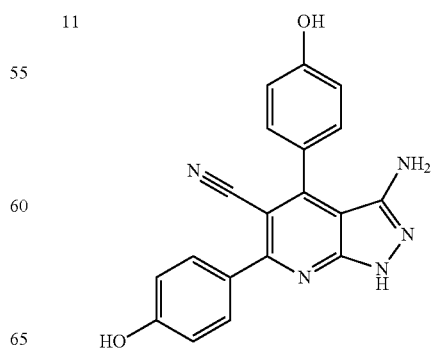

| 177 -continued | 178 -continued |
|---|---|
| 12 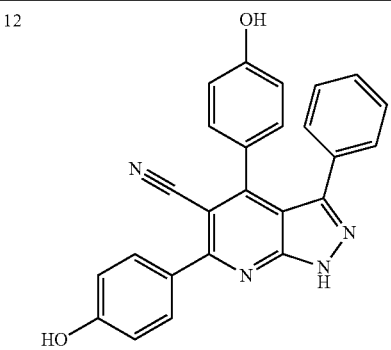 | 16 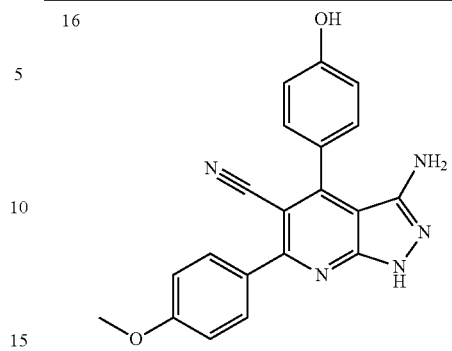 |
| 13 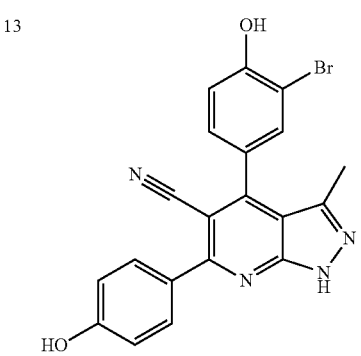 | 17 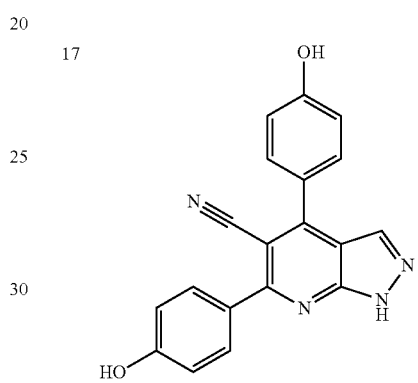 |
| 14 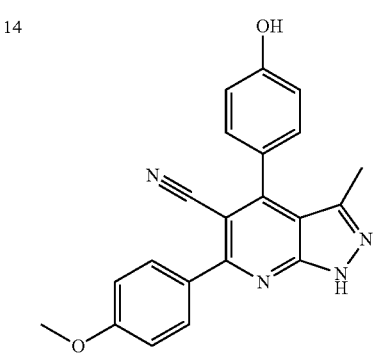 | 19 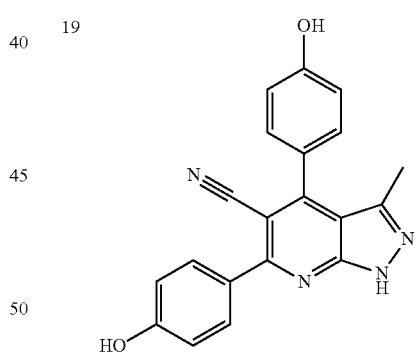 |
| 15 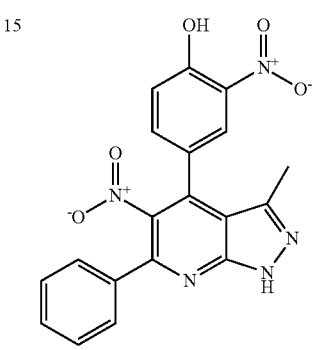 | 20 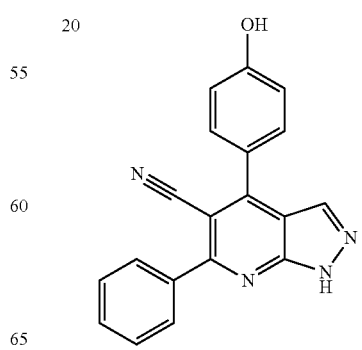 |

-continued
| | |
|---|---|
| 21 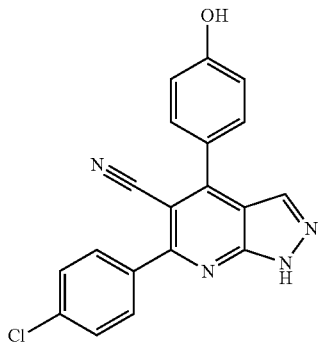 [SMILES: N#Cc1c(-c2ccc(Cl)cc2)nc2[nH]ncc2c1-c1ccc(O)cc1] | 26 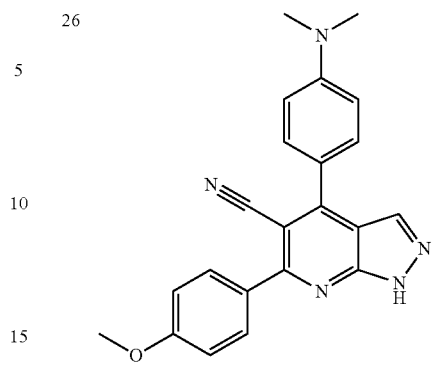 |
| 23 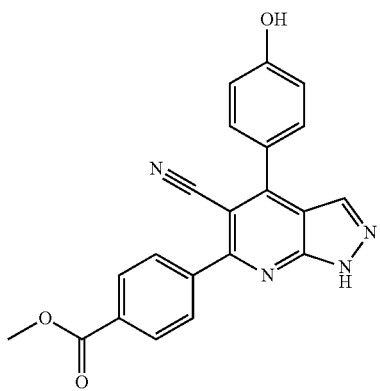 [SMILES: COC(=O)c1ccc(-c2nc3[nH]ncc3c(-c3ccc(O)cc3)c2C#N)cc1] | 27 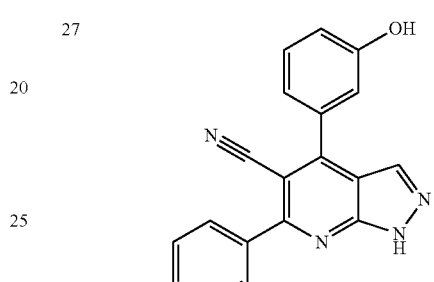 |
| | 28 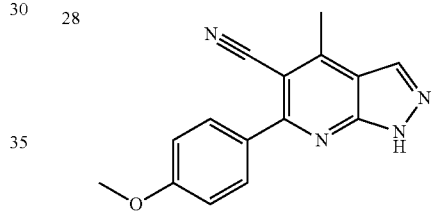 |
| 24 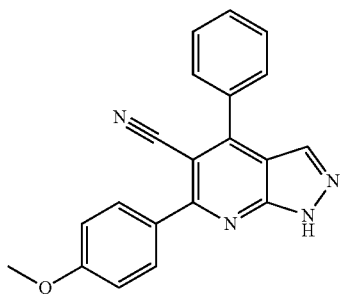 [SMILES: COc1ccc(-c2nc3[nH]ncc3c(-c3ccccc3)c2C#N)cc1] | 29 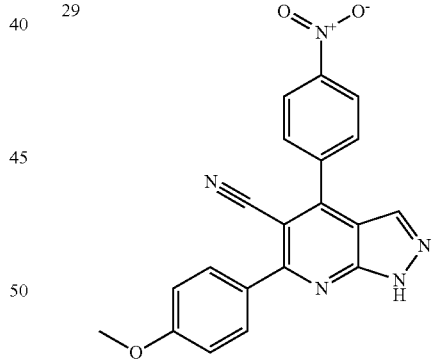 |
| 25 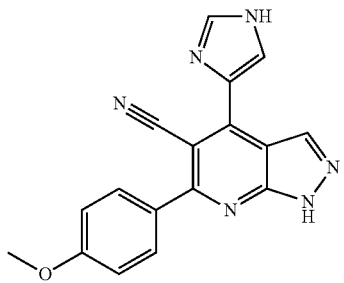 [SMILES: COc1ccc(-c2nc3[nH]ncc3c(-c3c[nH]cn3)c2C#N)cc1] | 31 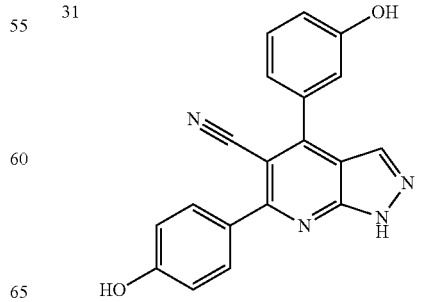 |

| 181 -continued | 182 -continued |
|---|---|
| 32 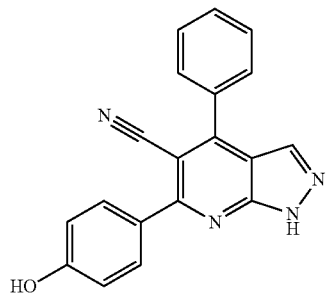 [SMILES: N#Cc1c(-c2ccc(O)cc2)nc2[nH]ncc2c1-c1ccccc1] | 38 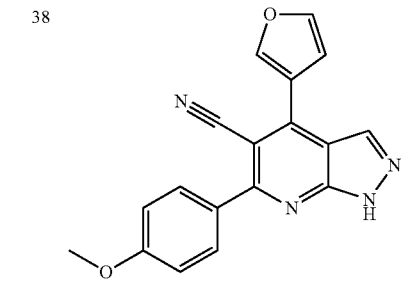 |
| 33 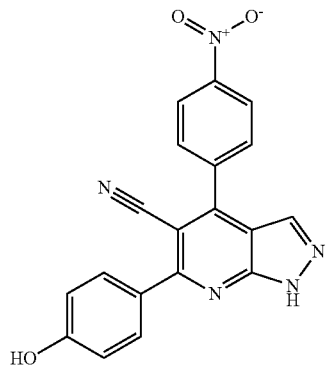 [SMILES: N#Cc1c(-c2ccc(O)cc2)nc2[nH]ncc2c1-c1ccc([N+](=O)[O-])cc1] | 39 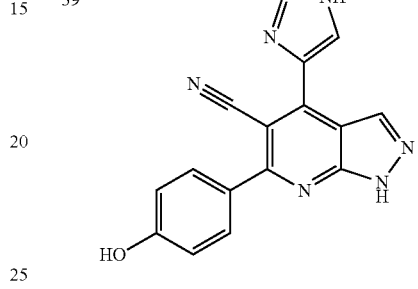 |
| | 40 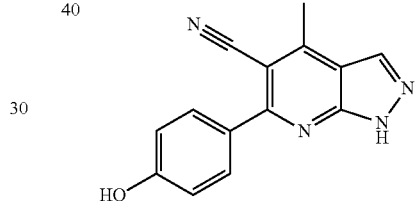 |
| 35 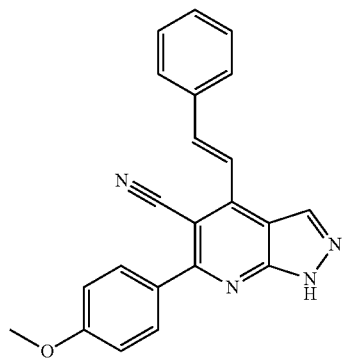 [SMILES: COc1ccc(-c2nc3[nH]ncc3c(/C=C/c3ccccc3)c2C#N)cc1] | 41 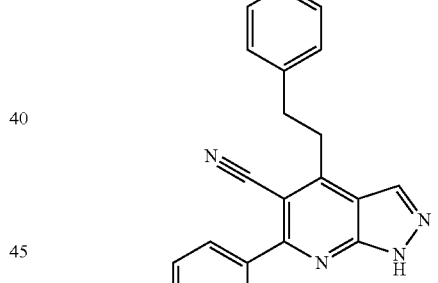 |
| 36 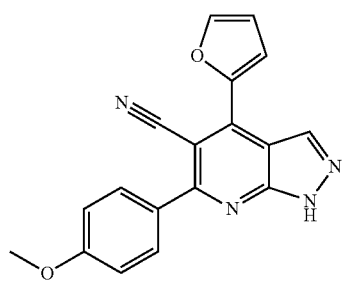 | 42 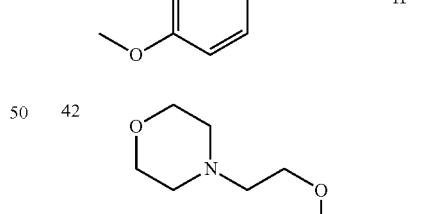 |
| 37 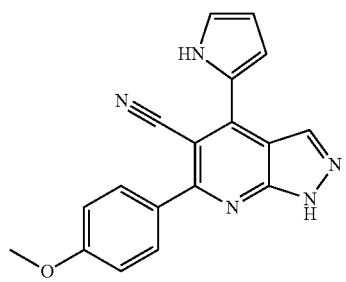 [SMILES: COc1ccc(-c2nc3[nH]ncc3c(-c3ccco3)c2C#N)cc1] | |

| 183 -continued | 184 -continued |
|---|---|
| 43 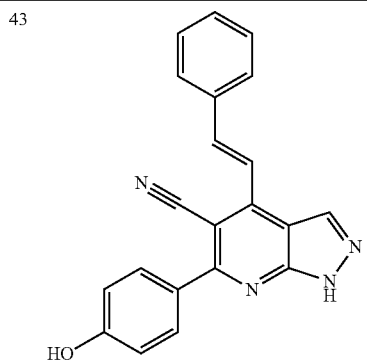 | 47 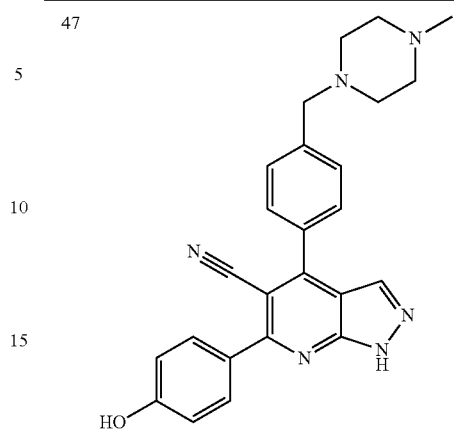 |
| 44 | 48 |
| 45 | 49 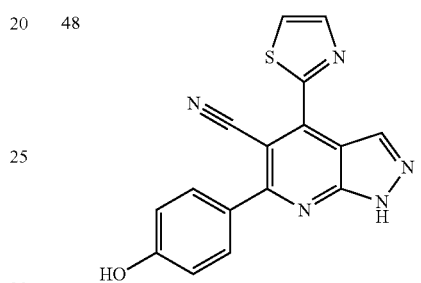 |
| 46 | 50 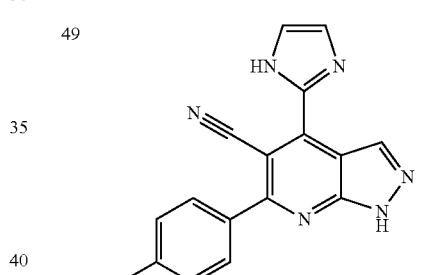 |
| | 51 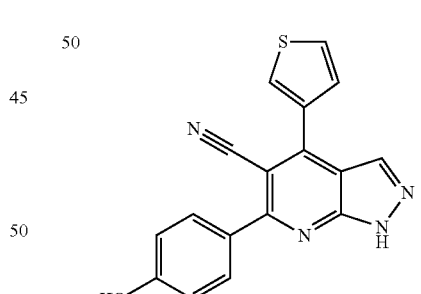 |
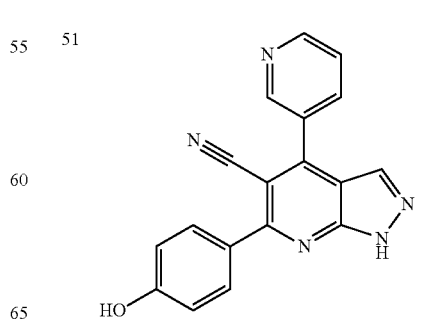

| 52 | 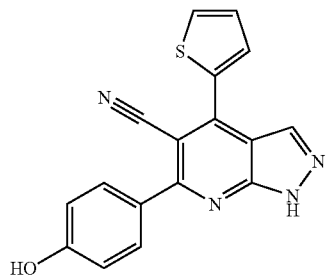 [SMILES: N#Cc1c(-c2ccc(O)cc2)nc2[nH]ncc2c1-c1ccco1] | 56 | 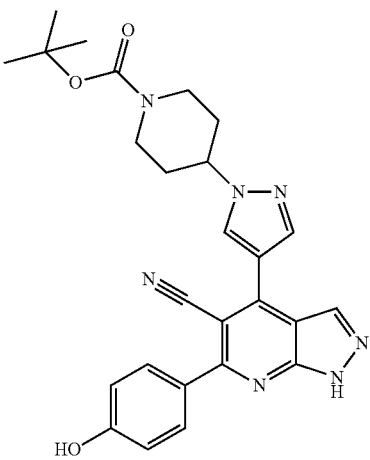 |
| --- | --- | --- | --- |
| 53 | 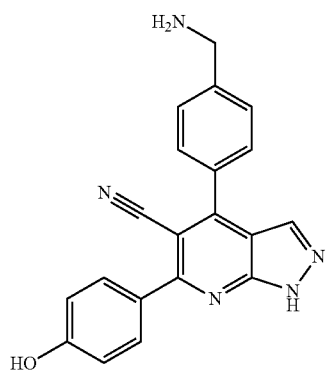 [SMILES: N#Cc1c(-c2ccc(O)cc2)nc2[nH]ncc2c1-c1ccc(CN)cc1] | 57 | 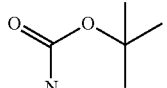 |
| 54 | 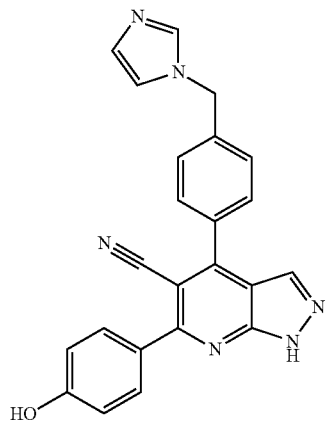 [SMILES: N#Cc1c(-c2ccc(O)cc2)nc2[nH]ncc2c1-c1ccc(Cn2ccnc2)cc1] | | |
| 55 | 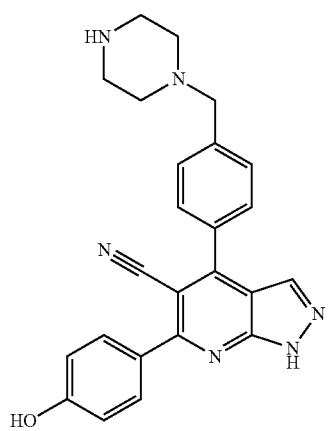 [SMILES: N#Cc1c(-c2ccc(O)cc2)nc2[nH]ncc2c1-c1ccc(CN2CCNCC2)cc1] | 58 | 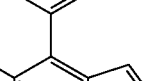 |

| 59 | 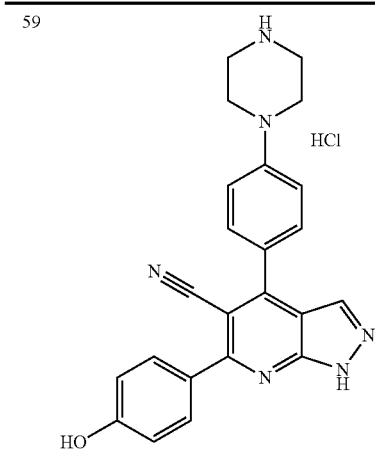 | 63 | 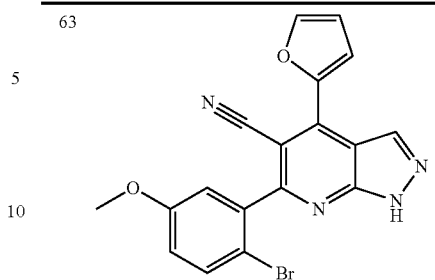 |
| --- | --- | --- | --- |
| 60 | | 67 | 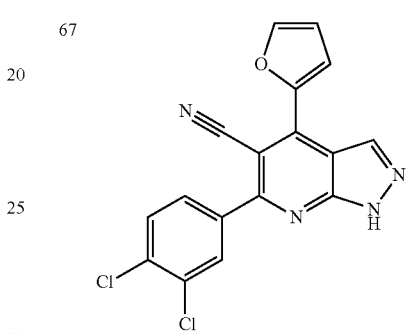 |
| 61 | | 68 | 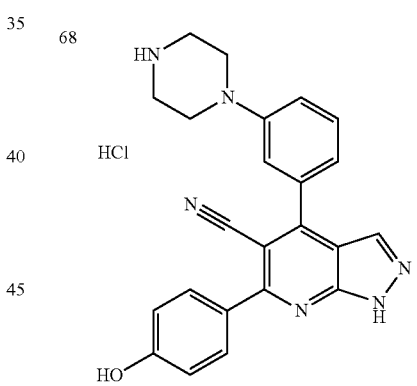 |
| 62 | | 69 | 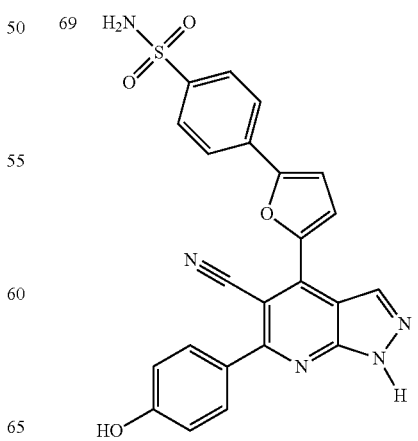 |

| 189 -continued | 190 -continued |
|---|---|
| 70 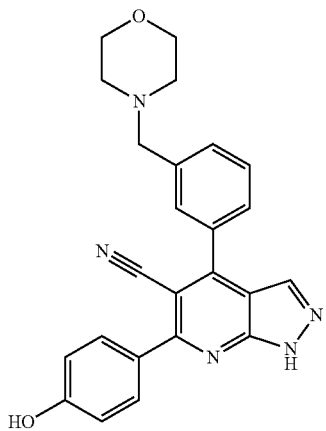 [SMILES: N#Cc1c(-c2ccc(O)cc2)nc2[nH]ncc2c1-c1cccc(CN2CCOCC2)c1] | 73 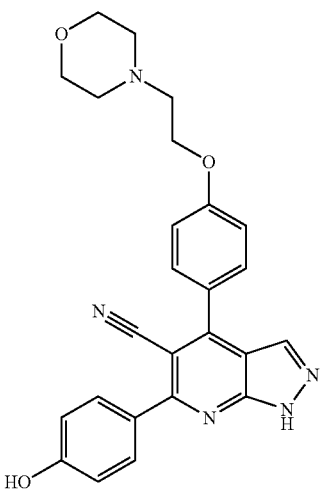 |
| 71 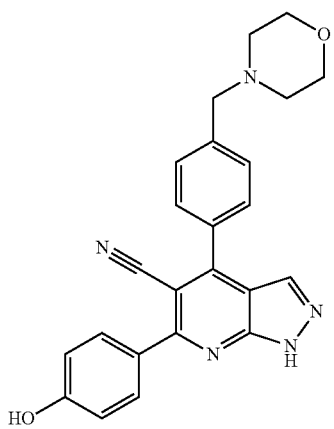 [SMILES: N#Cc1c(-c2ccc(O)cc2)nc2[nH]ncc2c1-c1ccc(CN2CCOCC2)cc1] | 74 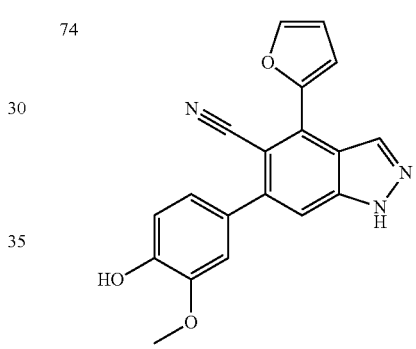 |
| 72 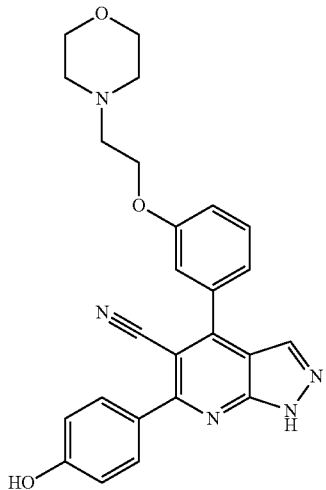 [SMILES: N#Cc1c(-c2ccc(O)cc2)nc2[nH]ncc2c1-c1cccc(OCCN2CCOCC2)c1] | 75 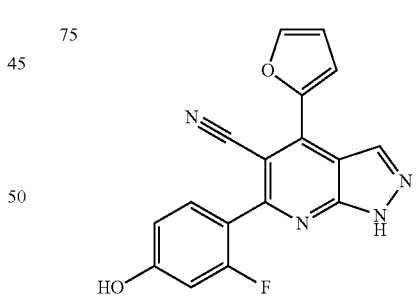 |
| | 76 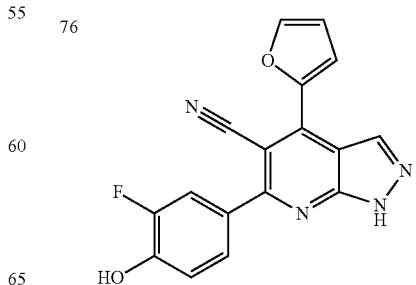 |

| 77 | 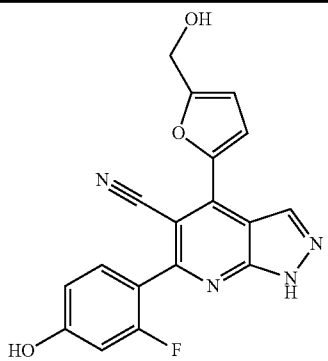 | 82 | 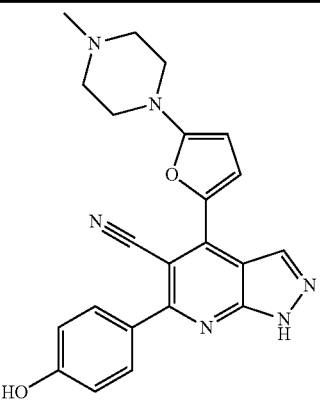 |
| --- | --- | --- | --- |
| 78 | 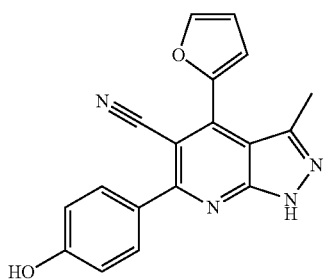 [SMILES: Cc1n[nH]c2nc(-c3ccc(O)cc3)c(C#N)c(-c3ccco3)c12] | 83 | |
| 79 | 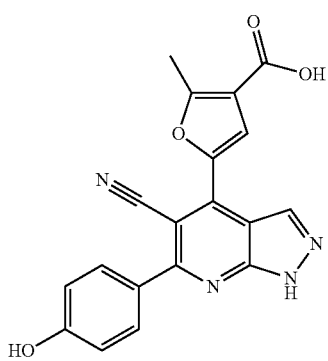 | 84 | |
| 80 | 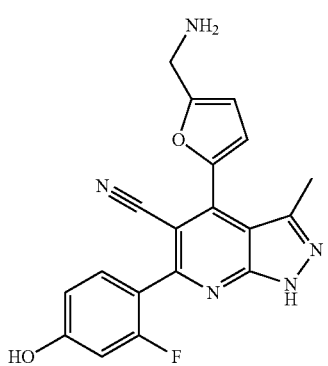 [SMILES: Cc1n[nH]c2nc(-c3ccc(O)cc3F)c(C#N)c(-c3ccc(CN)o3)c12] | 85 | |
| 81 | 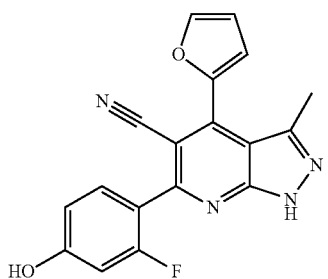 [SMILES: Cc1n[nH]c2nc(-c3ccc(O)cc3F)c(C#N)c(-c3ccco3)c12] | | |

| 193 -continued | 194 -continued |
|---|---|
| 86 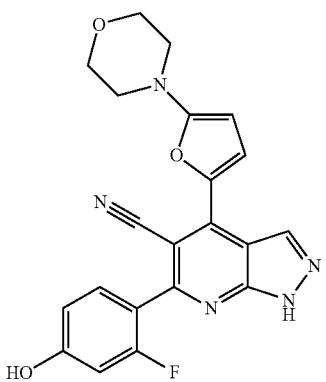 [SMILES: N#Cc1c(-c2ccc(O)cc2F)nc2[nH]ncc2c1-c1ccc(N2CCOCC2)o1] | 90 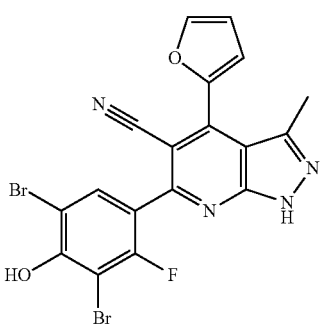 |
| 87 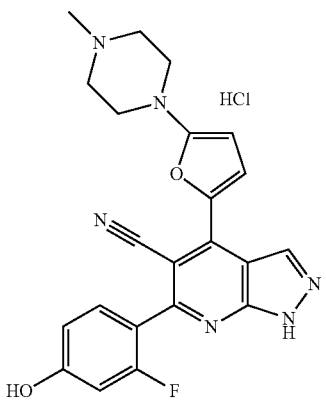 [SMILES: CN1CCN(c2ccc(-c3c(C#N)c(-c4ccc(O)cc4F)nc4[nH]ncc34)o2)CC1 ; Cl] | 91 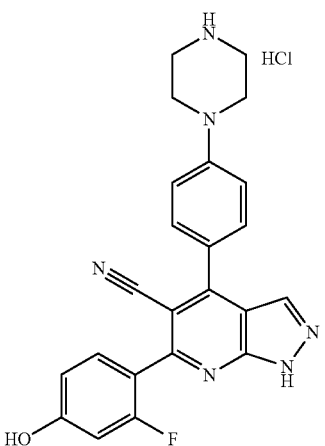 |
| 88 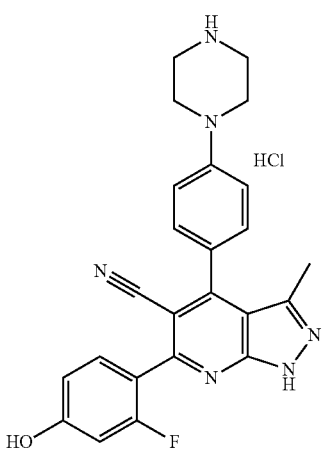 [SMILES: Cc1n[nH]c2nc(-c3ccc(O)cc3F)c(C#N)c(-c3ccc(N4CCNCC4)cc3)c12 ; Cl] | 92 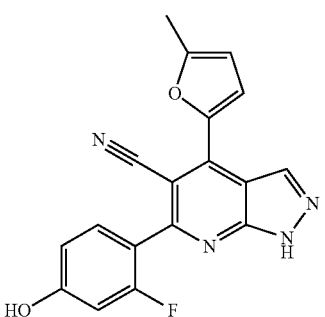 |
| 89 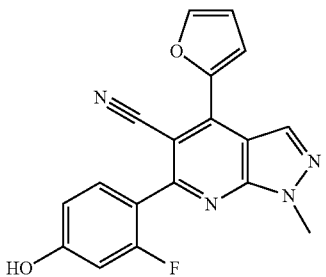 [SMILES: Cn1ncc2c(-c3ccco3)c(C#N)c(-c3ccc(O)cc3F)nc21] | 93 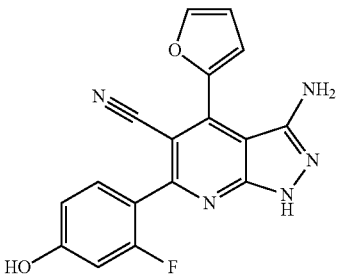 [SMILES: N#Cc1c(-c2ccc(O)cc2F)nc2[nH]nc(N)c2c1-c1ccco1] |

195
-continued
94
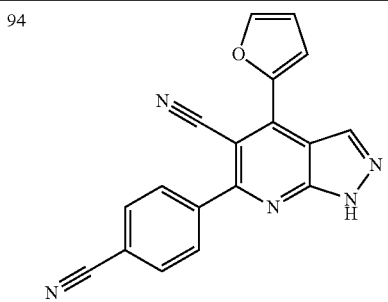
95
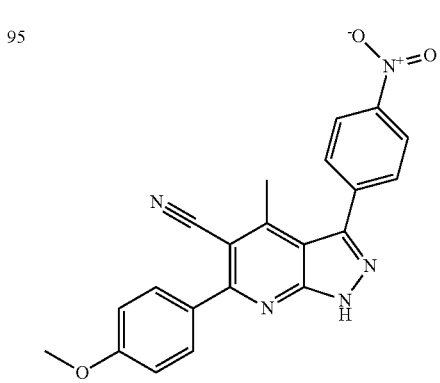
96
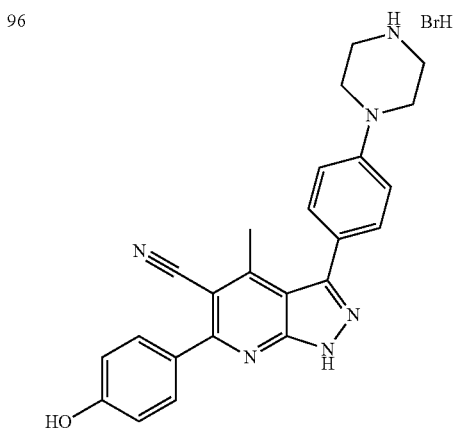
97
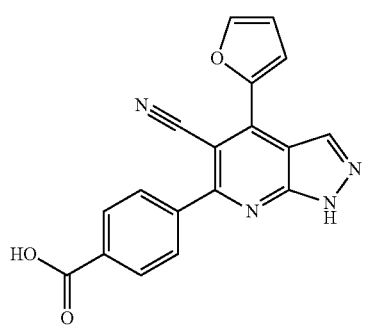 [SMILES: N#Cc1c(-c2ccc(C(=O)O)cc2)nc2[nH]ncc2c1-c1ccco1]
196
-continued
98
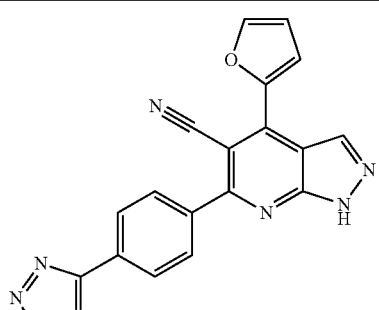
101
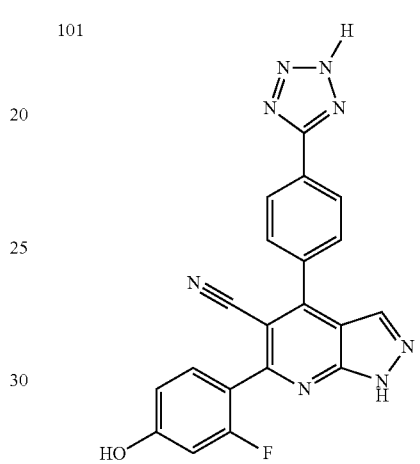
103
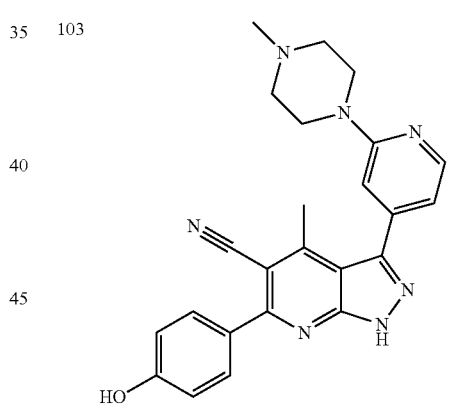
104
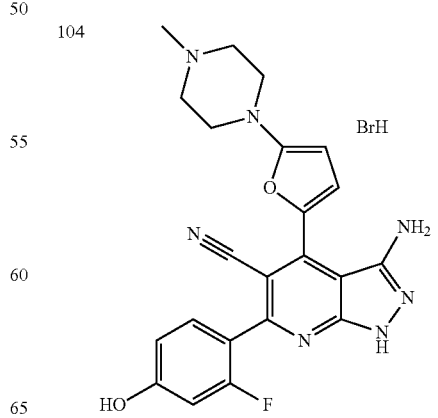

| 106 | 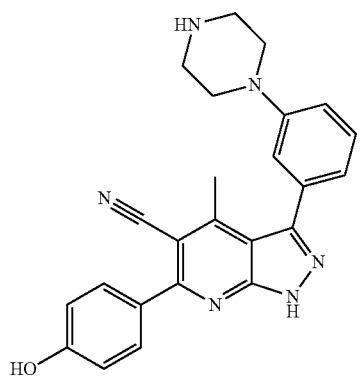 | 111 | 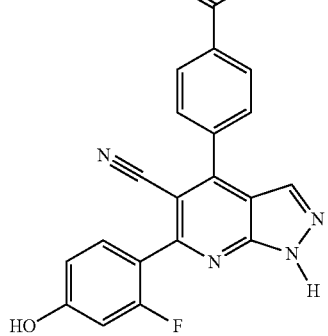 |
| --- | --- | --- | --- |
| 107 | 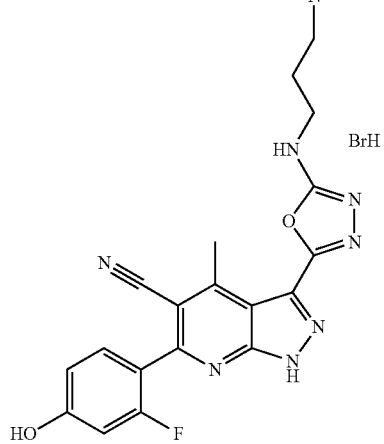 | 112 | 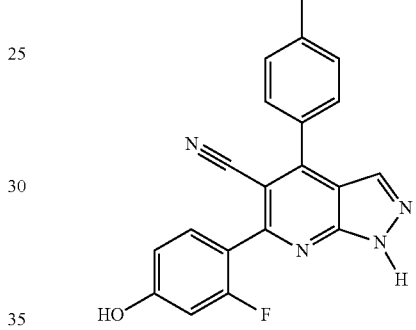 |
| 108 | 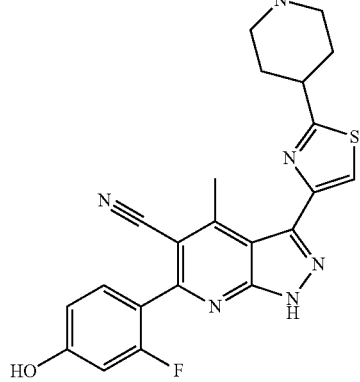 | 113 | 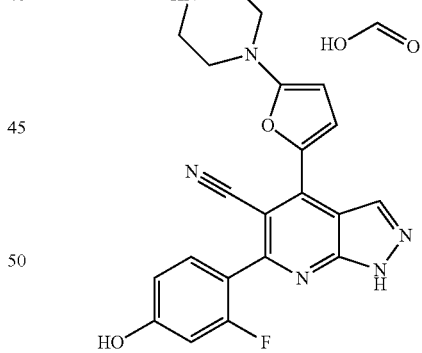 |
| 110 | 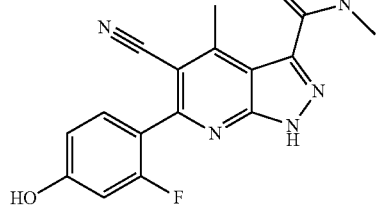 | 114 | 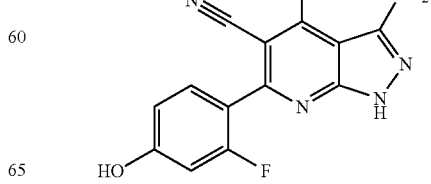 |

| 115 | 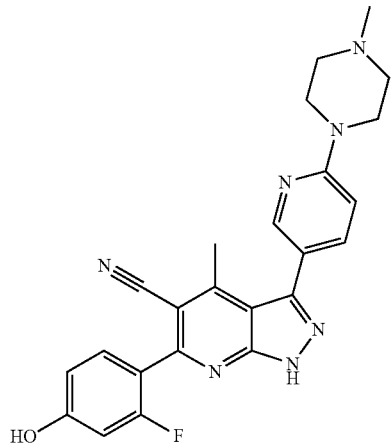 [SMILES: Cc1c(C#N)c(-c2ccc(O)cc2F)nc2[nH]nc(-c3ccc(N4CCN(C)CC4)nc3)c12] | 119 | 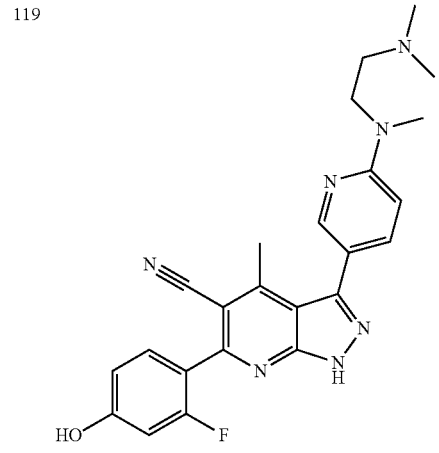 |
| 116 | 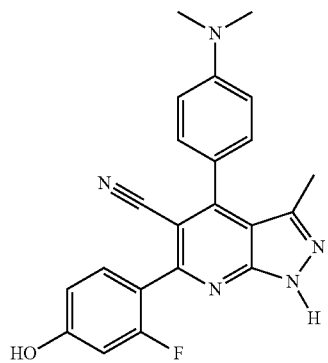 [SMILES: Cc1n[nH]c2nc(-c3ccc(O)cc3F)c(C#N)c(-c3ccc(N(C)C)cc3)c12] | 120 | 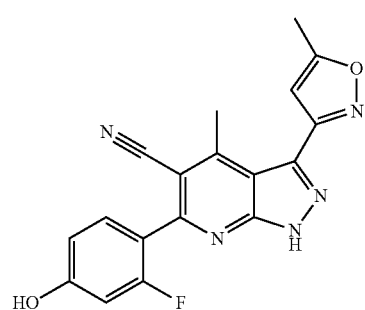 |
| 117 | 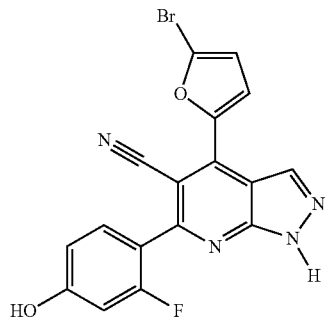 [SMILES: N#Cc1c(-c2ccc(O)cc2F)nc2[nH]ncc2c1-c1ccc(Br)o1] | 121 | 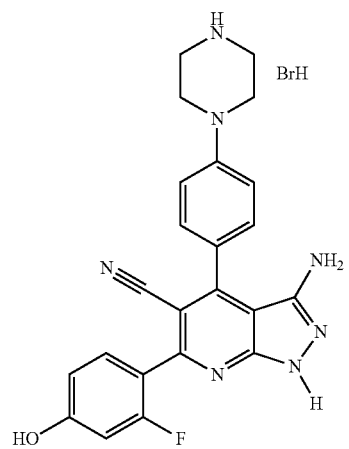 |
| 118 | 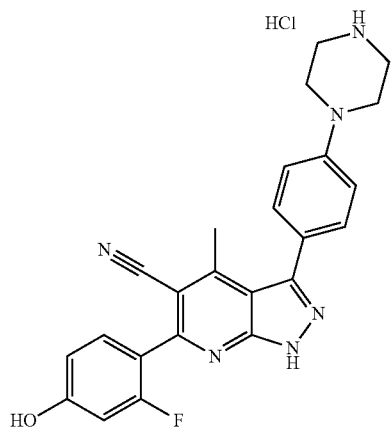 [SMILES: Cl ; Cc1c(C#N)c(-c2ccc(O)cc2F)nc2[nH]nc(-c3ccc(N4CCNCC4)cc3)c12] | 122 | 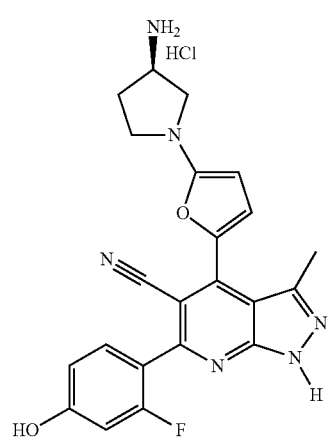 [SMILES: Cc1n[nH]c2nc(-c3ccc(O)cc3F)c(C#N)c(-c3ccc(N4CC[C@@H](N)C4)o3)c12 ; Cl] |

-continued
| | |
|---|---|
| 123 | 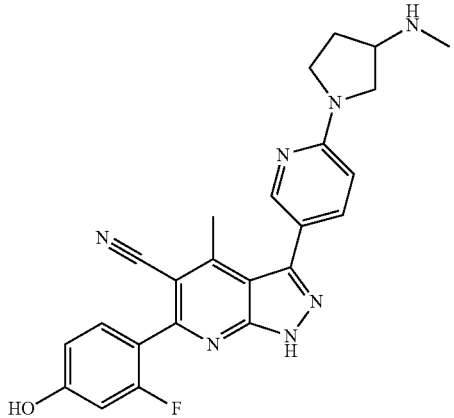 [SMILES: CNC1CCN(c2ccc(-c3n[nH]c4nc(-c5ccc(O)cc5F)c(C#N)c(C)c34)cn2)C1] |
| 124 | 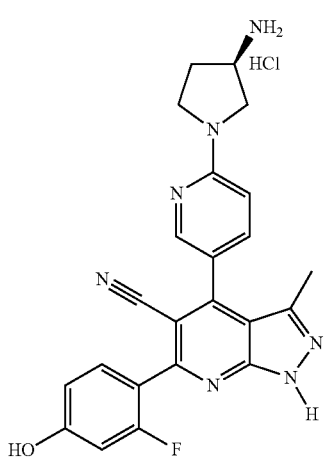 [SMILES: Cc1n[nH]c2nc(-c3ccc(O)cc3F)c(C#N)c(-c3ccc(N4CC[C@@H](N)C4)nc3)c12 ; Cl] |
| 125 | 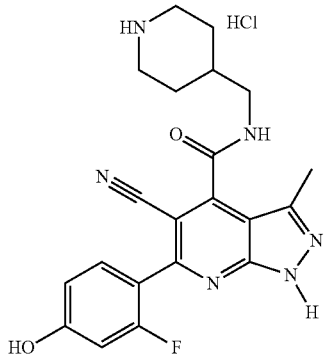 [SMILES: Cc1n[nH]c2nc(-c3ccc(O)cc3F)c(C#N)c(C(=O)NCC3CCNCC3)c12 ; Cl] |
| 126 | 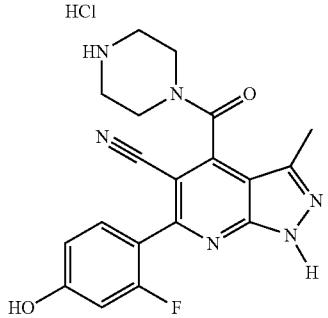 [SMILES: Cl ; Cc1n[nH]c2nc(-c3ccc(O)cc3F)c(C#N)c(C(=O)N3CCNCC3)c12] |
-continued
| | |
|---|---|
| 127 | 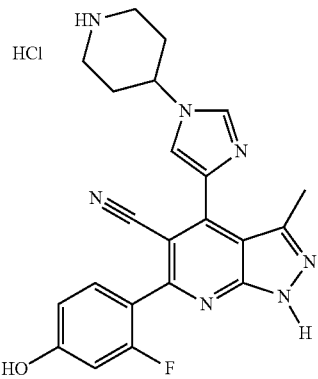 [SMILES: Cl ; Cc1n[nH]c2nc(-c3ccc(O)cc3F)c(C#N)c(-c3cn(C4CCNCC4)cn3)c12] |
| 128 | 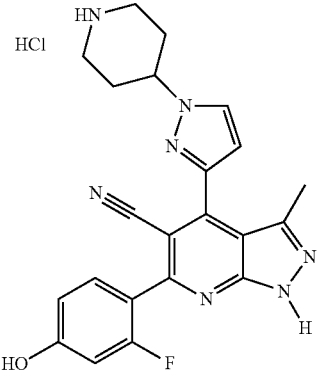 [SMILES: Cc1n[nH]c2nc(-c3ccc(O)cc3F)c(C#N)c(-c3ccn(C4CCNCC4)n3)c12 ; Cl] |
| 129 | 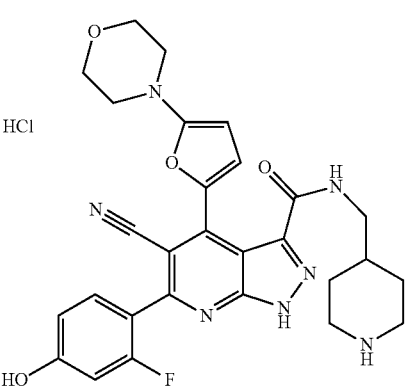 [SMILES: Cl ; N#Cc1c(-c2ccc(O)cc2F)nc2[nH]nc(C(=O)NCC3CCNCC3)c2c1-c1ccc(N2CCOCC2)o1] |
| 130 | 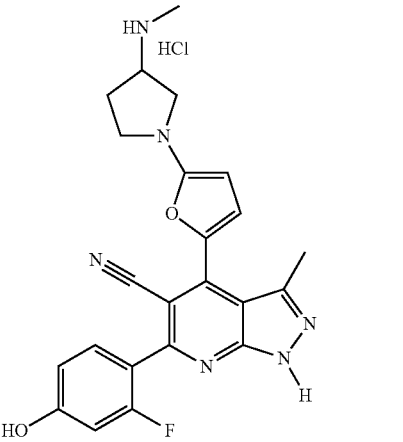 [SMILES: CNC1CCN(c2ccc(-c3c(C#N)c(-c4ccc(O)cc4F)nc4[nH]nc(C)c34)o2)C1 ; Cl] |

| 131 | 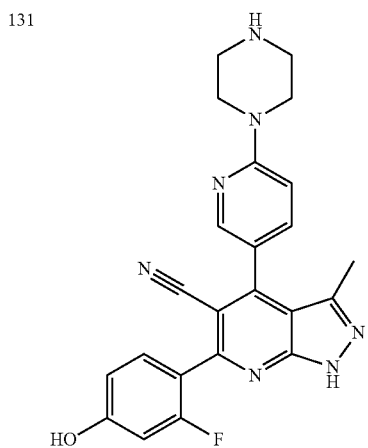 | 134 | 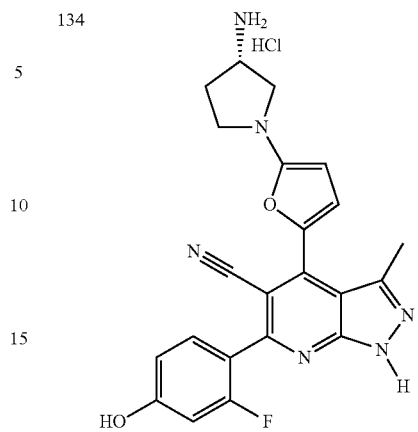 |
| 132 | 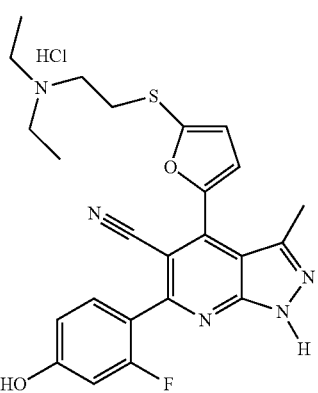 [SMILES: CCN(CC)CCSc1ccc(-c2c(C#N)c(-c3ccc(O)cc3F)nc3[nH]nc(C)c23)o1 ; Cl] | 135 | 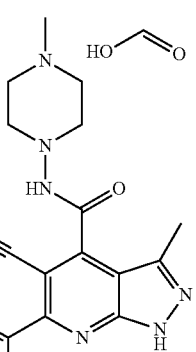 |
| | | 136 | 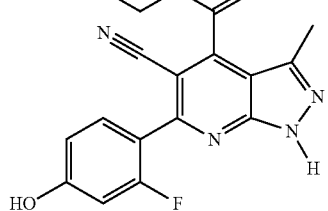 |
| 133 | 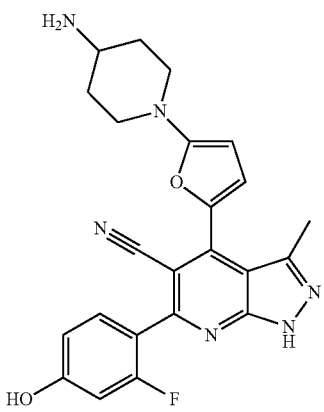 [SMILES: Cc1n[nH]c2nc(-c3ccc(O)cc3F)c(C#N)c(-c3ccc(N4CCC(N)CC4)o3)c12] | 137 | 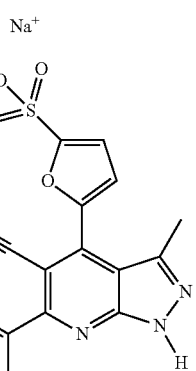 |

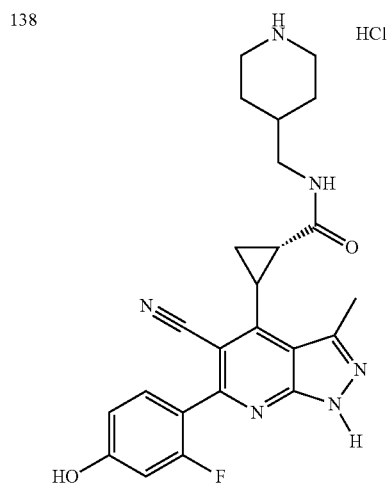
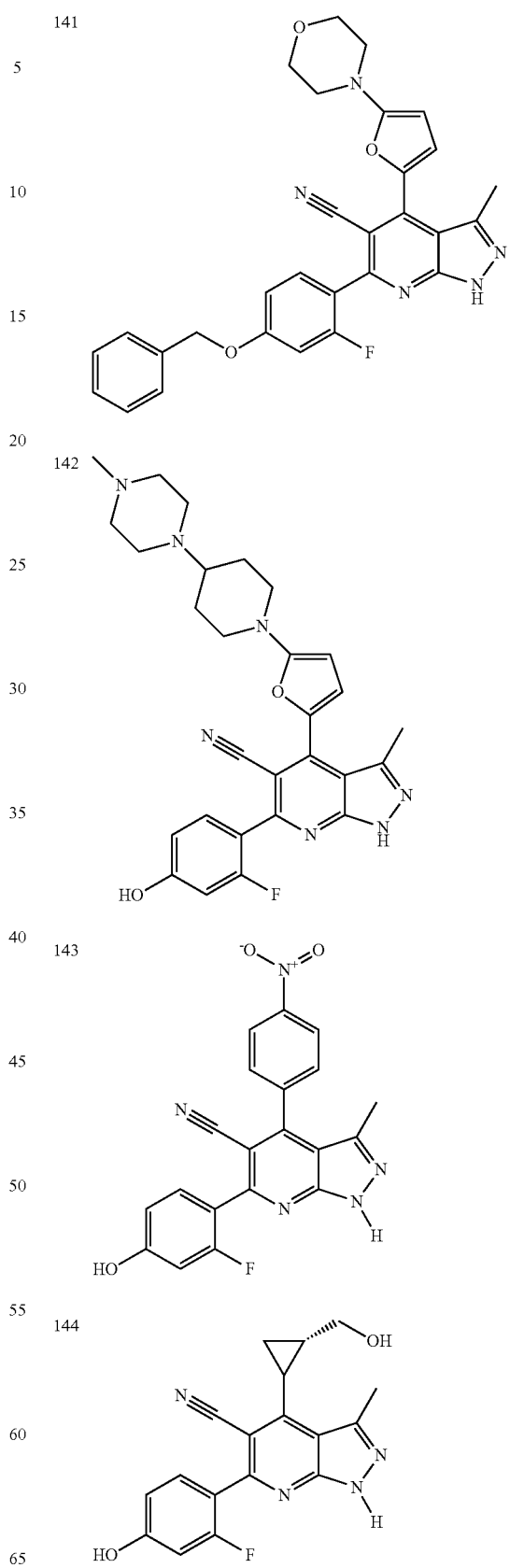

| 207 -continued | 208 -continued |
|---|---|
| 145 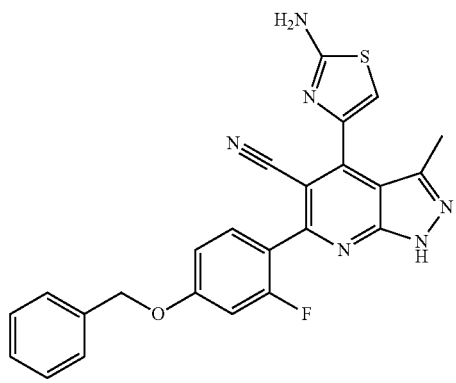 [SMILES: Cc1n[nH]c2nc(-c3ccc(OCc4ccccc4)cc3F)c(C#N)c(-c3csc(N)n3)c12] | 149 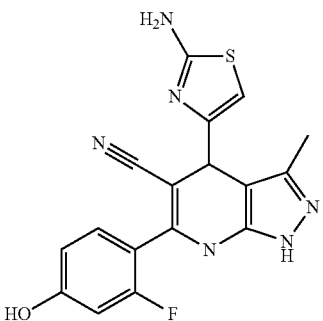 |
| 146 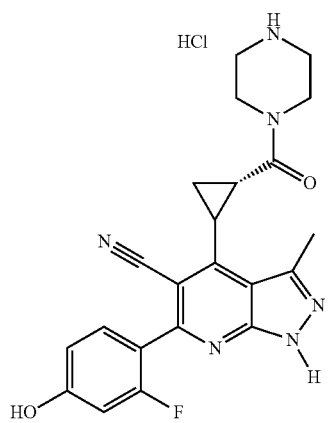 [SMILES: Cc1n[nH]c2nc(-c3ccc(O)cc3F)c(C#N)c(C3C[C@@H]3C(=O)N3CCNCC3)c12 ; Cl] | 150 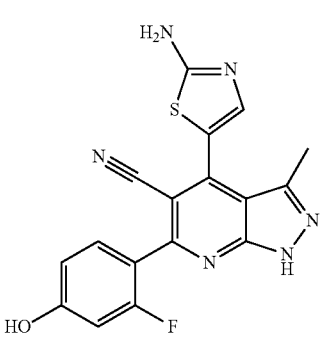 |
| 147 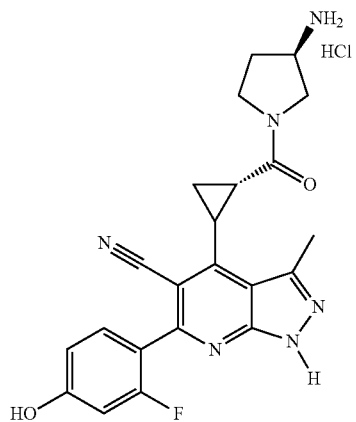 [SMILES: Cc1n[nH]c2nc(-c3ccc(O)cc3F)c(C#N)c(C3C[C@@H]3C(=O)N3CC[C@@H](N)C3)c12 ; Cl] | 151 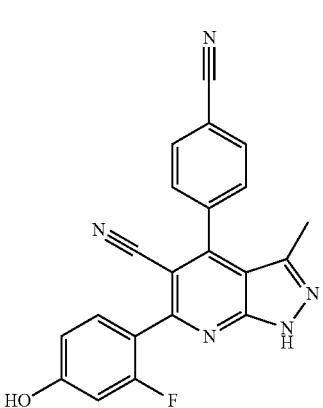 [SMILES: Cc1n[nH]c2nc(-c3ccc(O)cc3F)c(C#N)c(-c3ccc(C#N)cc3)c12] |
| 148 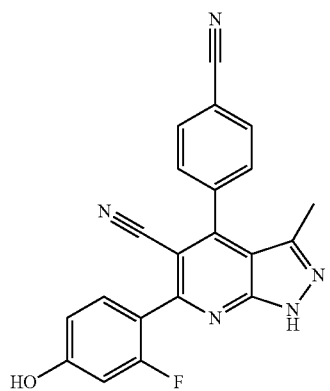 [SMILES: Cc1n[nH]c2nc(-c3ccc(O)cc3F)c(C#N)c(-c3ccc(C#N)cc3)c12] | 152 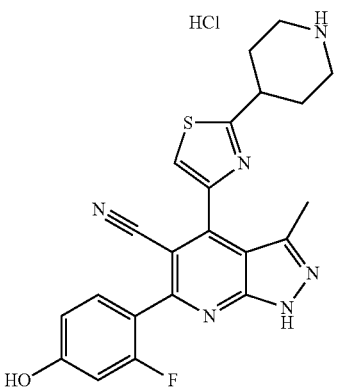 [SMILES: Cc1n[nH]c2nc(-c3ccc(O)cc3F)c(C#N)c(-c3csc(C4CCNCC4)n3)c12 ; Cl] |

| 209 -continued | 210 -continued |
|---|---|
| 153 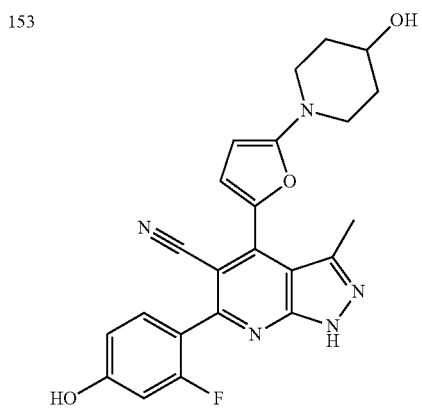 | 156 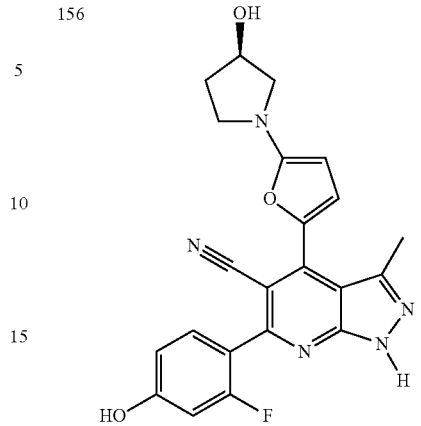 |
| 154 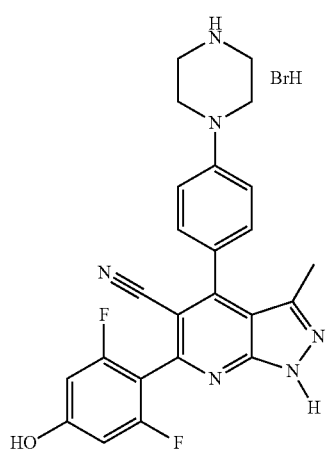 [SMILES: Cc1n[nH]c2nc(-c3c(F)cc(O)cc3F)c(C#N)c(-c3ccc(N4CCNCC4)cc3)c12 ; Br] | 158 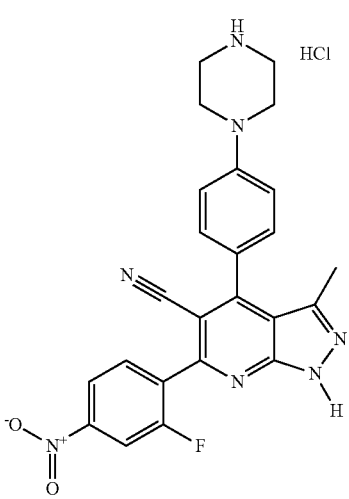 |
| 155 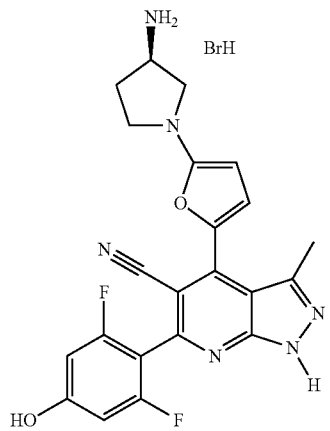 [SMILES: Cc1n[nH]c2nc(-c3c(F)cc(O)cc3F)c(C#N)c(-c3ccc(N4CC[C@@H](N)C4)o3)c12 ; Br] | 159 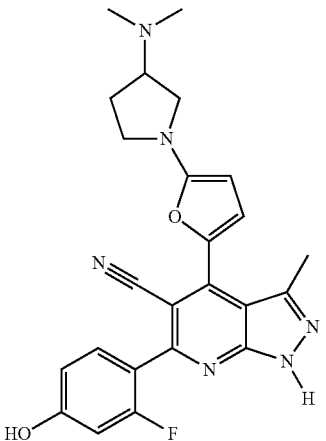 [SMILES: Cc1n[nH]c2nc(-c3ccc(O)cc3F)c(C#N)c(-c3ccc(N4CCC(N(C)C)C4)o3)c12] |

| 211 -continued | 212 -continued |
|---|---|
| 160 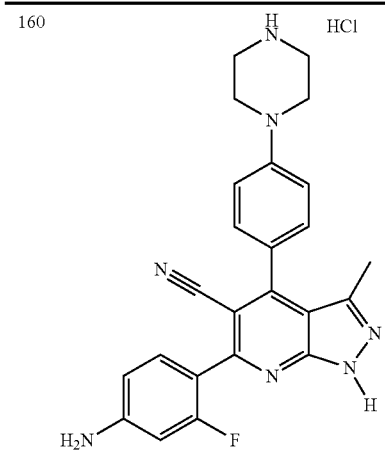 | 163 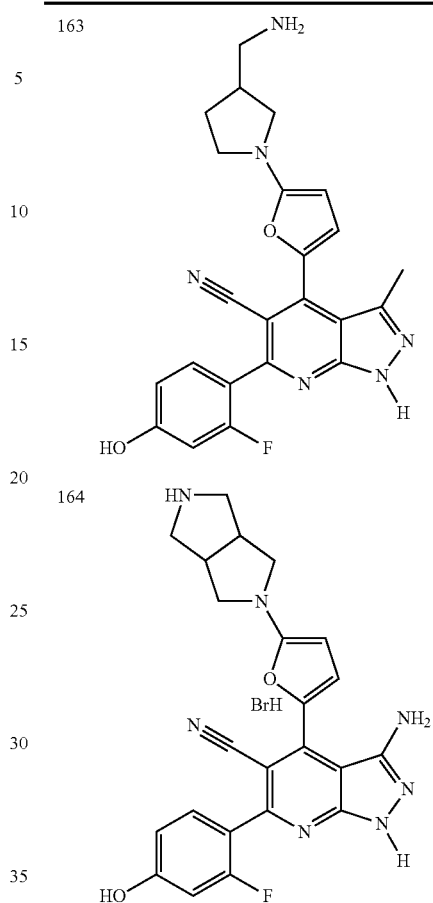 |
| 161 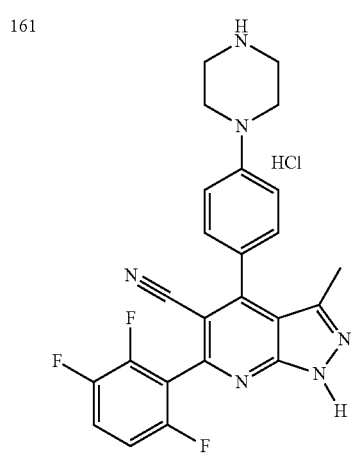 | 164 |
| 162 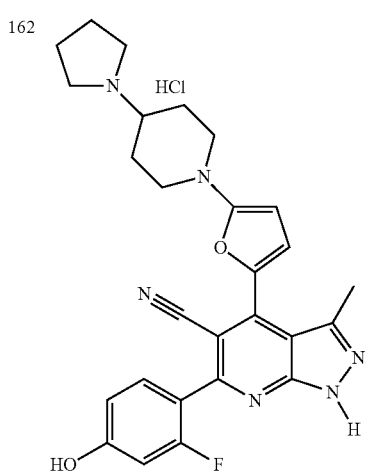 | 165 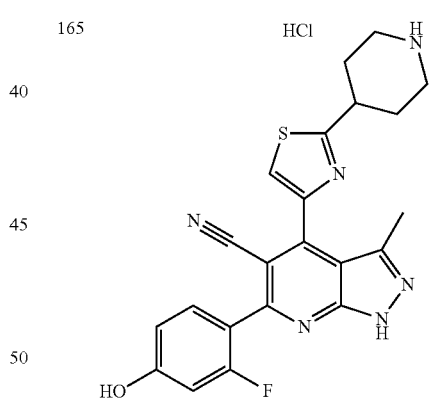 |
| | 166 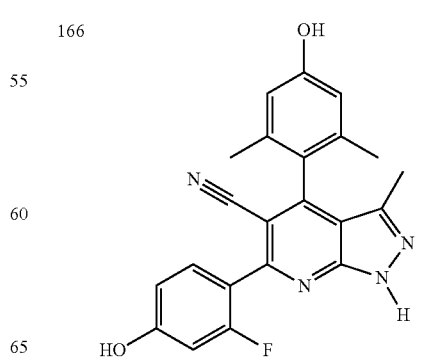 |

| 167 | 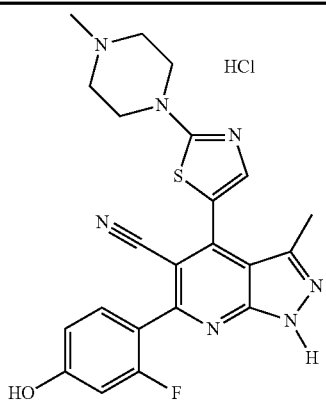 |
| 168 | 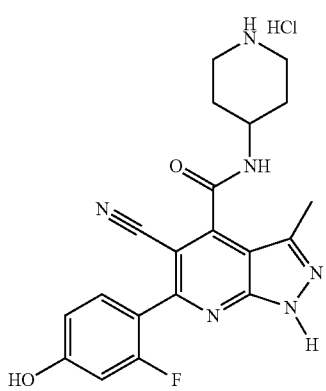 [SMILES: Cl ; Cc1n[nH]c2nc(-c3ccc(O)cc3F)c(C#N)c(C(=O)NC3CCNCC3)c12] |
| 169 | 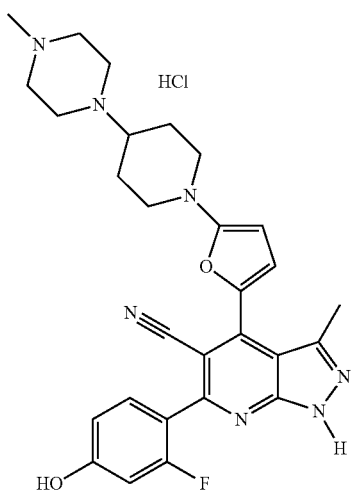 [SMILES: Cc1n[nH]c2nc(-c3ccc(O)cc3F)c(C#N)c(-c3ccc(N4CCC(N5CCN(C)CC5)CC4)o3)c12 ; Cl] |
| 170 | 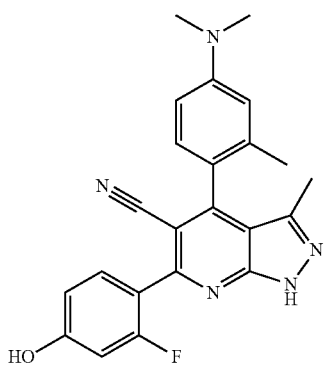 [SMILES: Cc1cc(N(C)C)ccc1-c1c(C#N)c(-c2ccc(O)cc2F)nc2[nH]nc(C)c12] |
| 171 | 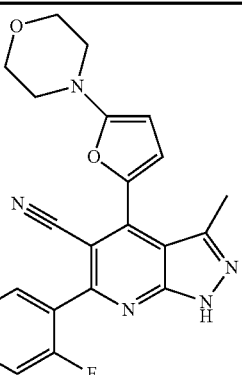 |
| 172 | 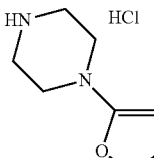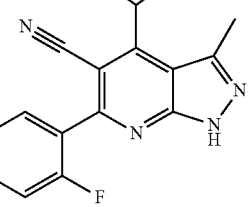 |
| 173 | |
| 174 | 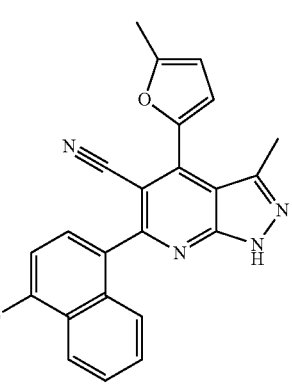 |

215
-continued
175
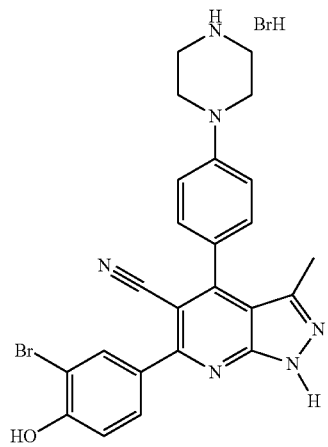 [SMILES: Br ; Cc1n[nH]c2nc(-c3ccc(O)c(Br)c3)c(C#N)c(-c3ccc(N4CCNCC4)cc3)c12]
176
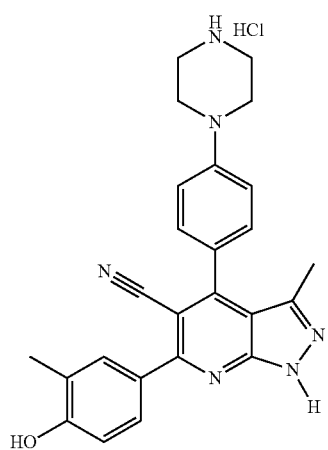 [SMILES: Cl ; Cc1cc(-c2nc3[nH]nc(C)c3c(-c3ccc(N4CCNCC4)cc3)c2C#N)ccc1O]
177
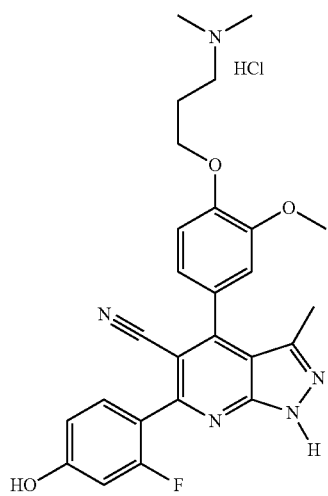 [SMILES: COc1cc(-c2c(C#N)c(-c3ccc(O)cc3F)nc3[nH]nc(C)c23)ccc1OCCCN(C)C ; Cl]
216
-continued
178
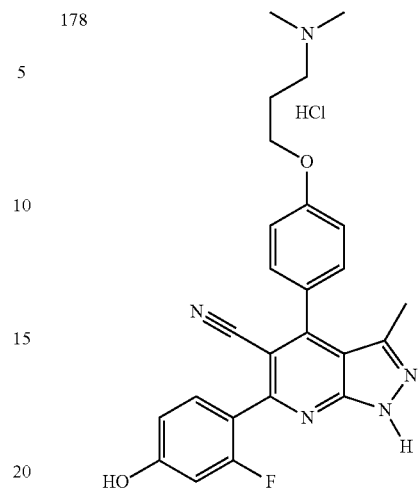
179
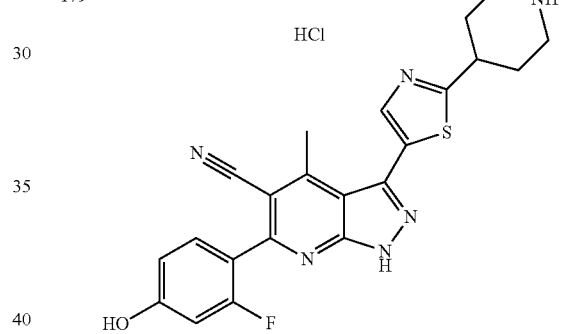
180
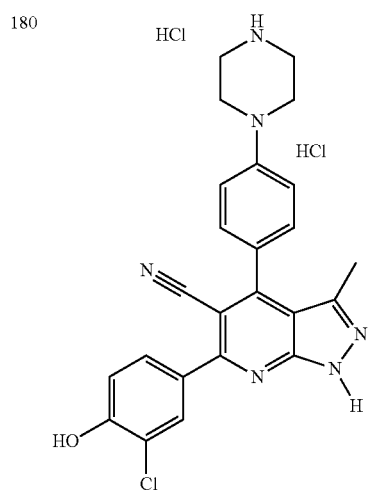

217
-continued
181 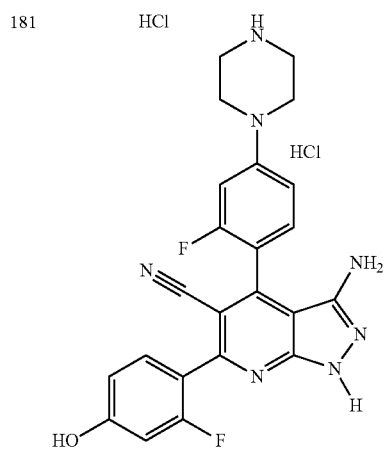
182 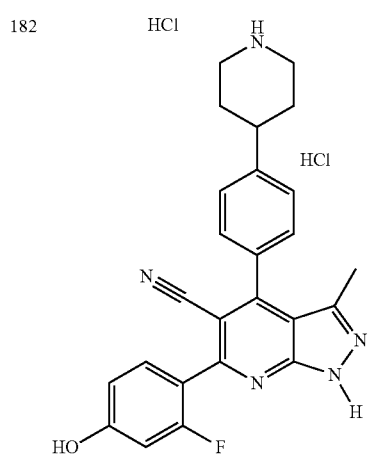
183 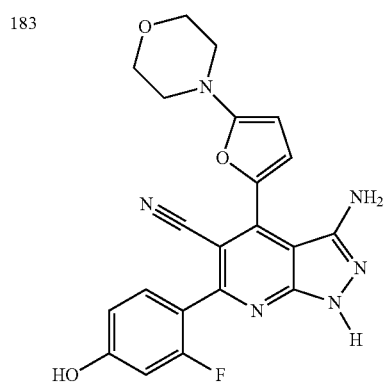
218
-continued
184 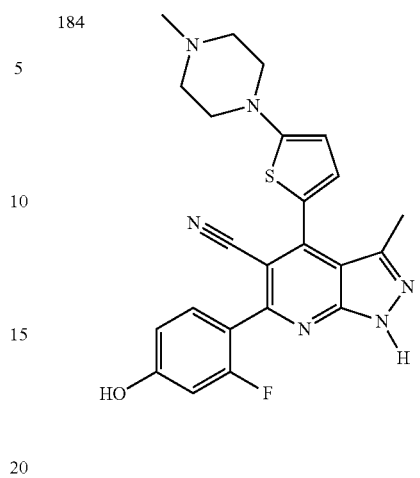
185 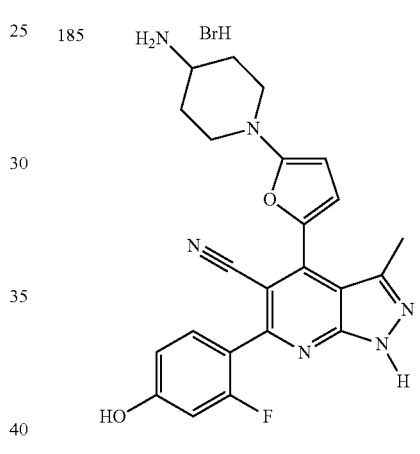
186 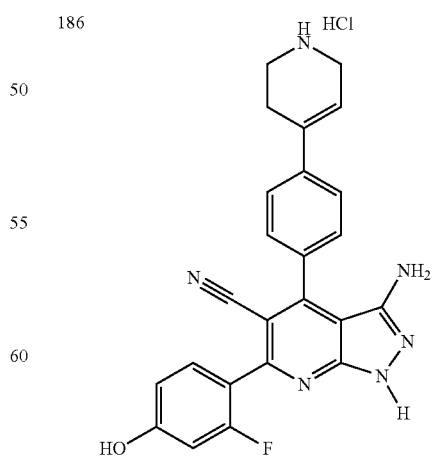

| 187 | 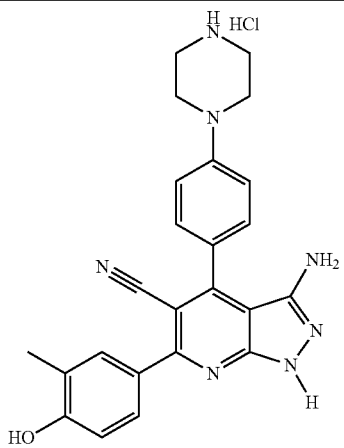 |
|---|---|
| 188 | 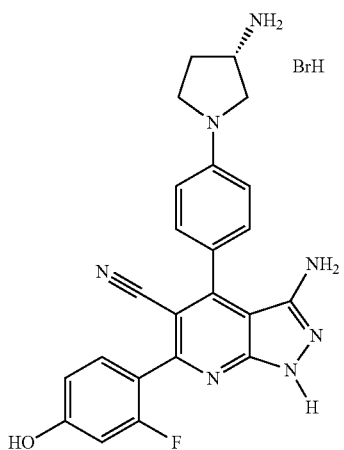 [SMILES: N#Cc1c(-c2ccc(O)cc2F)nc2[nH]nc(N)c2c1-c1ccc(N2CC[C@H](N)C2)cc1 ; Br] |
| 189 | 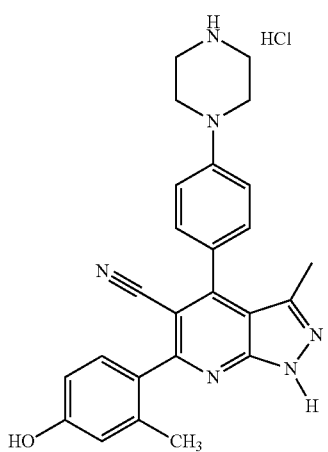 [SMILES: Cc1cc(O)ccc1-c1nc2[nH]nc(C)c2c(-c2ccc(N3CCNCC3)cc2)c1C#N ; Cl] |
| 190 | 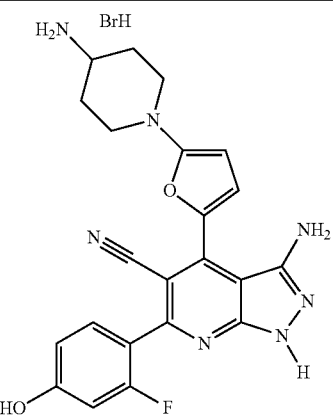 |
| 191 | 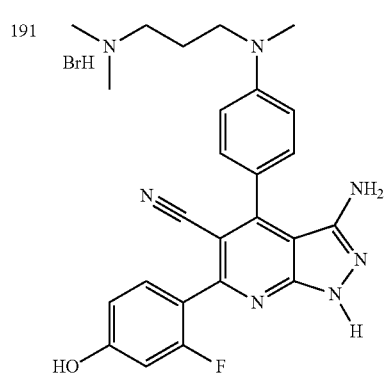 |
| 192 | 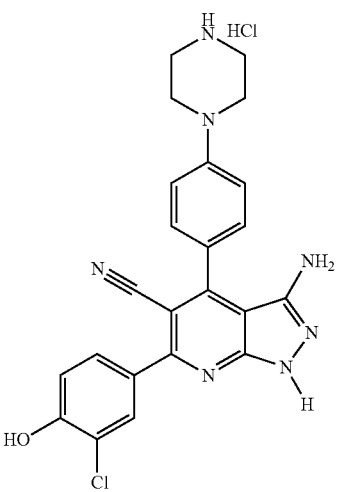 [SMILES: Cl ; N#Cc1c(-c2ccc(O)c(Cl)c2)nc2[nH]nc(N)c2c1-c1ccc(N2CCNCC2)cc1] |

221
-continued
193
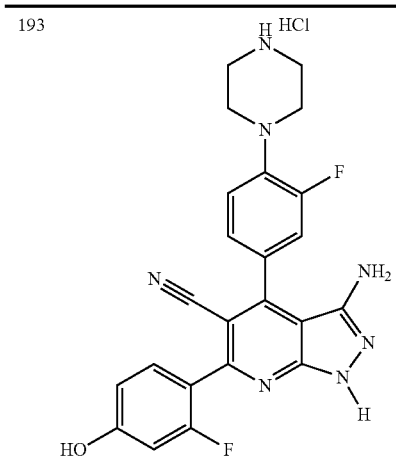
194
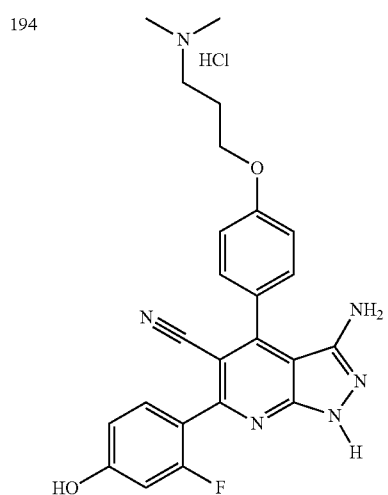
195
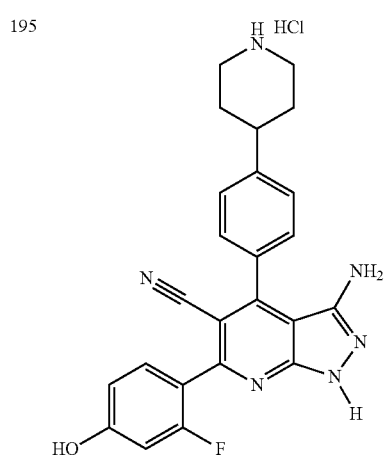
222
-continued
196
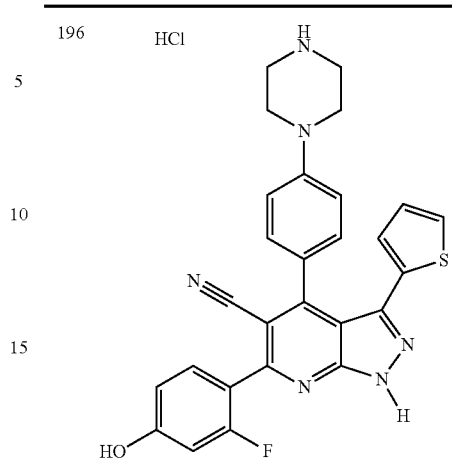
197
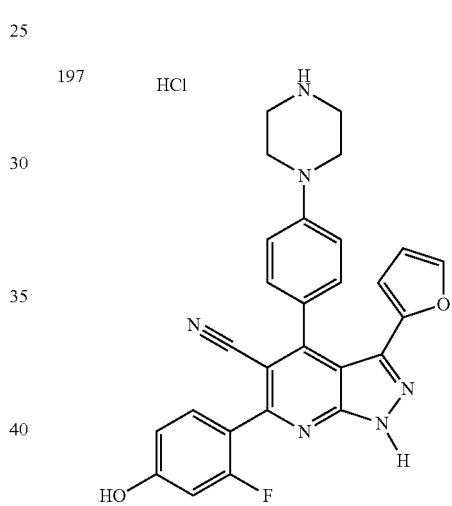
198
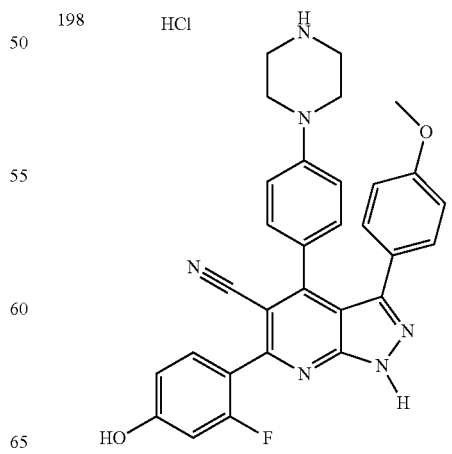

| 223 -continued | 224 -continued |
|---|---|
| 199 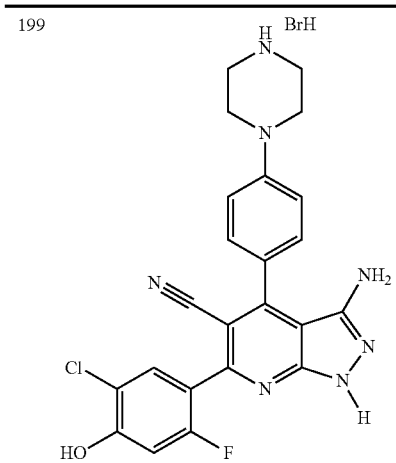 | 202 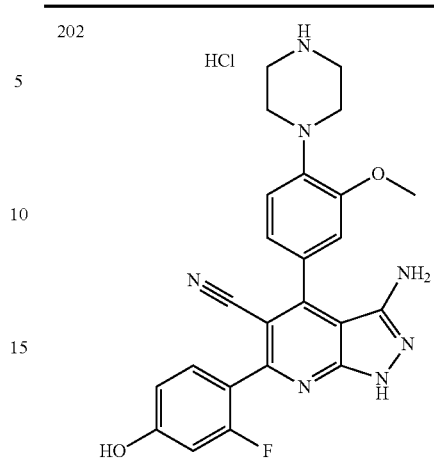 |
| 200 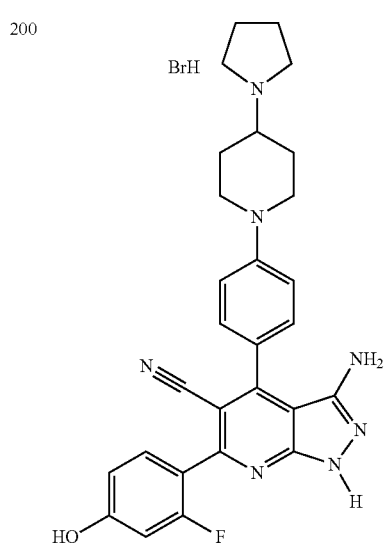 | 203 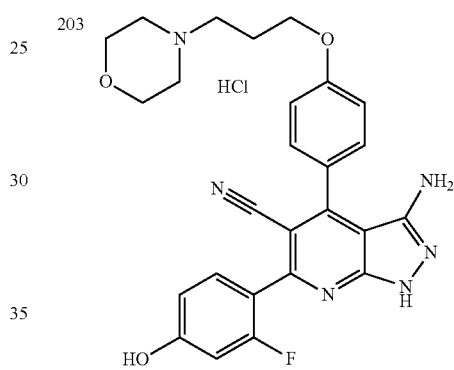 |
| | 204 |
| 201 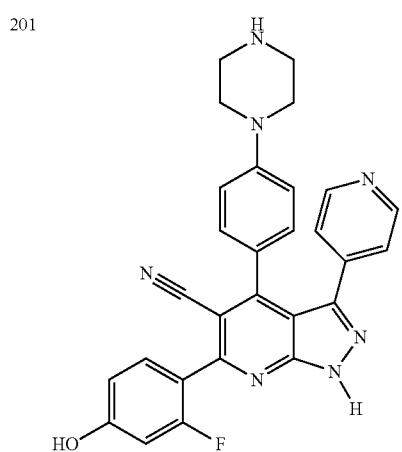 | 205 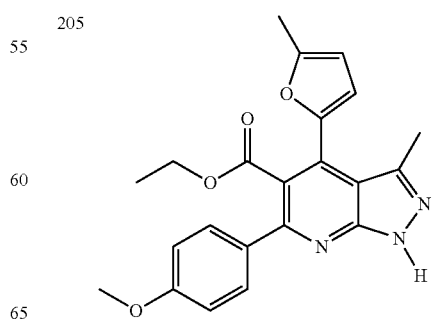 |

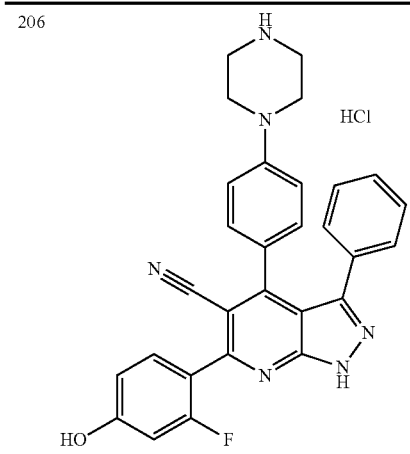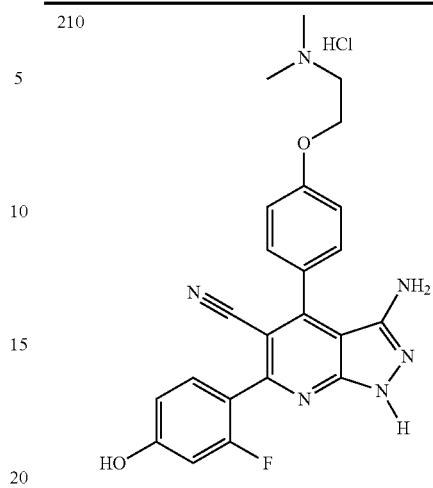

| 213 | 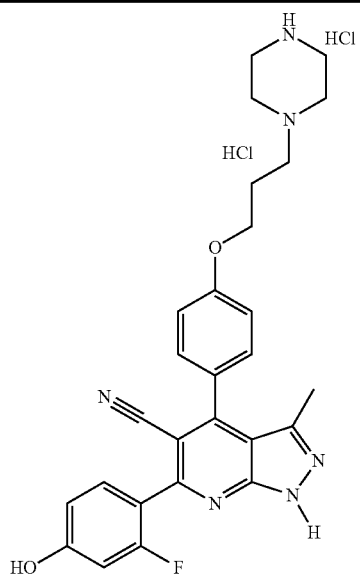 |
|---|---|
| 214 | 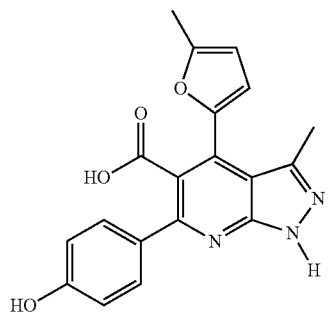 [SMILES: Cc1ccc(-c2c(C(=O)O)c(-c3ccc(O)cc3)nc3[nH]nc(C)c23)o1] |
| 215 | 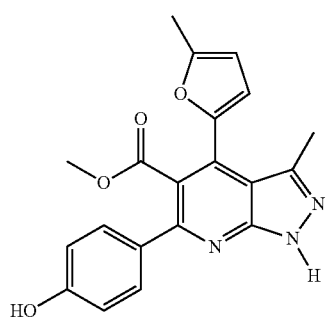 [SMILES: COC(=O)c1c(-c2ccc(O)cc2)nc2[nH]nc(C)c2c1-c1ccc(C)o1] |
| 216 | 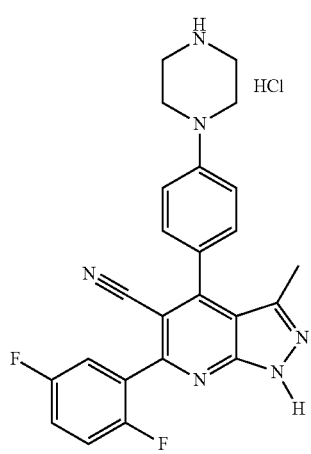 [SMILES: Cc1n[nH]c2nc(-c3cc(F)ccc3F)c(C#N)c(-c3ccc(N4CCNCC4)cc3)c12 ; Cl] |
| 217 | 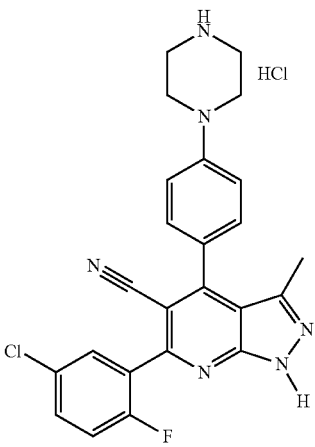 [SMILES: Cc1n[nH]c2nc(-c3cc(Cl)ccc3F)c(C#N)c(-c3ccc(N4CCNCC4)cc3)c12 ; Cl] |
|---|---|
| 218 | 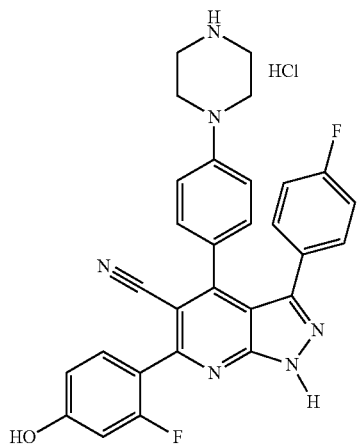 [SMILES: N#Cc1c(-c2ccc(O)cc2F)nc2[nH]nc(-c3ccc(F)cc3)c2c1-c1ccc(N2CCNCC2)cc1 ; Cl] |
| 219 | 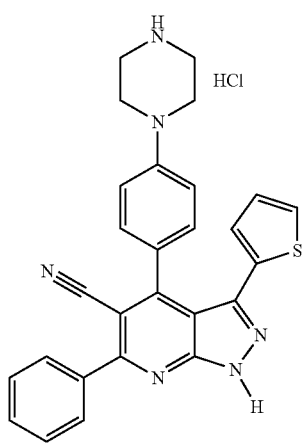 [SMILES: N#Cc1c(-c2ccccc2)nc2[nH]nc(-c3cccs3)c2c1-c1ccc(N2CCNCC2)cc1 ; Cl] |

| 220 | 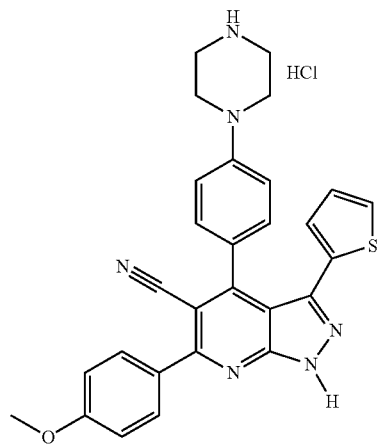 [SMILES: COc1ccc(-c2nc3[nH]nc(-c4cccs4)c3c(-c3ccc(N4CCNCC4)cc3)c2C#N)cc1 ; Cl] | 223 | 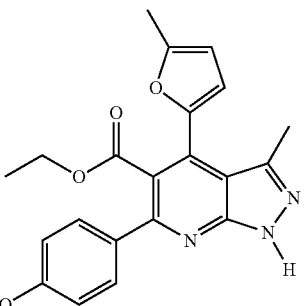 |
| --- | --- | --- | --- |
| 221 | 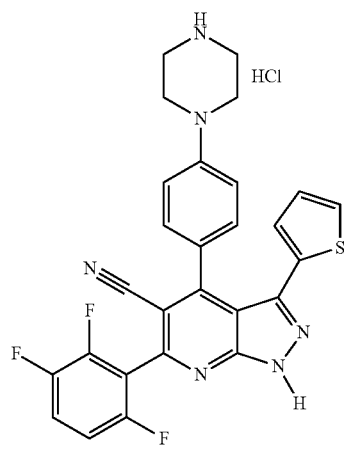 [SMILES: N#Cc1c(-c2c(F)ccc(F)c2F)nc2[nH]nc(-c3cccs3)c2c1-c1ccc(N2CCNCC2)cc1 ; Cl] | 224 | 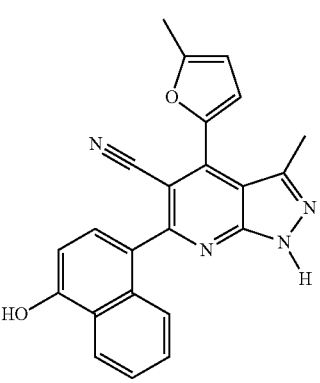 |
| | | 225 | 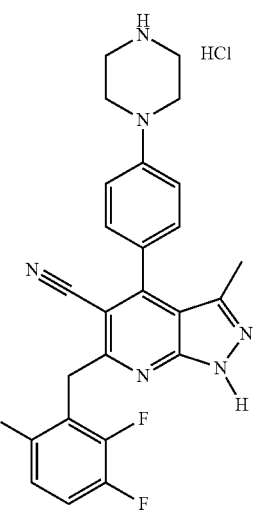 |
| 222 | 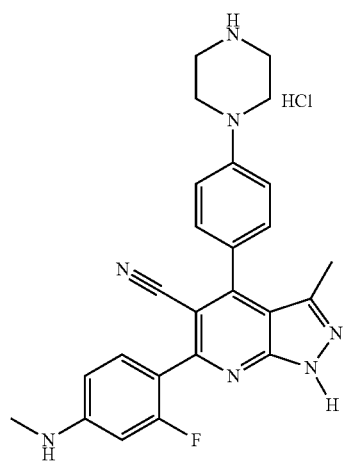 [SMILES: CNc1ccc(-c2nc3[nH]nc(C)c3c(-c3ccc(N4CCNCC4)cc3)c2C#N)c(F)c1 ; Cl] | 226 | 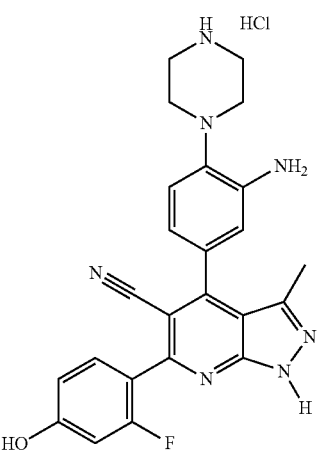 [SMILES: Cl ; Cc1n[nH]c2nc(-c3ccc(O)cc3F)c(C#N)c(-c3ccc(N4CCNCC4)c(N)c3)c12] |

| 231 -continued | 232 -continued |
|---|---|
| 227 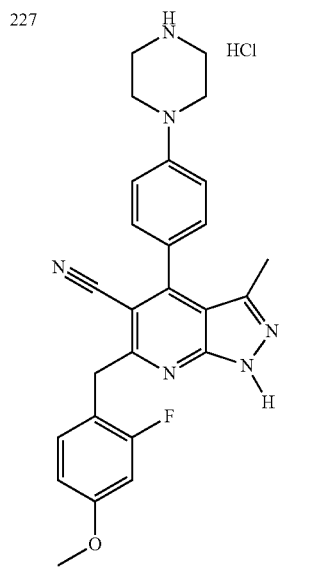 | 230 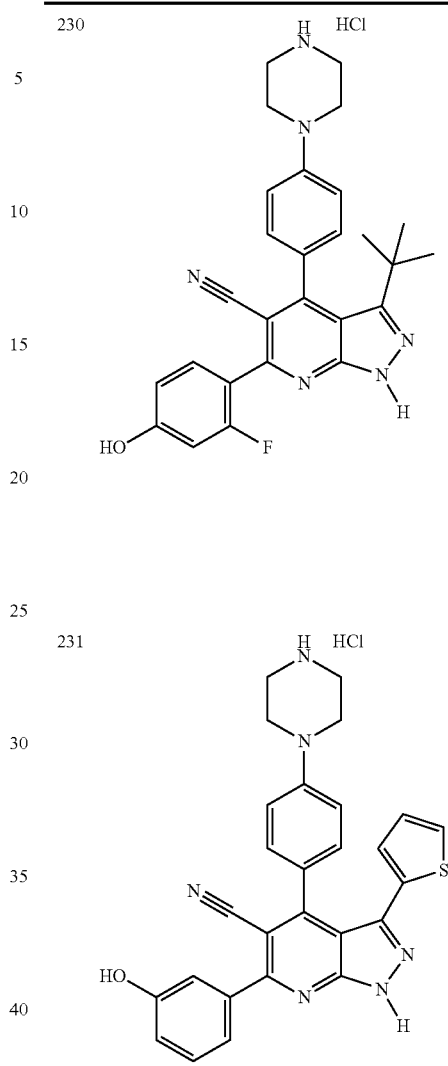 |
| 228 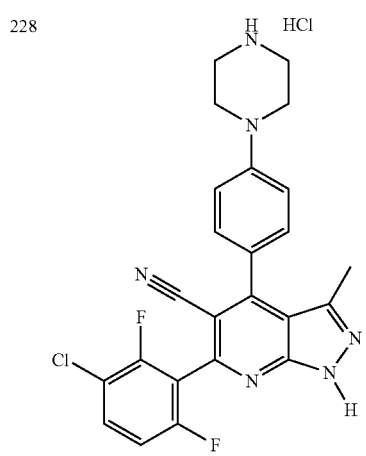 | 231 |
| 229 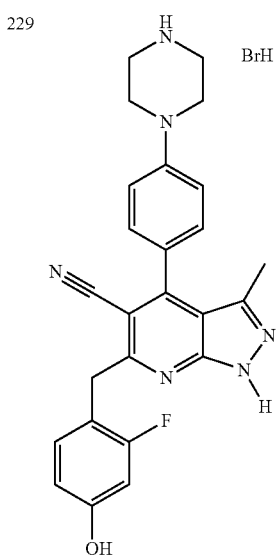 | 232 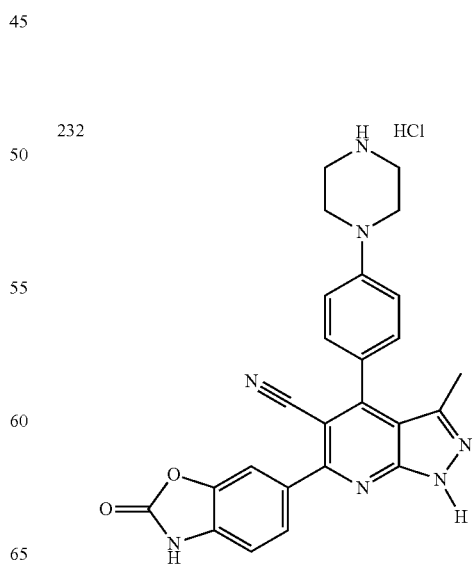 |

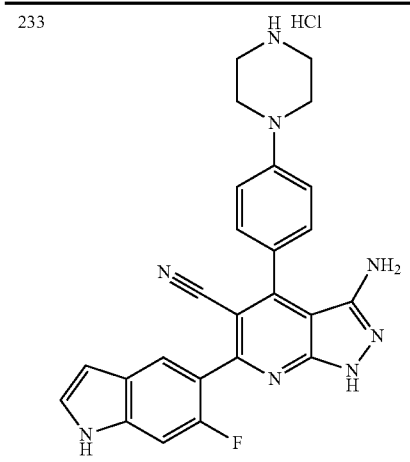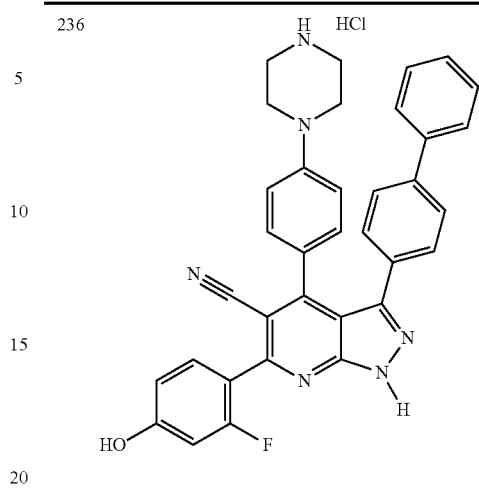

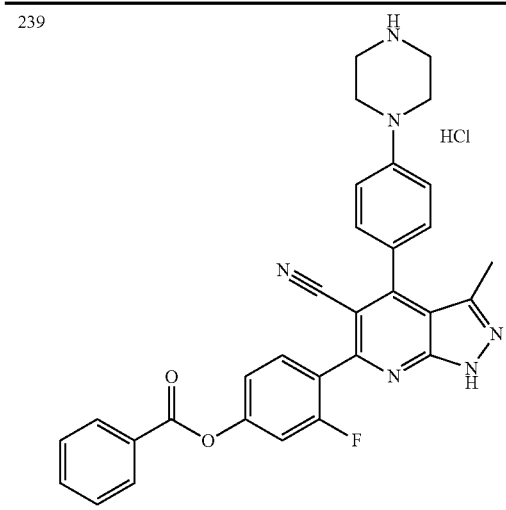
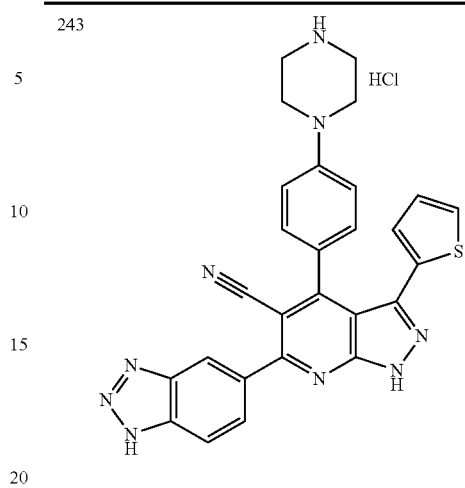

| 246 | 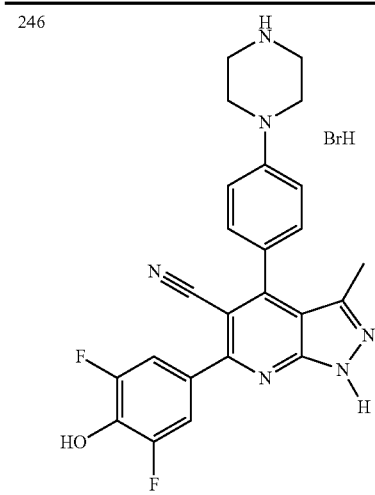 |
|---|---|
| 247 | 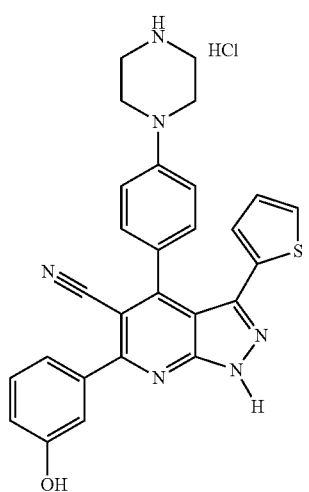 [SMILES: N#Cc1c(-c2cccc(O)c2)nc2[nH]nc(-c3cccs3)c2c1-c1ccc(N2CCNCC2)cc1 ; Cl] |
| 248 | 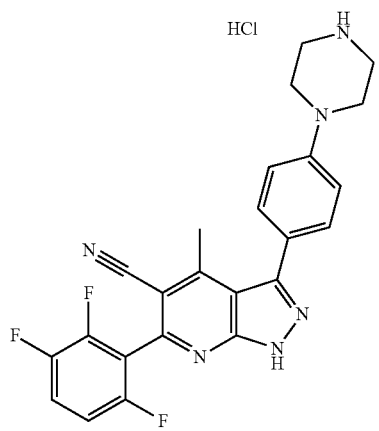 [SMILES: Cl ; Cc1c(C#N)c(-c2c(F)ccc(F)c2F)nc2[nH]nc(-c3ccc(N4CCNCC4)cc3)c12] |
| 249 | 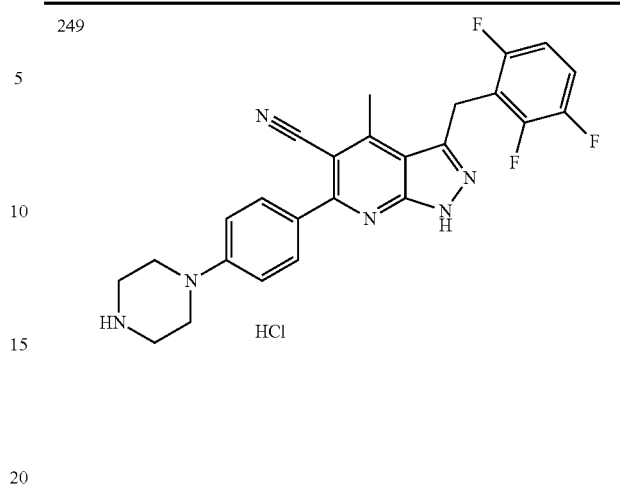 |
|---|---|
| 250 | 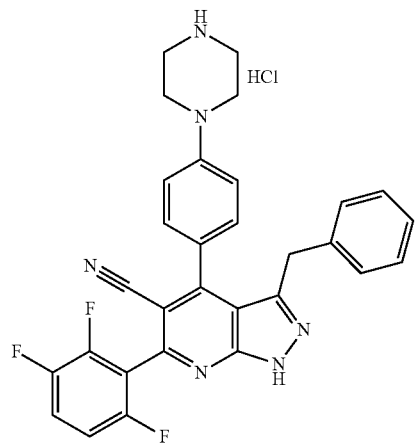 [SMILES: N#Cc1c(-c2c(F)ccc(F)c2F)nc2[nH]nc(Cc3ccccc3)c2c1-c1ccc(N2CCNCC2)cc1 ; Cl] |
| 251 | 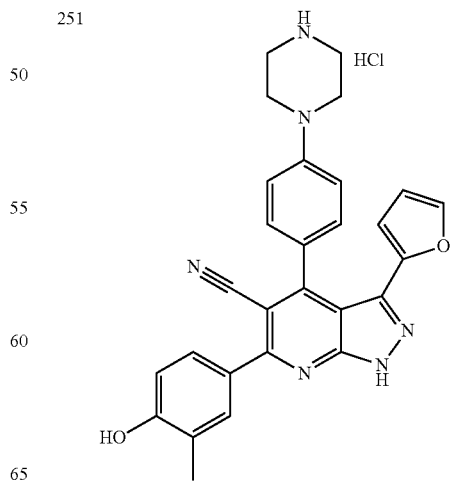 |

| 252 | 255 |
|---|---|
| 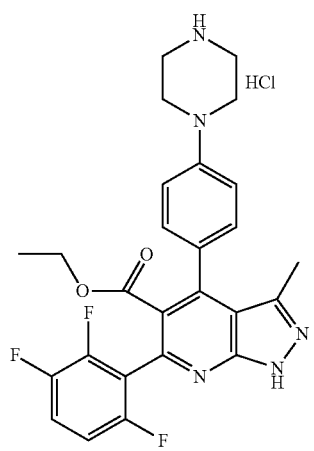 [SMILES: CCOC(=O)c1c(-c2c(F)ccc(F)c2F)nc2[nH]nc(C)c2c1-c1ccc(N2CCNCC2)cc1 ; Cl] | 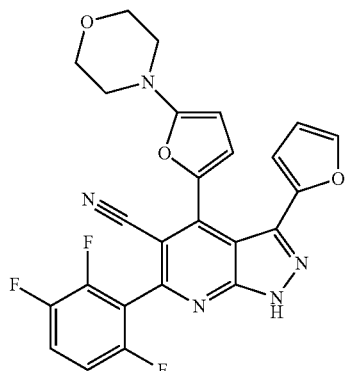 |
| 253 | 256 |
| 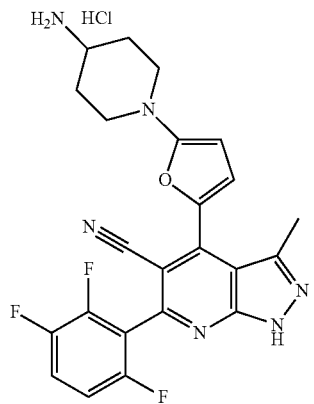 [SMILES: Cl ; Cc1n[nH]c2nc(-c3c(F)ccc(F)c3F)c(C#N)c(-c3ccc(N4CCC(N)CC4)o3)c12] | 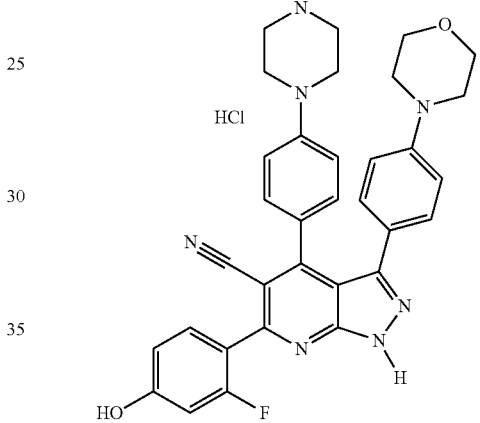 |
| 254 | 259 |
| 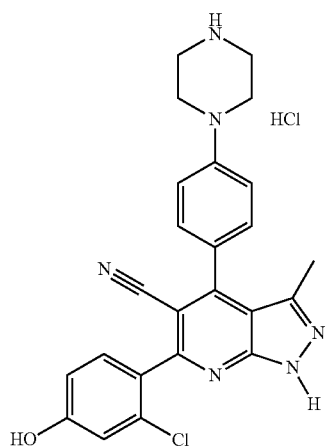 [SMILES: Cc1n[nH]c2nc(-c3ccc(O)cc3Cl)c(C#N)c(-c3ccc(N4CCNCC4)cc3)c12 ; Cl] | 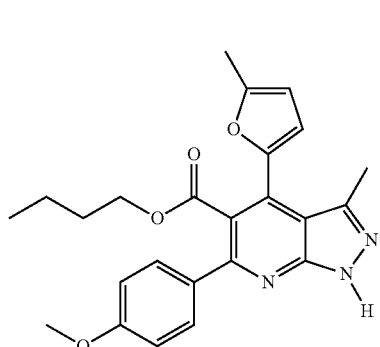 |
| | 262 |
| | 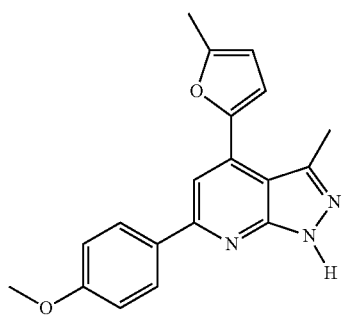 [SMILES: COc1ccc(-c2cc(-c3ccc(C)o3)c3c(C)n[nH]c3n2)cc1] |

| 241 -continued | 242 -continued |
|---|---|
| 263 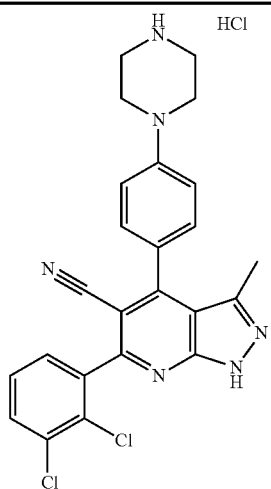 | 266 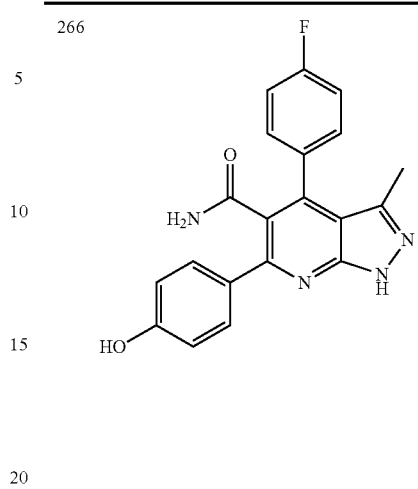 |
| 264 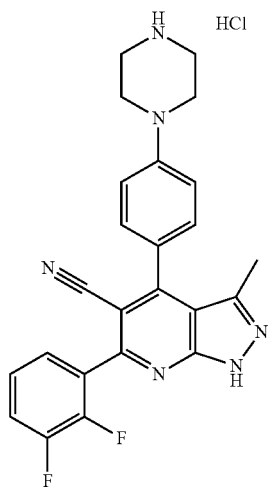 [SMILES: Cl ; Cc1n[nH]c2nc(-c3cccc(F)c3F)c(C#N)c(-c3ccc(N4CCNCC4)cc3)c12] | 267 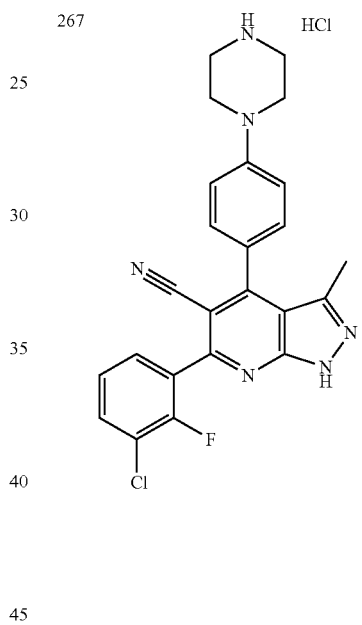 |
| 265 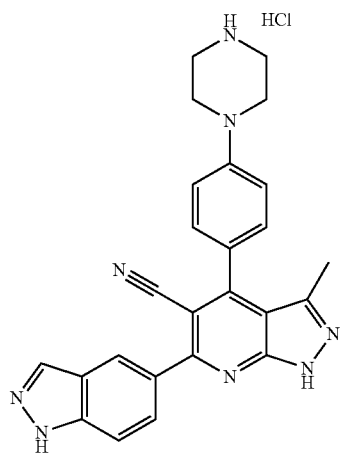 [SMILES: Cl ; Cc1n[nH]c2nc(-c3ccc4[nH]ncc4c3)c(C#N)c(-c3ccc(N4CCNCC4)cc3)c12] | 268 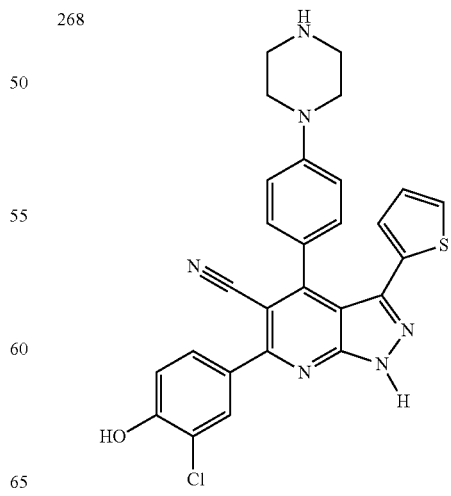 |

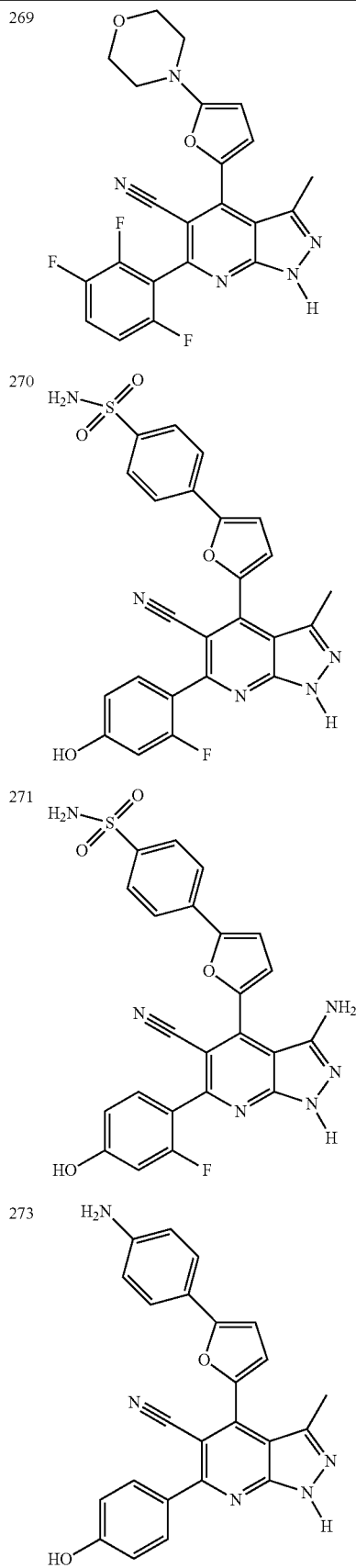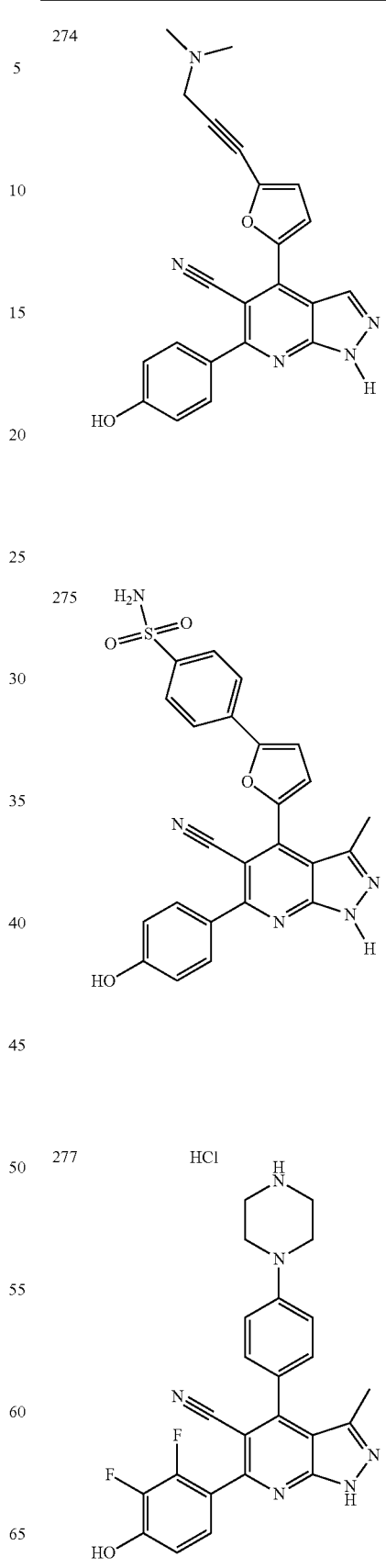

| 278 | 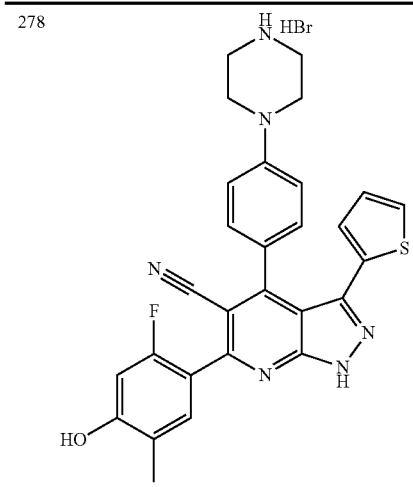 |
|---|---|
| 283 | 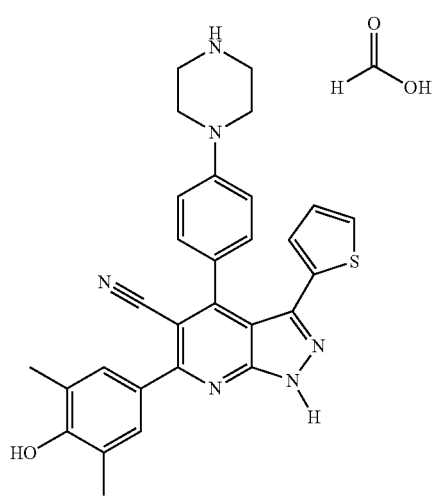 [SMILES: Cc1cc(-c2nc3[nH]nc(-c4cccs4)c3c(-c3ccc(N4CCNCC4)cc3)c2C#N)cc(C)c1O ; O=CO] |
| 284 | 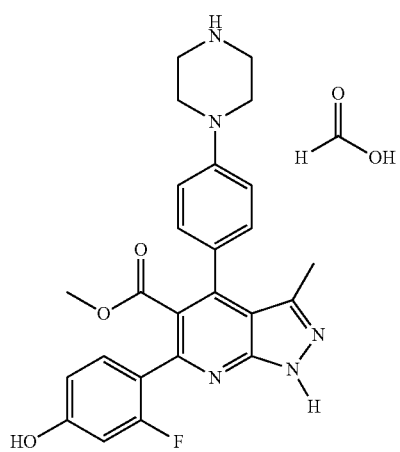 |
| 286 | 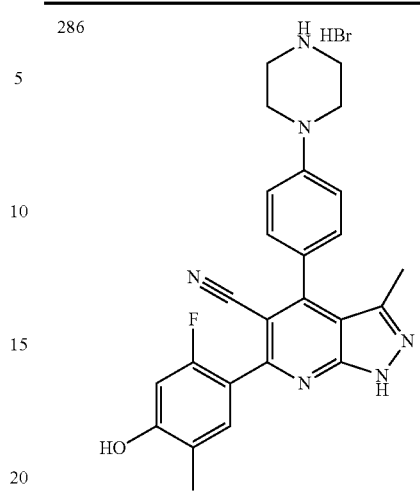 |
|---|---|
| 287 | 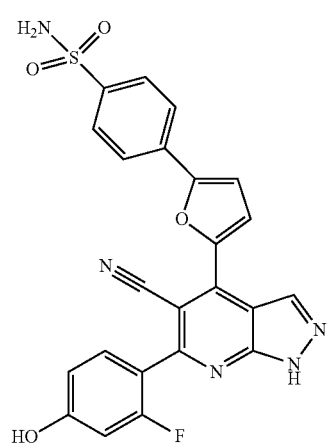 [SMILES: N#Cc1c(-c2ccc(O)cc2F)nc2[nH]ncc2c1-c1ccc(-c2ccc(S(N)(=O)=O)cc2)o1] |
| 288 | |
| 289 | 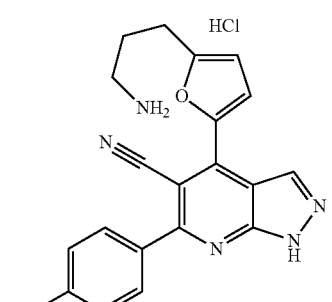 |

| 247 -continued | 248 -continued |
|---|---|
| 290 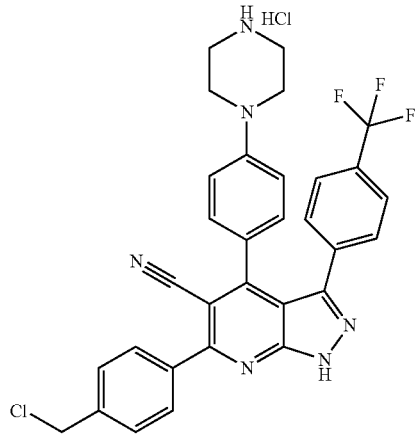 [SMILES: Cl ; N#Cc1c(-c2ccc(CCl)cc2)nc2[nH]nc(-c3ccc(C(F)(F)F)cc3)c2c1-c1ccc(N2CCNCC2)cc1] | 293 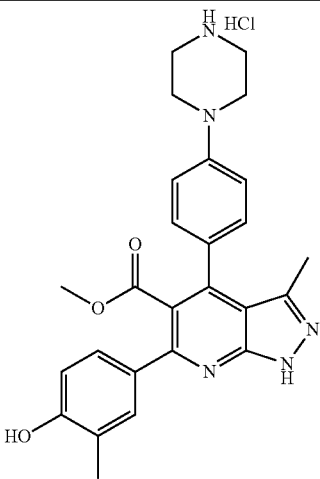 |
| 291 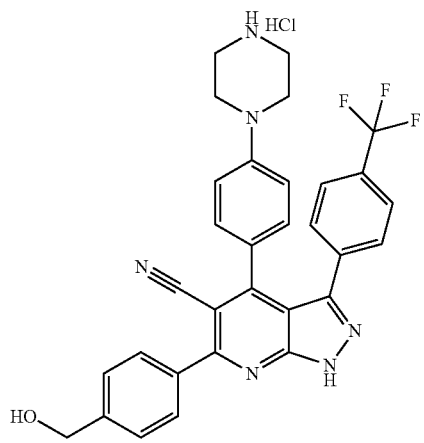 [SMILES: Cl ; N#Cc1c(-c2ccc(CO)cc2)nc2[nH]nc(-c3ccc(C(F)(F)F)cc3)c2c1-c1ccc(N2CCNCC2)cc1] | 294 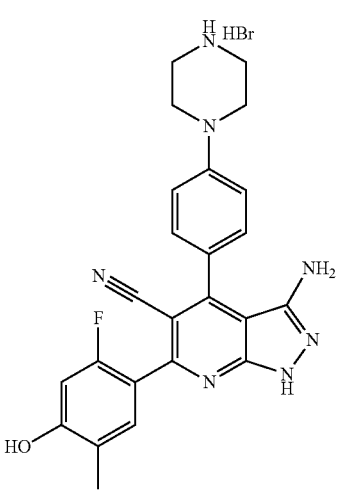 |
| 292 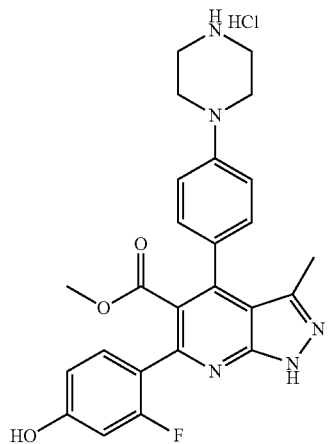 [SMILES: Cl ; COC(=O)c1c(-c2ccc(O)cc2F)nc2[nH]nc(C)c2c1-c1ccc(N2CCNCC2)cc1] | 295 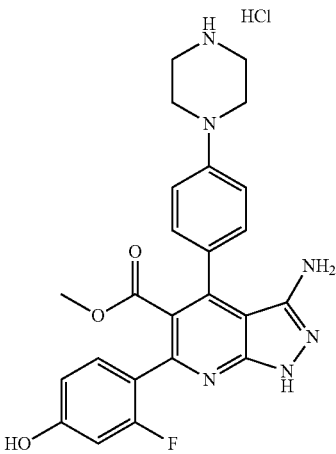 [SMILES: Cl ; COC(=O)c1c(-c2ccc(O)cc2F)nc2[nH]nc(N)c2c1-c1ccc(N2CCNCC2)cc1] |

249
-continued
250
-continued
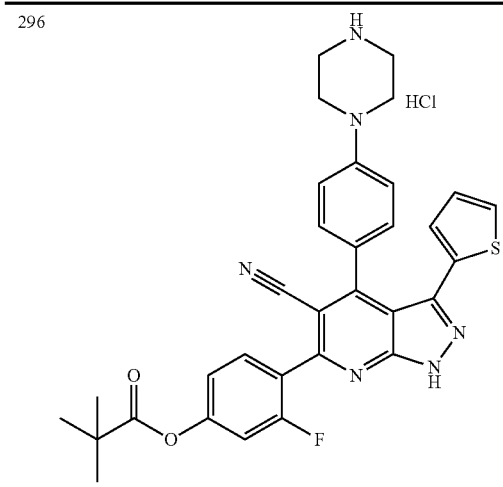
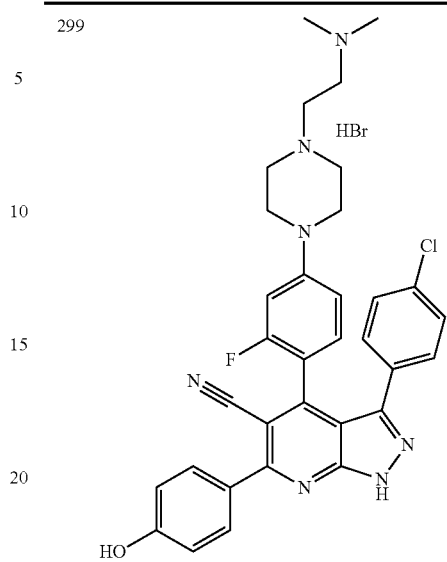

302 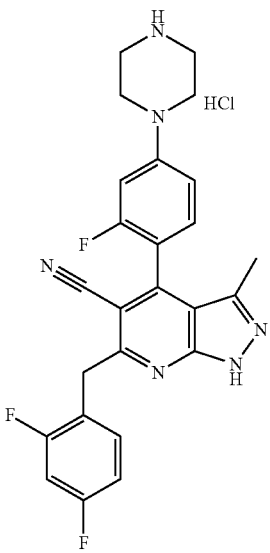 [SMILES: Cc1n[nH]c2nc(Cc3ccc(F)cc3F)c(C#N)c(-c3ccc(N4CCNCC4)cc3F)c12 ; Cl]

303 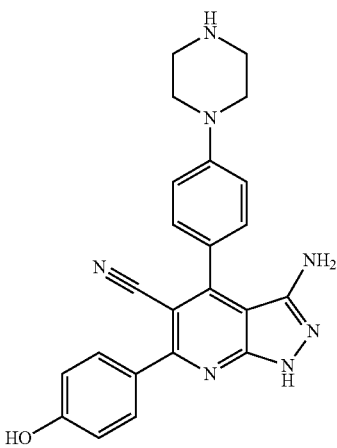 [SMILES: N#Cc1c(-c2ccc(O)cc2)nc2[nH]nc(N)c2c1-c1ccc(N2CCNCC2)cc1]

304 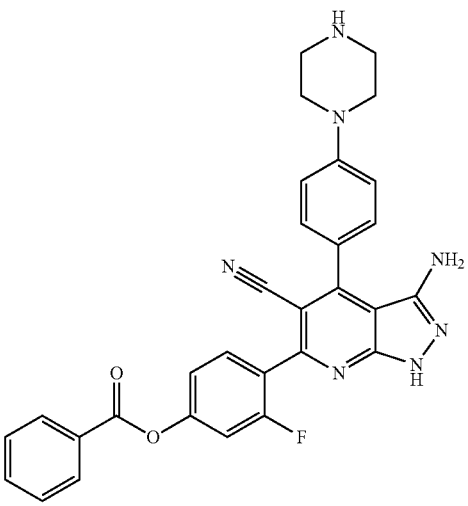 [SMILES: N#Cc1c(-c2ccc(OC(=O)c3ccccc3)cc2F)nc2[nH]nc(N)c2c1-c1ccc(N2CCNCC2)cc1]

305 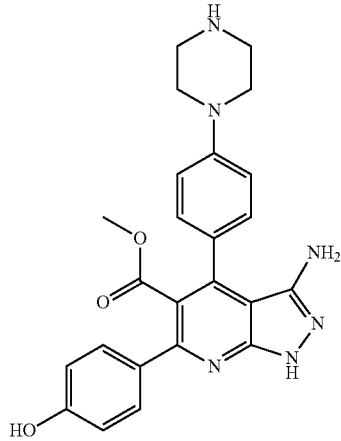

306 

307 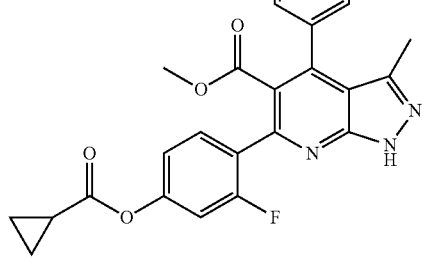

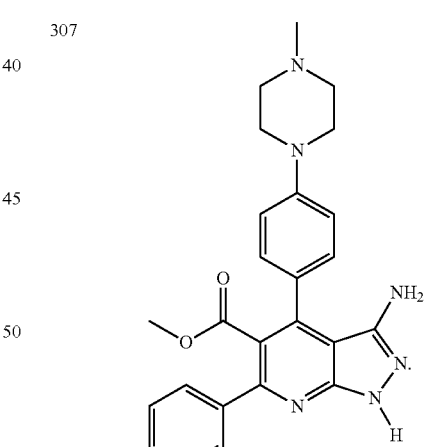

9. A pharmaceutical composition comprising at least one compound according to claim 1: and a pharmaceutically acceptable excipient.

10. The pharmaceutical composition according to claim 9, further comprising at least one other active ingredient.

11. A pharmaceutical composition containing:
(i) at least one compound according to claim 1, and
(ii) at least one other active ingredient, as a combination product for simultaneous, separate, or sequential use.

12. A method for preparing a compound according to claim 1, comprising a condensation reaction between $R^1$—C(O)—$CH_2$—$R^0$ (II), $R^2$—CHO (III) and

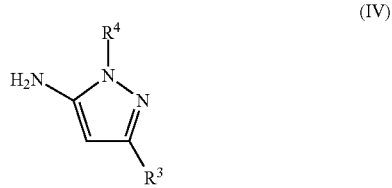
(IV)

to give the compound of following formula (V):

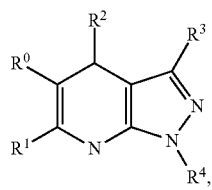
(V)

wherein $R^0$, $R^1$, $R^2$, $R^3$ and $R^4$ are as defined in claim 1, followed by an oxidation step.

13. The compound according to claim 3, wherein $R^1$ is a phenyl, naphtyl, furyl, thienyl, pyrrolyl, indolyl, benzoimidazolyl, indazolyl or benzotriazolyl, said group being optionally substituted with one or more groups chosen from among a halogen atom, a OH, CN, $NO_2$, $NH_2$, $CO_2H$, ($C_1$-$C_6$)alkyl optionally substituted with an OH group, ($C_1$-$C_6$)alcoxy, ($C_1$-$C_6$)haloalkyl, ($C_1$-$C_6$)haloalcoxy, aryl, aryloxy, aryl-($C_1$-$C_6$) alkyl, aryl-($C_1$-$C_6$)alcoxy, heteroaryl, heterocycle, —$CO_2$—(($C_1$-$C_6$)alkyl), aryl-carbonyloxy, —NH—(($C_1$-$C_6$)alkyl), and $NHSO_2$—(($C_1$-$C_6$) group.

14. The compound according to claim 13, wherein $R^1$ is a phenyl group, said group being optionally substituted with one or more groups chosen from among a halogen atom, a group OH, ($C_1$-$C_6$)alcoxy, ($C_1$-$C_6$)alkyl, and ($C_1$-$C_6$)haloalkyl.

15. The compound according to claim 5, wherein $R^3$ is a hydrogen atom, $NH_2$, ($C_1$-$C_6$)alkyl, an aryl which is phenyl, or an heteroaryl which is chosen from among furanyl, thienyl, pyridinyl, isoxazolyl, thiazolyl and oxadiazolyl, the aryl and heteroaryl rings being optionally substituted with one or more groups chosen from among a halogen atom, a group: $NO_2$, $CO_2H$, $NR^{16}R^{17}$, aryl, ($C_1$-$C_6$)alkyl, ($C_1$-$C_6$)haloalkyl, ($C_1$-$C_6$)alcoxy, $CO_2$—($C_1$-$C_6$)alkyl and heterocyle, the heterocycle ring being optionally substituted with a ($C_1$-$C_6$)alkyl, ($C_1$-$C_6$)alcoxy and NH—($C_1$-$C_6$)alkyl group.

16. The compound according to claim 6, wherein $R^3$ is a hydrogen atom, a $NH_2$, methyl, phenyl, thienyl, or furanyl group.

17. The compound according to claim 7, wherein $R^5$, $R^6$, $R^7$, $R^8$, and $R^9$ are each independently a hydrogen atom, a halogen atom, a group OH, ($C_1$-$C_6$)alcoxy, ($C_1$-$C_6$)alkyl, or ($C_1$-$C_6$)haloalkyl.

18. The pharmaceutical composition according to claim 10, wherein the at least one other active ingredient is an anticancer agent.

19. The pharmaceutical composition according to claim 11, wherein the at least one other active ingredient is an anticancer agent.

\* \* \* \* \*

UNITED STATES PATENT AND TRADEMARK OFFICE
CERTIFICATE OF CORRECTION

PATENT NO.       : 8,889,711 B2
APPLICATION NO.  : 13/500757
DATED            : November 18, 2014
INVENTOR(S)      : Karim Bedjeguelal et al.

It is certified that error appears in the above-identified patent and that said Letters Patent is hereby corrected as shown below:

Column 6, line 43, replace "$NHSO_2\text{-}((c1C6)alkyl$" with "$NHSO_2\text{-}((C1\text{-}C6)alkyl$--;

Signed and Sealed this
Twenty-seventh Day of October, 2015

Michelle K. Lee
*Director of the United States Patent and Trademark Office*

CERTIFICATE OF CORRECTION (continued)
U.S. Pat. No. 8,889,711 B2

Page 2 of 19

Column 26 through Column 27, the N atom is missing on the pyrazolopyridine moieties on the compounds 75 to 81.

Please replace the following:

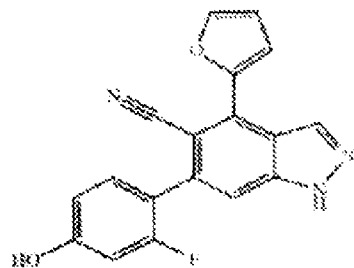
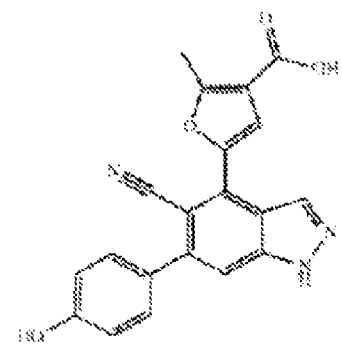
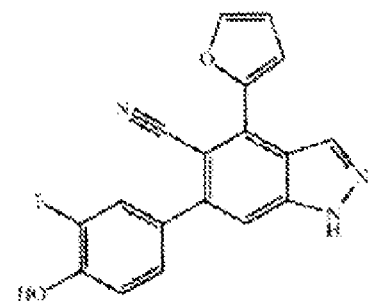
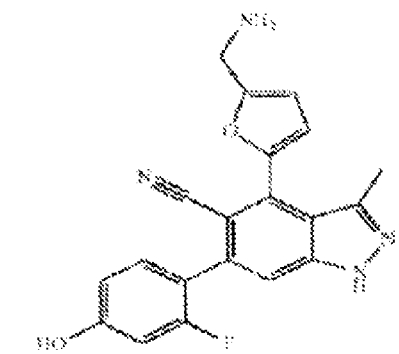
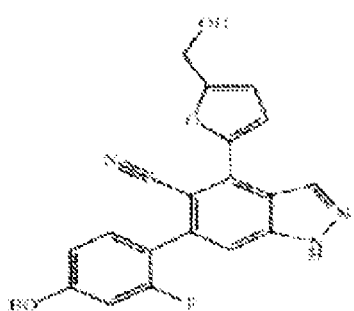
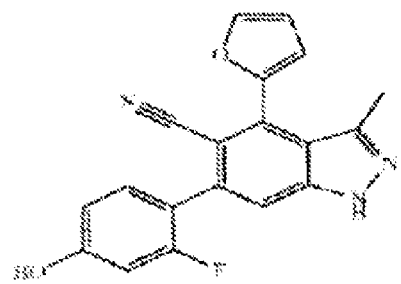
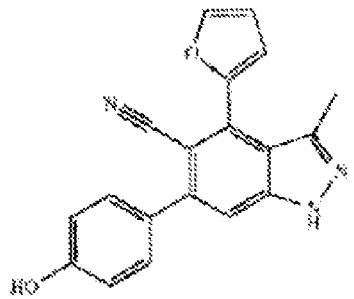

CERTIFICATE OF CORRECTION (continued)
U.S. Pat. No. 8,889,711 B2

With:

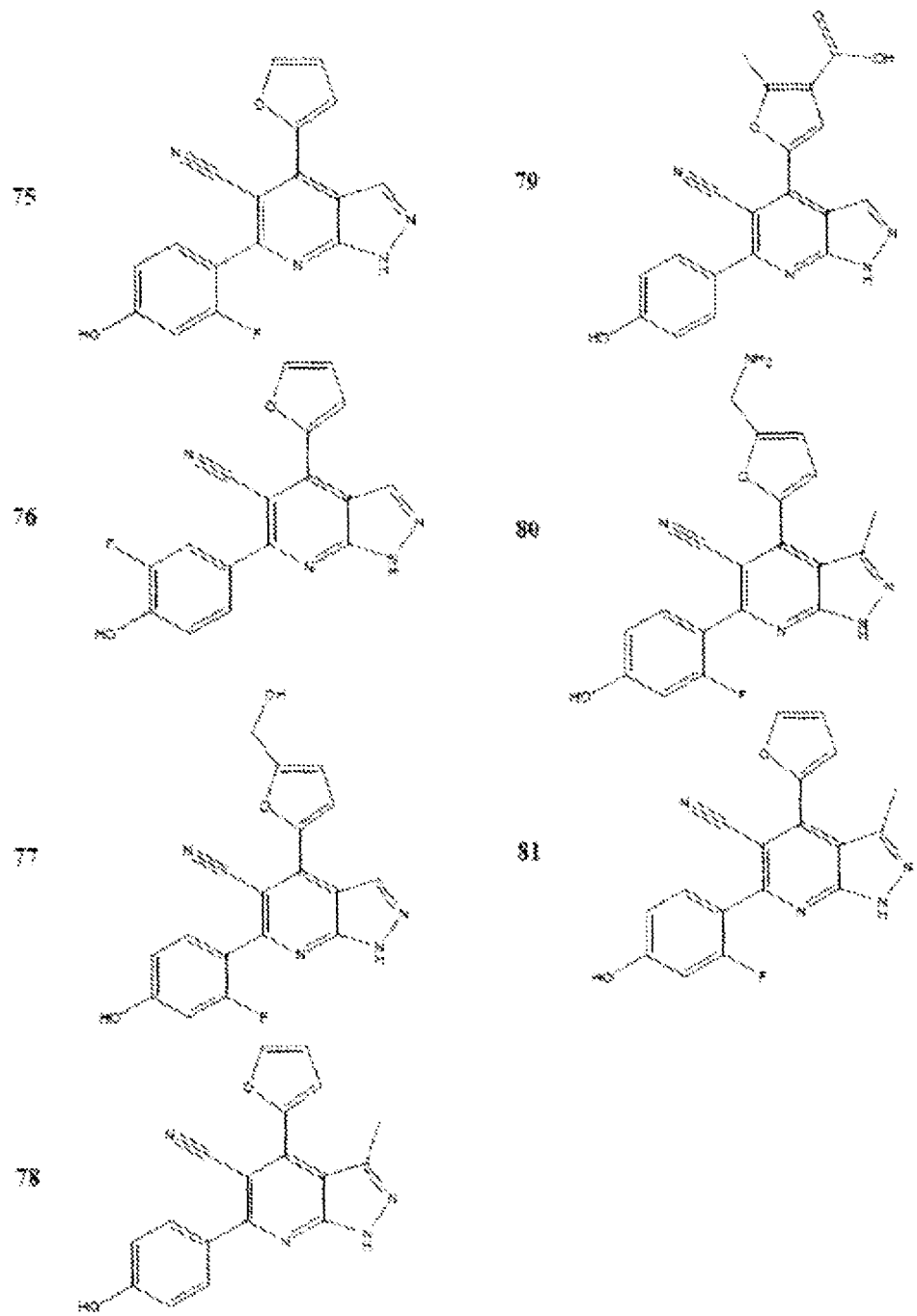

Column 39 through Column 40 - an H atom is missing on one of the azote atom of the pyrazolopyridines moieties of Compounds 127 and 128:
Replace:
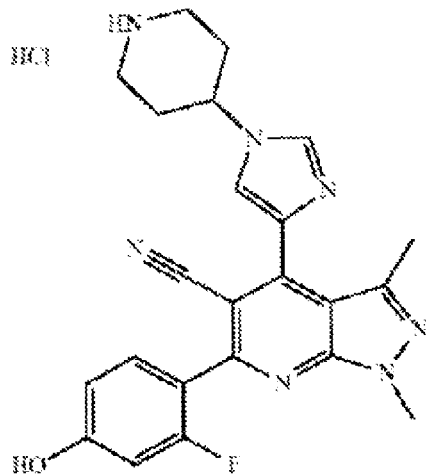 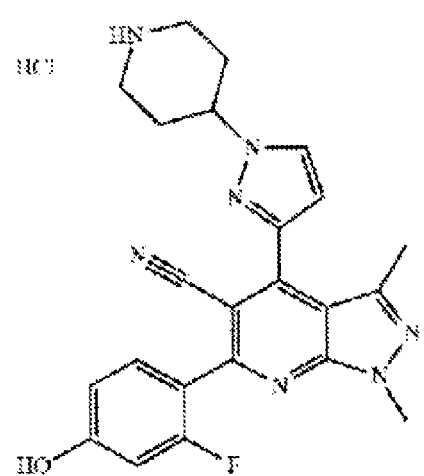
With:
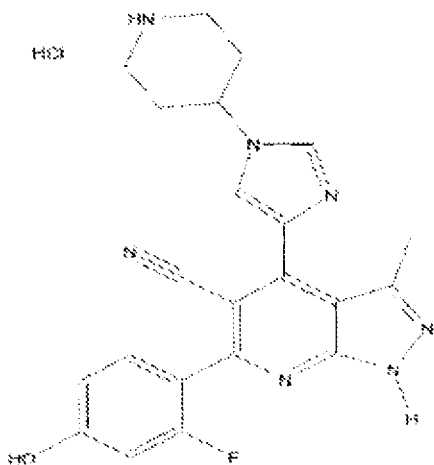 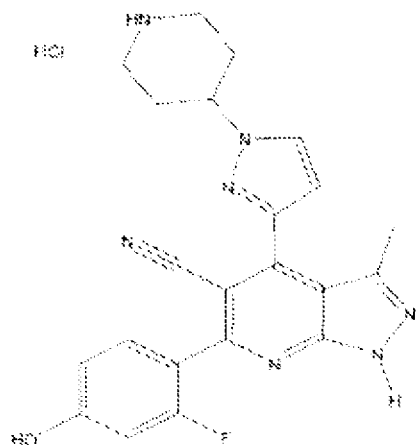
Column 52 - the O atom must be replaced by the S atom on the furan cycle of compound 173:

Please replace:
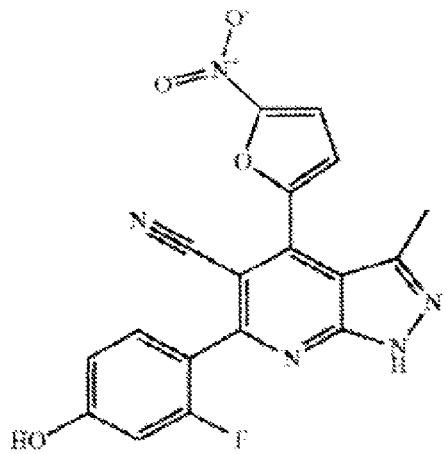
With:
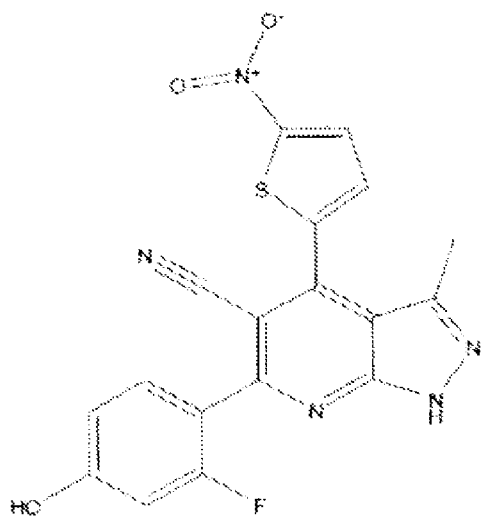
Column 54 - the N atom must be canceled on the piperazine cycle of compound 182.

CERTIFICATE OF CORRECTION (continued)
U.S. Pat. No. 8,889,711 B2

Please replace:

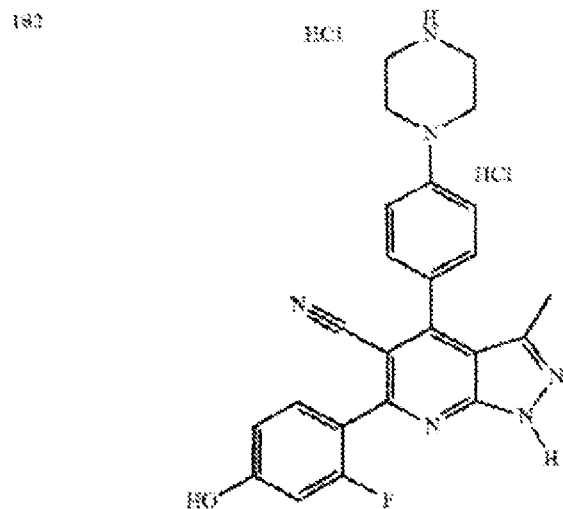

With:

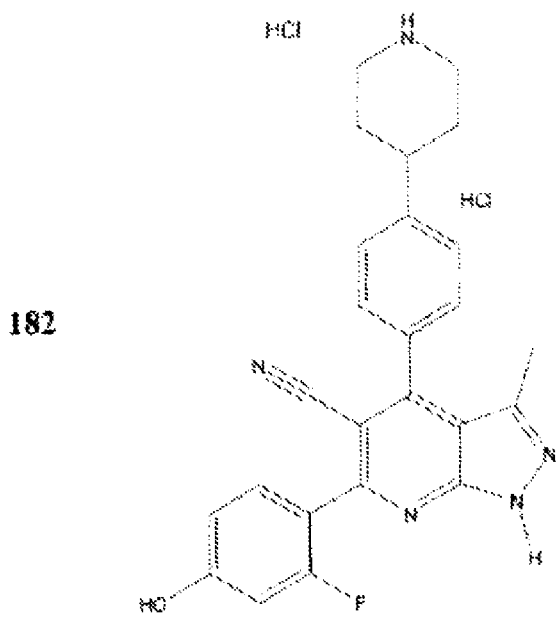

Column 59 - the HCl is missing on compound 196;

CERTIFICATE OF CORRECTION (continued)
U.S. Pat. No. 8,889,711 B2

Page 7 of 19

Please replace:

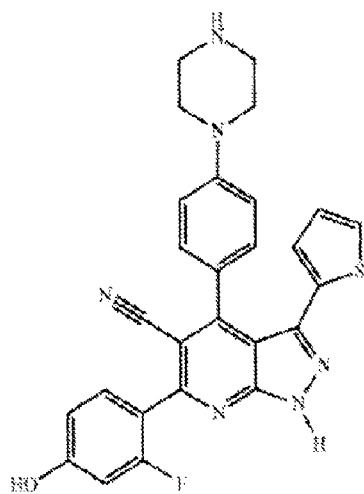

With:

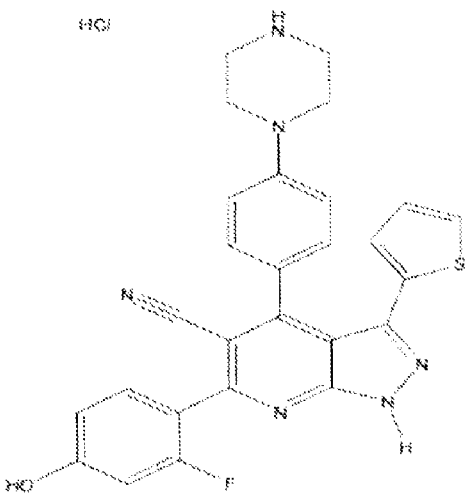

Column 61 - an O atom is missing on the piperidine cycle of compound 203.

CERTIFICATE OF CORRECTION (continued)   Page 8 of 19
U.S. Pat. No. 8,889,711 B2

Please replace:

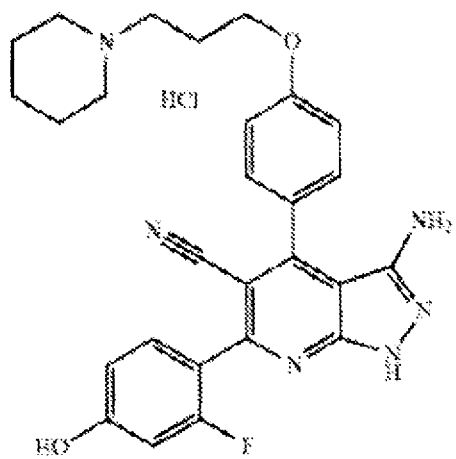

With:

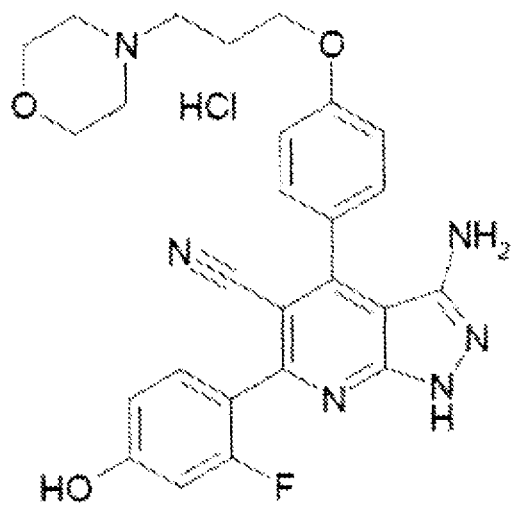

Column 71 - the N atom must be replaced by N+ in the group $NO_2$ of compound 235.

CERTIFICATE OF CORRECTION (continued)
U.S. Pat. No. 8,889,711 B2

Page 9 of 19

Please replace:

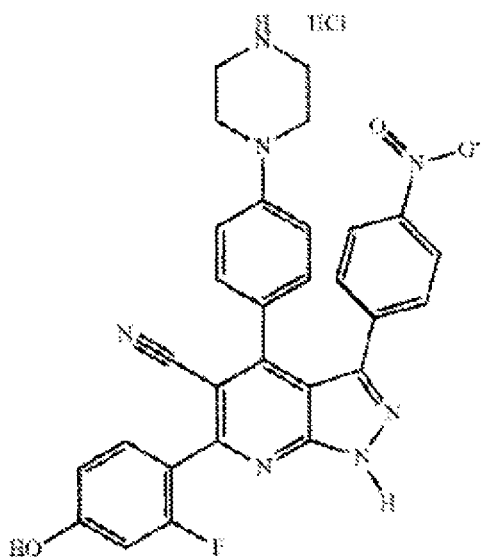

With:

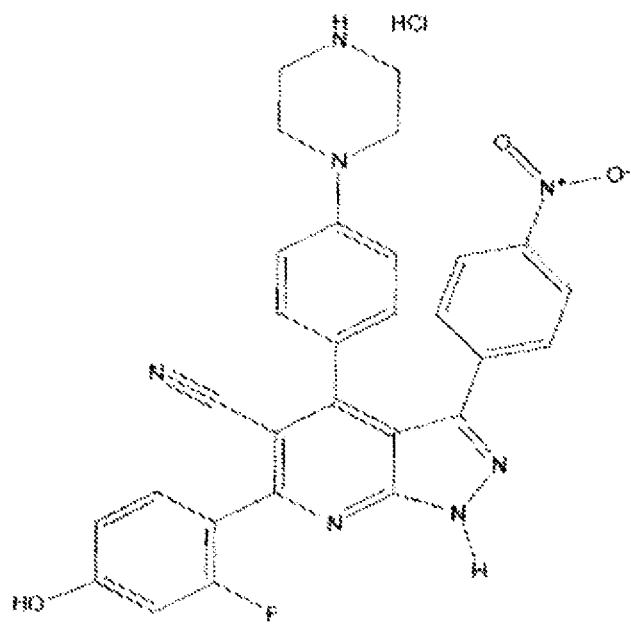

Column 77 - the Cl atom must be replaced by the F atom on compound 256.

288
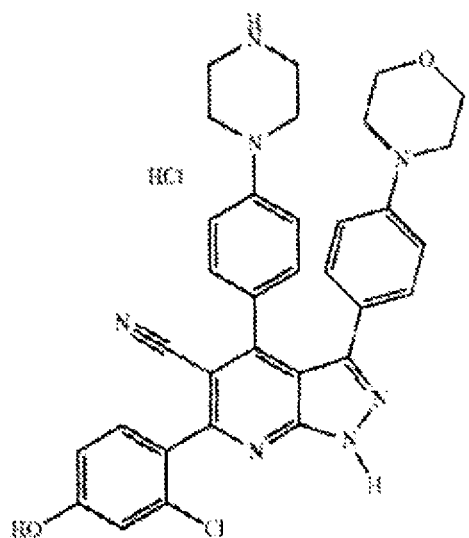
With:
256
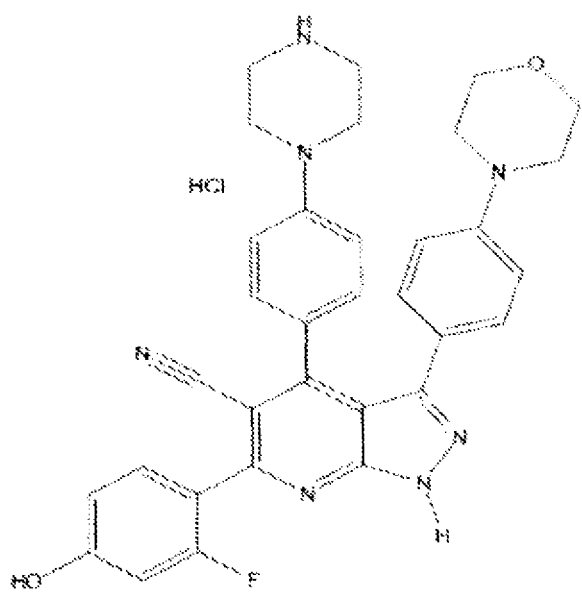
Column 85 - the HCl is missing on compound 279:

Please replace:
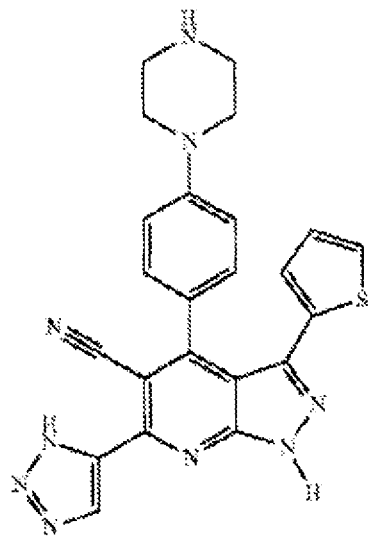
With:
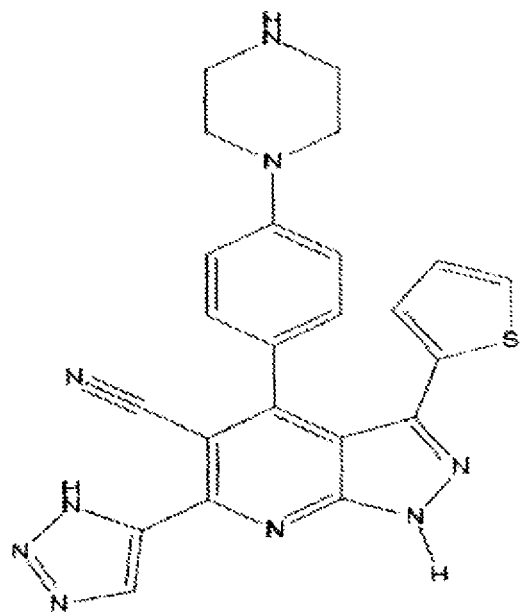
Column 123, Line 24 – please replace "caroxylate" with --carboxylate-- as correctly reflected below.

Please replace:

tert-butyl 4-((5-amino-1H-pyrazol-3-carboxamido)methyl)piperidine-1-caroxylate

With:

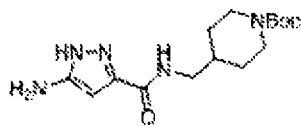

tert-butyl 4-((5-amino-1H-pyrazol-3-carboxamido)methyl)piperidine-1-carboxylate

Column 124, Line 11 – replace "piperzine" with --piperazine-- as correctly reflected below:

Please replace:

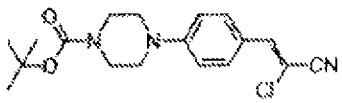

tert-butyl 4-(4-(2-chloro-2-cyanovinyl)phenyl)piperzine-1-carboxylate

With:

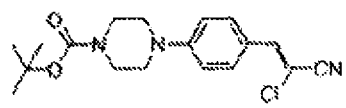

tert-butyl 4-(4-(2-chloro-2-cyanovinyl)phenyl)piperazine-1-carboxylate

Column 124, Line 54 – replace "piperzine" with --piperazine-- as correctly reflected below:

Please replace:

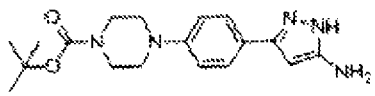

tert-butyl 4-(4-(5-amino-1H-pyrazol-3-yl)phenyl)piperzine-1-carboxylate

With:

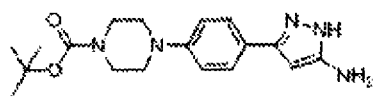

tert-butyl 4-(4-(5-amino-1H-pyrazol-3-yl)phenyl)piperazine-1-carboxylate

Column 125, Line 15 – replace "piperzine" with --piperazine-- as correctly reflected below:

Please replace:

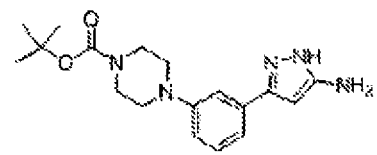

tert-butyl 4-(3-(5-amino-1H-pyrazol-3-yl)phenyl)piperazine-1-carboxylate

With:

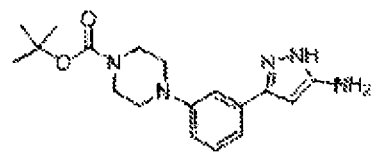

tert-butyl 4-(3-(5-amino-1H-pyrazol-3-yl)phenyl)piperazine-1-carboxylate

Column 125, Compound III - the O atom is missing:

Please replace:
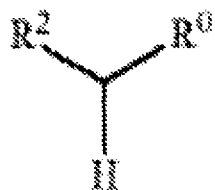
With:
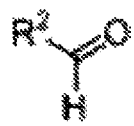
Column 129, Line 59 – the F atom needs to be removed:
Please replace:
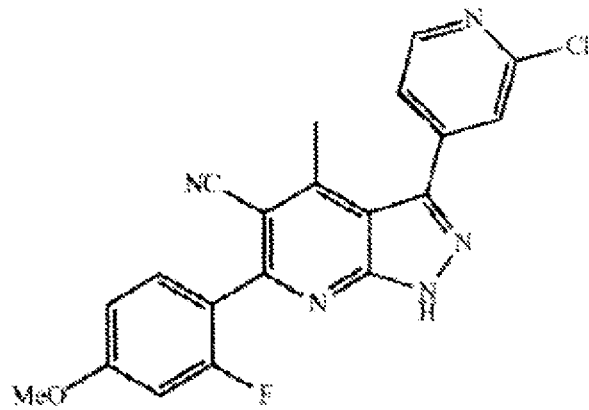
With:

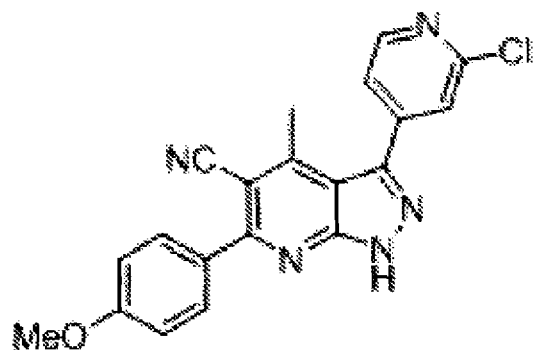
Column 130, Line 59 – the F atom needs to be removed:
Please replace:
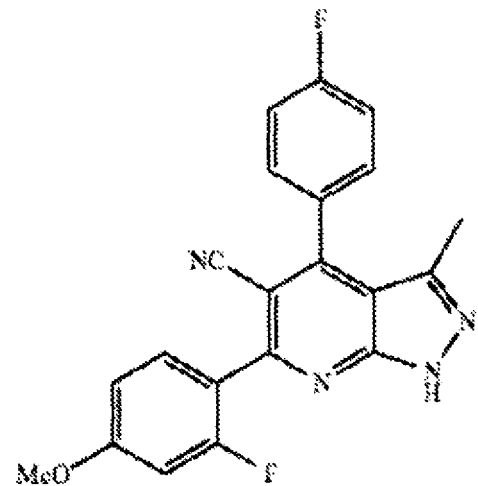
With:
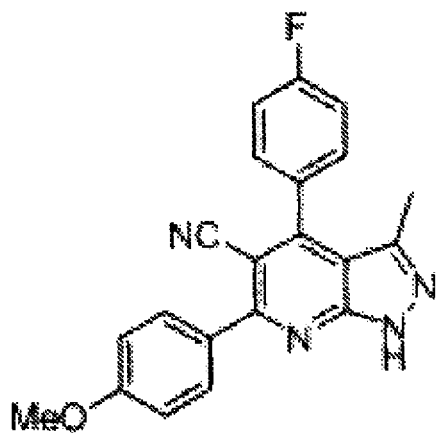
Column 142, Line 63 – replace "pyridine–4–carbohydrazide" with --pyridine–3–carbohydrazide-- as correctly reflected below:

Please replace:

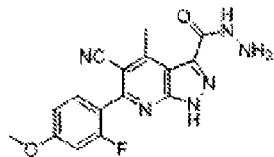

5-cyano-6-(2-fluoro-4-methoxyphenyl)-4-methyl-1H-pyrazolo[3,4-b]pyridine-4-carbohydrazide With:

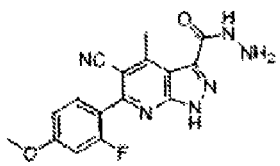

5-cyano-6-(2-fluoro-4-methoxyphenyl)-4-methyl-1H-pyrazolo[3,4-b]pyridine-3-carbohydrazide Column 147, line 31 – please replace "8.99 (1H, sl, NH), 7.53 (1H, t, $CH_{arom}$), 7.39 (1H, d, 7.00 (1H," with ---8.99(1 H, sl, NH), 7.53 (1H, t, $CH_{arom}$), 7.39 (1H, d, $CH_{arom}$), 7.00 (1H,--.

Column 149, Line 66 – replace "2-fluoro-4-methoxyphenyl" with --2-fluoro-4-methoxyphenol-- as indicated below:

Please replace:

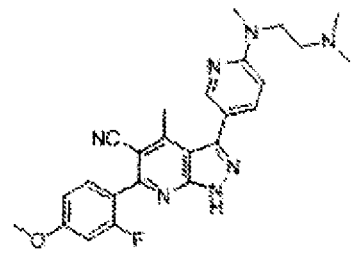

3-(6-((2-(dimethylamino)ethyl)(methyl)amino)pyridine-3-yl)-6-(2-fluoro-4-methoxyphenyl)-4-methyl-1H-pyrazolo[3,4-b]pyridine-5-carbonitrile With:

CERTIFICATE OF CORRECTION (continued)
U.S. Pat. No. 8,889,711 B2

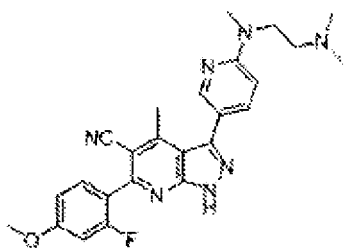

3-(6-((2-(dimethylamino)ethyl)(methyl)amino)pyridine-3-yl)-6-(2-fluoro-4-methoxyphenol)-4 methyl-1H-pyrazolo[3,4-b]pyridine-5-carbonitrile Column 152, Lines 4 through 40 need to be deleted because they are a duplicate of Column 153, Lines 18 through 55.

Column 166, Line 19 – the N atom on the pyridine ring in the second product needs to be removed as indicated below:

Please replace:

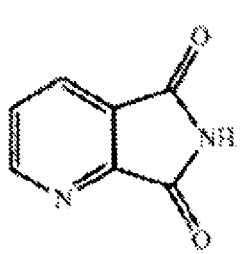

With:

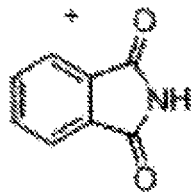

In the claims

Column 174, Claim 7 - the second $R^8$ group must be replaced by $R^9$ on compound (Ia) as indicated below:

Please replace:

CERTIFICATE OF CORRECTION (continued)
U.S. Pat. No. 8,889,711 B2

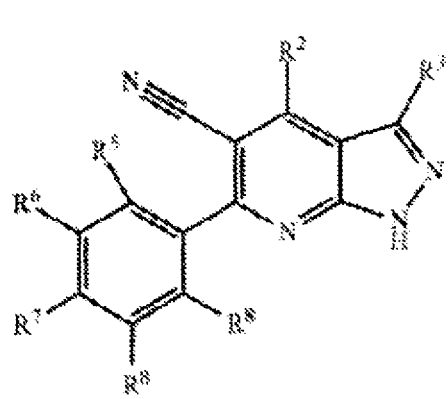

With:

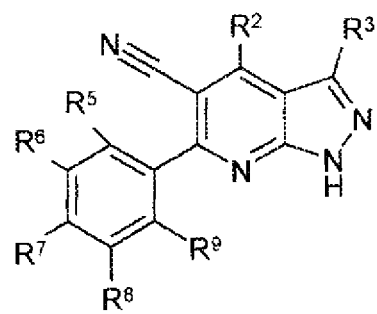

Column 208 – the N atom must be replaced by NH as indicated below:

Please replace:

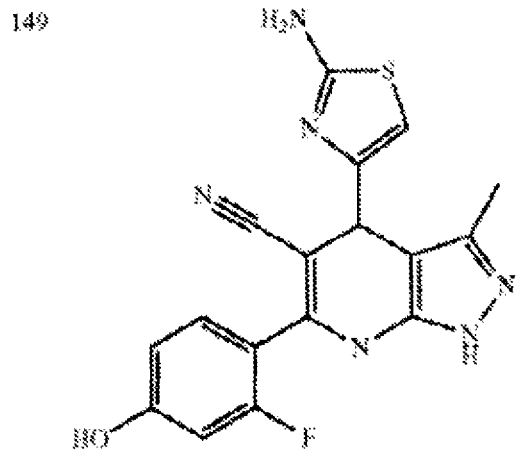

With: